US008916161B2

(12) United States Patent
Buckley

(10) Patent No.: US 8,916,161 B2
(45) Date of Patent: Dec. 23, 2014

(54) METHOD OF TREATING OR PREVENTING BENIGN PROSTATIC HYPERPLASIA USING MODIFIED PORE-FORMING PROTEINS

(75) Inventor: James Thomas Buckley, Victoria (CA)

(73) Assignee: Sophiris Bio Inc. (CA)

( * ) Notice: Subject to any disclaimer, the term of this patent is extended or adjusted under 35 U.S.C. 154(b) by 1968 days.

(21) Appl. No.: 11/921,964

(22) PCT Filed: Jun. 14, 2006

(86) PCT No.: PCT/CA2006/000971
§ 371 (c)(1),
(2), (4) Date: May 7, 2010

(87) PCT Pub. No.: WO2006/133553
PCT Pub. Date: Dec. 21, 2006

(65) Prior Publication Data

US 2010/0233191 A1 Sep. 16, 2010

Related U.S. Application Data

(60) Provisional application No. 60/690,269, filed on Jun. 14, 2005.

(51) Int. Cl.

| | |
|---|---|
| ***A61K 38/16*** | (2006.01) |
| ***A61K 39/395*** | (2006.01) |
| ***A61P 13/08*** | (2006.01) |
| ***C07K 14/195*** | (2006.01) |
| ***C07K 16/28*** | (2006.01) |
| *A61K 38/00* | (2006.01) |

(52) U.S. Cl.
CPC ............... *C07K 14/195* (2013.01); *A61K 38/00* (2013.01)
USPC .................. 424/183.1; 424/130.1; 424/154.1; 424/735; 424/737; 424/750; 424/758; 514/19.5; 514/21.1; 514/21.6; 514/12.2; 514/284; 514/602; 514/604; 514/258.1; 514/252.13; 514/21.9; 530/350

(58) Field of Classification Search
CPC ....... A61K 38/08; A61K 38/16; C07K 14/195
USPC ........... 424/183.1, 735, 737, 750, 758, 154.1, 424/130.1; 514/19.5, 284, 602, 604, 258.1, 514/252.13, 21.6, 21.9; 530/350
See application file for complete search history.

(56) References Cited

U.S. PATENT DOCUMENTS

| | | | | |
|---|---|---|---|---|
| 5,599,686 | A | 2/1997 | DeFeo-Jones et al. | |
| 5,677,274 | A | 10/1997 | Leppla et al. | |
| 5,777,078 | A | 7/1998 | Bayley et al. | |
| 5,798,218 | A | 8/1998 | Buckley | |
| 5,817,771 | A | 10/1998 | Bayley et al. | |
| 5,824,776 | A | 10/1998 | Bayley et al. | |
| 5,858,358 | A | 1/1999 | June et al. | |
| 5,866,679 | A | 2/1999 | DeFeo-Jones et al. | |
| 5,948,750 | A | 9/1999 | Garsky et al. | |
| 5,985,877 | A | 11/1999 | Dionne et al. | |
| 5,998,362 | A | 12/1999 | Feng et al. | |
| 6,143,864 | A | 11/2000 | DeFeo-Jones et al. | |
| 6,179,831 | B1 * | 1/2001 | Bliweis | 606/21 |
| 6,190,657 | B1 | 2/2001 | Pawelek et al. | |
| 6,200,573 | B1 * | 3/2001 | Locke | 424/727 |
| 6,265,540 | B1 | 7/2001 | Isaacs et al. | |
| 6,268,377 | B1 * | 7/2001 | Waldstreicher et al. | 514/284 |
| 6,331,415 | B1 | 12/2001 | Cabilly et al. | |
| 6,368,598 | B1 | 4/2002 | D'Amico et al. | |
| 6,391,305 | B1 | 5/2002 | Feng et al. | |
| 6,410,514 | B1 | 6/2002 | Isaacs et al. | |
| 6,495,315 | B2 | 12/2002 | Hildreth et al. | |
| 6,504,014 | B1 | 1/2003 | Isaacs et al. | |
| 6,545,131 | B1 | 4/2003 | Isaacs et al. | |
| 6,593,095 | B1 | 7/2003 | Buckley et al. | |
| 7,053,042 | B1 | 5/2006 | Denmeade et al. | |
| 7,282,476 | B2 | 10/2007 | Denmeade et al. | |
| 2002/0035090 | A1 * | 3/2002 | Zeldis et al. | 514/58 |
| 2002/0041880 | A1 | 4/2002 | DeFeo-Jones et al. | |
| 2002/0045736 | A1 | 4/2002 | Yu et al. | |

(Continued)

FOREIGN PATENT DOCUMENTS

| | | | |
|---|---|---|---|
| EP | 1052287 | A2 | 11/2000 |
| EP | 1052288 | A1 | 11/2000 |

(Continued)

OTHER PUBLICATIONS

Zlotta et al. (European Urology, vol. 44, Issue 1, pp. 89-93, Published 2003).*
Gerber et al. (BJU International, 94, pp. 338-344, Published 2004).*
Denmeade S. R. et al., Prostate-Specific Antigen-Activated Thapsigargin Prodrug as Targeted Therapy for Prostate Cancer, (2003) Journal of the National Cancer Institute, vol. 95, No. 13, pp. 990-1000.
Imagawa T. et al., Cloning, nucleotide sequence and expression of a hemolysin gene of *Clostridium septicum*, FEMS Microbiology Letters (1994) 117, 287-292.
Meza R. et al, Isolation of Cry1Ab protein mutants of *Bacillus thuringiensis* by a highly efficient PCR site-directed mutagenesis system, FEMS Microbiology Letters (1996) 145, 333-339.
Presti J. C. et al., Multicenter, Randomized, Double-blind, Placebo controlled study to investigate the effect of Finasteride (MK-906) on stage D prostate cancer, The Journal of Urology (1992), vol. 148, 1201-1204.
Williams S. A. et al., A Prostate-Specific Antigen-Activated Channel-Forming Toxin as Therapy for Prostatic Disease, J Natl Cancer Inst (2007); 99:376-385.

(Continued)

*Primary Examiner* — Richard Schnizer
*Assistant Examiner* — Alma Pipic
(74) *Attorney, Agent, or Firm* — Dennis A. Bennett

(57) ABSTRACT

The present invention provides a method of treating BPH using modified pore-forming proteins (MPPs). These MPPs are derived from naturally occurring cytotoxic proteins (nPPs) that kill cells by forming pores or channels in the cell membrane, resulting in cell death. The MPPs are generated by modification of the nPPs such that they are capable of being selectively activated at normal prostate cells. Such modification may include the addition of a prostate-specific protease cleavage site to the activation sequence, and/or the addition of a prostate-specific targeting domain to allow selective targeting of prostate cells. These MPPs are capable of selectively targeting and killing normal prostate cells in vivo. The MPPs may be used either alone or in combination with other therapies for the treatment of BPH.

9 Claims, 46 Drawing Sheets

(56) References Cited

U.S. PATENT DOCUMENTS

| | | | | |
|---|---|---|---|---|
| 2002/0077454 | A1 | 6/2002 | Yu et al. | |
| 2002/0082556 | A1* | 6/2002 | Cioanta et al. | 604/113 |
| 2003/0092689 | A1* | 5/2003 | Escandon et al. | 514/171 |
| 2004/0235095 | A1 | 11/2004 | Denmeade et al. | |
| 2005/0266512 | A1 | 12/2005 | Buckley | |

FOREIGN PATENT DOCUMENTS

| | | | |
|---|---|---|---|
| WO | 9425616 | A1 | 11/1994 |
| WO | 9526204 | A1 | 10/1995 |
| WO | 9602555 | A1 | 2/1996 |
| WO | 9620688 | A2 | 7/1996 |
| WO | 9740857 | A1 | 11/1997 |
| WO | 9811211 | A2 | 3/1998 |
| WO | 9818810 | A1 | 5/1998 |
| WO | 9820135 | A2 | 5/1998 |
| WO | 9837919 | A1 | 9/1998 |
| WO | 9840100 | A1 | 9/1998 |
| WO | WO 98/52581 | A1 | 11/1998 |
| WO | WO 98/52966 | A1 | 11/1998 |
| WO | WO 99/02175 | A1 | 1/1999 |
| WO | WO 99/20252 | A1 | 4/1999 |
| WO | WO 00/01419 | A1 | 1/2000 |
| WO | WO 01/09165 | A3 | 2/2001 |
| WO | WO 01/85777 | A2 | 11/2001 |
| WO | WO 02/26777 | A1 | 4/2002 |
| WO | WO 02/38799 | A2 | 5/2002 |
| WO | WO 02/43773 | A2 | 6/2002 |
| WO | WO 03/018611 | A2 | 3/2003 |
| WO | 2004060915 | A2 | 7/2004 |

OTHER PUBLICATIONS

Vallette F. et al., Construction of mutant and chimeric genes using the polymerase chain reaction, Nucleic Acids Research (1989), vol. 17, No. 2, 723-733.

Patri A. K. et al., Synthesis and In Vitro Testing of J591 Antibody—Dendrimer Conjugates for Targeted Prostate Cancer Therapy, Bioconjugate Chem. (2004), 15, 1174-1181.

Bander N. H. et al., Targeting Metastatic Prostate Cancer With Radiolabeled Monoclonal Antibody J591 to the Extracellular Domain of Prostate Specific Membrane Antigen, The Journal of Urology, (2003), vol. 170, 1717-1721.

Park H. S. et al., In vivo characterization of a prostate-specific antigen promoter-based suicide gene therapy for the treatment of benign prostatic hyperplasia, Gene Therapy, (2003),10:1129-1134.

Declaration of Dr. Samuel R. Denmeade in granted EP Patent Application No. 06761050.1, published as WO 2006/133553.

Panchal R. G. et al., Pore-Forming Proteins and their Application in Biotechnology, Current Pharmaceutical Biotechnology, (2002), 3:99-115.

Williams et al., "Tumoricidal Effects of a PSA-Activated Pore-Forming Toxin," *Proceedings of the American Association for Cancer Research 46*:1446 (2005).

Barry et al., "The Channel-Forming Protein Proaerolysin Remains a Dimer at Low Concentrations in Solution," *J Biol. Chem. 276*:551-554, 2001.

Audtho et al., "Production of Chymotrypsin-Resistant *Bacillus thuringiensis* Cry2Aa1 δ-Endotoxin by Protein Engineering," *Appl. Environ. Micriobiol. 65*:4601-4605 (1999).

Ballard et al., "The Primary Structure of *Clostridium septicum* Alpha-Toxin Exhibits Similarity with That of *Aeromonas hydrophila* Aerolysin," *Infect. Immun. 63*:340-344 (1995).

Chen et al., "Glycophosphatidylinositol-Anchored Protein Deficiency as a Marker of *Mutator* Phenotypes in Cancer," *Cancer Res. 61*:654-658 (2001).

Correale et al., "Generation of Human Cytolytic T Lymphocyte Lines Directed Against Prostate-Specific Antigen (PSA) Employing a PSA Oligoepitope Peptide," *J. Immunol. 161*:3186-3194 (1998).

Gong et al., "Overview of Evolving Strategies Incorporating Prostate-Specific Membrane Antigen as Target for Therapy," *Mol. Urol. 4*:217-222 (2000).

Gordon et al., "*Clostridium septicum* Alpha-Toxin Is Proteolytically Activated by Furin," *Infect. Immun. 65*:4130-4134 (1997).

Pang et al., "Activation and Fragmentation of *Bacillus thuringiensis* δ-Endotoxin by High Concentrations of Proteolytic Enzymes," *Can. J. Microbiol. 45*:816-825 (1999).

Rosen et al. "Enzymatic Activation of a Modified Proaerolysin Toxin by Prostate-Specific Antigen (PSA) as Treatment for Prostate Cancer," *Proceedings of the American Association for Cancer Research Annual Meeting 43*:92 (2002).

Rossjohn et al., "Aerolysin and Pertussis Toxin Share a Common Receptor-Binding Domain," *EMBO J. 16*:3426-3434 (1997).

Spyres et al., "Cytosolic Delivery and Characterization of the TcdB Glucosylating Domain by Using a Heterologous Protein Fusion," *Infection Immun. 69*:599-601 (2001).

Tanha et al., "Optimal Design Features of Camelized Human Single-Domain Antibody Libraries," *J. Biol. Chem. 276*:24774-24780 (2001).

Walker and Bayley, "A Pore-Forming Protein with a Protease-Activated Trigger," *Protein Eng. 7*:91-97 (1994).

Abrami et al. (1998) Journal of Biological Chemistry 273(49):32656-32661.

Denmeade et al. (1997) Cancer Research 57:4924-4930.

Mackenzie et al. (1999) Journal of Biological Chemistry 274(32):22604-22609.

Leskinen MJ et al., (2002) Adult Urology 60 (2):300-304.

Potts J et al., (2007) Cleveland Clinic Journal of Medicine, 74 (3) S63-S71.

Rich et al., (2008) American Family Physician, pp. 1-3.

* cited by examiner

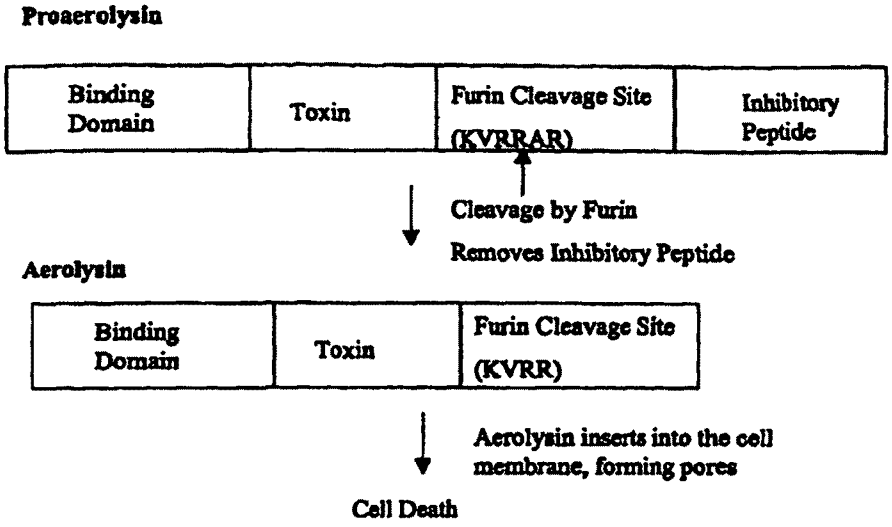

FIG. 1

Proaerolysin

| Binding Domain | Toxin | Furin Cleavage Site (KVRRAR) | Inhibitory Peptide |

↓ Cleavage by Furin
Removes Inhibitory Peptide

Aerolysin

| Binding Domain | Toxin | Furin Cleavage Site (KVRR) |

↓ Aerolysin inserts into the cell membrane, forming pores

Cell Death

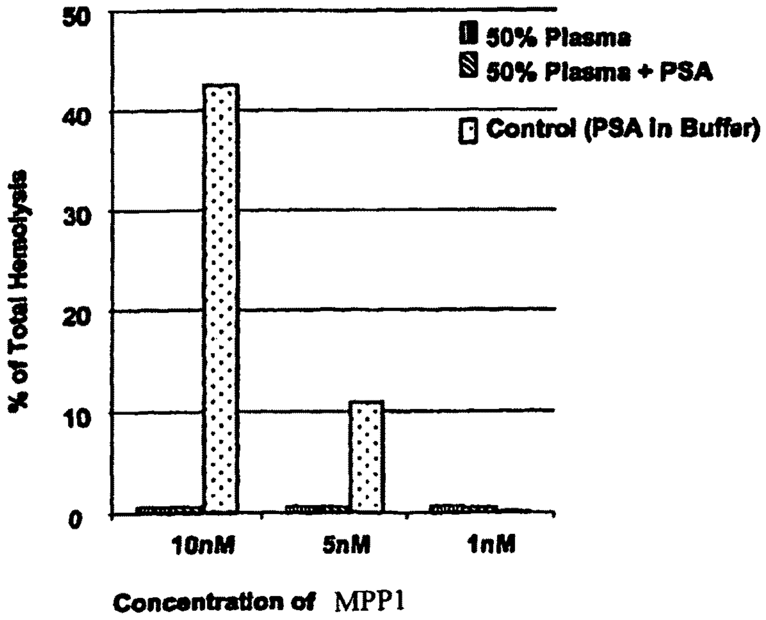

FIG. 2

Bar graph showing % of Total Hemolysis vs Concentration of MPP1 (10nM, 5nM, 1nM) with three conditions: 50% Plasma, 50% Plasma + PSA, Control (PSA in Buffer).

FIG. 4A:

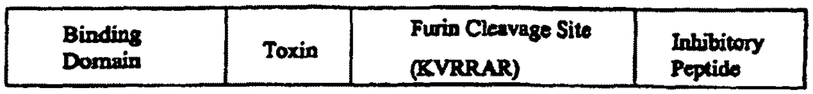

FIG. 4B:

FIG. 4C:

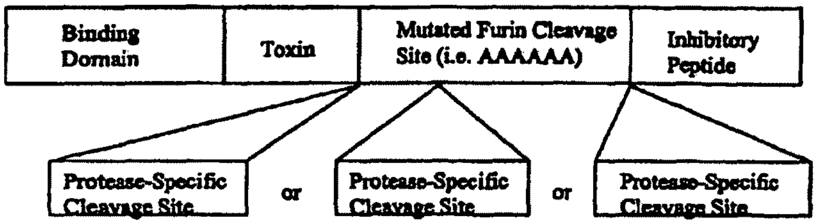

FIG. 4D:

FIG. 4E:

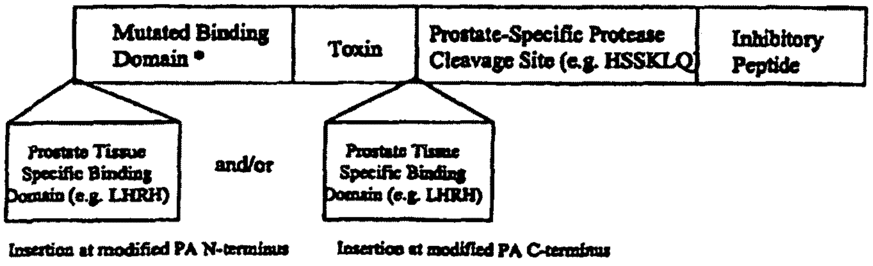

| Binding Domain | Toxin | Furin Cleavage Site (KVRRAR) | Inhibitory Peptide |
|---|---|---|---|

| Binding Domain | Toxin | Prostate-Specific Protease Cleavage Site (e.g. HSSKLQ) | Inhibitory Peptide |
|---|---|---|---|

| Binding Domain | Toxin | Mutated Furin Cleavage Site (i.e. AAAAAA) | Inhibitory Peptide |
|---|---|---|---|

Protease-Specific Cleavage Site   or   Protease-Specific Cleavage Site   or   Protease-Specific Cleavage Site

| Mutated Binding Domain * | Toxin | Prostate-Specific Protease Cleavage Site (e.g. HSSKLQ) | Inhibitory Peptide |
|---|---|---|---|

| Mutated Binding Domain * | Toxin | Prostate-Specific Protease Cleavage Site (e.g. HSSKLQ) | Inhibitory Peptide |
|---|---|---|---|

Prostate Tissue Specific Binding Domain (e.g. LHRH)   and/or   Prostate Tissue Specific Binding Domain (e.g. LHRH)

Insertion at modified PA N-terminus        Insertion at modified PA C-terminus

FIG. 5A

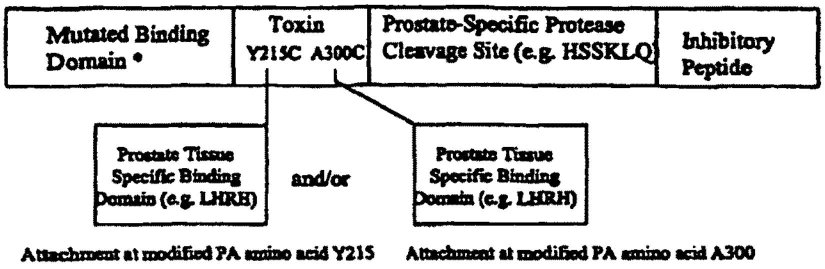

FIG. 5B

FIG. 5C

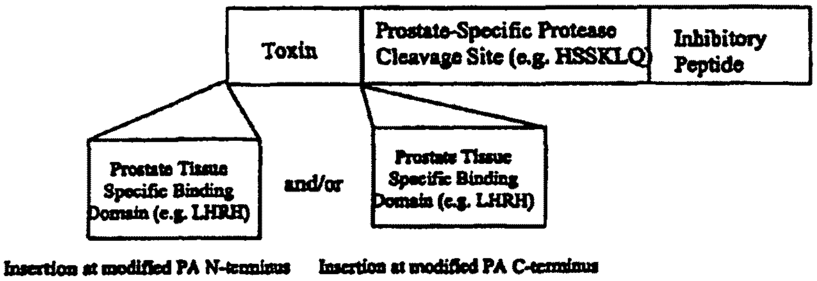

FIG. 5D

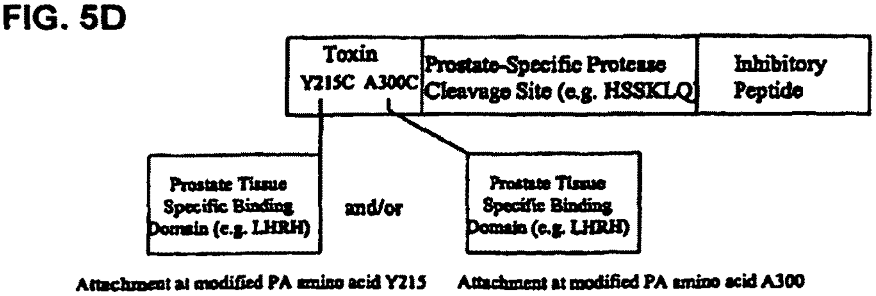

| Mutated Binding Domain * | Toxin Y215C A300C | Prostate-Specific Protease Cleavage Site (e.g. HSSKLQ) | Inhibitory Peptide |

| Prostate Tissue Specific Binding Domain (e.g. LHRH) | and/or | Prostate Tissue Specific Binding Domain (e.g. LHRH) |

Attachment at modified PA amino acid Y215    Attachment at modified PA amino acid A300

| Toxin | Prostate-Specific Protease Cleavage Site (e.g. HSSKLQ) | Inhibitory Peptide |

| Toxin | Prostate-Specific Protease Cleavage Site (e.g. HSSKLQ) | Inhibitory Peptide |

| Prostate Tissue Specific Binding Domain (e.g. LHRH) | and/or | Prostate Tissue Specific Binding Domain (e.g. LHRH) |

Insertion at modified PA N-terminus    Insertion at modified PA C-terminus

| Toxin Y215C A300C | Prostate-Specific Protease Cleavage Site (e.g. HSSKLQ) | Inhibitory Peptide |

| Prostate Tissue Specific Binding Domain (e.g. LHRH) | and/or | Prostate Tissue Specific Binding Domain (e.g. LHRH) |

Attachment at modified PA amino acid Y215    Attachment at modified PA amino acid A300

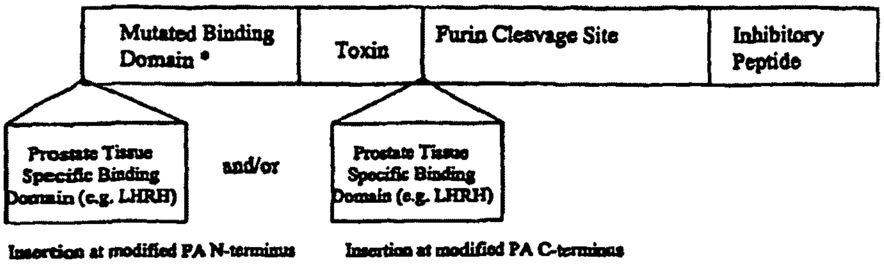

FIG. 6A

| Mutated Binding Domain * | Toxin | Furin Cleavage Site | Inhibitory Peptide |

Prostate Tissue Specific Binding Domain (e.g. LHRH) and/or Prostate Tissue Specific Binding Domain (e.g. LHRH)

Insertion at modified PA N-terminus    Insertion at modified PA C-terminus

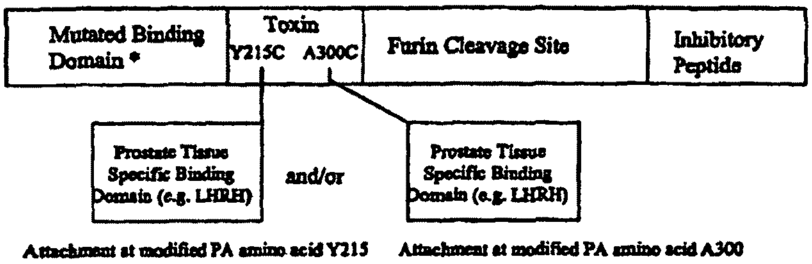

FIG. 6B

| Mutated Binding Domain * | Toxin Y215C A300C | Furin Cleavage Site | Inhibitory Peptide |

Prostate Tissue Specific Binding Domain (e.g. LHRH) and/or Prostate Tissue Specific Binding Domain (e.g. LHRH)

Attachment at modified PA amino acid Y215    Attachment at modified PA amino acid A300

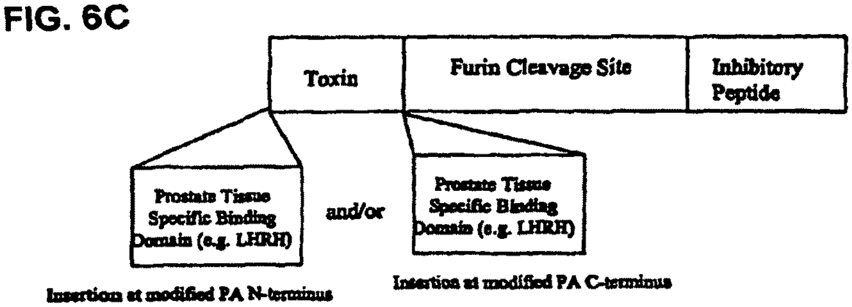

FIG. 6C

| Toxin | Furin Cleavage Site | Inhibitory Peptide |

Prostate Tissue Specific Binding Domain (e.g. LHRH) and/or Prostate Tissue Specific Binding Domain (e.g. LHRH)

Insertion at modified PA N-terminus    Insertion at modified PA C-terminus

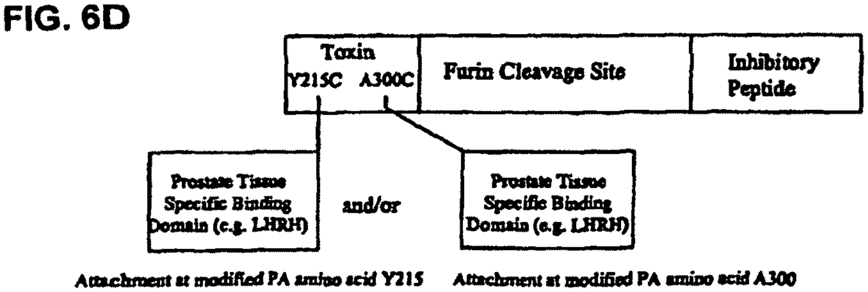

FIG. 6D

| Toxin Y215C A300C | Furin Cleavage Site | Inhibitory Peptide |

Prostate Tissue Specific Binding Domain (e.g. LHRH) and/or Prostate Tissue Specific Binding Domain (e.g. LHRH)

Attachment at modified PA amino acid Y215    Attachment at modified PA amino acid A300

FIG. 7

<210> SEQ ID NO 1
<211> LENGTH: 1410
<212> TYPE: DNA
<213> ORGANISM: Aeromonas hydrophila
<220> FEATURE:
<221> NAME/KEY: CDS
<222> LOCATION: (1)..(1410)
<223> OTHER INFORMATION:

<400> SEQUENCE: 1 gca gag ccc gtc tat cca gac cag ctt cgc ttg ttt tca ttg ggc caa 48
Ala Glu Pro Val Tyr Pro Asp Gln Leu Arg Leu Phe Ser Leu Gly Gln
1 5 10 15 ggg gtc tgt ggc gac aag tat cgc ccc gtc aat cga gaa gaa gcc caa 96
Gly Val Cys Gly Asp Lys Tyr Arg Pro Val Asn Arg Glu Glu Ala Gln
20 25 30 agc gtt aaa agc aat att gtc ggc atg atg ggg caa tgg caa ata agc 144
Ser Val Lys Ser Asn Ile Val Gly Met Met Gly Gln Trp Gln Ile Ser
35 40 45 ggg ctg gcc aac ggc tgg gtc att atg ggg ccg ggt tat aac ggt gaa 192
Gly Leu Ala Asn Gly Trp Val Ile Met Gly Pro Gly Tyr Asn Gly Glu
50 55 60 ata aaa cca ggg aca gcg tcc aat acc tgg tgt tat ccg acc aat cct 240
Ile Lys Pro Gly Thr Ala Ser Asn Thr Trp Cys Tyr Pro Thr Asn Pro
65 70 75 80 gtt acc ggt gaa ata ccg aca ctg tct gcc ctg gat att cca gat ggt 288
Val Thr Gly Glu Ile Pro Thr Leu Ser Ala Leu Asp Ile Pro Asp Gly
85 90 95 gac gaa gtc gat gtg cag tgg cga ctg gta cat gac agt gcg aat ttc 336
Asp Glu Val Asp Val Gln Trp Arg Leu Val His Asp Ser Ala Asn Phe
100 105 110 atc aaa cca acc agc tat ctg gcc cat tac ctc ggt tat gcc tgg gtg 384
Ile Lys Pro Thr Ser Tyr Leu Ala His Tyr Leu Gly Tyr Ala Trp Val
115 120 125 ggc ggc aat cac agc caa tat gtc ggc gaa gac atg gat gtg acc cgt 432

Gly Gly Asn His Ser Gln Tyr Val Gly Glu Asp Met Asp Val Thr Arg
130 135 140 gat ggc gac ggc tgg gtg atc cgt ggc aac aat gac ggc ggc tgt gac 480
Asp Gly Asp Gly Trp Val Ile Arg Gly Asn Asn Asp Gly Gly Cys Asp
145 150 155 160 ggc tat cgc tgt ggt gac aag acg gcc atc aag gtc agc aac ttc gcc 528
Gly Tyr Arg Cys Gly Asp Lys Thr Ala Ile Lys Val Ser Asn Phe Ala
165 170 175 tat aac ctg gat ccc gac agc ttc aag cat ggc gat gtc acc cag tcc 576
Tyr Asn Leu Asp Pro Asp Ser Phe Lys His Gly Asp Val Thr Gln Ser
180 185 190 gac cgc cag ctg gtc aag act gtg gtg ggc tgg gcg gtc aac gac agc 624
Asp Arg Gln Leu Val Lys Thr Val Val Gly Trp Ala Val Asn Asp Ser
195 200 205 gac acc ccc caa tcc ggc tat gac gtc acc ctg cgc tac gac aca gcc 672
Asp Thr Pro Gln Ser Gly Tyr Asp Val Thr Leu Arg Tyr Asp Thr Ala
210 215 220 acc aac tgg tcc aag acc aac acc tat ggc ctg agc gag aag gtg acc 720
Thr Asn Trp Ser Lys Thr Asn Thr Tyr Gly Leu Ser Glu Lys Val Thr
225 230 235 240

FIG. 7 CONT'D

```
acc aag aac aag ttc aag tgg cca ctg gtg ggg gaa acc caa ctc tcc      768
Thr Lys Asn Lys Phe Lys Trp Pro Leu Val Gly Glu Thr Gln Leu Ser
                245                 250                 255

atc gag att gct gcc aat cag tcc tgg gcg tcc cag aac ggg ggc tcg      816
Ile Glu Ile Ala Ala Asn Gln Ser Trp Ala Ser Gln Asn Gly Gly Ser
            260                 265                 270

acc acc acc tcc ctg tct cag tcc gtg cga ccg act gtg ccg gcc cgc      864
Thr Thr Thr Ser Leu Ser Gln Ser Val Arg Pro Thr Val Pro Ala Arg
        275                 280                 285

tcc aag atc ccg gtg aag ata gag ctc tac aag gcc gac atc tcc tat      912
Ser Lys Ile Pro Val Lys Ile Glu Leu Tyr Lys Ala Asp Ile Ser Tyr
    290                 295                 300

ccc tat gag ttc aag gcc gat gtc agc tat gac ctg acc ctg agc ggc      960
Pro Tyr Glu Phe Lys Ala Asp Val Ser Tyr Asp Leu Thr Leu Ser Gly
305                 310                 315                 320

ttc ctg cgc tgg ggc ggc aac gcc tgg tat acc cac ccg gac aac cgt     1008
Phe Leu Arg Trp Gly Gly Asn Ala Trp Tyr Thr His Pro Asp Asn Arg
                325                 330                 335

ccg aac tgg aac cac acc ttc gtc ata ggt ccg tac aag gac aag gcg     1056
Pro Asn Trp Asn His Thr Phe Val Ile Gly Pro Tyr Lys Asp Lys Ala
            340                 345                 350

agc agc att cgg tac cag tgg gac aag cgt tac atc ccg ggt gaa gtg     1104
Ser Ser Ile Arg Tyr Gln Trp Asp Lys Arg Tyr Ile Pro Gly Glu Val
        355                 360                 365

aag tgg tgg gac tgg aac tgg acc ata cag cag aac ggt ctg tct acc     1152
Lys Trp Trp Asp Trp Asn Trp Thr Ile Gln Gln Asn Gly Leu Ser Thr
    370                 375                 380

atg cag aac aac ctg gcc aga gtg ctg cgc ccg gtg cgg gcg ggg atc     1200
Met Gln Asn Asn Leu Ala Arg Val Leu Arg Pro Val Arg Ala Gly Ile
385                 390                 395                 400

acc ggt gat ttc agt gcc gag agc cag ttt gcc ggc aac ata gag atc     1248
Thr Gly Asp Phe Ser Ala Glu Ser Gln Phe Ala Gly Asn Ile Glu Ile
                405                 410                 415

ggt gct ccc gtg ccg ctc gcg gct gac agc aag gtg cgt cgt gct cgc     1296
Gly Ala Pro Val Pro Leu Ala Ala Asp Ser Lys Val Arg Arg Ala Arg
            420                 425                 430

agt gtg gac ggc gct ggt caa ggc ctg agg ctg gag atc ccg ctc gat     1344

Ser Val Asp Gly Ala Gly Gln Gly Leu Arg Leu Glu Ile Pro Leu Asp
        435                 440                 445

gcg caa gag ctc tcc ggg ctt ggc ttc aac aac gtc agc ctc agc gtg     1392
Ala Gln Glu Leu Ser Gly Leu Gly Phe Asn Asn Val Ser Leu Ser Val
    450                 455                 460

acc cct gct gcc aat caa                                             1410
Thr Pro Ala Ala Asn Gln
465                 470
```

FIG. 8

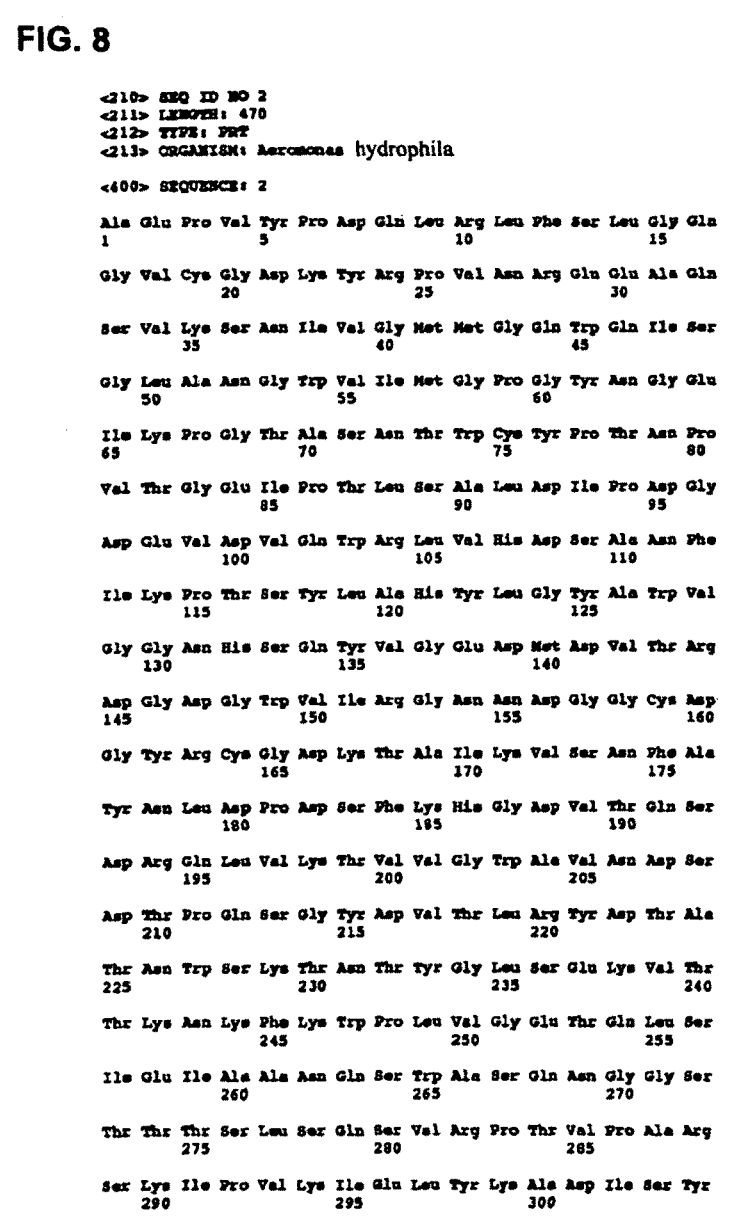

<210> SEQ ID NO 2
<211> LENGTH: 470
<212> TYPE: PRT
<213> ORGANISM: Aeromonas hydrophila

<400> SEQUENCE: 2

Ala Glu Pro Val Tyr Pro Asp Gln Leu Arg Leu Phe Ser Leu Gly Gln
1 5 10 15

Gly Val Cys Gly Asp Lys Tyr Arg Pro Val Asn Arg Glu Glu Ala Gln
20 25 30

Ser Val Lys Ser Asn Ile Val Gly Met Met Gly Gln Trp Gln Ile Ser
35 40 45

Gly Leu Ala Asn Gly Trp Val Ile Met Gly Pro Gly Tyr Asn Gly Glu
50 55 60

Ile Lys Pro Gly Thr Ala Ser Asn Thr Trp Cys Tyr Pro Thr Asn Pro
65 70 75 80

Val Thr Gly Glu Ile Pro Thr Leu Ser Ala Leu Asp Ile Pro Asp Gly
85 90 95

Asp Glu Val Asp Val Gln Trp Arg Leu Val His Asp Ser Ala Asn Phe
100 105 110

Ile Lys Pro Thr Ser Tyr Leu Ala His Tyr Leu Gly Tyr Ala Trp Val
115 120 125

Gly Gly Asn His Ser Gln Tyr Val Gly Glu Asp Met Asp Val Thr Arg
130 135 140

Asp Gly Asp Gly Trp Val Ile Arg Gly Asn Asn Asp Gly Gly Cys Asp
145 150 155 160

Gly Tyr Arg Cys Gly Asp Lys Thr Ala Ile Lys Val Ser Asn Phe Ala
165 170 175

Tyr Asn Leu Asp Pro Asp Ser Phe Lys His Gly Asp Val Thr Gln Ser
180 185 190

Asp Arg Gln Leu Val Lys Thr Val Val Gly Trp Ala Val Asn Asp Ser
195 200 205

Asp Thr Pro Gln Ser Gly Tyr Asp Val Thr Leu Arg Tyr Asp Thr Ala
210 215 220

Thr Asn Trp Ser Lys Thr Asn Thr Tyr Gly Leu Ser Glu Lys Val Thr
225 230 235 240

Thr Lys Asn Lys Phe Lys Trp Pro Leu Val Gly Glu Thr Gln Leu Ser
245 250 255

Ile Glu Ile Ala Ala Asn Gln Ser Trp Ala Ser Gln Asn Gly Gly Ser
260 265 270

Thr Thr Thr Ser Leu Ser Gln Ser Val Arg Pro Thr Val Pro Ala Arg
275 280 285

Ser Lys Ile Pro Val Lys Ile Glu Leu Tyr Lys Ala Asp Ile Ser Tyr
290 295 300

FIG. 8 CONT'D

Pro Tyr Glu Phe Lys Ala Asp Val Ser Tyr Asp Leu Thr Leu Ser Gly
305 310 315 320

Phe Leu Arg Trp Gly Gly Asn Ala Trp Tyr Thr His Pro Asp Asn Arg
325 330 335

Pro Asn Trp Asn His Thr Phe Val Ile Gly Pro Tyr Lys Asp Lys Ala
340 345 350

Ser Ser Ile Arg Tyr Gln Trp Asp Lys Arg Tyr Ile Pro Gly Glu Val
355 360 365

Lys Trp Trp Asp Trp Asn Trp Thr Ile Gln Gln Asn Gly Leu Ser Thr
370 375 380

Met Gln Asn Asn Leu Ala Arg Val Leu Arg Pro Val Arg Ala Gly Ile
385 390 395 400

Thr Gly Asp Phe Ser Ala Glu Ser Gln Phe Ala Gly Asn Ile Glu Ile
405 410 415

Gly Ala Pro Val Pro Leu Ala Ala Asp Ser Lys Val Arg Arg Ala Arg
420 425 430

Ser Val Asp Gly Ala Gly Gln Gly Leu Arg Leu Glu Ile Pro Leu Asp
435 440 445

Ala Gln Glu Leu Ser Gly Leu Gly Phe Asn Asn Val Ser Leu Ser Val
450 455 460

Thr Pro Ala Ala Asn Gln
465 470

FIG. 9

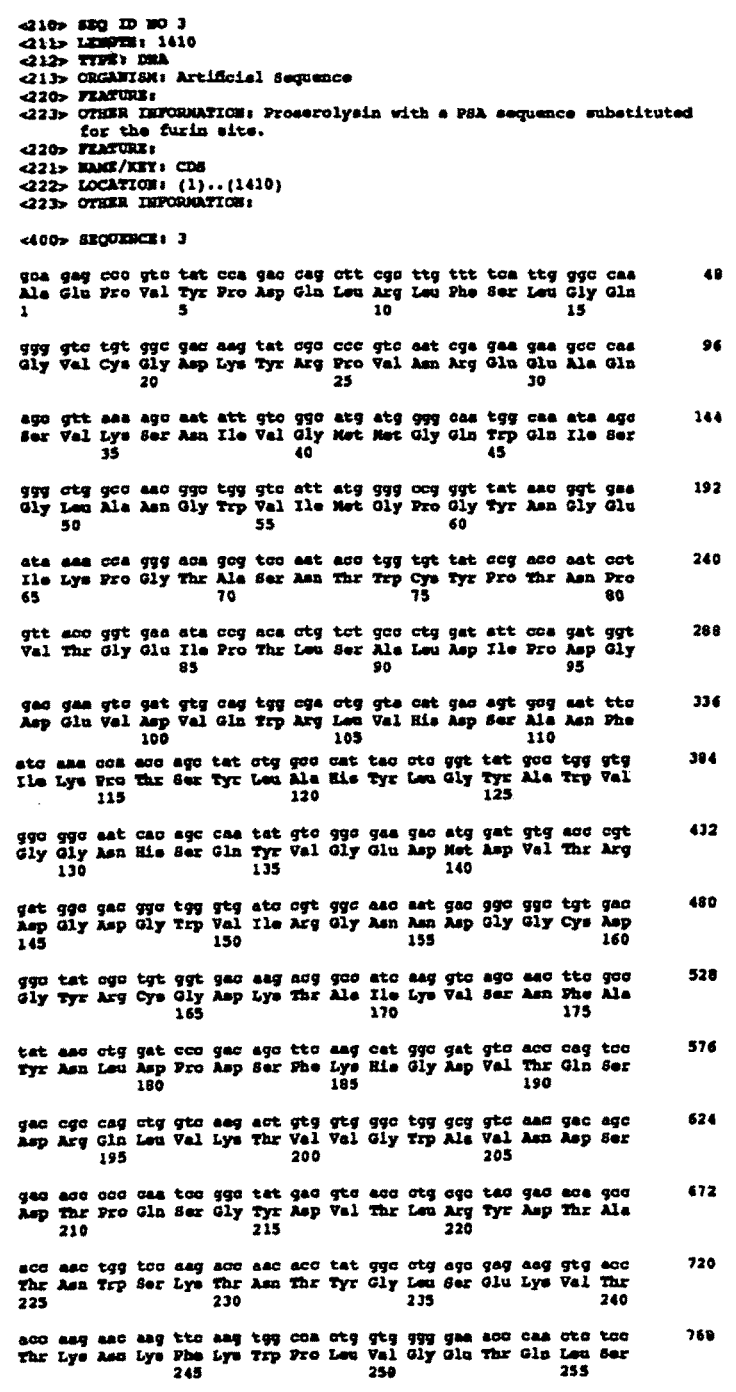

```
<210> SEQ ID NO 3
<211> LENGTH: 1410
<212> TYPE: DNA
<213> ORGANISM: Artificial Sequence
<220> FEATURE:
<223> OTHER INFORMATION: Proaerolysin with a PSA sequence substituted
      for the furin site.
<220> FEATURE:
<221> NAME/KEY: CDS
<222> LOCATION: (1)..(1410)
<223> OTHER INFORMATION:

<400> SEQUENCE: 3

gca gag ccc gtc tat cca gac cag ctt cgc ttg ttt tca ttg ggc caa        48
Ala Glu Pro Val Tyr Pro Asp Gln Leu Arg Leu Phe Ser Leu Gly Gln
1               5                   10                  15

ggg gtc tgt ggc gac aag tat cgc ccc gtc aat cga gaa gaa gcc caa        96
Gly Val Cys Gly Asp Lys Tyr Arg Pro Val Asn Arg Glu Glu Ala Gln
            20                  25                  30

agc gtt aaa agc aat att gtc ggc atg atg ggg caa tgg caa ata agc       144
Ser Val Lys Ser Asn Ile Val Gly Met Met Gly Gln Trp Gln Ile Ser
    35                  40                  45

ggg ctg gcc aac ggc tgg gtc att atg ggg ccg ggt tat aac ggt gaa       192
Gly Leu Ala Asn Gly Trp Val Ile Met Gly Pro Gly Tyr Asn Gly Glu
    50                  55                  60

ata aaa cca ggg aca gcg tcc aat acc tgg tgt tat ccg acc aat cct       240
Ile Lys Pro Gly Thr Ala Ser Asn Thr Trp Cys Tyr Pro Thr Asn Pro
65                  70                  75                  80

gtt acc ggt gaa ata ccg aca ctg tct gcc ctg gat att cca gat ggt       288
Val Thr Gly Glu Ile Pro Thr Leu Ser Ala Leu Asp Ile Pro Asp Gly
                85                  90                  95

gac gaa gtc gat gtg cag tgg cga ctg gta cat gac agt gcg aat ttc       336
Asp Glu Val Asp Val Gln Trp Arg Leu Val His Asp Ser Ala Asn Phe
            100                 105                 110

atc aaa cca acc agc tat ctg gcc cat tac ctc ggt tat gcc tgg gtg       384
Ile Lys Pro Thr Ser Tyr Leu Ala His Tyr Leu Gly Tyr Ala Trp Val
    115                 120                 125

ggc ggc aat cac agc caa tat gtc ggc gaa gac atg gat gtg acc cgt       432
Gly Gly Asn His Ser Gln Tyr Val Gly Glu Asp Met Asp Val Thr Arg
    130                 135                 140

gat ggc gac ggc tgg gtg atc cgt ggc aac aat gac ggc ggc tgt gac       480
Asp Gly Asp Gly Trp Val Ile Arg Gly Asn Asn Asp Gly Gly Cys Asp
145                 150                 155                 160

ggc tat cgc tgt ggt gac aag acg gcc atc aag gtc agc aac ttc gcc       528
Gly Tyr Arg Cys Gly Asp Lys Thr Ala Ile Lys Val Ser Asn Phe Ala
                165                 170                 175

tat aac ctg gat ccc gac agc ttc aag cat ggc gat gtc acc cag tcc       576
Tyr Asn Leu Asp Pro Asp Ser Phe Lys His Gly Asp Val Thr Gln Ser
            180                 185                 190

gac cgc cag ctg gtc aag act gtg gtg ggc tgg gcg gtc aac gac agc       624
Asp Arg Gln Leu Val Lys Thr Val Val Gly Trp Ala Val Asn Asp Ser
        195                 200                 205

gac acc ccc caa tcc ggc tat gac gtc acc ctg cgc tac gac aca gcc       672
Asp Thr Pro Gln Ser Gly Tyr Asp Val Thr Leu Arg Tyr Asp Thr Ala
    210                 215                 220

acc aac tgg tcc aag acc aac acc tat ggc ctg agc gag aag gtg acc       720
Thr Asn Trp Ser Lys Thr Asn Thr Tyr Gly Leu Ser Glu Lys Val Thr
225                 230                 235                 240

acc aag aac aag ttc aag tgg cca ctg gtg ggg gaa acc caa ctc tcc       768
Thr Lys Asn Lys Phe Lys Trp Pro Leu Val Gly Glu Thr Gln Leu Ser
                245                 250                 255
```

FIG. 9 CONT'D atc gag att gct gcc aat cag tcc tgg gcg tcc cag aac ggg ggc tcg 816
Ile Glu Ile Ala Ala Asn Gln Ser Trp Ala Ser Gln Asn Gly Gly Ser
260 265 270 acc acc acc tcc ctg tct cag tcc gtg cga ccg act gtg ccg gcc cgc 864
Thr Thr Thr Ser Leu Ser Gln Ser Val Arg Pro Thr Val Pro Ala Arg
275 280 285 tcc aag atc ccg gtg aag ata gag ctc tac aag gcc gac atc tcc tat 912
Ser Lys Ile Pro Val Lys Ile Glu Leu Tyr Lys Ala Asp Ile Ser Tyr
290 295 300 ccc tat gag ttc aag gcc gat gtc agc tat gac ctg acc ctg agc ggc 960
Pro Tyr Glu Phe Lys Ala Asp Val Ser Tyr Asp Leu Thr Leu Ser Gly
305 310 315 320 ttc ctg cgc tgg ggc ggc aac gcc tgg tat acc cac ccg gac aac cgt 1008
Phe Leu Arg Trp Gly Gly Asn Ala Trp Tyr Thr His Pro Asp Asn Arg
325 330 335 ccg aac tgg aac cac acc ttc gtc ata ggt ccg tac aag gac aag gcg 1056
Pro Asn Trp Asn His Thr Phe Val Ile Gly Pro Tyr Lys Asp Lys Ala
340 345 350 agc agc att cgg tac cag tgg gac aag cgt tac atc ccg ggt gaa gtg 1104
Ser Ser Ile Arg Tyr Gln Trp Asp Lys Arg Tyr Ile Pro Gly Glu Val
355 360 365 aag tgg tgg gac tgg aac tgg acc ata cag cag aac ggt ctg tct acc 1152
Lys Trp Trp Asp Trp Asn Trp Thr Ile Gln Gln Asn Gly Leu Ser Thr
370 375 380 atg cag aac aac ctg gcc aga gtg ctg cgc ccg gtg cgg gcg ggg atc 1200
Met Gln Asn Asn Leu Ala Arg Val Leu Arg Pro Val Arg Ala Gly Ile
385 390 395 400 acc ggt gat ttc agt gcc gag agc cag ttt gcc ggc aac ata gag atc 1248
Thr Gly Asp Phe Ser Ala Glu Ser Gln Phe Ala Gly Asn Ile Glu Ile
405 410 415 ggt gct ccc gtg ccg ctc gcg gct gac agc cat tcc tcc aag ctg cag 1296
Gly Ala Pro Val Pro Leu Ala Ala Asp Ser His Ser Ser Lys Leu Gln
420 425 430 agt gtg gac ggc gct ggt caa ggc ctg agg ctg gag atc ccg ctc gat 1344
Ser Val Asp Gly Ala Gly Gln Gly Leu Arg Leu Glu Ile Pro Leu Asp
435 440 445 gcg caa gag ctc tcc ggg ctt ggc ttc aac aac gtc agc ctc agc gtg 1392
Ala Gln Glu Leu Ser Gly Leu Gly Phe Asn Asn Val Ser Leu Ser Val
450 455 460 acc cct gct gcc aat caa 1410
Thr Pro Ala Ala Asn Gln
465 470

FIG.10

<210> SEQ ID NO 4
<211> LENGTH: 470
<212> TYPE: PRT
<213> ORGANISM: Artificial Sequence
<220> FEATURE:
<223> OTHER INFORMATION: Proaerolysin with a PSA sequence substituted for the furin site.

<400> SEQUENCE: 4

Ala Glu Pro Val Tyr Pro Asp Gln Leu Arg Leu Phe Ser Leu Gly Gln
1 5 10 15

Gly Val Cys Gly Asp Lys Tyr Arg Pro Val Asn Arg Glu Glu Ala Gln
20 25 30

Ser Val Lys Ser Asn Ile Val Gly Met Met Gly Gln Trp Gln Ile Ser
35 40 45

Gly Leu Ala Asn Gly Trp Val Ile Met Gly Pro Gly Tyr Asn Gly Glu
50 55 60

Ile Lys Pro Gly Thr Ala Ser Asn Thr Trp Cys Tyr Pro Thr Asn Pro
65 70 75 80

Val Thr Gly Glu Ile Pro Thr Leu Ser Ala Leu Asp Ile Pro Asp Gly
85 90 95

Asp Glu Val Asp Val Gln Trp Arg Leu Val His Asp Ser Ala Asn Phe
100 105 110

Ile Lys Pro Thr Ser Tyr Leu Ala His Tyr Leu Gly Tyr Ala Trp Val
115 120 125

Gly Gly Asn His Ser Gln Tyr Val Gly Glu Asp Met Asp Val Thr Arg
130 135 140

Asp Gly Asp Gly Trp Val Ile Arg Gly Asn Asn Asp Gly Gly Cys Asp
145 150 155 160

Gly Tyr Arg Cys Gly Asp Lys Thr Ala Ile Lys Val Ser Asn Phe Ala
165 170 175

Tyr Asn Leu Asp Pro Asp Ser Phe Lys His Gly Asp Val Thr Gln Ser
180 185 190

Asp Arg Gln Leu Val Lys Thr Val Val Gly Trp Ala Val Asn Asp Ser
195 200 205

Asp Thr Pro Gln Ser Gly Tyr Asp Val Thr Leu Arg Tyr Asp Thr Ala
210 215 220

Thr Asn Trp Ser Lys Thr Asn Thr Tyr Gly Leu Ser Glu Lys Val Thr
225 230 235 240

Thr Lys Asn Lys Phe Lys Trp Pro Leu Val Gly Glu Thr Gln Leu Ser
245 250 255

Ile Glu Ile Ala Ala Asn Gln Ser Trp Ala Ser Gln Asn Gly Gly Ser

FIG. 10 CONT'D

```
                260                 265                 270
Thr Thr Thr Ser Leu Ser Gln Ser Val Arg Pro Thr Val Pro Ala Arg
        275                 280                 285
Ser Lys Ile Pro Val Lys Ile Glu Leu Tyr Lys Ala Asp Ile Ser Tyr
    290                 295                 300
Pro Tyr Glu Phe Lys Ala Asp Val Ser Tyr Asp Leu Thr Leu Ser Gly
305                 310                 315                 320
Phe Leu Arg Trp Gly Gly Asn Ala Trp Tyr Thr His Pro Asp Asn Arg
                325                 330                 335
Pro Asn Trp Asn His Thr Phe Val Ile Gly Pro Tyr Lys Asp Lys Ala
            340                 345                 350
Ser Ser Ile Arg Tyr Gln Trp Asp Lys Arg Tyr Ile Pro Gly Glu Val
        355                 360                 365
Lys Trp Trp Asp Trp Asn Trp Thr Ile Gln Gln Asn Gly Leu Ser Thr
    370                 375                 380
Met Gln Asn Asn Leu Ala Arg Val Leu Arg Pro Val Arg Ala Gly Ile
385                 390                 395                 400
Thr Gly Asp Phe Ser Ala Glu Ser Gln Phe Ala Gly Asn Ile Glu Ile
                405                 410                 415
Gly Ala Pro Val Pro Leu Ala Ala Asp Ser His Ser Ser Lys Leu Gln
            420                 425                 430
Ser Val Asp Gly Ala Gly Gln Gly Leu Arg Leu Glu Ile Pro Leu Asp
        435                 440                 445
Ala Gln Glu Leu Ser Gly Leu Gly Phe Asn Asn Val Ser Leu Ser Val
    450                 455                 460
Thr Pro Ala Ala Asn Gln
465                 470
```

FIG. 11

```
<210> SEQ ID NO 5
<211> LENGTH: 6
<212> TYPE: PRT
<213> ORGANISM: Homo Sapiens

<400> SEQUENCE: 5

His Ser Ser Lys Leu Gln
1               5
```

FIG. 12

```
<210> SEQ ID NO 6
<211> LENGTH: 1410
<212> TYPE: DNA
<213> ORGANISM: Artificial Sequence
<220> FEATURE:
<223> OTHER INFORMATION: Proaerolysin with a PSA sequence substituted
      for the furin site
<220> FEATURE:
<221> NAME/KEY: CDS
<222> LOCATION: (1)..(1410)
<223> OTHER INFORMATION:

<400> SEQUENCE: 6

gca gag ccc gtc tat cca gac cag ctt cgc ttg ttt tca ttg ggc caa       48
Ala Glu Pro Val Tyr Pro Asp Gln Leu Arg Leu Phe Ser Leu Gly Gln
1               5                   10                  15

ggg gtc tgt ggc gac aag tat cgc ccc gtc aat cga gaa gaa gcc caa       96
Gly Val Cys Gly Asp Lys Tyr Arg Pro Val Asn Arg Glu Glu Ala Gln
            20                  25                  30

agc gtt aaa agc aat att gtc ggc atg atg ggg caa tgg caa ata agc      144
Ser Val Lys Ser Asn Ile Val Gly Met Met Gly Gln Trp Gln Ile Ser
        35                  40                  45

ggg ctg gcc aac ggc tgg gtc att atg ggg ccg ggt tat aac ggt gaa      192
Gly Leu Ala Asn Gly Trp Val Ile Met Gly Pro Gly Tyr Asn Gly Glu
    50                  55                  60

ata aaa cca ggg aca gcg tcc aat acc tgg tgt tat ccg acc aat cct      240
Ile Lys Pro Gly Thr Ala Ser Asn Thr Trp Cys Tyr Pro Thr Asn Pro
65                  70                  75                  80

gtt acc ggt gaa ata ccg aca ctg tct gcc ctg gat att cca gat ggt      288
Val Thr Gly Glu Ile Pro Thr Leu Ser Ala Leu Asp Ile Pro Asp Gly
                85                  90                  95

gac gaa gtc gat gtg cag tgg cga ctg gta cat gac agt gcg aat ttc      336
Asp Glu Val Asp Val Gln Trp Arg Leu Val His Asp Ser Ala Asn Phe
            100                 105                 110

atc aaa cca acc agc tat ctg gcc cat tac ctc ggt tat gcc tgg gtg      384
Ile Lys Pro Thr Ser Tyr Leu Ala His Tyr Leu Gly Tyr Ala Trp Val
        115                 120                 125
```

FIG. 12 CONT'D

```
ggc ggc aat cac agc caa tat gtc ggc gaa gac atg gat gtg acc cgt      432
Gly Gly Asn His Ser Gln Tyr Val Gly Glu Asp Met Asp Val Thr Arg
    130                 135                 140

gat ggc gac ggc tgg gtg atc cgt ggc aac aat gac ggc ggc tgt gac      480
Asp Gly Asp Gly Trp Val Ile Arg Gly Asn Asn Asp Gly Gly Cys Asp
145                 150                 155                 160

ggc tat cgc tgt ggt gac aag acg gcc atc aag gtc agc aac ttc gcc      528
Gly Tyr Arg Cys Gly Asp Lys Thr Ala Ile Lys Val Ser Asn Phe Ala
                165                 170                 175

tat aac ctg gat ccc gac agc ttc aag cat ggc gat gtc acc cag tcc      576
Tyr Asn Leu Asp Pro Asp Ser Phe Lys His Gly Asp Val Thr Gln Ser
            180                 185                 190

gac cgc cag ctg gtc aag act gtg gtg ggc tgg gcg gtc aac gac agc      624
Asp Arg Gln Leu Val Lys Thr Val Val Gly Trp Ala Val Asn Asp Ser
        195                 200                 205

gac acc ccc caa tcc ggc tat gac gtc acc ctg cgc tac gac aca gcc      672
Asp Thr Pro Gln Ser Gly Tyr Asp Val Thr Leu Arg Tyr Asp Thr Ala
    210                 215                 220

acc aac tgg tcc aag acc aac acc tat ggc ctg agc gag aag gtg acc      720
Thr Asn Trp Ser Lys Thr Asn Thr Tyr Gly Leu Ser Glu Lys Val Thr
225                 230                 235                 240

acc aag aac aag ttc aag tgg cca ctg gtg ggg gaa acc caa ctc tcc      768
Thr Lys Asn Lys Phe Lys Trp Pro Leu Val Gly Glu Thr Gln Leu Ser
                245                 250                 255

atc gag att gct gcc aat cag tcc tgg gcg tcc cag aac ggg ggc tcg      816
Ile Glu Ile Ala Ala Asn Gln Ser Trp Ala Ser Gln Asn Gly Gly Ser
            260                 265                 270

acc acc acc tcc ctg tct cag tcc gtg cga ccg act gtg ccg gcc cgc      864
Thr Thr Thr Ser Leu Ser Gln Ser Val Arg Pro Thr Val Pro Ala Arg
        275                 280                 285

tcc aag atc ccg gtg aag ata gag ctc tac aag gcc gac atc tcc tat      912
Ser Lys Ile Pro Val Lys Ile Glu Leu Tyr Lys Ala Asp Ile Ser Tyr
    290                 295                 300

ccc tat gag ttc aag gcc gat gtc agc tat gac ctg acc ctg agc ggc      960
Pro Tyr Glu Phe Lys Ala Asp Val Ser Tyr Asp Leu Thr Leu Ser Gly
305                 310                 315                 320

ttc ctg cgc tgg ggc ggc aac gcc tgg tat acc cac ccg gac aac cgt     1008
Phe Leu Arg Trp Gly Gly Asn Ala Trp Tyr Thr His Pro Asp Asn Arg
                325                 330                 335

ccg aac tgg aac cac acc ttc gtc ata ggt ccg tac aag gac aag gcg     1056
```

FIG. 12 CONT'D

```
Pro Asn Trp Asn His Thr Phe Val Ile Gly Pro Tyr Lys Asp Lys Ala
            340                 345                 350

agc agc att cgg tac cag tgg gac aag cgt tac atc ccg ggt gaa gtg     1104
Ser Ser Ile Arg Tyr Gln Trp Asp Lys Arg Tyr Ile Pro Gly Glu Val
        355                 360                 365

aag tgg tgg gac tgg aac tgg acc ata cag cag aac ggt ctg tct acc     1152
Lys Trp Trp Asp Trp Asn Trp Thr Ile Gln Gln Asn Gly Leu Ser Thr
    370                 375                 380

atg cag aac aac ctg gcc aga gtg ctg cgc ccg gtg cgg gcg ggg atc     1200
Met Gln Asn Asn Leu Ala Arg Val Leu Arg Pro Val Arg Ala Gly Ile
385                 390                 395                 400

acc ggt gat ttc agt gcc gag agc cag ttt gcc ggc aac ata gag atc     1248
Thr Gly Asp Phe Ser Ala Glu Ser Gln Phe Ala Gly Asn Ile Glu Ile
            405                 410                 415

ggt gct ccc gtg ccg ctc gcg gct gac agc cat tcc tcc aag ctg cag     1296
Gly Ala Pro Val Pro Leu Ala Ala Asp Ser His Ser Ser Lys Leu Gln
            420                 425                 430

agt gcc gac ggc gct ggt caa ggc ctg agg ctg gag atc ccg ctc gat     1344
Ser Ala Asp Gly Ala Gly Gln Gly Leu Arg Leu Glu Ile Pro Leu Asp
        435                 440                 445

gcg caa gag ctc tcc ggg ctt ggc ttc aac aac gtc agc ctc agc gtg     1392
Ala Gln Glu Leu Ser Gly Leu Gly Phe Asn Asn Val Ser Leu Ser Val
    450                 455                 460

acc cct gct gcc aat caa                                             1410
Thr Pro Ala Ala Asn Gln
465                 470
```

FIG. 13

<210> SEQ ID NO 7
<211> LENGTH: 470
<212> TYPE: PRT
<213> ORGANISM: Artificial Sequence
<220> FEATURE:
<223> OTHER INFORMATION: Proaerolysin with a PSA sequence substituted for the furin site

<400> SEQUENCE: 7

```
Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160
```

FIG. 13 CONT'D

Gly Tyr Arg Cys Gly Asp Lys Thr Ala Ile Lys Val Ser Asn Phe Ala
165 170 175

Tyr Asn Leu Asp Pro Asp Ser Phe Lys His Gly Asp Val Thr Gln Ser
180 185 190

Asp Arg Gln Leu Val Lys Thr Val Val Gly Trp Ala Val Asn Asp Ser
195 200 205

Asp Thr Pro Gln Ser Gly Tyr Asp Val Thr Leu Arg Tyr Asp Thr Ala
210 215 220

Thr Asn Trp Ser Lys Thr Asn Thr Tyr Gly Leu Ser Glu Lys Val Thr
225 230 235 240

Thr Lys Asn Lys Phe Lys Trp Pro Leu Val Gly Glu Thr Gln Leu Ser
245 250 255

Ile Glu Ile Ala Ala Asn Gln Ser Trp Ala Ser Gln Asn Gly Gly Ser
260 265 270

Thr Thr Thr Ser Leu Ser Gln Ser Val Arg Pro Thr Val Pro Ala Arg
275 280 285

Ser Lys Ile Pro Val Lys Ile Glu Leu Tyr Lys Ala Asp Ile Ser Tyr
290 295 300

Pro Tyr Glu Phe Lys Ala Asp Val Ser Tyr Asp Leu Thr Leu Ser Gly
305 310 315 320

Phe Leu Arg Trp Gly Gly Asn Ala Trp Tyr Thr His Pro Asp Asn Arg
325 330 335

Pro Asn Trp Asn His Thr Phe Val Ile Gly Pro Tyr Lys Asp Lys Ala
340 345 350

Ser Ser Ile Arg Tyr Gln Trp Asp Lys Arg Tyr Ile Pro Gly Glu Val
355 360 365

Lys Trp Trp Asp Trp Asn Trp Thr Ile Gln Gln Asn Gly Leu Ser Thr
370 375 380

Met Gln Asn Asn Leu Ala Arg Val Leu Arg Pro Val Arg Ala Gly Ile
385 390 395 400

Thr Gly Asp Phe Ser Ala Glu Ser Gln Phe Ala Gly Asn Ile Glu Ile
405 410 415

Gly Ala Pro Val Pro Leu Ala Ala Asp Ser His Ser Ser Lys Leu Gln
420 425 430

Ser Ala Asp Gly Ala Gly Gln Gly Leu Arg Leu Glu Ile Pro Leu Asp
435 440 445

Ala Gln Glu Leu Ser Gly Leu Gly Phe Asn Asn Val Ser Leu Ser Val
450 455 460

Thr Pro Ala Ala Asn Gln
465 470

FIG. 14

<210> SEQ ID NO 8
<211> LENGTH: 8
<212> TYPE: PRT
<213> ORGANISM: Artificial Sequence
<220> FEATURE:
<223> OTHER INFORMATION: PSA cleavage site

<400> SEQUENCE: 8

His Ser Ser Lys Leu Gln Ser Ala
1 5

FIG. 15

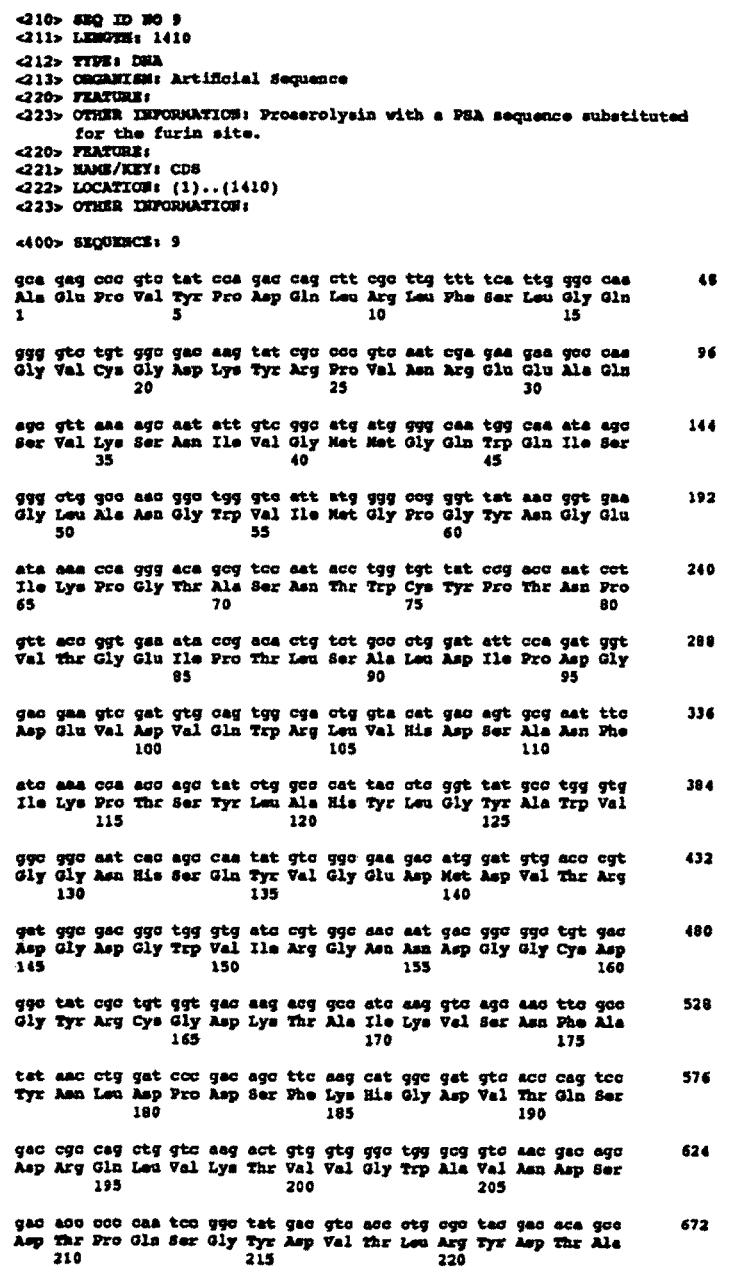

<210> SEQ ID NO 9
<211> LENGTH: 1410
<212> TYPE: DNA
<213> ORGANISM: Artificial Sequence
<220> FEATURE:
<223> OTHER INFORMATION: Proaerolysin with a PSA sequence substituted for the furin site.
<220> FEATURE:
<221> NAME/KEY: CDS
<222> LOCATION: (1)..(1410)
<223> OTHER INFORMATION:

<400> SEQUENCE: 9 gca gag ccc gtc tat cca gac cag ctt cgc ttg ttt tca ttg ggc caa 48
Ala Glu Pro Val Tyr Pro Asp Gln Leu Arg Leu Phe Ser Leu Gly Gln
1 5 10 15 ggg gtc tgt ggc gac aag tat cgc ccc gtc aat cga gaa gaa gcc caa 96
Gly Val Cys Gly Asp Lys Tyr Arg Pro Val Asn Arg Glu Glu Ala Gln
20 25 30 agc gtt aaa agc aat att gtc ggc atg atg ggg caa tgg caa ata agc 144
Ser Val Lys Ser Asn Ile Val Gly Met Met Gly Gln Trp Gln Ile Ser
35 40 45 ggg ctg gcc aac ggc tgg gtc att atg ggg ccg ggt tat aac ggt gaa 192
Gly Leu Ala Asn Gly Trp Val Ile Met Gly Pro Gly Tyr Asn Gly Glu
50 55 60 ata aaa cca ggg aca gcg tcc aat acc tgg tgt tat ccg acc aat cct 240
Ile Lys Pro Gly Thr Ala Ser Asn Thr Trp Cys Tyr Pro Thr Asn Pro
65 70 75 80 gtt acc ggt gaa ata ccg aca ctg tct gcc ctg gat att cca gat ggt 288
Val Thr Gly Glu Ile Pro Thr Leu Ser Ala Leu Asp Ile Pro Asp Gly
85 90 95 gac gaa gtc gat gtg cag tgg cga ctg gta cat gac agt gcg aat ttc 336
Asp Glu Val Asp Val Gln Trp Arg Leu Val His Asp Ser Ala Asn Phe
100 105 110 atc aaa cca acc agc tat ctg gcc cat tac ctc ggt tat gcc tgg gtg 384
Ile Lys Pro Thr Ser Tyr Leu Ala His Tyr Leu Gly Tyr Ala Trp Val
115 120 125 ggc ggc aat cac agc caa tat gtc ggc gaa gac atg gat gtg acc cgt 432
Gly Gly Asn His Ser Gln Tyr Val Gly Glu Asp Met Asp Val Thr Arg
130 135 140 gat ggc gac ggc tgg gtg atc cgt ggc aac aat gac ggc ggc tgt gac 480
Asp Gly Asp Gly Trp Val Ile Arg Gly Asn Asn Asp Gly Gly Cys Asp
145 150 155 160 ggc tat cgc tgt ggt gac aag acg gcc atc aag gtc agc aac ttc gcc 528
Gly Tyr Arg Cys Gly Asp Lys Thr Ala Ile Lys Val Ser Asn Phe Ala
165 170 175 tat aac ctg gat ccc gac agc ttc aag cat ggc gat gtc acc cag tcc 576
Tyr Asn Leu Asp Pro Asp Ser Phe Lys His Gly Asp Val Thr Gln Ser
180 185 190 gac cgc cag ctg gtc aag act gtg gtg ggc tgg gcg gtc aac gac agc 624
Asp Arg Gln Leu Val Lys Thr Val Val Gly Trp Ala Val Asn Asp Ser
195 200 205 gac acc ccc caa tcc ggc tat gac gtc acc ctg cgc tac gac aca gcc 672
Asp Thr Pro Gln Ser Gly Tyr Asp Val Thr Leu Arg Tyr Asp Thr Ala
210 215 220

FIG. 15 CONT'D

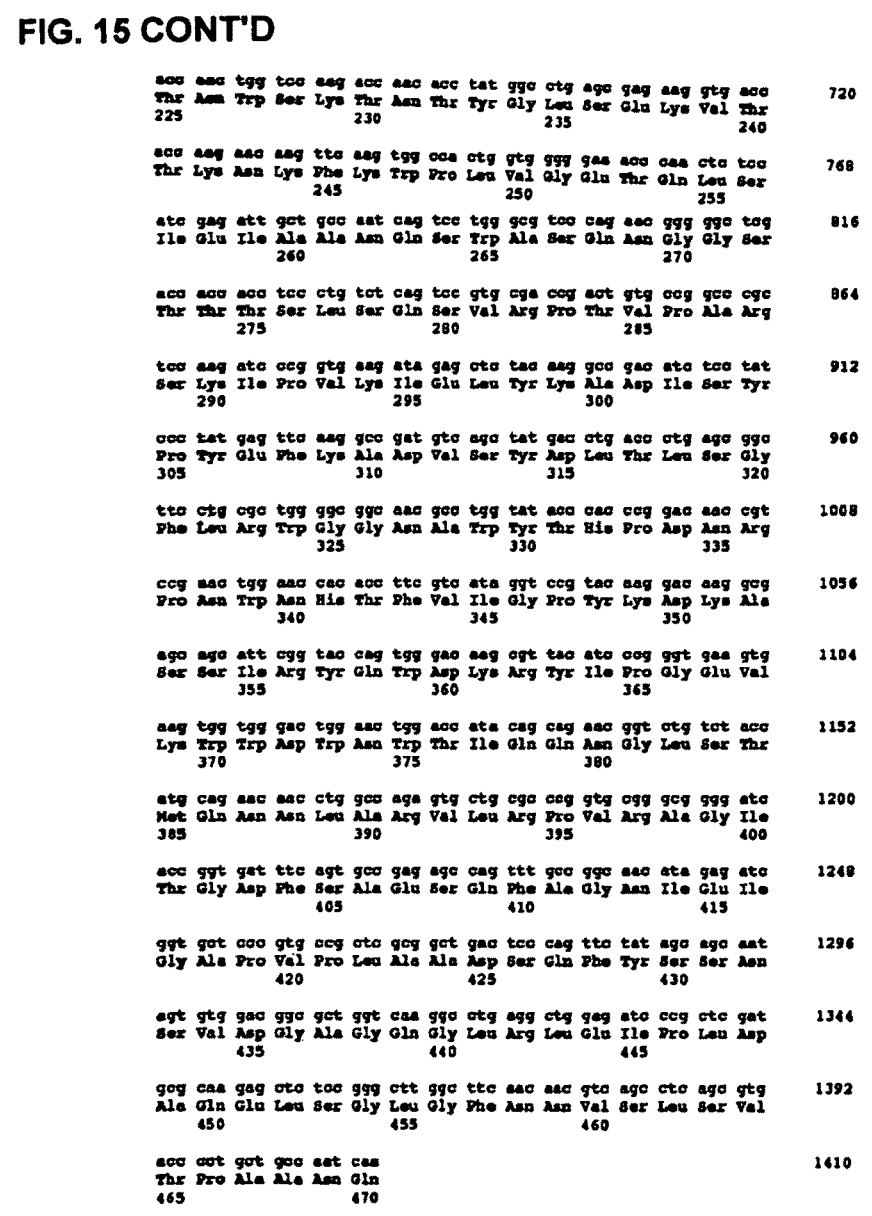

```
acc aac tgg tcc aag acc aac acc tat ggc ctg agc gag aag gtg acc      720
Thr Asn Trp Ser Lys Thr Asn Thr Tyr Gly Leu Ser Glu Lys Val Thr
225                 230                 235                 240

acc aag aac aag ttc aag tgg cca ctg gtg ggg gaa acc caa ctc tcc      768
Thr Lys Asn Lys Phe Lys Trp Pro Leu Val Gly Glu Thr Gln Leu Ser
                245                 250                 255

atc gag att gct gcc aat cag tcc tgg gcg tcc cag aac ggg ggc tcg      816
Ile Glu Ile Ala Ala Asn Gln Ser Trp Ala Ser Gln Asn Gly Gly Ser
            260                 265                 270

acc acc acc tcc ctg tct cag tcc gtg cga ccg act gtg ccg gcc cgc      864
Thr Thr Thr Ser Leu Ser Gln Ser Val Arg Pro Thr Val Pro Ala Arg
        275                 280                 285

tcc aag atc ccg gtg aag ata gag ctc tac aag gcc gac atc tcc tat      912
Ser Lys Ile Pro Val Lys Ile Glu Leu Tyr Lys Ala Asp Ile Ser Tyr
    290                 295                 300

ccc tat gag ttc aag gcc gat gtc agc tat gac ctg acc ctg agc ggc      960
Pro Tyr Glu Phe Lys Ala Asp Val Ser Tyr Asp Leu Thr Leu Ser Gly
305                 310                 315                 320

ttc ctg cgc tgg ggc ggc aac gcc tgg tat acc cac ccg gac aac cgt     1008
Phe Leu Arg Trp Gly Gly Asn Ala Trp Tyr Thr His Pro Asp Asn Arg
                325                 330                 335

ccg aac tgg aac cac acc ttc gtc ata ggt ccg tac aag gac aag gcg     1056
Pro Asn Trp Asn His Thr Phe Val Ile Gly Pro Tyr Lys Asp Lys Ala
            340                 345                 350

agc agc att cgg tac cag tgg gac aag cgt tac atc ccg ggt gaa gtg     1104
Ser Ser Ile Arg Tyr Gln Trp Asp Lys Arg Tyr Ile Pro Gly Glu Val
        355                 360                 365

aag tgg tgg gac tgg aac tgg acc ata cag cag aac ggt ctg tct acc     1152
Lys Trp Trp Asp Trp Asn Trp Thr Ile Gln Gln Asn Gly Leu Ser Thr
    370                 375                 380

atg cag aac aac ctg gcc aga gtg ctg cgc ccg gtg cgg gcg ggg atc     1200
Met Gln Asn Asn Leu Ala Arg Val Leu Arg Pro Val Arg Ala Gly Ile
385                 390                 395                 400

acc ggt gat ttc agt gcc gag agc cag ttt gcc ggc aac ata gag atc     1248
Thr Gly Asp Phe Ser Ala Glu Ser Gln Phe Ala Gly Asn Ile Glu Ile
                405                 410                 415

ggt gct ccc gtg ccg ctc gcg gct gac tcc cag ttc tat agc agc aat     1296
Gly Ala Pro Val Pro Leu Ala Ala Asp Ser Gln Phe Tyr Ser Ser Asn
            420                 425                 430

agt gtg gac ggc gct ggt caa ggc ctg agg ctg gag atc ccg ctc gat     1344
Ser Val Asp Gly Ala Gly Gln Gly Leu Arg Leu Glu Ile Pro Leu Asp
        435                 440                 445

gcg caa gag ctc tcc ggg ctt ggc ttc aac aac gtc agc ctc agc gtg     1392
Ala Gln Glu Leu Ser Gly Leu Gly Phe Asn Asn Val Ser Leu Ser Val
    450                 455                 460

acc cct gct gcc aat caa                                             1410
Thr Pro Ala Ala Asn Gln
465                 470
```

FIG. 16

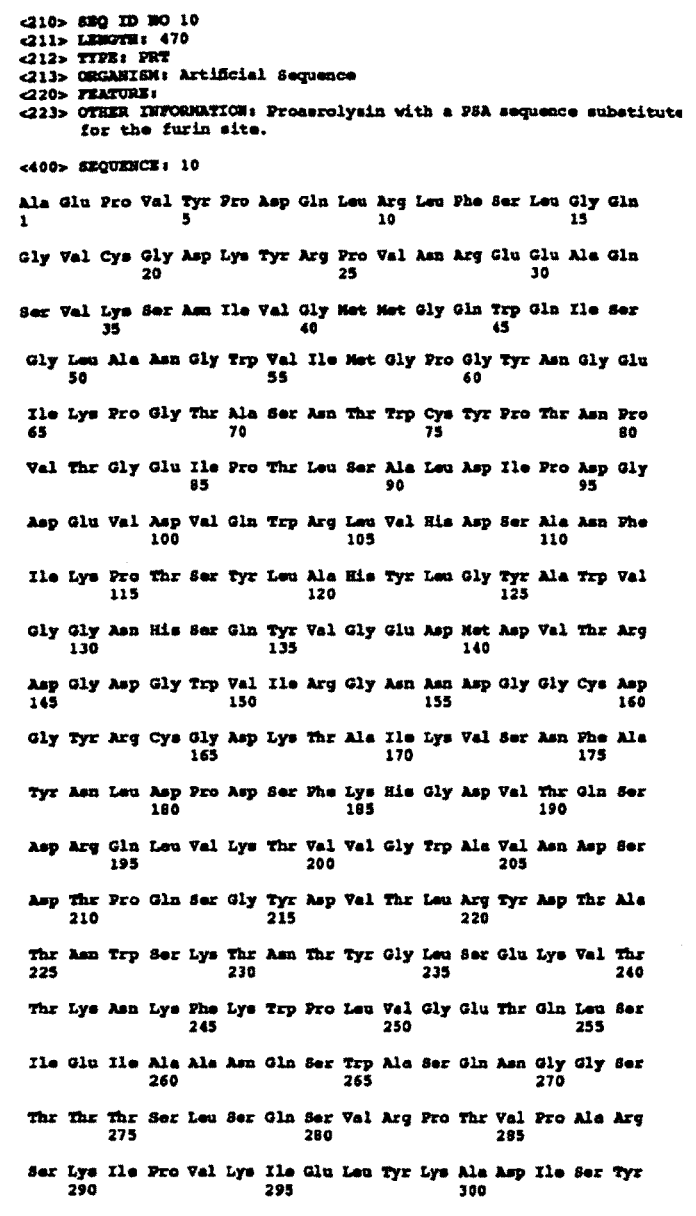

<210> SEQ ID NO 10
<211> LENGTH: 470
<212> TYPE: PRT
<213> ORGANISM: Artificial Sequence
<220> FEATURE:
<223> OTHER INFORMATION: Proaerolysin with a PSA sequence substitute for the furin site.

<400> SEQUENCE: 10

```
Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300
```

FIG. 16 CONT'D

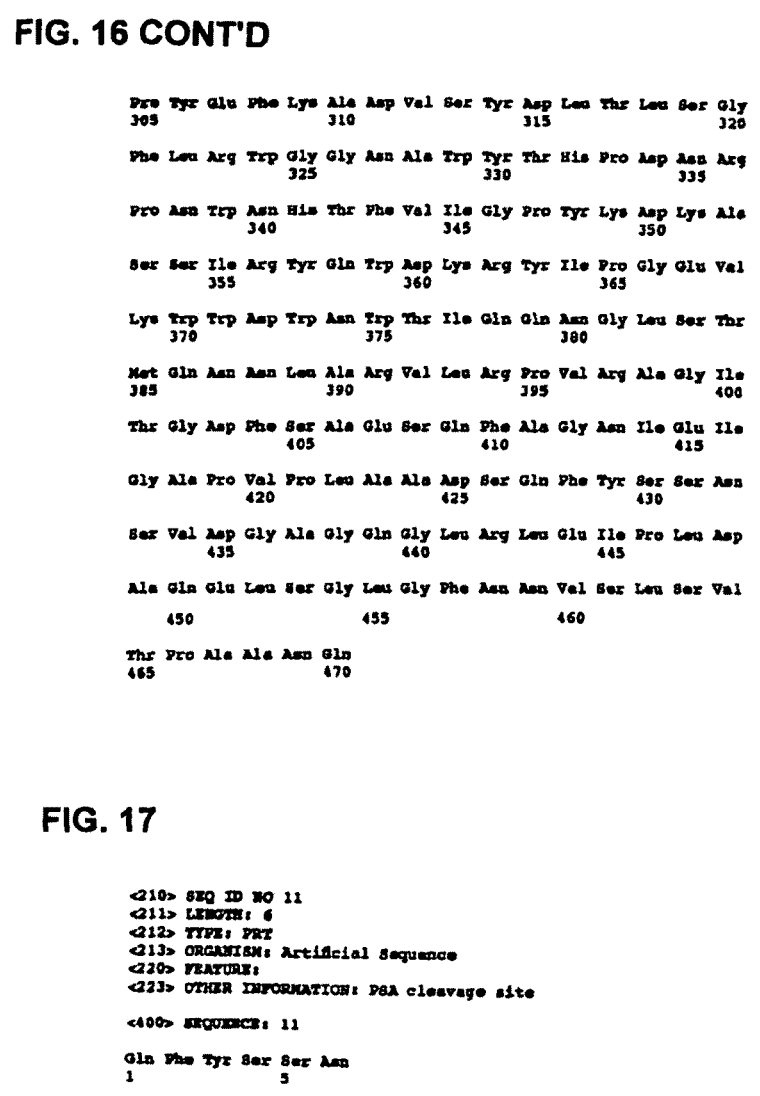

Pro Tyr Glu Phe Lys Ala Asp Val Ser Tyr Asp Leu Thr Leu Ser Gly
305 310 315 320

Phe Leu Arg Trp Gly Gly Asn Ala Trp Tyr Thr His Pro Asp Asn Arg
325 330 335

Pro Asn Trp Asn His Thr Phe Val Ile Gly Pro Tyr Lys Asp Lys Ala
340 345 350

Ser Ser Ile Arg Tyr Gln Trp Asp Lys Arg Tyr Ile Pro Gly Glu Val
355 360 365

Lys Trp Trp Asp Trp Asn Trp Thr Ile Gln Gln Asn Gly Leu Ser Thr
370 375 380

Met Gln Asn Asn Leu Ala Arg Val Leu Arg Pro Val Arg Ala Gly Ile
385 390 395 400

Thr Gly Asp Phe Ser Ala Glu Ser Gln Phe Ala Gly Asn Ile Glu Ile
405 410 415

Gly Ala Pro Val Pro Leu Ala Ala Asp Ser Gln Phe Tyr Ser Ser Asn
420 425 430

Ser Val Asp Gly Ala Gly Gln Gly Leu Arg Leu Glu Ile Pro Leu Asp
435 440 445

Ala Gln Glu Leu Ser Gly Leu Gly Phe Asn Asn Val Ser Leu Ser Val
450 455 460

Thr Pro Ala Ala Asn Gln
465 470

FIG. 17

<210> SEQ ID NO 11
<211> LENGTH: 6
<212> TYPE: PRT
<213> ORGANISM: Artificial Sequence
<220> FEATURE:
<223> OTHER INFORMATION: PSA cleavage site

<400> SEQUENCE: 11

Gln Phe Tyr Ser Ser Asn
1 5

FIG. 18

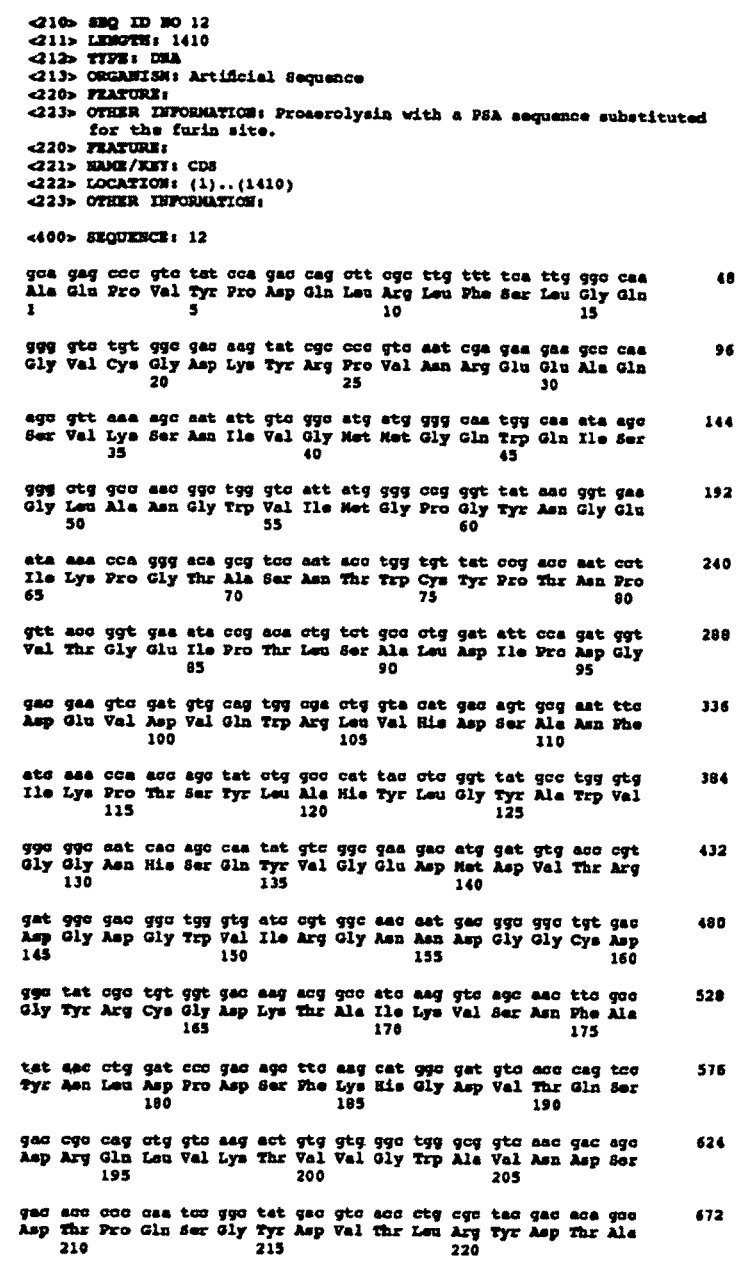

<210> SEQ ID NO 12
<211> LENGTH: 1410
<212> TYPE: DNA
<213> ORGANISM: Artificial Sequence
<220> FEATURE:
<223> OTHER INFORMATION: Proaerolysin with a PSA sequence substituted for the furin site.
<220> FEATURE:
<221> NAME/KEY: CDS
<222> LOCATION: (1)..(1410)
<223> OTHER INFORMATION:

<400> SEQUENCE: 12 gca gag ccc gtc tat cca gac cag ctt cgc ttg ttt tca ttg ggc caa 48
Ala Glu Pro Val Tyr Pro Asp Gln Leu Arg Leu Phe Ser Leu Gly Gln
1 5 10 15 ggg gtc tgt ggc gac aag tat cgc ccc gtc aat cga gaa gaa gcc caa 96
Gly Val Cys Gly Asp Lys Tyr Arg Pro Val Asn Arg Glu Glu Ala Gln
20 25 30 agc gtt aaa agc aat att gtc ggc atg atg ggg caa tgg caa ata agc 144
Ser Val Lys Ser Asn Ile Val Gly Met Met Gly Gln Trp Gln Ile Ser
35 40 45 ggg ctg gcc aac ggc tgg gtc att atg ggg ccg ggt tat aac ggt gaa 192
Gly Leu Ala Asn Gly Trp Val Ile Met Gly Pro Gly Tyr Asn Gly Glu
50 55 60 ata aaa cca ggg aca gcg tcc aat acc tgg tgt tat ccg acc aat cct 240
Ile Lys Pro Gly Thr Ala Ser Asn Thr Trp Cys Tyr Pro Thr Asn Pro
65 70 75 80 gtt acc ggt gaa ata ccg aca ctg tct gcc ctg gat att cca gat ggt 288
Val Thr Gly Glu Ile Pro Thr Leu Ser Ala Leu Asp Ile Pro Asp Gly
85 90 95 gac gaa gtc gat gtg cag tgg cga ctg gta cat gac agt gcg aat ttc 336
Asp Glu Val Asp Val Gln Trp Arg Leu Val His Asp Ser Ala Asn Phe
100 105 110 atc aaa cca acc agc tat ctg gcc cat tac ctc ggt tat gcc tgg gtg 384
Ile Lys Pro Thr Ser Tyr Leu Ala His Tyr Leu Gly Tyr Ala Trp Val
115 120 125 ggc ggc aat cac agc caa tat gtc ggc gaa gac atg gat gtg acc cgt 432
Gly Gly Asn His Ser Gln Tyr Val Gly Glu Asp Met Asp Val Thr Arg
130 135 140 gat ggc gac ggc tgg gtg atc cgt ggc aac aat gac ggc ggc tgt gac 480
Asp Gly Asp Gly Trp Val Ile Arg Gly Asn Asn Asp Gly Gly Cys Asp
145 150 155 160 ggc tat cgc tgt ggt gac aag acg gcc atc aag gtc agc aac ttc gcc 528
Gly Tyr Arg Cys Gly Asp Lys Thr Ala Ile Lys Val Ser Asn Phe Ala
165 170 175 tat aac ctg gat ccc gac agc ttc aag cat ggc gat gtc acc cag tcc 576
Tyr Asn Leu Asp Pro Asp Ser Phe Lys His Gly Asp Val Thr Gln Ser
180 185 190 gac cgc cag ctg gtc aag act gtg gtg ggc tgg gcg gtc aac gac agc 624
Asp Arg Gln Leu Val Lys Thr Val Val Gly Trp Ala Val Asn Asp Ser
195 200 205 gac acc ccc caa tcc ggc tat gac gtc acc ctg cgc tac gac aca gcc 672
Asp Thr Pro Gln Ser Gly Tyr Asp Val Thr Leu Arg Tyr Asp Thr Ala
210 215 220

FIG. 18 CONT'D

```
acc aac tgg tcc aag acc aac acc tat ggc ctg agc gag aag gtg acc        720
Thr Asn Trp Ser Lys Thr Asn Thr Tyr Gly Leu Ser Glu Lys Val Thr
225                 230                 235                 240

acc aag aac aag ttc aag tgg cca ctg gtg ggg gaa acc caa ctc tcc        768
Thr Lys Asn Lys Phe Lys Trp Pro Leu Val Gly Glu Thr Gln Leu Ser
                245                 250                 255

atc gag att gct gcc aat cag tcc tgg gcg tcc cag aac ggg ggc tcg        816
Ile Glu Ile Ala Ala Asn Gln Ser Trp Ala Ser Gln Asn Gly Gly Ser
            260                 265                 270

acc acc acc tcc ctg tct cag tcc gtg cga ccg act gtg ccg gcc cgc        864
Thr Thr Thr Ser Leu Ser Gln Ser Val Arg Pro Thr Val Pro Ala Arg
        275                 280                 285

tcc aag atc ccg gtg aag ata gag ctc tac aag gcc gac atc tcc tat        912
Ser Lys Ile Pro Val Lys Ile Glu Leu Tyr Lys Ala Asp Ile Ser Tyr
    290                 295                 300

ccc tat gag ttc aag gcc gat gtc agc tat gac ctg acc ctg agc ggc        960
Pro Tyr Glu Phe Lys Ala Asp Val Ser Tyr Asp Leu Thr Leu Ser Gly
305                 310                 315                 320

ttc ctg cgc tgg ggc ggc aac gcc tgg tat acc cac ccg gac aac cgt       1008
Phe Leu Arg Trp Gly Gly Asn Ala Trp Tyr Thr His Pro Asp Asn Arg
                325                 330                 335

ccg aac tgg aac cac acc ttc gtc ata ggt ccg tac aag gac aag gcg       1056
Pro Asn Trp Asn His Thr Phe Val Ile Gly Pro Tyr Lys Asp Lys Ala
            340                 345                 350

agc agc att cgg tac cag tgg gac aag cgt tac atc ccg ggt gaa gtg       1104
Ser Ser Ile Arg Tyr Gln Trp Asp Lys Arg Tyr Ile Pro Gly Glu Val
        355                 360                 365

aag tgg tgg gac tgg aac tgg acc ata cag cag aac ggt ctg tct acc       1152
Lys Trp Trp Asp Trp Asn Trp Thr Ile Gln Gln Asn Gly Leu Ser Thr
    370                 375                 380

atg cag aac aac ctg gcc aga gtg ctg cgc ccg gtg cgg gcg ggg atc       1200
Met Gln Asn Asn Leu Ala Arg Val Leu Arg Pro Val Arg Ala Gly Ile
385                 390                 395                 400

acc ggt gat ttc agt gcc gag agc cag ttt gcc ggc aac ata gag atc       1248
Thr Gly Asp Phe Ser Ala Glu Ser Gln Phe Ala Gly Asn Ile Glu Ile
                405                 410                 415

ggt gct ccc gtg ccg ctc gcg gct gac ggt ata agt agt ttc cag agt       1296
Gly Ala Pro Val Pro Leu Ala Ala Asp Gly Ile Ser Ser Phe Gln Ser
            420                 425                 430

agt gtg gac ggc gct ggt caa ggc ctg agg ctg gag atc ccg ctc gat       1344
Ser Val Asp Gly Ala Gly Gln Gly Leu Arg Leu Glu Ile Pro Leu Asp
        435                 440                 445

gcg caa gag ctc tcc ggg ctt ggc ttc aac aac gtc agc ctc agc gtg       1392
Ala Gln Glu Leu Ser Gly Leu Gly Phe Asn Asn Val Ser Leu Ser Val
    450                 455                 460

acc cct gct gcc aat caa                                               1410
Thr Pro Ala Ala Asn Gln
465                 470
```

FIG. 19

<210> SEQ ID NO 13
<211> LENGTH: 470
<212> TYPE: PRT
<213> ORGANISM: Artificial Sequence
<220> FEATURE:
<223> OTHER INFORMATION: Proaerolysin with a PSA sequence substituted for the furin site.

<400> SEQUENCE: 13

Ala Glu Pro Val Tyr Pro Asp Gln Leu Arg Leu Phe Ser Leu Gly Gln
1 5 10 15

Gly Val Cys Gly Asp Lys Tyr Arg Pro Val Asn Arg Glu Glu Ala Gln
20 25 30

Ser Val Lys Ser Asn Ile Val Gly Met Met Gly Gln Trp Gln Ile Ser
35 40 45

Gly Leu Ala Asn Gly Trp Val Ile Met Gly Pro Gly Tyr Asn Gly Glu
50 55 60

Ile Lys Pro Gly Thr Ala Ser Asn Thr Trp Cys Tyr Pro Thr Asn Pro
65 70 75 80

Val Thr Gly Glu Ile Pro Thr Leu Ser Ala Leu Asp Ile Pro Asp Gly
85 90 95

Asp Glu Val Asp Val Gln Trp Arg Leu Val His Asp Ser Ala Asn Phe
100 105 110

Ile Lys Pro Thr Ser Tyr Leu Ala His Tyr Leu Gly Tyr Ala Trp Val
115 120 125

Gly Gly Asn His Ser Gln Tyr Val Gly Glu Asp Met Asp Val Thr Arg
130 135 140

Asp Gly Asp Gly Trp Val Ile Arg Gly Asn Asn Asp Gly Gly Cys Asp
145 150 155 160

Gly Tyr Arg Cys Gly Asp Lys Thr Ala Ile Lys Val Ser Asn Phe Ala
165 170 175

Tyr Asn Leu Asp Pro Asp Ser Phe Lys His Gly Asp Val Thr Gln Ser
180 185 190

Asp Arg Gln Leu Val Lys Thr Val Val Gly Trp Ala Val Asn Asp Ser
195 200 205

Asp Thr Pro Gln Ser Gly Tyr Asp Val Thr Leu Arg Tyr Asp Thr Ala
210 215 220

Thr Asn Trp Ser Lys Thr Asn Thr Tyr Gly Leu Ser Glu Lys Val Thr
225 230 235 240

Thr Lys Asn Lys Phe Lys Trp Pro Leu Val Gly Glu Thr Gln Leu Ser
245 250 255

Ile Glu Ile Ala Ala Asn Gln Ser Trp Ala Ser Gln Asn Gly Gly Ser
260 265 270

Thr Thr Thr Ser Leu Ser Gln Ser Val Arg Pro Thr Val Pro Ala Arg
275 280 285

FIG. 19 CONT'D

```
Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala

            340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Gln Asn Gly Leu Ser Thr
    370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Gly Ile Ser Ser Phe Gln Ser
            420                 425                 430

Ser Val Asp Gly Ala Gly Gln Gly Leu Arg Leu Glu Ile Pro Leu Asp
        435                 440                 445

Ala Gln Glu Leu Ser Gly Leu Gly Phe Asn Asn Val Ser Leu Ser Val
    450                 455                 460

Thr Pro Ala Ala Asn Gln
465                 470
```

FIG. 20

```
<210> SEQ ID NO 14
<211> LENGTH: 7
<212> TYPE: PRT
<213> ORGANISM: Artificial Sequence
<220> FEATURE:
<223> OTHER INFORMATION: PSA cleavage site

<400> SEQUENCE: 14

Gly Ile Ser Ser Phe Gln Ser
1               5
```

FIG. 21

<210> SEQ ID NO 15
<211> LENGTH: 7
<212> TYPE: PRT
<213> ORGANISM: Homo sapiens

<400> SEQUENCE: 15

Lys Gly Ile Ser Ser Gln Tyr
1               5

FIG. 22

<210> SEQ ID NO 16
<211> LENGTH: 7
<212> TYPE: PRT
<213> ORGANISM: Homo sapiens

<400> SEQUENCE: 16

Ser Arg Lys Ser Gln Gln Tyr
1               5

FIG. 23

<210> SEQ ID NO 17
<211> LENGTH: 7
<212> TYPE: PRT
<213> ORGANISM: Homo sapiens

<400> SEQUENCE: 17

Ala Thr Lys Ser Lys Gln His
1               5

FIG. 24

<210> SEQ ID NO 18
<211> LENGTH: 7
<212> TYPE: PRT
<213> ORGANISM: Homo sapiens

<400> SEQUENCE: 18

Lys Gly Leu Ser Ser Gln Cys
1               5

FIG. 25

<210> SEQ ID NO 19
<211> LENGTH: 7
<212> TYPE: PRT
<213> ORGANISM: Homo sapiens

<400> SEQUENCE: 19

Leu Gly Gly Ser Ser Gln Leu
1 5

FIG. 26

<210> SEQ ID NO 20
<211> LENGTH: 7
<212> TYPE: PRT
<213> ORGANISM: Homo sapiens

<400> SEQUENCE: 20

Glu His Ser Ser Lys Leu Gln
1 5

FIG. 27

<210> SEQ ID NO 21
<211> LENGTH: 4
<212> TYPE: PRT
<213> ORGANISM: Homo sapiens

<400> SEQUENCE: 21

Ser Lys Leu Gln
1

FIG. 28

<210> SEQ ID NO 22
<211> LENGTH: 10
<212> TYPE: PRT
<213> ORGANISM: Homo sapiens

<400> SEQUENCE: 22

Gln His Trp Ser Tyr Gly Leu Arg Pro Gly
1 5 10

FIG. 29

<210> SEQ ID NO 23
<211> LENGTH: 10
<212> TYPE: PRT
<213> ORGANISM: Artificial Sequence
<220> FEATURE:
<223> OTHER INFORMATION: LHRH variant sequence.
<220> FEATURE:
<221> NAME/KEY: MISC_FEATURE
<222> LOCATION: (1)..(1)
<223> OTHER INFORMATION: Glu is a pyroglutamate
<220> FEATURE:
<221> NAME/KEY: MISC_FEATURE
<222> LOCATION: (6)..(6)
<223> OTHER INFORMATION: Lys is a D-Lys

<400> SEQUENCE: 23

Glu His Trp Ser Tyr Lys Leu Arg Pro Gly
1 5 10

FIG. 30

<210> SEQ ID NO 24
<211> LENGTH: 397
<212> TYPE: PRT
<213> ORGANISM: Artificial Sequence
<220> FEATURE:
<223> OTHER INFORMATION: Variant proaerolysin peptide.
<220> FEATURE:
<221> NAME/KEY: MISC_FEATURE
<222> LOCATION: (1)..(1)
<223> OTHER INFORMATION: pyroglutamate
<220> FEATURE:
<221> NAME/KEY: MISC_FEATURE
<222> LOCATION: (6)..(6)
<223> OTHER INFORMATION: D-Lys

<400> SEQUENCE: 24

Glu His Trp Ser Tyr Lys Leu Arg Pro Gly Glu Ile Pro Thr Leu Ser
1 5 10 15

Ala Leu Asp Ile Pro Asp Gly Asp Glu Val Asp Val Gln Trp Arg Leu
20 25 30

Val His Asp Ser Ala Asn Phe Ile Lys Pro Thr Ser Tyr Leu Ala His
35 40 45

Tyr Leu Gly Tyr Ala Trp Val Gly Gly Asn His Ser Gln Tyr Val Gly
50 55 60

Glu Asp Met Asp Val Thr Arg Asp Gly Asp Gly Trp Val Ile Arg Gly
65 70 75 80

Asn Asn Asp Gly Gly Cys Asp Gly Tyr Arg Cys Gly Asp Lys Thr Ala
85 90 95

Ile Lys Val Ser Asn Phe Ala Tyr Asn Leu Asp Pro Asp Ser Phe Lys
100 105 110

His Gly Asp Val Thr Gln Ser Asp Arg Gln Leu Val Lys Thr Val Val
115 120 125

Gly Trp Ala Val Asn Asp Ser Asp Thr Pro Gln Ser Gly Tyr Asp Val
130 135 140

Thr Leu Arg Tyr Asp Thr Ala Thr Asn Trp Ser Lys Thr Asn Thr Tyr
145 150 155 160

FIG. 30 CONT'D

Gly Leu Ser Glu Lys Val Thr Thr Lys Asn Lys Phe Lys Trp Pro Leu
165 170 175

Val Gly Glu Thr Gln Leu Ser Ile Glu Ile Ala Ala Asn Gln Ser Trp
180 185 190

Ala Ser Gln Asn Gly Gly Ser Thr Thr Thr Ser Leu Ser Gln Ser Val
195 200 205

Arg Pro Thr Val Pro Ala Arg Ser Lys Ile Pro Val Lys Ile Glu Leu
210 215 220

Tyr Lys Ala Asp Ile Ser Tyr Pro Tyr Glu Phe Lys Ala Asp Val Ser
225 230 235 240

Tyr Asp Leu Thr Leu Ser Gly Phe Leu Arg Trp Gly Gly Asn Ala Trp
245 250 255

Tyr Thr His Pro Asp Asn Arg Pro Asn Trp Asn His Thr Phe Val Ile
260 265 270

Gly Pro Tyr Lys Asp Lys Ala Ser Ser Ile Arg Tyr Gln Trp Asp Lys
275 280 285

Arg Tyr Ile Pro Gly Glu Val Lys Trp Trp Asp Trp Asn Trp Thr Ile
290 295 300

Gln Gln Asn Gly Leu Ser Thr Met Gln Asn Asn Leu Ala Arg Val Leu
305 310 315 320

Arg Pro Val Arg Ala Gly Ile Thr Gly Asp Phe Ser Ala Glu Ser Gln
325 330 335

Phe Ala Gly Asn Ile Glu Ile Gly Ala Pro Val Pro Leu Ala Ala Asp
340 345 350

Ser His Ser Ser Lys Leu Gln Ser Val Asp Gly Ala Gly Gln Gly Leu
355 360 365

Arg Leu Glu Ile Pro Leu Asp Ala Gln Glu Leu Ser Gly Leu Gly Phe
370 375 380

Asn Asn Val Ser Leu Ser Val Thr Pro Ala Ala Asn Gln
385 390 395

FIG. 31

<210> SEQ ID NO 25
<211> LENGTH: 397
<212> TYPE: PRT
<213> ORGANISM: Artificial Sequence
<220> FEATURE:
<223> OTHER INFORMATION: Variant proaerolysin peptide.
<220> FEATURE:
<221> NAME/KEY: MISC_FEATURE
<222> LOCATION: (1)..(1)
<223> OTHER INFORMATION: pyroglutamate
<220> FEATURE:
<221> NAME/KEY: MISC_FEATURE
<222> LOCATION: (6)..(6)
<223> OTHER INFORMATION: D-Lys

<400> SEQUENCE: 25

Glu His Trp Ser Tyr Lys Leu Arg Pro Gly Glu Ile Pro Thr Leu Ser
1 5 10 15

FIG. 31 CONT'D

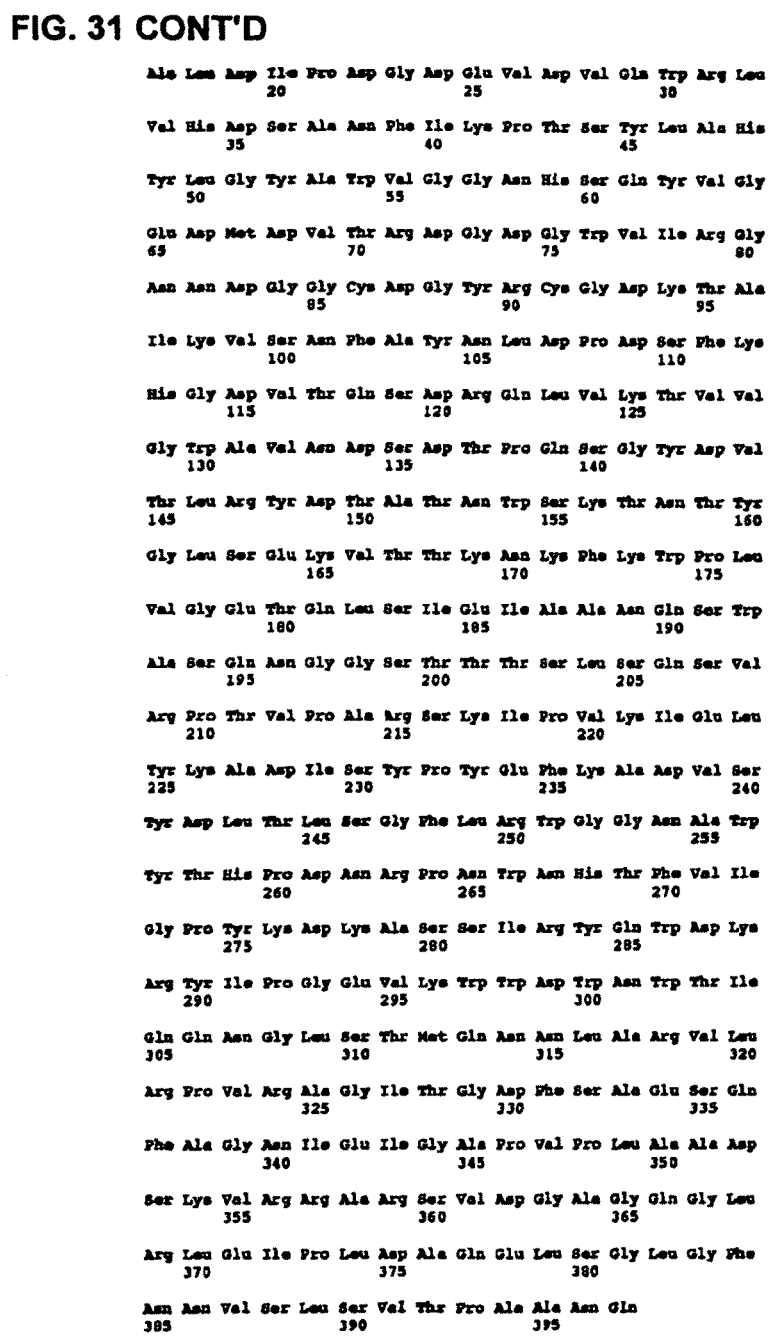

```
Ala Leu Asp Ile Pro Asp Gly Asp Glu Val Asp Val Gln Trp Arg Leu
            20                  25                  30

Val His Asp Ser Ala Asn Phe Ile Lys Pro Thr Ser Tyr Leu Ala His
        35                  40                  45

Tyr Leu Gly Tyr Ala Trp Val Gly Gly Asn His Ser Gln Tyr Val Gly
    50                  55                  60

Glu Asp Met Asp Val Thr Arg Asp Gly Asp Gly Trp Val Ile Arg Gly
65                  70                  75                  80

Asn Asn Asp Gly Gly Cys Asp Gly Tyr Arg Cys Gly Asp Lys Thr Ala
                85                  90                  95

Ile Lys Val Ser Asn Phe Ala Tyr Asn Leu Asp Pro Asp Ser Phe Lys
            100                 105                 110

His Gly Asp Val Thr Gln Ser Asp Arg Gln Leu Val Lys Thr Val Val
        115                 120                 125

Gly Trp Ala Val Asn Asp Ser Asp Thr Pro Gln Ser Gly Tyr Asp Val
    130                 135                 140

Thr Leu Arg Tyr Asp Thr Ala Thr Asn Trp Ser Lys Thr Asn Thr Tyr
145                 150                 155                 160

Gly Leu Ser Glu Lys Val Thr Thr Lys Asn Lys Phe Lys Trp Pro Leu
                165                 170                 175

Val Gly Glu Thr Gln Leu Ser Ile Glu Ile Ala Ala Asn Gln Ser Trp
            180                 185                 190

Ala Ser Gln Asn Gly Gly Ser Thr Thr Thr Ser Leu Ser Gln Ser Val
        195                 200                 205

Arg Pro Thr Val Pro Ala Arg Ser Lys Ile Pro Val Lys Ile Glu Leu
    210                 215                 220

Tyr Lys Ala Asp Ile Ser Tyr Pro Tyr Glu Phe Lys Ala Asp Val Ser
225                 230                 235                 240

Tyr Asp Leu Thr Leu Ser Gly Phe Leu Arg Trp Gly Gly Asn Ala Trp
                245                 250                 255

Tyr Thr His Pro Asp Asn Arg Pro Asn Trp Asn His Thr Phe Val Ile
            260                 265                 270

Gly Pro Tyr Lys Asp Lys Ala Ser Ser Ile Arg Tyr Gln Trp Asp Lys
        275                 280                 285

Arg Tyr Ile Pro Gly Glu Val Lys Trp Trp Asp Trp Asn Trp Thr Ile
    290                 295                 300

Gln Gln Asn Gly Leu Ser Thr Met Gln Asn Asn Leu Ala Arg Val Leu
305                 310                 315                 320

Arg Pro Val Arg Ala Gly Ile Thr Gly Asp Phe Ser Ala Glu Ser Gln
                325                 330                 335

Phe Ala Gly Asn Ile Glu Ile Gly Ala Pro Val Pro Leu Ala Ala Asp
            340                 345                 350

Ser Lys Val Arg Arg Ala Arg Ser Val Asp Gly Ala Gly Gln Gly Leu
        355                 360                 365

Arg Leu Glu Ile Pro Leu Asp Ala Gln Glu Leu Ser Gly Leu Gly Phe
    370                 375                 380

Asn Asn Val Ser Leu Ser Val Thr Pro Ala Ala Asn Gln
385                 390                 395
```

Group 1, 0 μg/g prostate, Animal 6002

Group 1, 0 μg/g prostate, Animal 7001

Group 2, 1 μg/g prostate, Animal 6004

Group 2, 1 μg/g prostate, Animal 9001

Group 3, 5 μg/g prostate, Animal 6006

Group 3, 5 μg/g prostate, Animal 7003

Group 4, 25 μg/g prostate, Animal 6008

Group 4, 25 μg/g prostate, Animal 7004

Group 1, 0 µg/g prostate, Animal 6001, Day 15

Group 1, 0 µg/g prostate, Animal 8001, Day 15

Group 2, 1 μg/g prostate, Animal 6003, Day 15

Group 2, 1 μg/g prostate, Animal 7002, Day 15

Group 3, 5 µg/g prostate, Animal 6005, Day 15

Group 3, 5 µg/g prostate, Animal 8002, Day 15

Group 4, 25 µg/g prostate, Animal 6007, Day 15

Group 4, 25 µg/g prostate, Animal 8003, Day 15

1 AAGCTTGCAT GCCTGCAGAA GAAGGAGATA TACATATGCA AAAAATAAAA CTAACTGGCT TGTCATTAAT
71 CATATCCGGC CTGCTGATGG CACAGGCGCA AGCGGCAGAG CCCGTCTATC CAGACCAGCT TCGCTTGTTT
141 TCATTGGGCC AAGGGGTCTG TGGCGACAAG TATCGCCCCG TCAATCGAGA AGAAGCCCAA AGCGTTAAAA
211 GCAATATTGT CGGCATGATG GGGCAATGGC AAATAAGCGG GCTGGCCAAC GGCTGGGTCA TTATGGGGCC
281 GGGTTATAAC GGTGAAATAA AACCAGGGAC AGCGTCCAAT ACCTGGTGTT ATCCGACCAA TCCTGTTACC
351 GGTGAAATAC CGACACTGTC TGCCCTGGAT ATTCCAGATG GTGACGAAGT CGATGTGCAG TGGCGACTGG
421 TACATGACAG TGCGAATTTC ATCAAACCAA CCAGCTATCT GGCCCATTAC CTCGGTTATG CCTGGGTGGG
491 CGGCAATCAC AGCCAATATG TCGGCGAAGA CATGGATGTG ACCCGTGATG GCGACGGCTG GGTGATCCGT
561 GGCAACAATG ACGGCGGCTG TGACGGCTAT CGCTGTGGTG ACAAGACGGC CATCAAGGTC AGCAACTTCG
631 CCTATAACCT AGATCCCGAC AGCTTCAAGC ATGGCGATGT CACCCAGTCC GACCGCCAGC TGGTCAAGAC
701 TGTGGTGGGC TGGGCGGTCA ACGACAGCGA CACCCCCCAA TCCGGCTATG ACGTCACCCT GCGCTACGAC
771 ACAGCCACCA ACTGGTCCAA GACCAACACC TATGGCCTGA GCGAGAAGGT GACCACCAAG AACAAGTTCA
841 AGTGGCCACT GGTGGGGGAA ACCGAACTCT CCATCGAGAT TGCTGCCAAT CAGTCCTGGG CGTCCCAGAA
911 CGGGGGCTCG ACCACCACCT CCCTGTCTCA GTCCGTGCGA CCGACTGTGC CGGCCCGCTC CAAGATCCCG
981 GTGAAGATAG AGCTCTACAA GGCCGACATC TCCTATCCCT ATGAGTTCAA GGCCGATGTC AGCTATGACC
1051 TGACCCTGAG CGGCTTCCTG CGCTGGGGCG GCAACGCCTG GTATACCCAC CCGGACAACC GTCCGAACTG
1121 GAACCACACC TTCGTCATAG GTCCGTACAA GGACAAGGCG AGCAGCATTC GGTACCAGTG GGACAAGCGT
1191 TACATCCCGG GTGAAGTGAA GTGGTGGGAC TGGAACTGGA CCATACAGCA GAACGGTCTG TCTACCATGC
1261 AGAACAACCT GGCCAGAGTG CTGCGCCCGG TGCGGGCGGG GATCACCGGT GATTTCAGTG CCGAGAGCCA
1331 GTTTGCCGGC AACATAGAGA TCGGTGCTCC CGTGCCGCTC GCGGCTGACA GCCATTCCTC CAAGCTGCAG
1401 AGTGTGGACG GCGCTGGTCA AGGCCTGAGG CTGGAGATCC CGCTCGATGC GCAAGAGCTC TCCGGGCTTG
1471 GCTTCAACAA CGTCAGCCTC AGCGTGACCC CTGCTGCCAA TCAA*CATCAT CATCATCATC AT*TAACGGCA
1541 GCGCTAACAA CATCATCATC ATCATCATTA ACGGCAGCGC GTTGTAGTGA TGGAACCGGG CCTCTGGCCC
1611 GGTTTTTGTT TGCACTGGTC GGGCTTGTTA AAGGCTTGTG CTTTCCATTT CCCCACTTAT ACTGGCGCCA
1681 TCTTGTCGGA GTGCCAACCG TCGAACGACG CGAGGCTGAG ACCGTTAATT CGGGATCCGT GGAACCTGAT
1751 CCCCGGGAAT TC

FIG. 34

1 AEPVYPDQLRLFSLGQGVCGDKYRPVNREEAQSVKSNIVGMMGQWQISGLANGWVIMGPG

61 YNGEIKPGTASNTWCYPTNPVTGEIPTLSALDIPDGDEVDVQWRLVHDSANFIKPTSYLA

121 HYLGYAWVGGNHSQYVGEDMDVTRDGDGWVIRGNNDGGCDGYRCGDKTAIKVSNFAYNLD

181 PDSFKHGDVTQSDRQLVKTVVGWAVNDSDTPQSGYDVTLRYDTATNWSKTNTYGLSEKVT

241 TKNKFKWPLVGETELSIEIAANQSWASQNGGSTTTSLSQSVRPTVPARSKIPVKIELYKA

301 DISYPYEFKADVSYDLTLSGFLRWGGNAWYTHPDNRPNWNHTFVIGPYKDKASSIRYQWD

361 KRYIPGEVKWWDWNWTIQQNGLSTMQNNLARVLRPVRAGITGDFSAESQFAGNIEIGAPV

421 PLAADSHSSKLQSVDGAGQGLRLEIPLDAQELSGLGFNNVSLSVTPAANQHHHHHH

<210> 73
<211> 1542
<212> DNA
<213> Clostridium septicum

<400> 73
tgttaataat atgttaatat tttgataaca tttattatat aataaattat ttattttaaa 60
attaaaggga gggatattta tgtcaaaaaa atcttttgct aaaaaagtaa tttgtacatc 120
tatgattgca attcagtgtg cggcagtagt accacatgta caagcttatg cacttacaaa 180
tcttgaagag gggggatatg caaatcataa taatgcttct tcaattaaaa tatttggata 240
tgaagacaat gaagatttaa aagctaaaat tattcaagat ccagagttta taagaaattg 300
ggcaaatgta gctcattcat taggatttgg atggtgcggt ggaacggcta atccaaacgt 360
tggacaaggt tttgaattta aaagagaagt tggggcaggt ggaaaagtat cttatttatt 420
atctgctaga tacaatccaa atgatcctta tgcaagtgga tatcgtgcaa aagatagact 480
ttctatgaaa atatcaaatg ttagatttgt tattgataat gattctataa aattaggtac 540
acctaaagtg aaaaaattag cacctttaaa ctctgctagt tttgatttaa taaatgaaag 600
taaaactgag tctaaattat caaaaacatt taattataca acttctaaaa cagtttctaa 660
aacagataac tttaaatttg gagaaaaaat aggagtaaaa acatcattta aagtaggtct 720
tgaagctata gctgacagta aagttgagac aagctttgaa tttaatgcag aacaaggttg 780
gtcaaataca aatagtacta ctgaaactaa acaagaaagt actacatata ctgcaacagt 840
ttctccacaa actaaaaaga gattattcct agatgtgtta ggatcacaaa ttgatattcc 900
ttatgaagga aaaatatata tggaatacga catagaatta atgggatttt taagatatac 960
aggaaatgct cgtgaagatc atactgaaga tagaccaaca gttaaactta aatttggtaa 1020
aaacggtatg agtgctgagg aacatcttaa agatttatat agtcataaga atattaatgg 1080
atattcagaa tgggattgga aatgggtaga tgagaaattt ggttatttat ttaaaaattc 1140
atacgatgct cttactagta gaaaattagg aggaataata aaaggctcat ttactaacat 1200
taatggaaca aaaatagtaa ttagagaagg taaagaaatt ccacttcctg ataagaagag 1260
aagaggaaaa cgttcagtag attctttaga tgctagatta caaaatgaag gtattagaat 1320
agaaaatatt gaaacacaag atgttccagg atttagacta aatagcataa catacaatga 1380
taaaaaattg atattaatta ataatatata attataattt attaaaatat gcttctctat 1440
actttatatt aatatttaaa gtataaaaac taacaaaatc tcacttagta ggtagaattg 1500
tataaaaaca aatctaccta ctattttttt attatttagt cg 1542

FIG. 41

<210> 74
<211> 443
<212> PRT
<213> Clostridium septicum

<400> 74
Met Ser Lys Lys Ser Phe Ala Lys Lys Val Ile Cys Thr Ser Met Ile
1 5 10 15
Ala Ile Gln Cys Ala Ala Val Val Pro His Val Gln Ala Tyr Ala Leu
20 25 30
Thr Asn Leu Glu Glu Gly Gly Tyr Ala Asn His Asn Asn Ala Ser Ser
35 40 45
Ile Lys Ile Phe Gly Tyr Glu Asp Asn Glu Asp Leu Lys Ala Lys Ile
50 55 60
Ile Gln Asp Pro Glu Phe Ile Arg Asn Trp Ala Asn Val Ala His Ser
65 70 75 80
Leu Gly Phe Gly Trp Cys Gly Gly Thr Ala Asn Pro Asn Val Gly Gln
85 90 95
Gly Phe Glu Phe Lys Arg Glu Val Gly Ala Gly Gly Lys Val Ser Tyr
100 105 110
Leu Leu Ser Ala Arg Tyr Asn Pro Asn Asp Pro Tyr Ala Ser Gly Tyr
115 120 125
Arg Ala Lys Asp Arg Leu Ser Met Lys Ile Ser Asn Val Arg Phe Val
130 135 140
Ile Asp Asn Asp Ser Ile Lys Leu Gly Thr Pro Lys Val Lys Lys Leu
145 150 155 160
Ala Pro Leu Asn Ser Ala Ser Phe Asp Leu Ile Asn Glu Ser Lys Thr
165 170 175
Glu Ser Lys Leu Ser Lys Thr Phe Asn Tyr Thr Thr Ser Lys Thr Val
180 185 190
Ser Lys Thr Asp Asn Phe Lys Phe Gly Glu Lys Ile Gly Val Lys Thr
195 200 205
Ser Phe Lys Val Gly Leu Glu Ala Ile Ala Asp Ser Lys Val Glu Thr
210 215 220
Ser Phe Glu Phe Asn Ala Glu Gln Gly Trp Ser Asn Thr Asn Ser Thr
225 230 235 240
Thr Glu Thr Lys Gln Glu Ser Thr Thr Tyr Thr Ala Thr Val Ser Pro
245 250 255
Gln Thr Lys Lys Arg Leu Phe Leu Asp Val Leu Gly Ser Gln Ile Asp
260 265 270
Ile Pro Tyr Glu Gly Lys Ile Tyr Met Glu Tyr Asp Ile Glu Leu Met
275 280 285
Gly Phe Leu Arg Tyr Thr Gly Asn Ala Arg Glu Asp His Thr Glu Asp
290 295 300
Arg Pro Thr Val Lys Leu Lys Phe Gly Lys Asn Gly Met Ser Ala Glu
305 310 315 320
Glu His Leu Lys Asp Leu Tyr Ser His Lys Asn Ile Asn Gly Tyr Ser
325 330 335
Glu Trp Asp Trp Lys Trp Val Asp Glu Lys Phe Gly Tyr Leu Phe Lys
340 345 350
Asn Ser Tyr Asp Ala Leu Thr Ser Arg Lys Leu Gly Gly Ile Ile Lys
355 360 365
Gly Ser Phe Thr Asn Ile Asn Gly Thr Lys Ile Val Ile Arg Glu Gly
370 375 380
Lys Glu Ile Pro Leu Pro Asp Lys Lys Arg Arg Gly Lys Arg Ser Val
385 390 395 400
Asp Ser Leu Asp Ala Arg Leu Gln Asn Glu Gly Ile Arg Ile Glu Asn
405 410 415
Ile Glu Thr Gln Asp Val Pro Gly Phe Arg Leu Asn Ser Ile Thr Tyr
420 425 430
Asn Asp Lys Lys Leu Ile Leu Ile Asn Asn Ile
435 440

METHOD OF TREATING OR PREVENTING BENIGN PROSTATIC HYPERPLASIA USING MODIFIED PORE-FORMING PROTEINS

This is the U.S. National Stage of International Application No. PCT/CA2006/000971, filed Jun. 14, 2006 (published in English under PCT Article 21(2)), which claims the benefit of U.S. provisional patent application No. 60/690,269 filed, Jun. 14, 2005, which is also incorporated herein by reference.

FIELD OF THE INVENTION

The present invention relates to the field of benign prostatic hypertrophy, and in particular to the use of modified pore-forming proteins for the treatment of benign prostatic hyperplasia (BPH).

BACKGROUND OF THE INVENTION

Many cytolytic proteins have been described (Lesieur et al. Mol. Membr. Biol. 14:45064, 1997). These naturally occurring cytotoxic proteins include mammalian proteins such as perforin, and bacterial proteins such as aerolysin (produced by *Aeromonas hydrophila*), α-hemolysin (produced by *Staphylococcus aureus*), alpha toxin (produced by *Clostridium septicum*), δ-toxin (produced by *Bacillus thuringiensis*), anthrax protective antigen, *Vibrio cholerae* VCC toxin, *Staphylococcus* leucocidins, LSL toxin from *Laetiporus sulphureus*, epsilon toxin from *Clostridium perfringens*, and hydralysins produced by *Cnidaria* spp.

Some of these cytotoxic proteins, for example, proaerolysin and alpha toxin, are synthesized as inactive protoxins. These protoxins contain discrete functionalities including a binding domain, which allows binding of the protoxin to a cell, a toxin domain, and either an N-terminal or a C-terminal inhibitory peptide domain that contains a protease cleavage site. Cleavage of the inhibitory peptide domain at the protease cleavage site results in activation of the protoxin, leading to oligomerization of the cytotoxin in the plasma membrane, producing pores that lead to rapid cytolytic cell death (Rossjohn et al. J. Struct. Biol. 121:92-100, 1998). Pore formation physically disrupts the cell membranes, and results in death of cells in all phases of the cell cycle, including non-proliferating cells (i.e. $G_0$ arrested). These cytotoxins are not specific in the type of cells they are able to kill, as their binding domains target molecules that are found on most cells, and they are generally activated by proteases that are not cell-specific.

Cytolytic pore-forming proteins or modified versions of these proteins have been proposed as potential therapeutics for the treatment of cancer. For example, U.S. Pat. No. 5,777,078 describes pore-forming agents that are activated at the surface of a cell by a number of conditions, including proteolysis, to lyse the cell. These pore-forming agents can be used generally to destroy unwanted cells associated with a pathological condition in an animal. Such cells include but are not limited to tumor cells, cells which are chronically infected with virus, or cells, which when improperly regulated or expressed, result in a disease state, e.g., cells of the immune system. WO 98/020135 describes methods and compositions relating to *Pseudomonas* exotoxin proproteins modified for selective toxicity. The exotoxin is modified to be activated by a desired protease by insertion of a protease susceptible sequence in the proprotein. In one example the exotoxin is modified to insert a prostate specific antigen (PSA) cleavage site for the purpose of targeting and killing prostate cancer cells.

U.S. Patent Application No. 2004/0235095 describes the use of modified cytolytic pore-forming proteins for the treatment of prostate and other cancers. The cytolytic proteins can be modified to include a prostate-specific cleavage site, and/or a prostate-specific targeting domain and can be used to selectively target and kill prostate cancer cells.

Cancer is characterized by an increase in the number of abnormal, or neoplastic cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites via a process called metastasis. In a cancerous state, a cell proliferates under conditions in which normal cells would not grow. Unlike normal cells, in general, cancer cells continue to reproduce, they do not specialize or become mature, and they have the ability to spread from the tissue of origin to other locations within the body. These characteristics of cancer cells generally result from changes in the relative pattern of gene expression within these cells compared to that in normal cells. Many strategies for developing therapeutics for the treatment of cancer have focused on taking advantage of the differences in gene expression between normal cells and cancer cells, and targeting cancer cells using molecular markers that are specific to cancer cells.

In contrast, benign prostatic hyperplasia (BPH, also known as benign prostatic hypertrophy) is a non-cancerous condition resulting from enlargement of the prostate gland as a consequence of the natural progression of prostate growth with age. Enlargement of the prostate can be a result of increased prostate cell proliferation, or an increase in prostate cell size. This progressive prostate growth does not usually cause problems until late in life. The National Institute of Health (NIH) estimates that 60% of American men in their sixties have some symptoms of BPH and that the condition affects more than 90% of men in their seventies and eighties. Approximately 115 million males worldwide in the 50+ age group have varying degrees of BPH. Due to the aging of the population, the prevalence is expected to increase substantially over the next 20 years. Severe BPH can cause serious problems such as urinary tract infections, bladder and kidney damage, including bladder stones, incontinence and most seriously, gross hematuria and renal failure due to obstructive uropathy.

There are several strategies currently available for treating BPH. These include watchful waiting, medical therapy such as alpha blocker therapy and finasteride therapy, balloon dilation and various surgical procedures such as transurethral incision of the prostate (TUIP), transurethral resection of the prostate (TURP), and open prostatectomy. Few treatments are without any adverse consequences, and this is particularly so with treatments for BPH, where there is a delicate balancing act between the benefits and demerits of the treatments available. The adverse events following currently available treatments for BPH include impotence (for various surgical procedures ranging from about 4% to 40%, the incidence of impotence is also increased after some medical treatments), incontinence (stress incontinence about 3% after surgery, with total urinary incontinence approaching 1%), and the need for re-treatment. Combined analysis of published data estimated that the mean probability for perioperative mortality (death within 90 days of a procedure) was 1.5% for TURP. For open surgery it was 2.4% and for balloon dilation it was 3.5%.

Currently, the most commonly used hormone therapy is oral administration of finasteride. Finasteride, commercially available under the tradename Proscar™ from Merck & Co. Inc., Whitehouse Station, N.J., is a synthetic 4-azasteroid compound, a specific inhibitor of steroid Type II 5α-reductase, and an intracellular enzyme that converts the androgen testosterone into 5α-dihydrotestosterone (DHT). Finasteride helps to shrink the enlarged prostate and reduces elevated PSA due to benign prostate conditions. However, finasteride is known to cause undesirable side effects, which include impotence or lessened desire for sex, problems with ejaculation, and breast enlargement and/or tenderness. Dutasteride (Duagen) is another drug for the treatment of BPH and it is capable of blocking both types I and II 5α-reductase. Sexual side effects are similar to those of finasteride.

Alpha-1 adrenoceptor blocking agents are also currently used for clinical treatment of benign prostatic hyperplasia. Examples include tamsulasin hydrochloride, terazosin hydrochloride, alfuzosin hydrochloride and doxazosin mesylate. The reduction in symptoms of BPH and improvement in urine flow rates following administration of an alpha-1 adrenoceptor blocking agent are related to relaxation of smooth muscle produced by blockage of alpha-1 adrenoceptors in the bladder neck and prostate.

Furthermore, plant sterols and extracts have also been used for the treatment of benign prostatic hyperplasia.

United States Patent Application No. 20040081659 describes conjugates useful to treat BPH comprising 1) oligopeptides with amino acid sequences which are selectively and proteolytically cleaved by PSA, chemically linked to 2) vinca alkaloid cytotoxic agents. Theoretically, the cytotoxic activity of the alkaloid is low in the conjugate and increased when the linkage is cleaved by PSA.

European Patent Application 0652014 describes a treatment for BPH comprising administration of PSA (prostate-specific antigen) linked to an immunogenic carrier to induce the production of anti-PSA antibodies. Anti-PSA antibodies may also be used. The immunogenic carrier can be tetanus toxin, diphtheria toxin or cholera toxin chain B.

U.S. Pat. No. 6,379,669 describes a method of targeting a specific organ by coupling a therapeutic agent to an antibody or fragments thereof. Such coupled therapeutic agents (or immunocongugates) can be used to treat prostate cancer, BPH, or prostatitis. The immunoconjugates included are antibodies against PSA that are linked to various bioactive agents. The bioactive agents may include bacterial toxins. Similarly, in United States Patent Application No. 20020001588, the chemical linkage of antibodies and various bioactive therapeutic agents is explored further.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a method of treating or preventing benign prostatic hyperplasia using modified pore-forming proteins.

In accordance with one aspect of the present invention, there is provided a modified pore-forming protein for use in decreasing prostate size in a subject, said modified pore-forming protein derived from a naturally-occurring pore-forming protein and comprising one or more prostate-selective modifications selected from an activation sequence cleavable by a prostate-specific protease, and one or more prostate-specific targeting domains capable of selectively targeting prostate cells, wherein said modified pore-forming protein is capable of selectively killing prostate cells.

In accordance with another aspect of the present invention, there is provided a modified pore-forming protein for use in the treatment of benign prostatic hyperplasia (BPH), said modified pore-forming protein derived from a naturally-occurring pore-forming protein and comprising one or more prostate-selective modifications selected from an activation sequence cleavable by a prostate-specific protease, and one or more prostate-specific targeting domains capable of selectively targeting prostate cells, wherein said modified pore-forming protein is capable of selectively killing prostate cells.

In accordance with another aspect of the present invention, there is provided a use of a modified pore-forming protein in the preparation of a medicament for decreasing prostate size in a subject, said modified pore-forming protein derived from a naturally-occurring pore-forming protein and comprising one or more prostate-selective modifications selected from an activation sequence cleavable by a prostate-specific protease, and one or more prostate-specific targeting domains capable of selectively targeting prostate cells, wherein said modified pore-forming protein is capable of selectively killing prostate cells.

In accordance with another aspect of the present invention, there is provided a use of a modified pore-forming protein in the preparation of a medicament for the treatment of benign prostatic hyperplasia (BPH), said modified pore-forming protein derived from a naturally-occurring pore-forming protein and comprising one or more prostate-selective modifications selected from an activation sequence cleavable by a prostate-specific protease, and one or more prostate-specific targeting domains capable of selectively targeting prostate cells, wherein said modified pore-forming protein is capable of selectively killing prostate cells.

In accordance with another aspect of the present invention, there is provided a method of decreasing prostate size in a subject comprising administering to said subject an effective amount of a modified pore-forming protein, said modified pore-forming protein derived from a naturally-occurring pore-forming protein and comprising one or more prostate-selective modifications selected from an activation sequence cleavable by a prostate-specific protease, and one or more prostate-specific targeting domains capable of selectively targeting prostate cells, wherein said modified pore-forming protein is capable of selectively killing prostate cells.

In accordance with another aspect of the present invention, there is provided a method of treating benign prostatic hyperplasia (BPH) in a subject, comprising administering to said subject an effective amount of a modified pore-forming protein, said modified pore-forming protein derived from a naturally-occurring pore-forming protein and comprising one or more prostate-selective modifications selected from an activation sequence cleavable by a prostate-specific protease, and one or more prostate-specific targeting domains capable of selectively targeting prostate cells, wherein said modified pore-forming protein is capable of selectively killing prostate cells.

In accordance with another aspect of the present invention, there is provided a modified proaerolysin protein comprising one or more mutations in a large lobe binding domain, and one or more prostate-specific modifications selected from a prostate-specific targeting domain capable of selectively targeting prostate cells and an activation sequence cleavable by a prostate-specific protease, wherein said modified proaerolysin is capable of selectively killing prostate cells.

BRIEF DESCRIPTION OF THE DRAWINGS

These and other features of the invention will become more apparent in the following detailed description in which reference is made to the appended drawings.

FIG. 1 presents a schematic of proaerolysin domains (not drawn to scale) and shows the result of activation by furin.

FIG. 2 depicts a bar graph showing the results of a hemolysis assay in which MPP1 is preincubated with human plasma or human plasma spiked with enzymatically active PSA (10,000 ng/ml).

FIGS. 4A-4E are schematic drawings (not to scale) showing how a proaerolysin protein can be altered to generate several different MPPs derived from proaerolysin according to embodiments of the present invention. The "*" symbol represents one or more point mutations, and/or one or more deletions which decrease proaerolysin binding domain function (i.e. the ability to concentrate in a cell membrane).

FIG. 4A represents a schematic drawing of a wild-type proaerolysin. FIG. 4B represents a schematic drawing of an MPP derived from proaerolysin, with an activation sequence modified to include a prostate-specific protease cleavage site. FIG. 4C represents a schematic drawing of an MPP derived from proaerolysin, with an activation sequence modified to include one or more prostate-specific protease cleavage sites. FIG. 4D represents a schematic drawing of an MPP derived from proaerolysin, with an activation sequence modified to include a prostate-specific protease cleavage site and with a functionally deleted native binding domain. The functionally deleted native binding domain is generated by one or more point mutations or one or more deletions. FIG. 4E represents a schematic drawing of an MPP derived from proaerolysin, with an activation sequence modified to include a prostate-specific protease cleavage site and with a functionally replaced native binding domain. The functionally deleted native binding domain is generated as described for FIG. 4D. One or more prostate-specific targeting domains may be attached at the N-terminus of the MPP, or at the C-terminal end of the toxin domain of the MPP, in this embodiment.

FIG. 5A represents a schematic drawing of an MPP derived from proaerolysin, with an activation sequence modified to include a prostate-specific protease cleavage site and with a functionally replaced native binding domain. The native binding domain is modified by one or more point mutations or one or more deletions. One or more prostate-specific targeting domains can be optionally attached to the MPP at Y215C, or A300C. FIG. 5B represents a schematic drawing of an MPP derived from proaerolysin, with an activation sequence modified to include a prostate-specific protease cleavage site and with a functionally deleted native binding domain. The native binding domain is functionally deleted by deletion of one of the native binding domains of proaerolysin. FIG. 5C represents a schematic drawing of an MPP derived from proaerolysin, with an activation sequence modified to include a prostate-specific protease cleavage site and with a functionally replaced native binding domain. One or more prostate-specific targeting domains may be attached to either the N-terminus of the toxin domain of the MPP, or to the C-terminal end of the toxin domain of the MPP in this embodiment. One of the native binding domains of the MPP is deleted as described in FIG. 5B. FIG. 5D represents a schematic drawing of an MPP derived from proaerolysin, with an activation sequence modified to include a prostate-specific protease cleavage site and with a functionally replaced native binding domain. One or more prostate-specific targeting domains may be attached to the MPP at Y215C, or A300C. One of the native binding domains of the MPP is deleted as described in FIG. 5B.

FIG. 6A represents a schematic drawing of an MPP according to one embodiment of the invention derived from proaerolysin with a functionally replaced native binding domain. The MPP further comprises one or more prostate-specific targeting domains. A native binding domain of the MPPP is functionally deleted by mutation or deletion of one or more amino acid residues. FIG. 6B represents a schematic drawing of an MPP according to one embodiment of the invention derived from proaerolysin with a functionally replaced native binding domain. The MPP further comprises one or more prostate-specific targeting domains attached to proaerolysin at Y215C or A300C. A native binding domain of the MPPP is functionally deleted by mutation or deletion of one or more amino acid residues. FIG. 6C represents a schematic drawing of an MPP according to one embodiment of the invention derived from proaerolysin with a functionally replaced native binding domain. The MPP further comprises one or more prostate-specific targeting domains. The native binding domain is functionally deleted by deletion of one of the native binding domains of proaerolysin. FIG. 6D represents a schematic drawing of an MPP according to another embodiment of the invention derived from proaerolysin with a functionally replaced native binding domain. The MPP further comprises one or more prostate-specific targeting domains attached to proaerolysin at Y215C or A300C. The native binding domain is functionally deleted by deletion of one of the native binding domains of proaerolysin.

FIG. 7 depicts a wild-type proaerolysin cDNA sequence (SEQ ID NO:1).

FIG. 8 depicts a wild-type proaerolysin amino acid sequence (SEQ ID NO:2).

FIG. 9 depicts the cDNA sequence (SEQ ID NO:3) of an MPP according to one embodiment of the invention (MPP1), wherein the furin site of proaerolysin has been replaced with a PSA cleavage site.

FIG. 10 depicts the amino acid sequence (SEQ ID NO:4) of an MPP according to one embodiment of the invention (MPP1), wherein the furin site of proaerolysin has been replaced with a PSA cleavage site.

FIG. 11 depicts the amino acid sequence (SEQ ID NO:5) of a PSA cleavage site found in human semenogelin I and II proteins.

FIG. 12 depicts the cDNA sequence (SEQ ID NO:6) of an MPP according to one embodiment of the invention (MPP2), wherein the furin site of proaerolysin has been replaced with a PSA cleavage site.

FIG. 13 depicts the amino acid sequence (SEQ ID NO:7) of an MPP according to one embodiment of the invention (MPP2), wherein the furin site of proaerolysin has been replaced with a PSA cleavage site.

FIG. 14 depicts an example of a PSA cleavage site (SEQ ID NO:8).

FIG. 15 depicts the cDNA sequence (SEQ ID NO:9) of an MPP according to one embodiment of the invention (MPP3), wherein the furin site of proaerolysin has been replaced with a PSA cleavage site.

FIG. 16 depicts the amino acid sequence (SEQ ID NO:10) of an MPP according to one embodiment of the invention (MPP3), wherein the furin site of proaerolysin has been replaced with a PSA cleavage site.

FIG. 17 depicts a second example of a PSA cleavage site (SEQ ID NO:11).

FIG. 18 depicts the cDNA sequence (SEQ ID NO:12) of an MPP according to one embodiment of the invention (MPP4), wherein the furin site of proaerolysin has been replaced with a PSA cleavage site.

FIG. 19 depicts the amino acid sequence (SEQ ID NO:13) of an MPP according to one embodiment of the invention (MPP4), wherein the furin site of proaerolysin has been replaced with a PSA cleavage site.

FIGS. 20-27 depict the amino acid sequences of alternative PSA cleavage sites according to the present invention (SEQ ID NOs:14-21, respectively).

FIG. 28 depicts a native luteinizing hormone releasing hormone (LHRH) amino acid sequence (SEQ ID NO:22).

FIG. 29 depicts a modified luteinizing hormone releasing hormone (LHRH) amino acid sequence (SEQ ID NO:23).

FIG. 30 depicts the amino acid sequence (SEQ ID NO:24) of an MPP according to one embodiment of the present invention (MPP6), in which the furin site of proaerolysin has been replaced with a PSA cleavage site, and wherein the native binding domain of proaerolysin has been modified.

FIG. 31 depicts the amino acid sequence of an MPP according to one embodiment of the present invention (MPP7), in which the furin site of proaerolysin is retained, and the native binding domain of proaerolysin has been deleted and replaced with SEQ ID NO:23 (SEQ ID NO:25).

FIG. 34 depicts the nucleotide sequence of MPP5 (SEQ ID NO:30). The ATG start codon and TAA stop codon are underlined and in bold. The HindIII and EcoRI restriction sites are in bold text. The PSA cut site is underlined and the 6 His tag is in bold italicized text.

FIG. 35 depicts the amino acid sequence of MPP5 (SEQ ID NO:31). The amino acid sequence was derived from the nucleic acid sequence shown in FIG. 34. Amino acids 427-432 (the PSA cut site) are underlined and in bold. The 6 His tag is in bold text.

FIG. 40 depicts the nucleotide sequence (SEQ ID NO:73) of a wild-type *Clostridium septicum* alpha toxin.

FIG. 41 depicts the amino acid sequence (SEQ ID NO:74) of a wild-type *Clostridium septicum* alpha toxin.

DETAILED DESCRIPTION OF THE INVENTION

Figure 3:
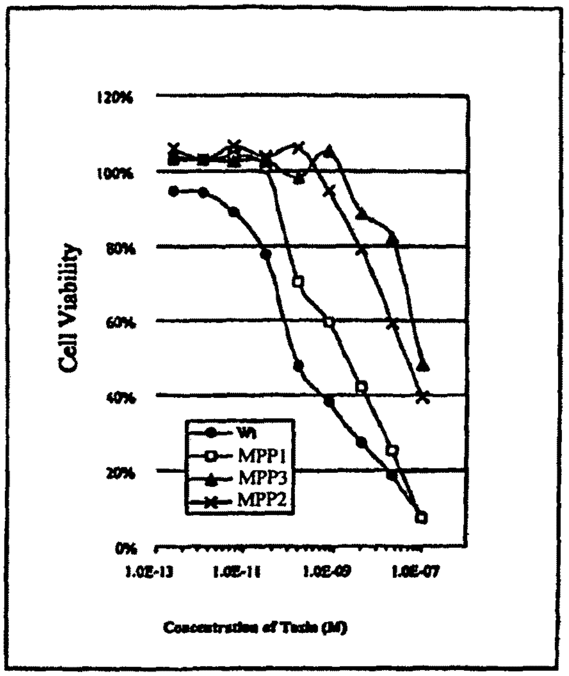
FIG. 3 depicts a graph comparing the in vitro toxicity of several MPPs according to embodiments of the invention to that of proaerolysin. The MPPs are derived from proaerolysin, and include a PSA cleavage site in place of the native furin site.
Figure 32A:
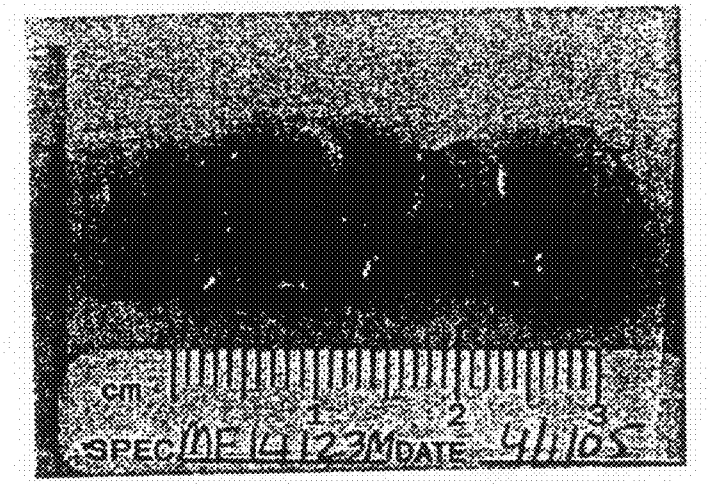
FIG. 32 depicts the effects of an MPP according to one embodiment of the invention (MPP5) in the prostate gland of monkeys after treatment for 3 days. A and B depict the prostate glands of control monkeys treated with vehicle alone; C and D depict the prostate glands of monkeys treated with 1 μg of the MPP; E and F depict the prostate glands of monkeys treated with 5 μg of the MPP; and G and H depict the prostate glands of monkeys treated with 25 μg of the MPP.
Figure 32B:
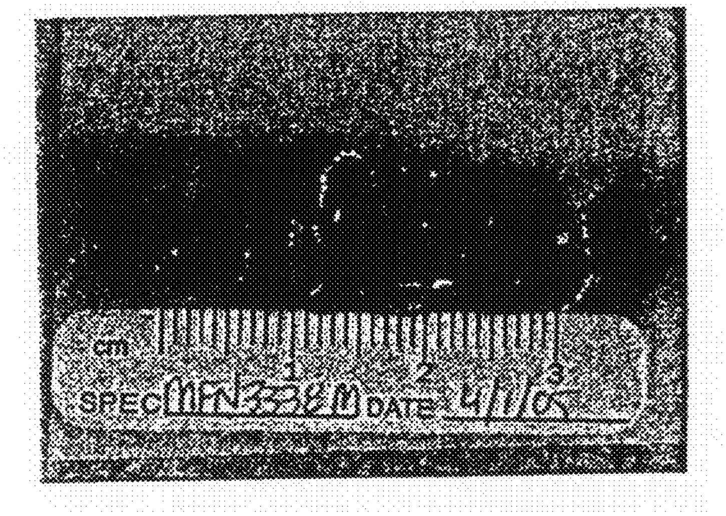
Figure 32C:
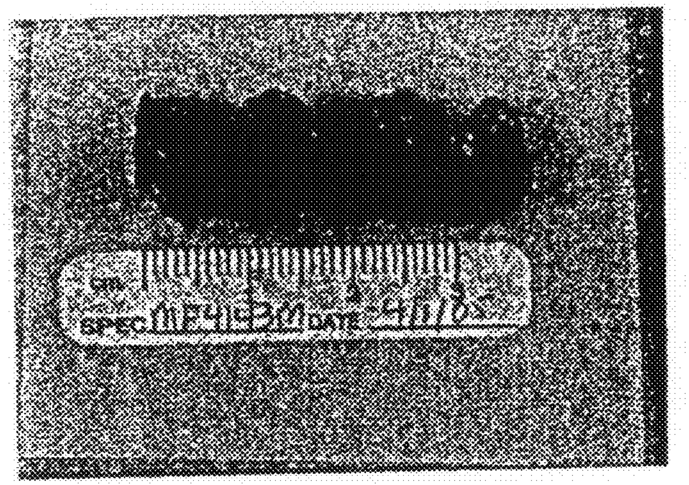
Figure 32D:
Figure 32E:
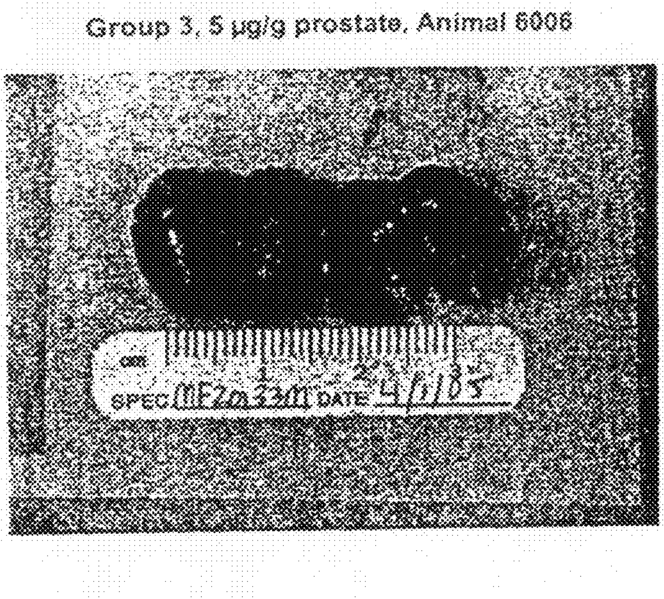
Figure 32F:
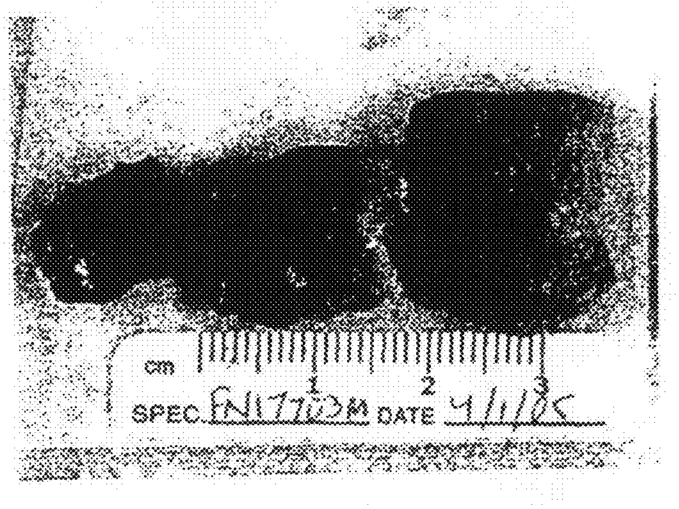
Figure 32G:
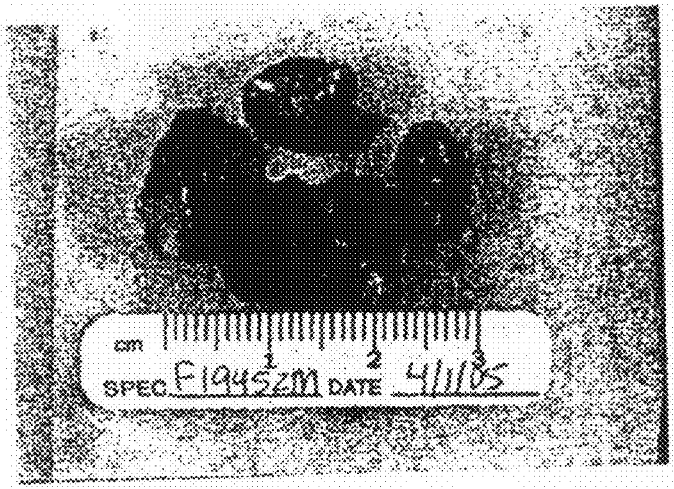
Figure 32H:
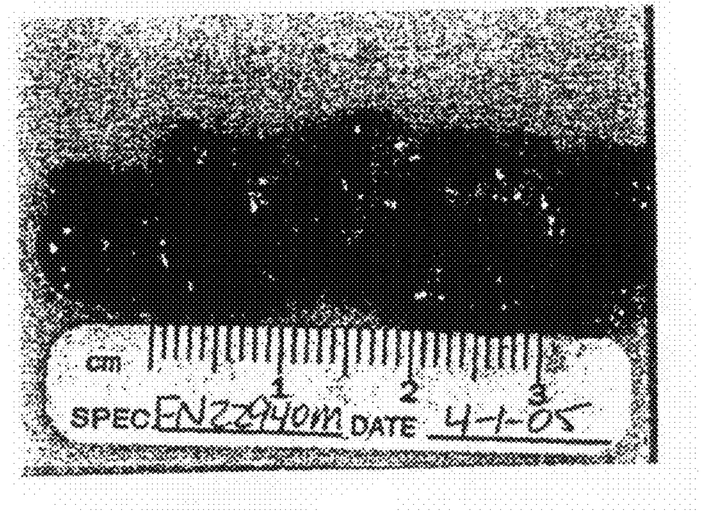
Figure 33A:
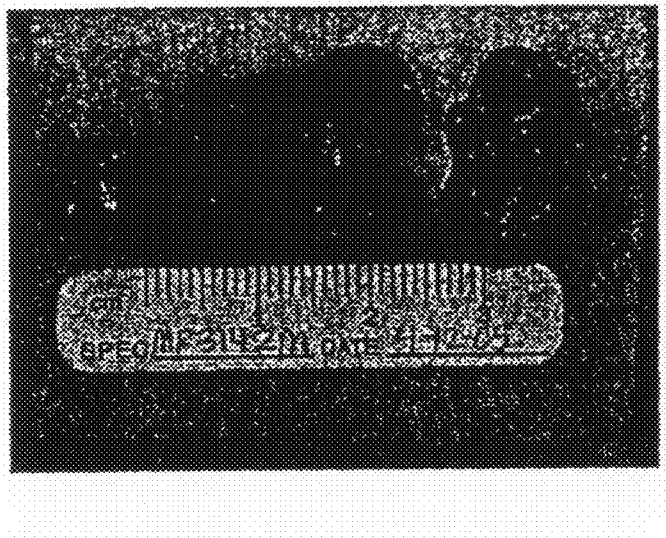
FIG. 33 depicts the effects of an MPP according to one embodiment of the invention (MPP5) in the prostate gland of monkeys treated for 15 days. A and B depict the prostate glands of control monkeys treated with vehicle alone; C and D depict the prostate glands of monkeys treated with 1 μg of the MPP; E and F depict the prostate glands of monkeys treated with 5 μg of the MPP; and G and H depict the prostate glands of monkeys treated with 25 μg of the MPP.
Figure 33B:
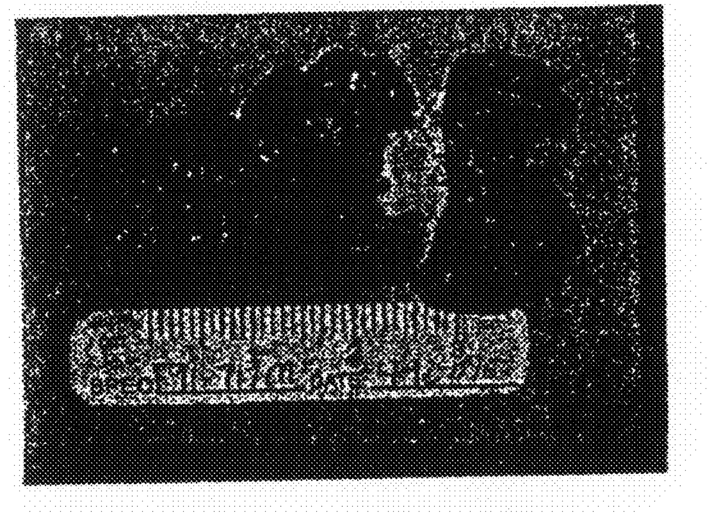
Figure 33C:
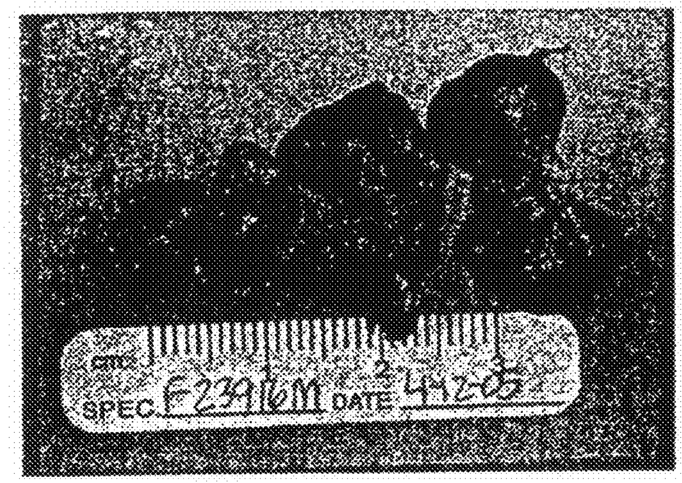
Figure 33D:
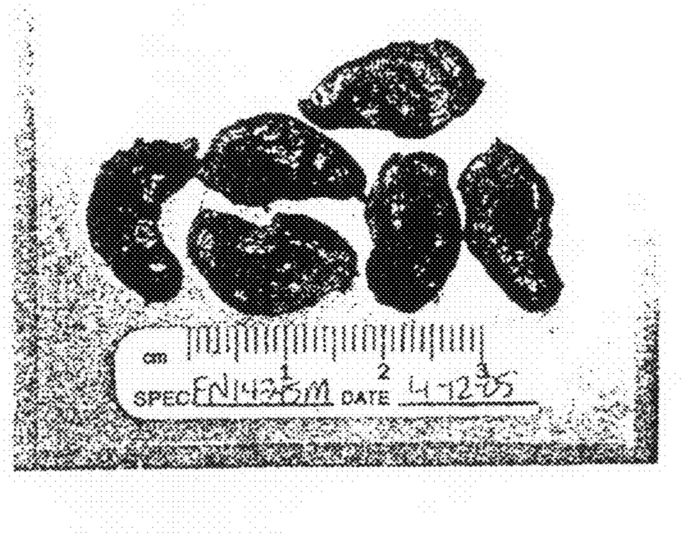
Figure 33E:
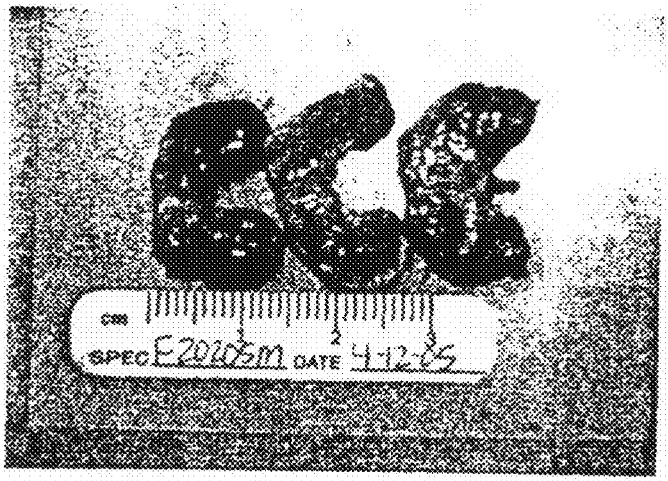
Figure 33F:
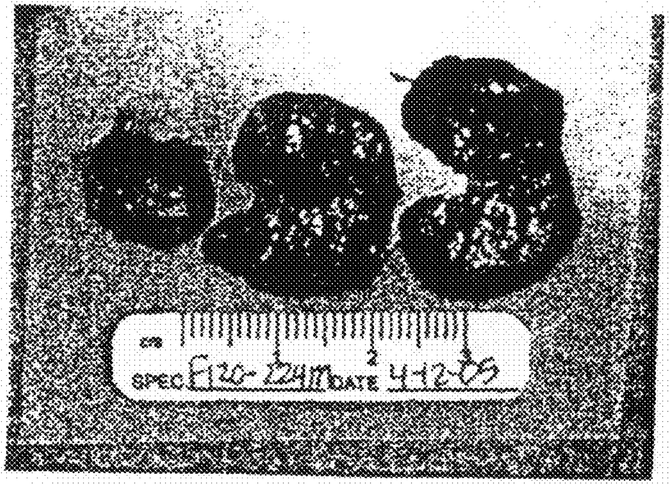
Figure 33G:
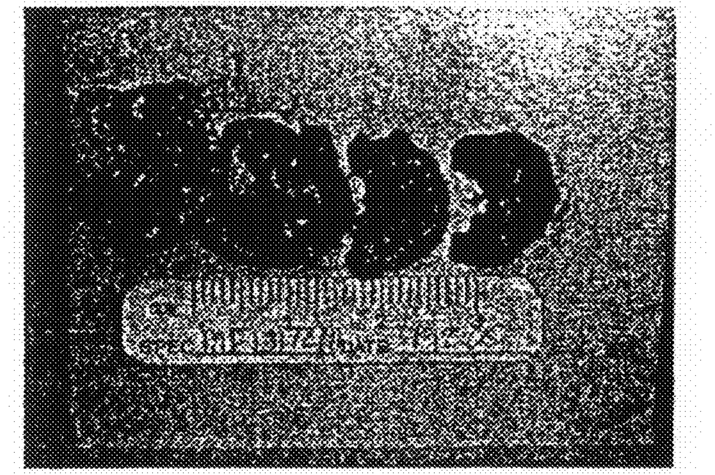
Figure 33H:
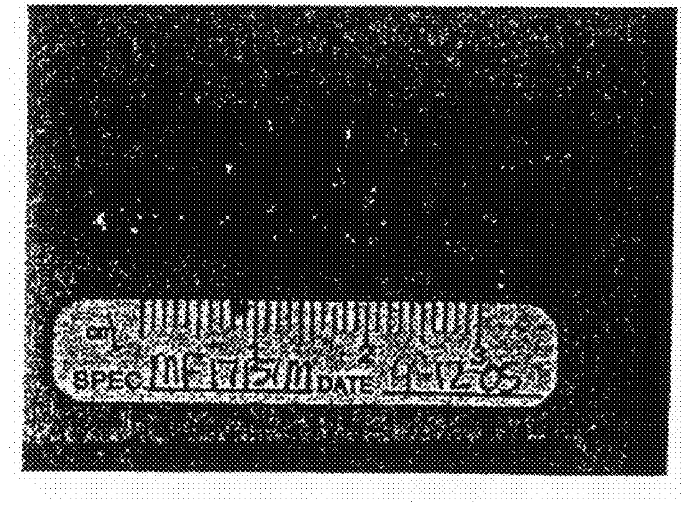

The present invention relates to the use of modified pore-forming proteins for the treatment of BPH. The MPPs are derived from naturally-occurring pore-forming proteins (nPPs) that kill cells by inserting into the membrane and forming pores or channels in the cell membranes of target cells, resulting in cell death. In one embodiment, the MPP inserts into the cell membrane, irreversibly, and thus bystander cells are not affected. The MPPs comprise prostate-selective modifications that result in the ability of the MPPs to selectively target normal prostate cells relative to cells from other tissues. The MPPs are capable of selectively killing normal prostate cells in vivo, and are capable of decreasing the weight or volume of normal prostate gland in vivo. Thus, the MPPs according to the present invention may be used alone, or in combination with other therapies for the treatment of BPH. This is in contrast to the molecules described in U.S. Patent Application No. 20040235095 which describes the use of modified cytolytic proteins to treat localized or metastatic prostate cancer.

Definitions

Unless defined otherwise, all technical and scientific terms used herein have the same meaning as commonly understood by one of ordinary skill in the art to which this invention belongs.

The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., and Lakowicz, J. R. Principles of Fluorescence Spectroscopy, New York: Plenum Press (1983) for fluorescence techniques). Standard techniques are used for chemical syntheses, chemical analyses, and biological assays. As employed throughout the disclosure, the following terms, unless otherwise indicated, shall be understood to have the following meanings.

As used herein, the term "about" refers to a +/−10% variation from the nominal value. It is to be understood that such a variation is always included in any given value provided herein, whether or not it is specifically referred to.

The term "prostate-specific" as used herein with reference to an entity or moiety indicates that the entity/moiety, or a property of the entity/moiety, is selective to prostate cells when compared to other cell types. For example, a prostate specific entity/moiety can be selectively expressed by prostate cells, selectively associated with prostate cells, selectively activated by prostate cells, be capable of selectively binding to prostate cells, or the like.

The term "prostate-specific activation sequence," as used herein, refers to a sequence of amino acid residues which incorporates one or more prostate-specific protease cleavage sites, which are selectively cleaved or hydrolysed by a prostate-specific protease.

The term "prostate-specific targeting domain," as used herein, refers to a molecule such as a peptide ligand, toxin, or antibody, which is capable of selectively binding to a prostate cell when compared to its ability to bind to other cell types.

The term "gene," as used herein, refers to a segment of nucleic acid that encodes an individual protein or RNA (also referred to as a "coding sequence" or "coding region") together with associated regulatory regions such as promoters, operators, terminators and the like, that may be located upstream or downstream of the coding sequence.

The term "selectively hybridize," as used herein, refers to the ability of a nucleic acid to bind detectably and specifically to a second nucleic acid. Polynucleotides, oligonucleotides and fragments thereof selectively hybridize to target nucleic acid strands under hybridization and wash conditions that minimize appreciable amounts of detectable binding to non-specific nucleic acids. High stringency conditions can be used to achieve selective hybridization conditions as known in the art and discussed herein. Typically, hybridization and washing conditions are performed at high stringency according to conventional hybridization procedures. Washing conditions are typically 1-3×SSC, 0.1-1% SDS, 50-70° C. with a change of wash solution after about 5-30 minutes.

The terms "corresponding to" or "corresponds to" indicates that a polynucleotide sequence is identical to all or a portion of a reference polynucleotide sequence. In contradistinction, the term "complementary to" is used herein to indicate that the polynucleotide sequence is identical to all or a portion of the complementary strand of a reference polynucleotide sequence. For illustration, the nucleotide sequence "TATAC" corresponds to a reference sequence "TATAC" and is complementary to a reference sequence "GTATA."

The following terms are used herein to describe the sequence relationships between two or more polynucleotides or two or more polypeptides: "reference sequence," "window of comparison," "sequence identity," "percent sequence identity," and "substantial identity." A "reference sequence" is a defined sequence used as a basis for a sequence comparison; a reference sequence may be a subset of a larger sequence, for example, as a segment of a full-length cDNA, gene or protein sequence, or may comprise a complete cDNA, gene or protein sequence. Generally, a reference polynucleotide sequence is at least 20 nucleotides in length, and often at least 50 nucleotides in length. A reference polypeptide sequence is generally at least 7 amino acids in length and often at least 17 amino acids in length.

A "window of comparison", as used herein, refers to a conceptual segment of the reference sequence of at least 15 contiguous nucleotide positions or at least 5 contiguous amino acid positions over which a candidate sequence may be compared to the reference sequence and wherein the portion of the candidate sequence in the window of comparison may comprise additions or deletions (i.e. gaps) of 20 percent or less as compared to the reference sequence (which does not comprise additions or deletions) for optimal alignment of the two sequences. The present invention contemplates various lengths for the window of comparison, up to and including the full length of either the reference or candidate sequence. Optimal alignment of sequences for aligning a comparison window may be conducted using the local homology algorithm of Smith and Waterman (*Adv. Appl. Math.* (1981) 2:482), the homology alignment algorithm of Needleman and Wunsch (*J. Mol. Biol.* (1970) 48:443), the search for similarity method of Pearson and Lipman (*Proc. Natl. Acad. Sci.* (U.S.A.) (1988) 85:2444), using computerized implementations of these algorithms (such as GAP, BESTFIT, FASTA, and TFASTA in the Wisconsin Genetics Software Package Release 7.0, Genetics Computer Group, 573 Science Dr., Madison, Wis.), using publicly available computer software such as ALIGN or Megalign (DNASTAR), or by inspection. The best alignment (i.e. resulting in the highest percentage of identity over the comparison window) is then selected.

The term "sequence identity" means that two polynucleotide or polypeptide sequences are identical (i.e. on a nucleotide-by-nucleotide or amino acid-by-amino acid basis) over the window of comparison.

The term "percent (%) sequence identity," as used herein with respect to a reference sequence is defined as the percentage of nucleotide or amino acid residues in a candidate sequence that are identical with the residues in the reference polypeptide sequence over the window of comparison after optimal alignment of the sequences and introducing gaps, if necessary, to achieve the maximum percent sequence identity, without considering any conservative substitutions as part of the sequence identity.

The term "substantial identity" as used herein denotes a characteristic of a polynucleotide or polypeptide sequence, wherein the polynucleotide or polypeptide comprises a sequence that has at least 50% sequence identity as compared to a reference sequence over the window of comparison. Polynucleotide and polypeptide sequences which have at least 60% sequence identity, at least 70% sequence identity, at least 80% sequence identity, or at least 90% sequence identity as compared to a reference sequence over the window of comparison are also considered to have substantial identity with the reference sequence.

The term "functional deletion" as used herein denotes a mutation, partial or complete deletion, insertion, or other variation made to a gene sequence which renders that part of the gene sequence non-functional. For example, functional deletion of a proaerolysin (PA) binding domain results in a decrease in the ability of PA to bind to and concentrate on the cell membrane. This functional deletion can be reversed by inserting another functional binding domain into proaerolysin, such as a prostate-specific targeting domain, for example, an LHRH peptide. Such reversal of a functional deletion is referred to herein as "functional replacement." In another example, functional deletion of a native PA furin cleavage site results in a decrease in the ability of PA to be cleaved and activated by furin, when compared to a wild-type PA molecule.

The terms "therapy" and "treatment," as used interchangeably herein, refer to an intervention performed with the intention of improving a subject's status. The improvement can be subjective or objective and is related to ameliorating the symptoms associated with, preventing the development of, or altering the pathology of a disease or disorder being treated. Thus, the terms therapy and treatment are used in the broadest sense, and include the prevention (prophylaxis), moderation, reduction, and curing of a disease or disorder at various stages. Preventing deterioration of a subject's status is also encompassed by the term. Subjects in need of therapy/treatment thus include those already having the disease or disorder as well as those prone to, or at risk of developing, the disease or disorder and those in whom the disease or disorder is to be prevented.

The term "ameliorate" includes the arrest, prevention, decrease, or improvement in one or more the symptoms, signs, and features of the disease or disorder being treated, both temporary and long-term.

The term "subject" or "patient" as used herein refers to an animal in need of treatment.

The term "animal," as used herein, refers to both human and non-human animals, including, but not limited to, mammals, birds and fish.

Administration of the proteins or polypeptides of the invention "in combination with" one or more further therapeutic agents or additional treatment, is intended to include simultaneous (concurrent) administration and consecutive administration. Consecutive administration is intended to encompass administration of the therapeutic agent(s) or additional treatment and the compound(s) of the invention to the subject in various orders and via various routes.

The terms "antigen" and "antigenic material," are used interchangeably herein to refer to a molecule, molecules, a portion or portions of a molecule, or a combination of molecules, up to and including whole cells and tissues, which are capable of inducing an immune response in an animal. The antigenic material may comprise a single epitope or antigenic determinant or it may comprise a plurality of epitopes or antigenic determinants.

The term "immune response," as used herein, refers to an alteration in the reactivity of the immune system of an animal in response to an antigen or antigenic material and may involve antibody production, induction of cell-mediated immunity, complement activation and/or development of immunological tolerance.

The term "inhibit," as used herein, means to decrease, reduce, slow-down or prevent.

"Binding pair" refers to two moieties (e.g. chemical or biochemical) that have an affinity for one another. Examples of binding pairs include homo-dimers, hetero-dimers, antigen/antibodies, lectin/avidin, target polynucleotide/probe, oligonucleotide, antibody/anti-antibody, receptor/ligand, enzyme/ligand and the like. "One member of a binding pair" refers to one moiety of the pair, such as an antigen or ligand.

"Isolated polynucleotide" refers to a polynucleotide of genomic, cDNA, or synthetic origin or some combination thereof, which by virtue of its origin the "isolated polynucleotide" (1) is not associated with the cell in which the "isolated polynucleotide" is found in nature, or (2) is operably linked to a polynucleotide which it is not linked to in nature.

The term "polypeptide" is used herein as a generic term to refer to an amino acid sequence of at least 20 amino acids in length that can be a wild-type (naturally-occurring) protein sequence, a fragment of a wild-type protein sequence, a variant of a wild-type protein sequence, a derivative of a wild-type protein sequence, or an analogue of a wild-type protein sequence. Hence, native protein sequences and fragments, variants, derivatives and analogues of native protein sequences, as defined herein, are considered to be species of the polypeptide genus.

The term "isolated polypeptide," as used herein, refers to a polypeptide which by virtue of its origin is not associated with other polypeptides with which it is normally associated with in nature, and/or is isolated from the cell in which it normally occurs and/or is free of other polypeptides from the same cellular source and/or is expressed by a cell from a different species, and/or does not occur in nature.

"Naturally-occurring" or "native" as used herein, as applied to an object, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

"Control sequence" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequences. The term "control sequences" is intended to include, at a minimum, components whose presence can influence expression, and can also include additional components whose presence is advantageous, for example, leader sequences and fusion partner sequences.

"Polynucleotide" refers to a polymeric form of nucleotides of at least 10 bases in length, either ribonucleotides or deoxynucleotides or a modified form of either type of nucleotide. The term includes single and double stranded forms of DNA or RNA.

"Polypeptide fragment" refers to a polypeptide that has an amino-terminal and/or carboxy-terminal deletion, but where the remaining amino acid sequence is usually identical to the corresponding positions in the naturally-occurring sequence deduced, for example, from a full-length cDNA sequence. Fragments typically are at least 5, 6, 8 or 10 amino acids long. In one embodiment, a fragment is at least 14 amino acids long. In another embodiment, a fragment is at least 20 amino acids long. In still another embodiment, a fragment is at least 50 amino acids long. In yet another embodiment the fragment is at least 70 amino acids long.

The term "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^{3}H$, $^{14}C$, $^{35}S$, $^{125}I$, $^{131}I$), fluorescent labels (e.g., FITC, rhodamine, lanthanide phosphors), enzymatic labels (or reporter genes) (e.g., horseradish peroxidase, β-galactosidase, (β-latamase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

Naturally-occurring amino acids are identified throughout by the conventional three-letter or one-letter abbreviations indicated below, which are as generally accepted in the peptide art and are recommended by the IUPAC-IUB commission in biochemical nomenclature:

TABLE 1

Amino acid codes

| Name | 3-letter code | 1-letter code |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The peptide sequences set out herein are written according to the generally accepted convention whereby the N-terminal amino acid is on the left and the C-terminal amino acid is on the right. By convention, L-amino acids are represented by upper case letters and D-amino acids by lower case letters.

Modified Pore-forming Proteins (MPPs)

The modified pore-forming proteins (MPPs) of the present invention are derived from naturally-occurring pore-forming proteins (nPPs), and have been modified to include one or more prostate-selective modifications such that they are capable of selectively killing normal prostate cells relative to cells from other normal tissues. By selective killing of normal prostate cells relative to cells from other normal tissues is meant that the MPPs are capable of killing normal prostate cells more effectively than other types of normal cells such as, for example, lung, spleen, or blood cells. Suitable MPPs include those described in United States Patent Application No. 20040235095.

1. Naturally-Occurring Pore-forming Proteins (nPPs)

Suitable mPPs from which the MPPs of the present invention can be derived include various bacterial toxins that are capable of forming pores or channels in the membrane of a target cell leading to cell death. Suitable bacterial toxins include those that are produced as protoxins and are subsequently activated by proteolytic cleavage as well as those that are produced in an active from and do not require additional processing. In one embodiment, the nPPs are large cytotoxic proteins that are synthesized as protoxins which are activated by protease cleavage at an activation sequence to form pores or channels in the cell membrane of target cells, thus leading to rapid cytolytic cell death. Suitable nPPs in accordance with this embodiment have the following features: a pore-forming activity that is activated by removal of an inhibitory domain via protease cleavage, and the ability to bind to receptors that are present on cell membranes through one or more binding domains. Numerous such nPPs have been cloned and recombinant forms produced (see, for example, Imagawa et al., FEMS. Microbiol. Lett. 17:287-92, 1994; Meza et al. FEMS Microbiol. Lett. 145:333-9, 1996).

In one embodiment, the MPPs are derived from nPPs such as aerolysin or aerolysin-related polypeptides. Examples include, but are not limited to, aerolysin homologues such as proaerolysin from *Aeromonas hydrophila, Aeromonas trota* and *Aeromonas salmonicida*, and alpha toxin from *Clostridium septicum* (Ballard et al., Infect. Immun. 63:340-4, 1995; Gordon et al. J. Biol. Chem. 274:27274-80, 1999; Genbank Accession No. S75954), as well as the following polypeptides: *Bacillus anthraces* protective antigen, *Vibrio cholerae* VCC toxin, epsilon toxin from *Clostridium perfringens*, and *Bacillus thuringiensis* delta toxins (Genbank Accession No. D00117).

Proaerolysin (PA) polypeptides from the *Aeromonas* species noted above have been characterized. These polypeptides exhibit greater than 80% pairwise sequence identity between them (Parker et al., Progress in Biophysics & Molecular Biology 88 (2005) 91-142). Each of these PA polypeptides is an approximately 52 kDa protoxin with approximately 470 amino acid residues. The cDNA sequence for wild-type PA from *A. hydrophila* is shown in SEQ ID NO: 1 (FIG. 7) and the corresponding amino acid sequence of this wild-type PA is shown in SEQ ID NO:2 (FIG. 8). The nucleotide and protein sequences for numerous naturally occurring nPPs are known in the art. Non-limiting examples are listed in the following Table:

TABLE 2

Exemplary nPPs and corresponding GenBank ™ Accession Numbers

| nPP | Nucleotide sequence (GenBank ™ Accession No.) | Amino acid sequence (GenBank ™ Accession No.) |
|---|---|---|
| *Aeromonas hydrophila* aerolysin | Buckley AerA, not corrected: M16495 | Buckley AerA corrected P09167 |
| *A. sobria* proaerolysin[1] | Y00559 | CAA68642 |
| *A. sobria* hemolysin[2] | X65046 | CAA46182 |
| *A. trota* proaerolysin[3] | AF064068 | AAC26217 |
| *A. salmonicida* hemolysin[4], | X65048 | CAA46184 |

[1]Husslein et al., Mol. Microbiol. 2 (4), 507-517 (1988)
[2]Hirono et al., Microb. Pathog. 13 (6), 433-446 (1992)
[3]Kahn et al., Appl. Environ. Microbiol. 64 (7), 2473-2478 (1998)
[4]Hirono et al., Microb. Pathog. 15 (4), 269-282 (1993)

The *A. hydrophila* PA protein includes a binding domain (approximately amino acids 1-83 of SEQ ID NO: 2) in what is known as the small lobe of the polypeptide and referred to herein as the small lobe binding domain (SBD), and a C-terminal inhibitory peptide (CIP) domain (approximately amino acids 427-470 of SEQ ID NO: 2) that is removed by protease cleavage at an activation sequence to activate PA. Cleavage at the activation sequence to remove the CIP domain can be carried out by a number of ubiquitous proteases including furin and trypsin. The amino acid residues from approximately 84-426 of SEQ ID NO: 2 are known as the large lobe of the PA polypeptide, and contain a toxin domain and other functional domains, including a second binding domain, referred to herein as the large lobe binding domain (LBD). The cDNA sequence for wild-type *A. hydrophila* PA is shown in SEQ ID NO: 1.

Alpha toxin from *C. septicum* is considered to be a homologue of proaerolysin based on significant sequence identity and other similarities (Parker et al., supra). Alpha toxin is secreted as a 46,450 Da protoxin (approximately 443 amino acids) that is activated by protease cleavage at an activation sequence to remove a C-terminal inhibitory peptide (CIP) domain, and it also binds to glycosyl-phosphatidylinositol (GPI)-anchored proteins. Alpha toxin, however, does not have a region corresponding to the small lobe of PA. Activation of this polypeptide occurs by protease cleavage at a furin cleavage site (Gordon et al., Infect. Immun. 65:4130-4, 1997). An example of a *Clostridium septicum* alpha toxin nucleic acid sequence is provided in GenBank™ Accession No. S75954 (SEQ ID NO:73, FIG. 40), and an example of a *Clostridium septicum* alpha toxin protein sequence is provided in GenBank™ Accession No. AAB32892 (SEQ ID NO:74, FIG. 41). Based on the sequence homology, alpha toxin is thought to have a similar structure and similar ability to bind to GPI-anchored proteins.

The activation sequence of *Bacillus thuringiensis* delta-toxin is cleaved by proteases in the midgut of certain insects to produce active endotoxin (Miranda et al., Insect Biochem. Mol. Biol. 31:1155-63, 2001). The structure of this endotoxin has been solved and shown to consist of three domains, a channel-forming domain, a binding domain, and a stabilizing domain.

In one embodiment, the MPPs according to the present invention are derived from proaerolysin polypeptides. In a further embodiment, the MPPs are derived from proaerolysin polypeptides from *A. hydrophila*. In another embodiment of the invention, the MPPs are derived from alpha toxin polypeptides.

In another embodiment, the MPPs are derived from nPPs that do not require protease cleavage for activation, and thus do not have an activation sequence. These nPPs can be modified to insert a prostate-specific protease cleavage site into the nPP resulting in an MPP that is capable of being selectively activated to kill prostate cells. Examples of such nPPs include *Staphylococcus aureus* a hemolysin. In the case of this nPP, an activation sequence can be inserted inot the center of the pore-forming domain as known in the art (Panchal et al., (1996) Nat. Biotech. 14:852-856).

The present invention further includes MPPs that are derived from biologically active fragments of nPPs. Biologically active fragments of nPPs are those that are capable of forming pores and killing cells. Suitable fragments include those that are capable of being activated to form pores in target cells by removal of a CIP domain. For example, in the case of PA, a suitable fragment would be one that comprised a binding domain of the protein as well as the CIP domain and activation sequence. Thus, in one embodiment of the invention, the MPP is derived from a fragment of proaerolysin that includes a binding domain, the CIP domain and the activation sequence. In another embodiment, the MPP is derived from a fragment of proaerolysin that comprises the binding domain, the activation sequence, but only part of a CIP domain.

2. Prostate-specific Modifications

In accordance with the present invention, the selected nPP is modified to form a MPP by inclusion of one or more prostate-specific modifications. Prostate-specific modifications contemplated by the present invention include incorporation of a prostate-specific activation sequence and/or functional deletion (including functional replacement) of one or more binding domains, and/or addition of a prostate-specific targeting domain.

In one embodiment, the MPPs according to the present invention comprise a prostate-specific activation sequence that allows for selective activation of the MPPs in prostate cells. A prostate-specific activation sequence may be generated by modification of the naturally-occurring activation sequence of a nPP, or it may be generated by the addition of a prostate-specific activation sequence to a nPP that does not have a naturally-occurring activation sequence. In another embodiment, the MPPs comprise a prostate-specific activation sequence and one or more prostate-specific targeting domains. In another embodiment, the MPPs comprise a prostate-specific activation sequence and a modification to the SBD. In another embodiment, the MPPs comprise a prostate-specific activation sequence and a modification to the LBD.

In one embodiment, the MPPs according to the present invention comprise one or more prostate-specific targeting domains that allow for selective activation of the MPPs in prostate cells. In another embodiment, the MPPs comprise one or more prostate-specific targeting domain and a modification to the SBD. In another embodiment, the MPPs comprise a prostate-specific targeting domain and a modification to the LBD.

In still another embodiment, the MPPs comprise a prostate-specific activation sequence, one or more prostate-specific targeting domain and a modification to the LBD. In another embodiment, the MPPs comprise a prostate-specific activation sequence, one or more prostate-specific targeting domains, and a modification to the SBD.

In one embodiment, the MPP comprises a prostate-specific activation sequence and one or more modifications to the native binding domain. In another embodiment, the MPP comprises a prostate-specific targeting domain and one or more modifications to the native binding domain. In still another embodiment, the MPP comprises a prostate-specific activation sequence, a prostate-specific targeting domain, and one or more modifications to the native binding domain.

Representative, non-limiting examples of combinations of prostate-specific modifications that can be made to proaerolysin are shown in FIGS. 4, 5, and 6.

Modification of Activation Sequence

As indicated above, a nPP can be modified to incorporate a prostate-specific activation sequence by modification of the naturally occurring activation sequence to provide a prostate-specific activation sequence, or a prostate-specific activation sequence can be added to an nPP that does not have a naturally occurring activation sequence. A prostate-specific activation sequence is accordance with the present invention is a sequence of amino acids that incorporates one or more prostate-specific protease cleavage sites. A prostate-specific protease cleavage site is a sequence of amino acids which is recognized and selectively and efficiently hydrolyzed (cleaved) by a prostate-specific protease. In one embodiment, a prostate-specific protease is a protease that is expressed at higher levels in prostate cells than in other cell types. Examples of prostate-specific proteases include, but are not limited to: PSA (prostate-specific antigen), PSMA (prostate-specific membrane antigen), and HK2 (human glandular kallikrein 2) cleavage sequences. Numerous examples of cleavage sites recognized by these prostate-specific proteases are known in the art and will be described further below.

Modifications to the naturally-occurring activation sequence to provide a prostate-specific protease activation sequence may be achieved as is known in the art. Modification of the naturally occurring activation sequence results in functional deletion of the native activation sequence. Functional deletion can be achieved by mutation, partial or complete deletion, insertion, or other variation made to the naturally occurring activation sequence that renders it inactive. In one embodiment, the naturally-occurring activation sequence of the nPP is functionally deleted by insertion of a prostate-specific activation sequence. In another embodiment, functional deletion of the naturally occurring activation sequence is achieved via mutations in one or more amino acid residues of the native activation sequence which produce a prostate-specific activation sequence. In an alternate embodiment, the naturally occurring activation sequence of the nPP is functionally deleted by replacing the native protease cleavage site of the activation sequence with a prostate-specific protease cleavage site.

In one embodiment, the one or more prostate-specific protease cleavage sites functionally replace the native protease cleavage site of the MPP. For example, a prostate-specific protease cleavage site can functionally replace the native furin cleavage site of PA (see FIG. 4B). This replacement results in a MPP that becomes cytolytically active in the presence of an enzymatically active prostate-specific protease, such as PSA, PSMA, or HK2. Suitable PSA, PSMA, or HK2 cleavage sites are known in the art and are described below.

In another embodiment of the invention, the MPPs according to the present invention can be generated by deleting the native protease cleavage site of the nPP and inserting a prostate-specific activation sequence. For example the furin cleavage site of PA (amino acids 427-432 of SEQ ID NO: 2) can be deleted and a prostate-specific protease cleavage site, such as a PSA cleavage site, inserted (see FIG. 4B).

In a further embodiment, the native protease cleavage site of the nPP is mutated such that it is no longer functional and a prostate-specific activation sequence is inserted within the mutated protease cleavage site, or added to the N- or C-terminus of the native protease cleavage site. For example, the furin cleavage site of PA can be mutated and a prostate-specific protease cleavage site, such as a PSA cleavage site, inserted within, or added to the N- or C-terminus of the mutated furin site (see FIG. 4C).

In still another embodiment, a prostate-specific activation sequence is added to an nPP that does not have a naturally occurring activation sequence. For example, *Staphylococcus aureus* α-hemolysin, which does not require protease cleavage in order to be activated to kill cells, may be engineered to include one or more prostate-specific protease cleavage sites, thus rendering it capable of being selectively activated to kill prostate cells.

Prostate-specific Cleavage Sites

As noted above, various prostate-specific proteases and the protease cleavage sites they recognize are known in the art. Examples include, but are not limited to, PSA, PSMA and HK2.

In one embodiment, the MPP is modified to include a prostate-specific activation sequence that includes a PSA-specific cleavage site. A PSA-specific cleavage site is a sequence of amino acids which is recognized and selectively and efficiently hydrolyzed (cleaved) by prostate specific antigen (PSA). PSA is a serine protease with the ability to recognize and hydrolyze specific peptide sequences. It is secreted by prostate cells in an enzymatically active form and becomes inactivated upon entering the circulation. Since neither blood nor normal tissue other than the prostate contains enzymatically active PSA, the proteolytic activity of PSA can be used to activate MPPs at the prostate gland. Various PSA-specific cleavage sites are known in the art. Examples, include, but are not limited to, those shown in SEQ ID NOs: 5, 8, 11, and 14-21, and those disclosed in U.S. Pat. Nos. 5,866,679, 5,948,750, 5,998,362, 6,265,540, 6,368,598, and 6,391,305. In one embodiment, the MPP has an activation sequence that includes the PSA cleavage site shown in SEQ ID NO: 5.

Additional PSA-specific cleavage sites are known, based on the PSA-cleavage map of human seminal proteins semenogelin I and II, and a cellulose membrane based assay (see Table 3 and Denmeade et al., Cancer Res., 57:4924-30, 1997) and can be used to produce the modified MPPs according to the present invention. For example, the MPPs according to the present invention can be modified to include one of the PSA-cleavage sites as shown in Table 3, which can substitute for the wild-type furin protease activation site of proaerolysin (amino acids 427-432 of SEQ ID NO: 2), as is known in the art.

In one embodiment, the MPP has an amino acid sequence of any one of SEQ ID NOs: 3, 4, 6, 7, 9, 10, 12, 13, and 24, which include an activation sequence containing a PSA cleavage site.

TABLE 3

PSA substrates (PSA cleavage sites) and kinetics of PSA hydrolysis.*

| PSA substrate (SEQ ID NO) | $K_m$ (μM) | $K_{cat}$ ($s^{-1}$) | $K_{cat}/K_m$ ($s^{-1}$ $M^{-1}$) |
|---|---|---|---|
| KGISSQY (15) | 160 | 0.043 | 270 |
| SRKSQQY (16) | 90 | 0.023 | 260 |
| ATKSKQH (17) | 1310 | 0.0091 | 6.9 |
| KGLSSQC (18) | 300 | 0.0017 | 5.6 |
| LGGSSQL (19) | 900 | 0.0037 | 4.1 |
| EHSSKLQ (20) | 1165 | 0.012 | 10.6 |
| HSSKLQ (5) | 470 | 0.011 | 23.6 |
| SKLQ (21) | 813 | 0.020 | 24.6 |

*Peptides were fluorescently labeled (aminomethyl coumarin). Assays were performed in 50 mM Tris, 0.1M NaCl, pH 7.8.

In another embodiment, the MPP comprises a prostate-specific activation sequence that includes a PSMA-specific cleavage site. Examples of suitable PSMA-specific cleavage sites are known in the art and can be found, for example, in International Publication No. WO 02/43773. In general terms, a PSMA cleavage site includes at least the dipeptide $X_1X_2$. The dipeptide contains the amino acids Glu or Asp at position $X_1$. $X_2$ can be Glu, Asp, Gln, or Asn. Tripeptides $X_1X_2X_3$ are also suitable, with $X_1$ and $X_2$ defined as before, with $X_3$ as Glu, Asp, Gln or Asn. Tetrapeptides $X_1X_2X_3X_4$ are also suitable, with $X_{1-3}$ defined as above, and with $X_4$ as Glu, Asp, Gln or Asn. Pentapeptides $X_1X_2X_3X_4X_5$ are also suitable, with $X_{1-4}$ defined as above, and with $X_5$ as Glu, Asp, Gln or Asn. Hexapeptides $X_1X_2X_3X_4X_5X_6$ are also suitable, with $X_{1-5}$ defined as above, and with $X_6$ as Glu, Asp, Gln or Asn. Further peptides of longer sequence length can be constructed in similar fashion. Generally, the peptides are of the following sequence: $X_1 \ldots X_n$, where n is 2 to 30, 2 to 20, 2 to 15, or 2 to 6, where $X_1$ is Glu, Asp, Gln or Asn. In one embodiment, $X_1$ is Glu or Asp, and $X_2$-$X_n$ are independently selected from Glu, Asp, Gln and Asn. Other possible peptide sequences are as above, except that $X_2$-$X_{n-1}$ are independently selected from Glu, and Asp, and $X_n$ is independently selected from Glu, Asp, Gln and Asn. Examples of PSMA cleavage sites are Asp-Glu, Asp-Asp, Asp-Asn, Asp-Gln, Glu-Glu-Glu, Glu-Asp-Glu, Asp-Glu-Glu, Glu-Glu-Asp, Glu-Asp-Asp, Asp-Glu-Asp, Asp-Asp-Glu, Asp-Asp-Asp, Glu-Glu-Gln, Glu-Asp-Gln, Asp-Glu-Gln, Glu-Glu-Asn, Glu-Asp-Asn, Asp-Glu-Asn, Asp-Asp-Gln, and Asp-Asp-Asn.

In an additional embodiment, the MPP comprises a prostate-specific activation sequence that includes an HK2-specific cleavage site. Examples of HK2-specific cleavage sites are also known in the art and described, for example, in International Publication No. WO01/09165. The cleavage site recognized by HK2 is flanked by at least an amino acid sequence $X_4X_3X_2X_1$. This amino acid sequence contains the amino acid arginine, histidine or lysine at position $X_1$. $X_2$ can be arginine, phenylalanine, lysine, or histidine. $X_3$ can be lysine, serine, alanine, histidine or glutamine. $X_4$ can be from 0 to 20 further amino acids, and can be at least two further amino acids. In an embodiment, the HK2 cleavage site includes a sequence for $X_4$ that is substantially identical to the 20 amino acids in the wild type semenogelin I or semenogelin II sequence that are the from fourth to twenty fourth amino acids to the N-terminal side of recognized semenogelin cleavage sites. The amino acid sequence can further comprise $X_1$, which is linked to the carboxy terminus of $X_1$ to create the amino acid sequence $X_4X_3X_2X_1X_1$. $X_1$ is up to a further 10 amino acids, and can include various amino acids. $X_1$ may have a leucine, alanine or serine linked to the carboxy terminus of $X_1$. $X_1$ can include L- or D-amino acids. The HK2 cleavage site is located at the carboxy terminal side of $X_1$.

Examples of HK2 cleavage sites are shown in Table 4 (Note that the symbol][denotes an Hk2 cleavage site):

TABLE 4

| Exemplary HK2 Cleavage sites | | | |
|---|---|---|---|
| Lys-Arg-Arg ][ | SEQ ID NO: 32 | Ser-Arg-Arg ][ Leu | SEQ ID NO: 53 |
| Ser-Arg-Arg ][ | SEQ ID NO: 33 | Ala-Arg-Arg ][ Leu | SEQ ID NO: 54 |
| Ala-Arg-Arg ][ | SEQ ID NO: 34 | Ala-Arg-Arg ][ Ser | SEQ ID NO: 55 |
| His-Arg-Arg ][ | SEQ ID NO: 35 | His-Arg-Arg ][ Ala | SEQ ID NO: 56 |
| Gln-Arg-Arg ][ | SEQ ID NO: 36 | Gln-Arg-Arg ][ Leu | SEQ ID NO: 57 |
| Ala-Phe-Arg ][ | SEQ ID NO: 37 | Ala-Phe-Arg ][ Leu | SEQ ID NO: 58 |
| Ala-Gln-Arg ][ | SEQ ID NO: 38 | Ala-Gln-Arg ][ Leu | SEQ ID NO: 59 |
| Ala-Lys-Arg ][ | SEQ ID NO: 39 | Ala-Lys-Arg ][ Leu | SEQ ID NO: 60 |
| Ala-Arg-Lys ][ | SEQ ID NO: 40 | Ala-Arg-Lys ][ Leu | SEQ ID NO: 61 |
| Ala-His-Arg ][ | SEQ ID NO: 41 | Ala-His-Arg ][ Leu | SEQ ID NO: 62 |
| Gln-Lys-Arg-Arg ][ | SEQ ID NO: 42 | His-Ala-Gln-Lys-Arg-Arg ][ Leu | SEQ ID NO: 63 |
| Lys-Ser-Arg-Arg ][ | SEQ ID NO: 43 | Gly-Gly-Lys-Ser-Arg-Arg ][ Leu | SEQ ID NO: 64 |
| Ala-Lys-Arg-Arg ][ | SEQ ID NO: 44 | His-Glu-Gln-Lys-Arg-Arg ][ Leu | SEQ ID NO: 65 |
| Lys-Lys-Arg-Arg ][ | SEQ ID NO: 45 | His-Glu-Ala-Lys-Arg-Arg ][ Leu | SEQ ID NO: 66 |
| His-Lys-Arg-Arg ][ | SEQ ID NO: 46 | Gly-Gly-Gln-Lys-Arg-Arg ][ Leu | SEQ ID NO: 67 |
| Lys-Ala-Phe-Arg ][ | SEQ ID NO: 47 | His-Glu-Gln-Lys-Arg-Arg ][ Ala | SEQ ID NO: 68 |
| Lys-Ala-Gln-Arg ][ | SEQ ID NO: 48 | Gly-Gly-Ala-Lys-Arg-Arg ][ Leu | SEQ ID NO: 69 |
| Lys-Ala-Lys-Arg ][ | SEQ ID NO: 49 | His-Glu-Gln-Lys-Arg-Arg ][ Ser | SEQ ID NO: 70 |
| Lys-Ala-Arg-Lys ][ | SEQ ID NO: 50 | Gly-Gly-Lys-Lys-Arg-Arg ][ Leu | SEQ ID NO: 71 |
| Lys-Ala-His-Arg ][ | SEQ ID NO: 51 | Gly-Gly-His-Lys-Arg-Arg ][ Leu | SEQ ID NO: 72 |
| Lys-Arg-Arg ][ Leu | SEQ ID NO: 52 | | |

Addition of Prostate-specific Targeting Domain

In one embodiment of the invention, the MPPs comprise one or more prostate-specific targeting domains to allow selective targeting of prostate cells. The prostate-specific targeting domain is capable of directing the MPP to the prostate cell, where the MPP can be activated and subsequently kill the prostate cell. The targeting domain can be located at the N- or C-terminus of the MPP, or both. Alternatively, the targeting domain can located at another region of the MPP, as long as it does not interfere with the pore-forming activity of the MPP.

Examples of suitable prostate-specific targeting domains include, but are not limited to molecules such as a peptide ligand, toxin, or antibody, which have a higher specificity for prostate cells than for other cell types. In one embodiment, a prostate tissue specific binding domain has a lower $K_D$ in prostate tissue or cells than in other cell types, (i.e. binds selectively to prostate tissues as compared to other normal tissues), for example at least a 10-fold lower $K_D$, such as an at least 20-, 50-, 75-, 100- or even 200-fold lower $K_D$. Such molecules can be used to target a MPP to the prostate. Examples include, but are not limited to: antibodies which recognize proteins that are relatively prostate-specific such as PSA, PSMA, HK2, prostasin, and hepsin; ligands which have prostate-specific receptors such as natural and synthetic luteinizing hormone releasing hormone (LHRH); and endothelin (binding to cognate endothelin receptor).

In one embodiment of the invention, addition of the prostate-specific targeting domain results in functional deletion of the native binding domain of the nPP. In another embodiment, the native non-specific GPI-anchor protein binding domain of proaerolysin is functionally deleted and replaced with a prostate-specific targeting domain. Specific examples of MPPs derived from proaerolysin that have a functionally deleted native binding domain are depicted in FIGS. 4D and 5B. Examples of MPPs derived from proaerolysin that include a prostate-specific targeting domain which functionally substitutes for the native proaerolysin binding domain are shown in FIGS. 4E, 5A, 5C and 5D and 6A-6D.

One or more prostate tissue-specific binding domains can be linked to one or more amino acids of the MPPs, but ideally, do not interfere significantly with the ability to form pores in cell membranes, or, where applicable, with the ability of the MPP to be activated by a prostate-specific protease such as PSA. Methods of conjugating proteins or peptides to MPPs are known in the art and include for example, changing the N-terminal amino acid of the protein to be modified to a Cys or other amino acid before attaching the prostate-tissue specific binding domain, to assist in linking the prostate-tissue specific binding domain to the MPP.

In one embodiment, prostate tissue specific binding domains are linked or inserted at the N-and/or C-terminus of an MPP derived from proaerolysin (for example, see FIGS. 4E and 5C). In some examples, the native binding domain of proaerolysin is deleted (i.e. amino acids 1-83 of SEQ ID NO: 2 or 4), such that attachment or linking of a prostate tissue specific binding domain to the N-terminus results in attachment to amino acid 84 of SEQ ID NO: 2 or 4 (for example, see FIGS. 5C and 6C). In other examples, smaller deletions or point mutations are introduced into the native binding domain of proaerolysin, such that attachment or linking of a prostate tissue specific binding domain to the N-terminus results in attachment to amino acid 1 of SEQ ID NO: 2 or 4 (or whichever amino acid is N-terminal following functional deletion of the native proaerolysin binding domain) (for example, see FIGS. 4E and 5D).

Antibodies as Prostate-specific Targeting Domains

In one embodiment, the prostate specific targeting domain is an antibody or antibody fragment that specifically binds to an antigen that is associated with prostate cells, thus targeting the MPP to prostate cells. Antigens associated with prostate cells that may be specifically bound by such prostate-specific targeting domains include PSA, and PSMA and the LHRH receptor, the expression of which is elevated in prostate cells. Antibodies can be attached to the N- or C-terminus of the MPP using gene fusion methods well known in the art (for example see Debinski and Pastan, Clin. Cancer Res. 1:1015-22, 1995). Alternatively, antibodies can be attached to an MPP by covalent crosslinking (for example see Woo et al., Arch. Pharm. Res. 22(5):459-63, 1999 and Debinski and Pastan, Clin. Cancer Res. 1(9):1015-22, 1995). Crosslinking can be non-specific, for example by using a homobifunctional-lysine-reactive crosslinking agent, or it can be specific, for example by using a crosslinking agent that reacts with amino groups on the antibody and with cysteine residues located in the MPP. In one embodiment, proaerolysin amino acids such as amino acids Cys19, Cys75, Cys159, and/or Cys164 of SEQ ID NO: 2 can be used to crosslink antibodies to the modified proaerolysin molecule. For example, the antibody could replace the native binding domain of the nPP to be modified, or the antibody could be added to an MPP already having mutations in the native binding domain. Such an MPP can also include a prostate-specific activation sequence to increase specificity. In one embodiment, the antibody is a single chain antibody to PSMA fused to the toxin domain of PA.

Suitable antibodies include intact antibodies as well as antibody fragments such as, for example, (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., Nature 341:544-6, 1989) which consists of a VH domain; (v) an isolated complementarity determining region (CDR); and (vi) an F(ab')2 fragment, a bivalent fragment comprising two Fab fragments linked by a disulfide bridge at the hinge region. Suitable antibodies include single chain Fv antibodies, which are prepared by recombinant methods resulting in the two domains of an Fv fragment being linked via a synthetic linker (Bird et al. Science 242:423-6, 1988; and Huston et al., Proc. Natl. Acad. Sci. 85:5879-83, 1988), and camelized antibodies (for example see Tanha et al., J. Biol. Chem. 276:24774-80, 2001).

In another embodiment, the antibody fragments are capable of crosslinking their target antigen, e.g., bivalent fragments such as F(ab')2 fragments. Alternatively, an antibody fragment which does not itself crosslink its target antigen (e.g., a Fab fragment) can be used in conjunction with a secondary antibody which serves to crosslink the antibody fragment, thereby crosslinking the target antigen. Antibodies can be fragmented using conventional techniques and the fragments screened for utility in the same manner as described for whole antibodies, and as is known in the art. An antibody is further intended to include nanobodies, and bispecific and chimeric molecules that specifically bind the target antigen.

"Specifically binds," when used in reference to an antibody, refers to the ability of individual antibodies to specifically immunoreact with a specific antigen. The binding is a non-random binding reaction between an antibody molecule and an antigenic determinant of the antigen. The desired binding specificity is typically determined from the reference point of the ability of the antibody to differentially bind the specific and an unrelated antigen, and therefore distinguish between two different antigens, particularly where the two antigens have unique epitopes. An antibody that specifically binds to a particular epitope is referred to as a "specific antibody".

Small Peptide Ligands as Prostate-specific Targeting Domains

In one embodiment, the prostate-specific targeting domain is a small peptide ligand that binds to its cognate prostate-specific receptor expressed on the membrane of prostate cells. Examples include, but are not limited to, natural and synthetic luteinizing hormone releasing hormone (LHRH) agonist peptides (for example see Genbank Accession No. CAA25526 and SEQ ID NOS: 22 and 23), which bind with high affinity to LHRH receptors, and peptides that can bind selectively to PSMA. LHRH receptors are displayed by prostate cells, and only a few other cells. This differential expression provides binding specificity.

Small peptide ligands may be modified as is known in the art in order to facilitate their attachment to the MPP. For example, certain residues of LHRH, such as the Gly at the 6th position (Gly6), can be substituted without compromising receptor binding affinity (Janaky et al., Proc. Natl. Acad. Sci. USA 89:972-6, 1992; Nechushtan et al., J. Biol. Chem., 272: 11597-603, 1997). Therefore, an MPP (in which the native binding domain is functionally deleted) can be produced which is covalently coupled to purified LHRH D-Lys6 (at the epsilon amine of this lysine).

LHRH D-Lys6 (SEQ ID NO: 23) can be attached at various positions within an nPP to provide an MPP having a prostate-specific targeting domain. As noted above, attachment of the small peptide ligand will not significantly interfere with the ability of the toxin to insert into the membrane to form a pore. For example, the epsilon amine of the D-Lys6 analog can be coupled to the amino terminus of the MPP using methods known in the art such as for example via a dicarboxylic acid linker. Activation of the MPP by cleavage of the activation sequence will result in release of the C-terminal inhibitory portion while the toxin remains bound to the LHRH receptor.

Alternatively or in addition, the small peptide ligand can be coupled directly to the C-terminus of the MPP. For example, the epsilon amine of the D-Lys6 analog of LHRH can be coupled directly to the C-terminal carboxyl of the MPP by the addition of a Cys to the C-terminus of the MPP, then crosslinking this Cys to the epsilon amine of the D-Lys6 analog of LHRH. This coupling will produce an MPP in which the LHRH peptide is attached to the C-terminal inhibitory domain. Activation of the MPP by cleavage of the activation sequence will liberate the MPP and leave the inhibitory fragment bound to the LHRH receptor. In addition, recombinant fusion proteins can be produced in which modified LHRH peptides are fused to both the N- and C-terminus of the MPP.

It is also contemplated that the small peptide ligand may be attached to an MPP via a disulfide bridge. For example, a cysteine residue is introduced into the 6th position of the LHRH peptide and the peptide attached to an MPP via a disulfide bridge. The cysteine with which the peptide forms a disulphide bridge can be present in the native nPP sequence or the nPP can be mutated to include a cysteine residue. In one embodiment, an MPP derived from PA can have a cysteine residue introduced, for example at amino acids 215 and/or 300 of SEQ ID NO: 2, wherein amino acid 215 and/or 300 has been mutated to a cysteine.

In another embodiment, a recombinant protein is produced in which LHRH peptide is fused to the amino terminus of the MPP.

Alternatively or in addition, an MPP may be produced by attaching or linking one or more prostate-specific targeting domains to other amino acids of the MPP. For example, for MPPs derived from proaerolysin, amino acids such as amino acid 215 or 300 of SEQ ID NO: 2 or 4 (for example, see FIGS. 5A, 5D, 6B and 6D) may be used to attach the one or more prostate specific targeting domains. In some examples, a Cys amino acid replaces the native amino acid at that position. For example, the following changes can be made to SEQ ID NO: 2 or 4: Tyr215Cys or Ala300Cys. Alternatively, cysteine residues present in the native sequence of the nPP can be utilized. For MPPs derived from proaerolysin, amino acids such as amino acids Cys19, Cys75, Cys159, and/or Cys164 of SEQ ID NO: 2, are suitable for this purpose.

In one embodiment the MPP is derived from proaerolysin and has a sequence selected from SEQ ID NOs:24 and 25, which comprises LHRH as a prostate-specific targeting domain.

Modifications to the Native Binding Domain of MPPs

MPPs according to the present invention are derived from nPPs that comprise one or more binding domains, as known in the art. In the context of the present invention, when an nPP comprises one binding domain, it is considered to be a "large lobe binding domain." MPPs according to the present invention may comprise modifications to one or more binding domains, as applicable. For example, native proaerolysin from *Aeromonas* species comprises two binding domains, a small lobe binding domain, and a large lobe binding domain. In contrast, native alpha toxin from *Clostridium septicum* comprises only a large lobe binding domain. In one embodiment, modifications of the binding domains include functional deletion of a binding domain. A functionally deleted binding domain in an MPP results in an MPP that has an attenuated ability to bind to its cell surface receptor, yet still retains pore-forming ability. Functional deletions can be made by deleting or mutating one or more binding domains of an MPP. In one embodiment, the entire binding domain or portions thereof, may be deleted. In an additional embodiment, insertion of heterologous sequences into the binding domain may also be used to functionally delete the binding domain. Addition of these heterologous sequences may confer an additional functionality to the MPP (i.e. functional replacement of the binding domain). For example, addition of a heterologous sequence can result in the addition of a region that can function as a prostate-specific targeting domain as described herein. In still another embodiment, point mutations to the amino acid sequence of the native binding domain of the nPP can also be made to decrease the ability of the binding domain to bind to its receptor. Further details regarding these modifications are described below.

MPPs lacking a binding domain retain their cytolytic activity, but may need to be administered at higher doses to ensure concentration of the toxin in the cell membrane. MPPs with functional deletions in the binding domain may be prepared using methods known in the art. These methods include the use of recombinant DNA technology as described in Sambrook et al., supra. Alternatively, functional deletions of the binding domain may also be achieved by direct modification of the protein itself according to methods known in the art, such as proteolysis to generate fragments of the MPP, which can then be chemically linked together.

In one embodiment of the invention, the MPP is modified by functional deletion of its small lobe binding domain (SBD). Exemplary functional deletions of the SBD may be made in the *A. hydrophila* proaerolysin polypeptide as follows. The entire SBD, corresponding to amino acid 1-83 of SEQ ID NO:2 may be deleted, or portions of this region may be deleted, for example amino acids 45-66 of SEQ ID NO:2. Alternatively, point mutations can be made as follows W45A, I47E, M57A, Y61A, K66Q (amino acid numbers refer to SEQ ID NO: 2 or SEQ ID NO:4) and as described in Mackenzie et al. J. Biol. Chem. 274: 22604-22609, 1999. A schematic diagram representing an example of an MPP with one or more mutations in a binding domain is shown in FIG. 4D, where * represents one or more mutations or deletions.

In one embodiment of the invention, the nPP is modified by functional deletion of its large lobe binding domain (LBD). Exemplary functional deletions of the LBD of proaerolysin (contained in approximately amino acid residues 84-426 of SEQ ID NO:2) that may be made to provide MPPs are as follows. The entire LBD of proaerolysin may be deleted. Alternatively, in one embodiment of the invention, the MPP derived from proaerolysin comprises one or more point mutations in the LBD to amino acid residues Y162, W324, R323, R336, and/or W127. In another embodiment of the invention, the MPP derived from proaerolysin comprises one or more point mutations at positions W127 and/or R336. In still another embodiment, the MPP derived from proaerolysin comprises the point mutations Y162A and/or W324A. In a further embodiment the MPP derived from proaerolysin comprises the point mutations R336A, R336c, and/or W127T. In another embodiment, MPPs comprise mutations to other residues that interact directly with the GPI-protein ligand.

Exemplary mutations to the LBD of MPPs derived from alpha toxin are noted below and include at least one substituted amino acid in the receptor binding domains of the alpha toxin which include amino acid residues 53, 54, 62, 84-102, 259-274 and 309-315 of the sequence of the native alpha toxin as shown in SEQ ID NO: 33. In one embodiment of the invention, MPPs derived from alpha toxin include mutations to one or more of the following residues: W85, Y128, R292, Y293, and 8305.

Further Modifications of MPPs

The present invention contemplates further modification of MPPs that do not affect the ability of the MPPs to selectively target prostate cells. Such modifications include amino acid substitutions, insertions or deletions, modifications to reduce antigenicity, and modifications to enhance the stability or improve the pharmacokinetics of the MPPs. In one embodiment, further modifications to MPPs result in a polypeptide that differs by only a small number of amino acids from the MPP. Such modifications include deletions (for example of 1-3 or more amino acids), insertions (for example of 1-3 or more residues), or substitutions that do not interfere with the ability of the MPPs to selectively target and kill normal prostate cells. In one embodiment, further modifications to the MPPs result in a polypeptide that retains at least 70%, 80%, 85%, 90%, 95%, 98%, or greater sequence identity to the MPP and maintains the ability of the MPP to selectively target and kill normal prostate cells.

MPPs may be modified by substitution whereby at least one residue in the amino acid sequence has been removed and a different residue inserted in its place. In one embodiment, the substitution is a conservative substitution. A conservative substitution is one in which one or more amino acids (for example 2, 5 or 10 residues) are substituted with amino acid residues having similar biochemical properties. Typically, conservative substitutions have little to no impact on the activity of a resulting polypeptide. For example, ideally, an MPP including one or more conservative substitutions retains the activity of the corresponding nPP. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

An MPP can be modified to include one or more conservative substitutions by manipulating the nucleotide sequence that encodes that polypeptide using, for example, standard procedures such as site-directed mutagenesis or PCR. Further information about conservative substitutions can be found in, among other locations, Ben-Bassat et al., (J. Bacteriol. 169: 751-7, 1987), O'Regan et al., (Gene 77:237-51, 1989), Sahin-Toth et al., (Protein Sci. 3:240-7, 1994), Hochuli et al., (Bio/Technology 6:1321-5, 1988), WO 00/67796 (Curd et al.) and in standard textbooks of genetics and molecular biology.

In another embodiment the substitution is a permissive substitution. Permissive substitutions are non-conservative amino acid substitutions, but also do not significantly alter MPP activity. An example is substitution of Cys for Ala at position 300 of SEQ ID NO: 2 or 4 in a proaerolysin polypeptide.

In one embodiment, MPPs are modified to include 1 or more amino acid substitutions of single residues. In another embodiment, the MPPs are modified to include 1 amino acid substitution. In another embodiment, the MPPs are modified to include from about 2 to about 10 amino acid substitutions. In another embodiment, the MPPs are modified to include about 3 to about 5 amino acid substitutions.

Non-limiting examples of further modifications to MPPs derived from proaerolysin are listed in Table 5.

TABLE 5

Exemplary single mutations of MPPs derived from a native proaerolysin polypeptide

| | | | | |
|---|---|---|---|---|
| H107N | G202C | G251C | T284C | H341N |
| K22C | H121N | W203C | E252C | V285C |
| W127T | T253S | V293C | K361C | N459C |
| C164S | D216C | T253C | K294C | K369Q |
| Q254C | K294Q | W371L | D372N | I445C |
| Y135A | R220Q | E296C | K299C | K349C |
| Y135F | K171C | K238C | W373L | A418C |
| K22C | A300C | S256C | K309C | H332N |
| H186N | P248C | E258C | I416C | Q263C |
| K198C | L249C | I259C | G417C | |
| K114C | C159S | V201C | V250C | |

Peptidomimetic and organomimetic embodiments are also contemplated, whereby the three-dimensional arrangement of the chemical constituents of such peptido- and organomimetics mimic the three-dimensional arrangement of the polypeptide backbone and component amino acid side chains in the polypeptide, resulting in such peptido- and organomimetics of an MPP which have the ability to lyse prostate cells. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165-174 and Principles of Pharmacology (ed. Munson, 1995), chapter 102 for a description of techniques used in CADD.

Other modifications that may be made to the MPPs include, for example, modifications to the carboxylic acid groups of the MPP, whether carboxyl-terminal or side chain, in which these groups are in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the polypeptide, whether amino-terminal or side chain, can be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Other modifications include conversion of hydroxyl groups of the polypeptide side chain to $C_1$-$C_{16}$ alkoxy or to a $C_1$-$C_{16}$ ester using well-recognized techniques. Phenyl and phenolic rings of the polypeptide side chain can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the polypeptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the polypeptides described herein to select and provide conformational constraints to the structure that result in enhanced stability. For example, a carboxyl-terminal or amino-terminal cysteine residue can be added to the polypeptide, so that when oxidized the polypeptide will contain a disulfide bond, generating a cyclic peptide. Other peptide cyclizing methods include the formation of thioethers and carboxyl- and amino-terminal amides and esters.

The present invention also contemplates further modifications to MPPs in which the MPPs are linked or immobilized to a surface, such as a bead. The bead can also include a prostate-specific ligand to enhance targeting to a prostate cell. Immobilized refers to binding to a surface, such as a solid surface. A solid surface can be polymeric, such as polystyrene or polypropylene. The solid surface may be in the form of a bead. In one embodiment, the surface includes an immobilized MPP, and in other embodiments further includes one or more prostate-specific binding ligands, such as LHRH peptide, PSMA antibody, and PSMA single chain antibody. In another embodiment, the MPP is liberated from the bead once the bead reaches the prostate cell target. Methods of immobilizing peptides on a solid surface are known in the art and can be found in WO 94/29436, and U.S. Pat. No. 5,858,358.

The present invention further contemplates that the MPP can comprise further modifications intended to improve the pharmacokinetic properties of the molecule when administered to a subject. Various modifications to reduce immunogenicity and/or improve the half-life of therapeutic proteins are known in the art. For example, the MMPs can undergo glycosylation, isomerization, or deglycosylation according to standard methods known in the art. Similarly, the MPP can be modified by non-naturally occurring covalent modification for example by addition of polyethylene glycol moieties (pegylation) or lipidation. In one embodiment, the MPPs of the invention are conjugated to polyethylene glycol (PEGylated) to improve their pharmacokinetic profiles. Conjugation can be carried out by techniques known to those skilled in the art (see, for example, Deckert et al., Int. J. Cancer 87: 382-390, 2000; Knight et al., Platelets 15: 409-418, 2004; Leong et al., Cytokine 16: 106-119, 2001; and Yang et al., Protein Eng. 16: 761-770, 2003). In one embodiment, antigenic epitopes can be identified and altered by mutagenesis. Methods of identifying antigenic epitopes are known in the art (see for example, Sette et al., Biologicals 29:271-276), as are methods of mutating such antigenic epitopes.

Methods of Preparing MPPs

MPPs according to the present invention can be prepared by many standard methods, as known in the art. Modifications to the MPP can be made, for example, by engineering the nucleic acid encoding the MPP using recombinant DNA technology. Alternatively, modifications to the MPP may be made by modifying the MPP polypeptide itself, using chemical modifications and/or limited proteolysis. Combinations of these methods may also be used to prepare the MPPs according to the present invention, as is also known in the art.

Preparation of MPPs Using Recombinant Methods

As is known in the art, genetic engineering of a protein generally requires that the nucleic acid encoding the protein first be isolated and cloned. Sequences for various nPPs are available from GenBank as noted herein. Isolation and cloning of the nucleic acid sequence encoding these proteins can thus be achieved using standard techniques [see, for example, Ausubel et al., *Current Protocols in Molecular Biology*, Wiley & Sons, NY (1997 and updates); Sambrook et al., *Molecular Cloning: A Laboratory Manual*, Cold-Spring Harbor Press, NY (2001)]. For example, the nucleic acid sequence can be obtained directly from a suitable organism, such as *Aeromonas hydrophila*, by extracting the mRNA by standard techniques and then synthesizing cDNA from the mRNA template (for example, by RT-PCR). Alternatively, the nucleic acid sequence encoding the nPP can be obtained from an appropriate cDNA or genomic DNA library by standard procedures. The isolated cDNA or genomic DNA is then inserted into a suitable vector. One skilled in the art will appreciate that the precise vector used is not critical to the instant invention. Examples of suitable vectors include, but are not limited to, plasmids, phagemids, cosmids, bacteriophage, baculoviruses, retroviruses or DNA viruses. The vector may be a cloning vector or it may be an expression vector.

Once the nucleic acid sequence encoding the nPP has been obtained, mutations in one or more of the binding domain or activation sequence can be introduced at specific, pre-selected locations by in vitro site-directed mutagenesis techniques well-known in the art. Mutations can be introduced by deletion, insertion, substitution, inversion, or a combination thereof, of one or more of the appropriate nucleotides making up the coding sequence. This can be achieved, for example, by PCR based techniques for which primers are designed that incorporate one or more nucleotide mismatches, insertions or deletions. The presence of the mutation can be verified by a number of standard techniques, for example by restriction analysis or by DNA sequencing.

If desired, after introduction of the appropriate mutation or mutations, the nucleic acid sequence encoding the MPP can be inserted into a suitable expression vector. Examples of suitable expression vectors include, but are not limited to, plasmids, phagemids, cosmids, bacteriophages, baculoviruses and retroviruses, and DNA viruses.

One skilled in the art will understand that the expression vector may further include regulatory elements, such as transcriptional elements, required for efficient transcription of the MPP-encoding sequences. Examples of regulatory elements that can be incorporated into the vector include, but are not limited to, promoters, enhancers, terminators, and polyadenylation signals. The present invention, therefore, provides vectors comprising a regulatory element operatively linked to a nucleic acid sequence encoding a genetically engineered MPP. One skilled in the art will appreciate that selection of suitable regulatory elements is dependent on the host cell chosen for expression of the genetically engineered MPP and that such regulatory elements may be derived from a variety of sources, including bacterial, fungal, viral, mammalian or insect genes.

For example, a prostate-specific promoter responsive to testosterone and other androgens, can be used to promote gene expression in prostate cells. Examples include, but are not limited to the probasin promoter; the prostate specific antigen (PSA) promoter; the prostate specific membrane antigen (PSMA) promoter; and the human glandular kallikrein 2 (HK2) promoter.

In the context of the present invention, the expression vector may additionally contain heterologous nucleic acid sequences that facilitate the purification of the expressed MPP. Examples of such heterologous nucleic acid sequences include, but are not limited to, affinity tags such as metal-affinity tags, histidine tags, avidin/strepavidin encoding sequences, glutathione-S-transferase (GST) encoding sequences and biotin encoding sequences. The amino acids corresponding to expression of the nucleic acids can be removed from the expressed MPP prior to use according to methods known in the art. Alternatively, the amino acids corresponding to expression of heterologous nucleic acid sequences can be retained on the MPP, provided that they do not interfere with the ability of the MPP to target and kill prostate cells.

In one embodiment of the invention, the MPP is expressed as a histidine tagged protein. In another embodiment, the histidine tag is located at the carboxyl terminus of the MPP.

The expression vectors can be introduced into a suitable host cell or tissue by one of a variety of methods known in the art. Such methods can be found generally described in Ausubel et al., *Current Protocols in Molecular Biology*, Wiley & Sons, NY (1997 and updates); Sambrook et al., *Molecular Cloning: A Laboratory Manual*, Cold-Spring Harbor Press, NY (2001) and include, for example, stable or transient transfection, lipofection, electroporation, and infection with recombinant viral vectors. One skilled in the art will understand that selection of the appropriate host cell for expression of the MPP will be dependent upon the vector chosen. Examples of host cells include, but are not limited to, bacterial, yeast, insect, plant and mammalian cells.

In addition, a host cell may be chosen which modulates the expression of the inserted sequences, or modifies and processes the gene product in a specific, desired fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, and for post-translational modifications such as glycosylation and phosphorylation of the gene product can be used. Such mammalian host cells include, but are not limited to, CHO, VERO, BHK, HeLa, COS, MDCK, 293, 3T3, WI38.

Methods of cloning and expressing proteins are well-known in the art, detailed descriptions of techniques and systems for the expression of recombinant proteins can be found, for example, in *Current Protocols in Protein Science* (Coligan, J. E., et al., Wiley & Sons, New York). Those skilled in the field of molecular biology will understand that a wide variety of expression systems can be used to provide the recombinant protein. The precise host cell used is not critical to the invention. Accordingly, the present invention contemplates that the MPPs can be produced in a prokaryotic host (e.g., *E. coli, A. salmonicida* or *B. subtilis*) or in a eukaryotic host (e.g., *Saccharomyces* or *Pichia*; mammalian cells, e.g., COS, NIH 3T3, CHO, BHK, 293, or HeLa cells; or insect cells).

The MPPs can be purified from the host cells by standard techniques known in the art. If desired, the changes in amino acid sequence engineered into the protein can be determined by standard peptide sequencing techniques using either the intact protein or proteolytic fragments thereof.

As an alternative to a directed approach to introducing mutations into naturally occurring pore-forming proteins, a cloned gene expressing a pore-forming protein can be subjected to random mutagenesis by techniques known in the art. Subsequent expression and screening of the mutant forms of the protein thus generated would allow the identification and isolation of MPPs according to the present invention.

The MPPs according to the present invention can also be prepared as fragments or fusion proteins. A fusion protein is one which includes an MPP linked to other amino acid sequences that do not inhibit the ability of the MPP to selectively target and kill normal prostate cells. In one embodiment, the other amino acid sequences are no more than 5, 6, 7, 8, 9, 10, 20, 30, or 50 amino acid residues in length.

Methods for making fusion proteins are well known to those skilled in the art. For example U.S. Pat. No. 6,057,133 discloses methods for making fusion molecules composed of human interleukin-3 (hIL-3) variant or mutant proteins functionally joined to a second colony stimulating factor, cytokine, lymphokine, interleukin, hematopoietic growth factor or IL-3 variant. U.S. Pat. No. 6,072,041 to Davis et al. discloses the generation of fusion proteins comprising a single chain Fv molecule directed against a transcytotic receptor covalently linked to a therapeutic protein.

Similar methods can be used to generate fusion proteins comprising MPPs (or variants, fragments, etc. thereof) linked to other amino acid sequences, such as a prostate specific targeting domain (for example LHRH or an antibody). Linker regions can be used to space the two portions of the protein from each other and to provide flexibility between them. The linker region is generally a polypeptide of between 1 and 500 amino acids in length, for example less than 30 amino acids in length. In general, the linker joining the two molecules can be designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and/or (4) provide steric separation of the two regions. Typically surface amino acids in flexible protein regions include Gly, Asn and Ser. Other neutral amino acids, such as Thr and Ala, can also be used in the linker sequence. Additional amino acids can be included in the linker to provide unique restriction sites in the linker sequence to facilitate construction of the fusions. Other moieties can also be included, as desired. These can include a binding region, such as avidin or an epitope, or a tag such as a polyhistidine tag, which can be useful for purification and processing of the fusion protein. In addition, detectable markers can be attached to the fusion protein, so that the traffic of the fusion protein through a body or cell can be monitored conveniently. Such markers include radionuclides, enzymes, fluorophores, and the like.

Fusing of the nucleic acid sequences of the MPP with the nucleic acid sequence of another protein (or variant, fragment etc. thereof), can be accomplished by the use of intermediate vectors. Alternatively, one gene can be cloned directly into a vector containing the other gene. Linkers and adapters can be used for joining the nucleic acid sequences, as well as replacing lost sequences, where a restriction site was internal to the region of interest. Genetic material (DNA) encoding one polypeptide, peptide linker, and the other polypeptide is inserted into a suitable expression vector which is used to transform prokaryotic or eukaryotic cells, for example bacteria, yeast, insect cells or mammalian cells. The transformed organism is grown and the protein isolated by standard techniques, for example by using a detectable marker such as nickel-chelate affinity chromatography, if a polyhistidine tag is used. The resulting product is therefore a new protein, a fusion protein, which has the MPP joined to a second protein, optionally via a linker. To confirm that the fusion protein is expressed, the purified protein can be, for example, subjected to electrophoresis in SDS-polyacrylamide gels, and transferred onto nitrocellulose membrane filters using established methods. The protein products can be identified by Western blot analysis using antibodies directed against the individual components, i.e., polyhistidine tag and/or the MPP.

If the MPPs according to the present invention are produced by expression of a fused gene, a peptide bond serves as the linker between the MPP and the prostate-specific targeting domain. For example, a recombinant fusion protein of a single chain Fv fragment of an antibody and a pore-forming protein toxin can be made according to methods known in the art, e.g., Huston et al., Meth. Enzymol. 203:46-88, 1991.

One of ordinary skill in the art will appreciate that the DNA can be altered in numerous ways without affecting the biological activity of the encoded protein. For example, PCR can be used to produce variations in the DNA sequence which encodes an MPP. Such variations in the DNA sequence encoding an MPP can be used to optimize for codon preference in a host cell used to express the protein, or may contain other sequence changes that facilitate expression.

Other Methods of Preparing MPPs

The prostate-specific targeting domains and optional linkers noted above may be added to the MPPs of the present invention via a covalent or non-covalent bond, or both. Non-covalent interactions can be ionic, hydrophobic, or hydrophilic, such as interactions involved in a leucine-zipper or antibody-Protein G interaction (Derrick et al., Nature 359: 752, 1992). Examples of additional non-covalent interactions include but are not restricted to the following binding pairs: antigen or hapten with antibody; antibody with anti-antibody; receptor with ligand; enzyme or enzyme fragment with substrate, substrate analogue or ligand; biotin or lectin with avidin or streptavidin; lectin with carbohydrate; pairs of leucine zipper motifs (see, for example, U.S. Pat. No. 5,643,731), as well as various homodimers and heterodimers known in the art. As is known in the art, the MPP may be modified to include one member of the binding pair, and the prostate-specific targeting domain may be modified to include the other member of the binding pair.

A covalent linkage may take the form of a disulfide bond. The DNA encoding one of the components can be engineered to contain a unique cysteine codon. Alternatively, use can be made of a naturally occurring cysteine residue. The second component can be derivatized with a sulfhydryl group reactive with the cysteine of the first component. Alternatively, a sulfhydryl group, either by itself or as part of a cysteine residue, can be introduced using solid phase polypeptide techniques. For example, the introduction of sulfhydryl groups into peptides is described by Hiskey (Peptides 3:137, 1981).

Proteins can be chemically modified by standard techniques to add a sulfhydryl group. For example, Traut's reagent (2-iminothiolane-HCl) (Pierce Chemicals, Rockford, Ill.) can be used to introduce a sulfhydryl group on primary amines, such as lysine residues or N-terminal amines. A protein or peptide modified with Traut's reagent can then react with a protein or peptide which has been modified with reagents such as N-succinimidyl 3-(2-pyridyldithio) propionate (SPDP) or succinimidyl 4-(N-maleimidomethyl)cyclohexane-1-carboxylate (SMCC) (Pierce Chemicals, Rockford, Ill.).

Once the correct sulfhydryl groups are present on each component, the two components are purified, sulfur groups on each component are reduced; the components are mixed; and disulfide bond formation is allowed to proceed to completion at room temperature. To improve the efficiency of the coupling reaction, the cysteine residue of one of the components, e.g., cysteine-MPP, can be activated prior to addition to the reaction mixture with 5,5'-dithiobis(2-nitrobenzoic) acid (DTNB) or 2,2'-dithiopyridine, using methods known in the art. Following the reaction, the mixture is dialyzed against phosphate buffered saline to remove unconjugated molecules. Sephadex chromatography or the like is then carried out to separate the compound of the invention from its constituent parts on the basis of size.

The components can also be joined using the polymer, monomethoxy-polyethylene glycol (mPEG), as described in Maiti et al., Int. J. Cancer Suppl. 3:17-22, 1988.

The prostate-specific targeting domain and the nPP or MPP can also be conjugated through the use of standard conjugation chemistries as is known in the art, such as, carbodiimide-mediated coupling (for example, DCC, EDC or activated EDC), and the use of 2-iminothiolane to convert epsilon amino groups to thiols for crosslinking and m-maleimidobenzoyl-n-hydroxysuccinimidyl ester (MBS) as a crosslinking agent. Various other methods of conjugation known in the art can be employed to join the prostate-specific targeting domain and the nPP or MPP.

Large Scale Preparation of MPPs

The preparation of the MPPs can also be conducted on a large scale, for example for manufacturing purposes, using standard techniques known in the art, such as large scale fermentation processes for production of recombinant proteins, and ultrafiltration, ion exchange chromatography, immobilized metal ion affinity chromatography for purification of recombinant proteins.

Methods of Testing MPPs

The MPPs according to the present invention retain their pore-forming activity and selectively kill prostate cells. The ability of the MPPs to selectively kill prostate cells can be tested using standard techniques known in the art. Exemplary methods of testing candidate MPPs are provided below and in the Examples included herein. One skilled in the art will understand that other methods of testing candidate MPPs are known in the art and are also suitable for testing the MPPs according to the present invention.

In Vitro Methods

MPPs according to the present invention that contain a prostate-specific activation sequence can be tested for their ability to be cleaved by the appropriate prostate-specific protease according to methods known in the art. For example, the MPP can be incubated with varying concentrations of the appropriate protease and the incubation products can be electrophoresed on SDS-PAGE gels and cleavage of the MPP can be assessed by examining the size of the polypeptide on the gel.

In order to determine if the MPPs that have been incubated with protease retain pore-forming activity, and thus the ability to kill cells after incubation with the protease, the reaction products can be tested in a hemolysis assay as is known in the art. An example of a suitable assay is described in Howard, S. P., and Buckley, J. T. 1985. Activation of the hole-forming toxin aerolysin by extracellular processing. J. Bacteriol. 163: 336-340.

MPPs according to the present invention can be tested for their ability to kill prostate cells as is known in the art. For example, the ability of the MPPs to kill prostate cells can be assayed in vitro using a suitable prostate cell line. In general, cells of the selected test cell line are grown to an appropriate density and the candidate MPP is added. After an appropriate incubation time (for example, about 48 to 72 hours), cell survival is assessed. Methods of determining cell survival are well known in the art and include, but are not limited to, the resazurin reduction test (see Fields & Lancaster (1993) *Am. Biotechnol. Lab.* 11:48-50; O'Brien et al., (2000) *Eur. J. Biochem.* 267:5421-5426 and U.S. Pat. No. 5,501,959), the sulforhodamine assay (Rubinstein et al., (1990) *J. Natl. Cancer Inst.* 82:113-118) or the neutral red dye test (Kitano et al., (1991) *Euro. J. Clin. Investg.* 21:53-58; West et al., (1992) *J. Investigative Derm.* 99:95-100) or trypan blue assay. Numerous commercially available kits may also be used, for example the CellTiter 96® AQueous One Solution Cell Proliferation Assay (Promega). Cytotoxicity is determined by comparison of cell survival in the treated culture with cell survival in one or more control cultures, for example, untreated cultures and/or cultures pre-treated with a control compound (typically a known therapeutic), or other appropriate control. MPPs considered to be effective in killing normal prostate cells are capable of decreasing cell survival, for example, by at least 10%, at least 20%, at least 30%, at least 40%, or at least 50%.

MPPs comprising a prostate-specific targeting domain can be assessed for their ability to selectively target prostate cells, for example, by comparing the ability of the MPP to kill normal prostate cells to its ability to kill cells from other tissues. Alternatively, flow cytometric methods, as is known in the art, may be used to determine if an MPP comprising prostate-specific targeting domain is able to selectively target prostate cells. As yet another alternative, the binding ligand for the prostate-specific targeting domain can be incorporated into artificial lipid membranes and the ability of the MPP to form channels can be measured using methods familiar to those skilled in the art.

Assays which can be used to test the MPPs according to the present invention for their ability to specifically lyse prostate cells are described for example, in Examples 2 and 3. For example, an MPP having a PSA cleavage site can be assessed for its ability to specifically lyse PSA-producing cells compared to its ability to lyse non-PSA producing cells. MPPs according to the present invention when contacted with a PSA-producing cell (such as a prostate cell), promote lysis and death of the cell, at lower concentrations than are required to kill a non-PSA producing cell, for example, by at least 2-fold, 5-fold, 10-fold or 100-fold lower concentrations.

A variety of prostate cell-lines suitable for testing the candidate MPPs are known in the art and many are commercially available (for example, from the American Type Culture Collection, Manassas, Va.). Examples of suitable prostate cell-lines for in vitro testing include, but are not limited to PNT1A, PNT2, BPH-1, DuK50, NRP152, PS-1 cell lines.

If necessary, the toxicity of the MPPs to non-prostate cells can also be initially assessed in vitro using standard techniques. For example, human primary fibroblasts can be transfected in vitro with the MPP and then tested at different time points following treatment for their viability using a standard viability assay, such as the assays described above, or the trypan-blue exclusion assay. Cells can also be assayed for their ability to synthesize DNA, for example, using a thymidine incorporation assay, and for changes in cell cycle dynamics, for example, using a standard cell sorting assay in conjunction with a fluorocytometer cell sorter (FACS).

The activity of MPPs according to the present invention in plasma or serum can also be tested as known in the art. For example, the MPPs can be incubated with serum for a suitable period of time, after which the degree of activation of the MPP is measured using, for example, electrophoresis and densitometric analysis of electrophoresed bands corresponding to activated MPP.

In vivo Methods

The toxicity of the MPPs according to the present invention can be tested in vivo according to methods known in the art. For example, the overall systemic toxicity of the MPPs can be tested by determining the dose that kills 100% of mice (i.e. $LD_{100}$) following a single intravenous injection as described in Example 4. Toxicity due to systemic or intraprostatic administration of an MPP can also be assessed in vivo, for example, by administering the MPP to dogs, rats or monkeys.

The ability of the MPPs according to the present invention to decrease the size of the prostate, thus indicating suitability for the treatment of BPH can be tested in vivo using animal models known in the art. For, example, the in vivo activity of MPPs can be tested using dogs, or non-human primates such as the cynomologous monkey, chimpanzee and baboon. The MPPs can be administered, for example, by perianal intraprostatic injection. Changes in prostate volume after administration can be evaluated, for example, by magnetic resonance imaging or by postmortem examination of the prostate tissue and/or determination of prostate weight.

As noted above, MPPs capable of decreasing the size of the prostate gland in an animal model, or attenuating further growth of the prostate gland are considered to be suitable for the treatment of BPH. Decreasing the size of the prostate gland refers to a decrease in the weight or volume of a prostate gland, and attenuating of further growth of the prostate gland refers to the situation where there is minimal or no increase in the weight or volume of a prostate gland in an animal subsequent to administration of the test compound. In one embodiment, MPPs contemplated by the present invention, when administered to an animal, are capable of decreasing prostate gland size, for example, by at least 10%, 20%, 30%, 40%, or 50%.

Determination and Reduction of MPP Antigenicity

Therapeutic proteins may elicit some level of antibody response when adminstered to a subject, which in some cases can lead to potentially serious side effects. Therefore, if necessary, the antigenicity of the MPPs can be assessed as known in the art and described below. In addition, methods to reduce potential antigenicity are described.

The kinetics and magnitude of the antibody response to the MPPs described herein can be determined, for example, in immunocompetent mice, and can be used to facilitate the development of a dosing regimen that can be used in an immunocompetent human. Immunocompetent mice such as the strain C57-BL6 are administered intravenous doses of the MPP. Mice are sacrificed at varying intervals (e.g. following single dose, following multiple doses) and serum obtained. An ELISA-based assay can be used to detect the presence of anti-MPP antibodies.

To decrease antigenicity of MPPs according to the present invention, the native binding domain of the MPP can be functionally deleted and replaced, for example with a prostate-specific targeting domain as described above. The antigenicity of such MPPs can be determined following exposure to varying schedules of the MPP which lack portions of the native binding domain using the methods described above. Another method that can be used to allow continued treatment with MPPs is to use sequentially administered alternative MPPs derived from other nPPs with non-overlapping antigenicity. For example, an MPP derived from proaerolysin can be used alternately with an MPP derived from *Clostridium septicum* alpha toxin or *Bacillus thuringiensis* delta-toxin. All of these MPPs would target prostate cells, but would not be recognized or neutralized by the same antibodies. Another example is to use an MPP derived from human tissues, such as human perforin produced by cytolytic human T cells. Such MPPs, can be administered and not produce an antibody response because the proteins are of human origin.

Pharmaceutical Compositions

The present invention provides for pharmaceutical compositions comprising an MPP and one or more non-toxic pharmaceutically acceptable carriers, diluents, excipients and/or adjuvants. If desired, other active ingredients may be included in the compositions. As indicated above, such compositions are used in the treatment of BPH.

The pharmaceutical compositions may comprise from about 1% to about 95% of a MPP of the invention. Compositions formulated for administration in a single dose form may comprise, for example, about 20% to about 90% of the MPPs of the invention, whereas compositions that are not in a single dose form may comprise, for example, from about 5% to about 20% of the MPPs of the invention. Concentration of the MPP in the final formulation can be as low as 0.01 μg/mL. For example, the concentration in the final formulation can be between about 0.01 μg/mL and about 1,000 μg/mL. In one embodiment, the concentration in the final formulation is between about 0.01 μg/mL and about 100 μg/mL. Non-limiting examples of unit dose forms include dragées, tablets, ampoules, vials, suppositories and capsules. Non-limiting examples of unit dose forms include dragées, tablets, ampoules, vials, suppositories and capsules.

The composition can be a liquid solution, suspension, emulsion, tablet, pill, capsule, sustained release formulation, or powder. For solid compositions (e.g., powder, pill, tablet, or capsule forms), conventional non-toxic solid carriers can include, for example, pharmaceutical grades of mannitol, lactose, starch, sodium saccharine, cellulose, magnesium carbonate, or magnesium stearate. The composition can be formulated as a suppository, with traditional binders and carriers such as triglycerides.

For administration to an animal, the pharmaceutical compositions can be formulated for administration by a variety of routes. For example, the compositions can be formulated for oral, topical, rectal or parenteral administration or for administration by inhalation or spray. The term parenteral as used herein includes subcutaneous injections, intravenous, intramuscular, intrathecal, intrasternal injection or infusion techniques. Direct injection or infusion into the prostate gland is also contemplated. Convection enhanced delivery, a standard administration technique for protein toxins, is also contemplated by the present invention.

The MPPs can be delivered along with a pharmaceutically acceptable vehicle. Ideally, such a vehicle would enhance the stability and/or delivery properties. Thus, the present invention also provides for formulation of the MPP with a suitable vehicle, such as an artificial membrane vesicle (including a liposome, noisome, nanosome and the like), microparticle or microcapsule, or as a colloidal formulation that comprises a pharmaceutically acceptable polymer. The use of such vehicles/polymers may be beneficial in achieving sustained release of the MPPs. Alternatively, or in addition, the MPP formulations can include additives to stabilise the protein in vivo, such as human serum albumin, or other stabilisers for protein therapeutics known in the art.

Pharmaceutical compositions for oral use can be formulated, for example, as tablets, troches, lozenges, aqueous or oily suspensions, dispersible powders or granules, emulsion hard or soft capsules, or syrups or elixirs. Such compositions can be prepared according to standard methods known to the art for the manufacture of pharmaceutical compositions and may contain one or more agents selected from the group of sweetening agents, flavoring agents, colouring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatine or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monostearate or glyceryl distearate may be employed.

Pharmaceutical compositions for oral use can also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium such as peanut oil, liquid paraffin or olive oil.

Pharmaceutical compositions formulated as aqueous suspensions contain the active compound(s) in admixture with one or more suitable excipients, for example, with suspending agents, such as sodium carboxymethylcellulose, methyl cellulose, hydropropylmethylcellulose, sodium alginate, polyvinylpyrrolidone, hydroxypropyl-β-cyclodextrin, gum tragacanth and gum acacia; dispersing or wetting agents such as a naturally-occurring phosphatide, for example, lecithin, or condensation products of an alkylene oxide with fatty acids, for example, polyoxyethyene stearate, or condensation products of ethylene oxide with long chain aliphatic alcohols, for example, hepta-decaethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxy-benzoate, one or more colouring agents, one or more flavoring agents or one or more sweetening agents, such as sucrose or saccharin.

Pharmaceutical compositions can be formulated as oily suspensions by suspending the active compound(s) in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and/or flavoring agents may be added to provide palatable oral preparations. These compositions can be preserved by the addition of an anti-oxidant such as ascorbic acid.

The pharmaceutical compositions can be formulated as a dispersible powder or granules, which can subsequently be used to prepare an aqueous suspension by the addition of water. Such dispersible powders or granules provide the active ingredient in admixture with one or more dispersing or wetting agents, suspending agents and/or preservatives. Suitable dispersing or wetting agents and suspending agents are exemplified by those already mentioned above. Additional excipients, for example, sweetening, flavoring and coloring agents, can also be included in these compositions.

Pharmaceutical compositions of the invention can also be formulated as oil-in-water emulsions. The oil phase can be a vegetable oil, for example, olive oil or arachis oil, or a mineral oil, for example, liquid paraffin, or it may be a mixture of these oils. Suitable emulsifying agents for inclusion in these compositions include naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the said partial esters with ethylene oxide, for example, polyoxyethylene sorbitan monoleate. The emulsions can also optionally contain sweetening and flavoring agents.

Pharmaceutical compositions can be formulated as a syrup or elixir by combining the active ingredient(s) with one or more sweetening agents, for example glycerol, propylene glycol, sorbitol or sucrose. Such formulations can also optionally contain one or more demulcents, preservatives, flavoring agents and/or coloring agents.

The pharmaceutical compositions can be formulated as a sterile injectable aqueous or oleaginous suspension according to methods known in the art and using suitable one or more dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, Pa. (2000).

The pharmaceutical compositions of the present invention described above include one or more MPPs of the invention in an amount effective to achieve the intended purpose. Thus the term "therapeutically effective dose" refers to the amount of the MPP that ameliorates the symptoms or characteristics of BPH. Determination of a therapeutically effective dose of a compound is well within the capability of those skilled in the art. For example, the therapeutically effective dose can be estimated initially either in cell culture assays, or in animal models, such as those described herein. Animal models can also be used to determine the appropriate concentration range and route of administration. Such information can then be used to determine useful doses and routes for administration in other animals, including humans, using standard methods known in those of ordinary skill in the art.

Therapeutic efficacy and toxicity can also be determined by standard pharmaceutical procedures such as, for example, by determination of the median effective dose, or $ED_{50}$ (i.e. the dose therapeutically effective in 50% of the population) and the median lethal dose, or $LD_{50}$ (i.e. the dose lethal to 50% of the population). The dose ratio between therapeutic and toxic effects is known as the "therapeutic index," which can be expressed as the ratio, $LD_{50}/ED_{50}$. The data obtained from cell culture assays and animal studies can be used to formulate a range of dosage for human or animal use. The dosage contained in such compositions is usually within a range of concentrations that include the $ED_{50}$ and demonstrate little or no toxicity. The dosage varies within this range depending upon the dosage form employed, sensitivity of the subject, and the route of administration and the like.

The exact dosage to be administered to a subject can be determined by the practitioner, in light of factors related to the subject requiring treatment. Dosage and administration are adjusted to provide sufficient levels of the MPP and/or to maintain the desired effect. Factors which may be taken into account when determining an appropriate dosage include the severity of the disease state, general health of the subject, age, weight, and gender of the subject, diet, time and frequency of administration, drug combination(s), reaction sensitivities, and tolerance/response to therapy. Dosing regimens can be designed by the practitioner depending on the above factors as well as factors such as the half-life and clearance rate of the particular formulation.

Pharmaceutically effective amounts MPPs of the present invention can be formulated with pharmaceutically acceptable carriers for parenteral, oral, nasal, rectal, topical, transdermal administration or the like, according to conventional methods. Formulations may further include one or more diluents, fillers, emulsifiers, preservatives, buffers, excipients, and the like, and may be provided in such forms as liquids, powders, emulsions, suppositories, liposomes, transdermal patches and tablets, for example. Slow or extended-release delivery systems, including any of a number of biopolymers (biological-based systems), systems employing liposomes, and polymeric delivery systems, can also be utilized with the compositions described herein to provide a continuous or long-term source of MPP. Such slow release systems are applicable to formulations, for example, for oral, topical and parenteral use. The term "pharmaceutically acceptable carrier" refers to a carrier medium which does not interfere with the effectiveness of the biological activity of the active ingredients and which is not toxic to the host or patient. One skilled in the art may formulate the compounds of the present invention in an appropriate manner, and in accordance with accepted practices, such as those disclosed in Remington: The Science and Practice of Pharmacy, Gennaro, ed., Mack Publishing Co., Easton Pa., 19th ed., 1995

In one embodiment, the MPP is conjugated to a water-soluble polymer, e.g., to increase stability or circulating half life or reduce immunogenicity. Clinically acceptable, water-soluble polymers include, but are not limited to, polyethylene glycol (PEG), polyethylene glycol propionaldehyde, carboxymethylcellulose, dextran, polyvinyl alcohol (PVA), polyvinylpyrrolidone (PVP), polypropylene glycol homopolymers (PPG), polyoxyethylated polyols (POG) (e.g., glycerol) and other polyoxyethylated polyols, polyoxyethylated sorbitol, or polyoxyethylated glucose, and other carbohydrate polymers. Methods for conjugating polypeptides to water-soluble polymers such as PEG are described, e.g., in U.S. patent Pub. No. 20050106148 and references cited therein.

Use of MPPs for Treatment of Benign Prostatic Hyperplasia (BPH)

The MPPs according to the present invention selectively kill normal prostate cells relative to cells from other normal tissues. Thus, the MPPs according to the present invention are useful in the treatment or prevention of BPH.

In one embodiment, treatment of BPH refers to a decrease in the size of the prostate gland, in a subject with BPH. The size of the prostate gland can be measured in terms of its volume, by methods known in the art including, for example, planimetry, prolate ellipse volume calculation (HWL), and an ellipsoid volume measurement technique. Prostate size can also be measured directly, for example by digital rectal examination, or rectal ultrasound or cytoscopy, or indirectly, for example, by measuring changes in the levels of blood PSA or changes in the proportions of free and total PSA in the blood.

In one embodiment, administration of MPP decreases the volume of the prostate gland in a subject. For example, the disclosed methods can reduce prostate volume, for example, by at least 10%, by at least 20%, or by at least 30% by at least 40%, or by at least 50%.

In another embodiment, treatment of BPH refers to the decrease in the degree of severity of one or more symptoms of BPH. Symptoms of BPH include changes or problems with urination, such as a hesitant, interrupted or weak stream, urgency and leaking or dribbling, or more frequent urination, especially at night. These symptoms are also known as lower urinary tract symptoms (LUTS). LUTS can be measured as known in the art using the American Urological Association (AUA) Symptom Index, the Madsen-Iversen Scoring System, or the Boyarsky System.

In another embodiment, treatment of BPH refers to the prevention or inhibition of continued growth of the prostate gland and can be measured by a reduction in the rate of increase in the volume or the rate of increase of blood PSA or reduction in symptoms of BPH as described above.

Combination Therapy

The MPPs according to the present invention can be used alone or in combination with one or more additional treatments for BPH. The additional treatments for BPH include administration of drugs such as α-1-adrenoreceptor antagonists and 5-α reductase inhibitors, phytotherapies, surgical procedures, and minimally invasive techniques.

Examples of α-1-adrenoreceptor antagonists are alfuzosin/prazosin, tamsulosin, terazosin, and doxazosin. Examples of 5-α reductase inhibitors are finasteride and dutasteride.

Examples of phytotherapies include Saw palmetto berry/dwarf palm (*Serenoa repens*), African plum bark (*Pygeum africanum*), South African star grass/beta-sitosterol (*Hipoxis rooperi*), Purple cone flower (*Echinacea purpurea*), Pumpkin seeds (*Cucurbita pepo*), Rye (*Secale cereale*), and Stinging nettle (*Urtica dioica*).

Examples of surgical procedures are transurethral resection of the prostate (TURP), transurethral needle ablation (TUNA), transurethral incision of the prostate (TUIP), transurethral microwave thermotherapy (TUMT), laser prostatectomy, balloon dilation, electrical vaporization and open prostatectomy.

If necessary to reduce a systemic immune response to the MPPs, immunosuppressive therapies can be administered in combination with the MPPs. Examples of immunosuppressive therapies include, but are not limited to, systemic or topical corticosteroids (Suga et al., Ann. Thorac. Surg. 73:1092-7, 2002), cyclosporin A (Fang et al., Hum. Gene Ther. 6:1039-44, 1995), cyclophosphamide (Smith et al., Gene Ther. 3:496-502, 1996), deoxyspergualin (Kaplan et al., Hum. Gene Ther. 8:1095-1104, 1997) and antibodies to T and/or B cells [e.g. anti-CD40 ligand, anti CD4 antibodies, anti-CD20 antibody (Rituximab)] (Manning et al., Hum. Gene Ther. 9:477-85, 1998). Such agents can be administered before, during, or subsequent to administration of the MPP. The MPPs of the present invention may be administered separately, sequentially or simultaneously with the above noted treatments.

Administration of MPPs

A therapeutically effective amount of an MPP according to the present invention, or a nucleic acid encoding an MPP, can be administered locally or systemically using methods known in the art, to subjects having BPH.

In one embodiment, the MPPs are injected into the prostate gland (intraprostatically) in a subject having BPH. For example, an administration approach similar to the multiple injection approach of brachytherapy can be used, in which multiple aliquots of the purified peptides, adapted as compositions or formulations and in the appropriate dosage form, may be injected using a needle through the perineum.

In addition, or alternatively, the MPPs can be administered systemically, for example intravenously, intramuscularly, subcutaneously, or orally, to a subject having BPH.

A therapeutically effective amount of an MPP refers to an amount sufficient to achieve a desired biological effect, for example an amount that is effective to decrease the size (i.e. volume and/or weight) of the prostate gland, or attenuate further growth of the prostate gland, or decrease symptoms of BPH. In one embodiment, it is an amount sufficient to decrease the signs or symptoms of BPH in a subject. In particular examples, it is an amount effective to decrease the volume of a prostate gland by at least 10%, 20%, 30%, 40%, or 50%. In another embodiment, it is an amount sufficient to prevent further increase in volume or weight of the prostate gland. Effective doses can be extrapolated from dose-response curves derived from in vitro or animal model test systems.

An effective amount of an MPP can be administered in a single dose, or in several doses, for example daily, during a course of treatment. However, the effective amount of MPP will be dependent on the subject being treated, the severity and type of the condition being treated, and the manner of administration. In one embodiment, a therapeutically effective amount of an MPP can vary from about 0.01 to 50 μg per gram prostate weight, administered intraprostatically. In another embodiment, a therapeutically effective amount of an MPP can vary from about 0.02 to 40 μg per gram prostate weight, administered intraprostatically. In another embodiment, a therapeutically effective amount of an MPP can vary from about 0.02 to 35 μg per gram prostate weight, administered intraprostatically. In another embodiment, a therapeutically effective amount of an MPP can vary from about 0.03 to 25 μg per gram prostate weight, administered intraprostatically. In another embodiment, a therapeutically effective amount of an MPP can vary from about 0.04 to 20 μg per gram prostate weight, administered intraprostatically. In another embodiment, a therapeutically effective amount of an MPP can vary from about 0.04 to 10 μg per gram prostate weight, administered intraprostatically.

In one embodiment, an effective intravenous dose intraprostatically an MPP for a 70 kg human is from about 1 mg to about 10 mg of MPP. In another embodiment an effective intravenous dose is from about 1 mg to about 5 mg. In another embodiment, an effective intravenous dose is from about 1 mg to about 3 mg. In still another embodiment, an effective intravenous dose is about 2.8 mg. In one embodiment, an effective intraprostatic dose of an MPP for a 70 kg human is from about 10 mg to about 100 mg of MPP. In another embodiment, an effective intraprostatic dose of an MPP for a 70 kg human is from about 10 mg to about 50 mg of MPP. In another embodiment, an effective intraprostatic dose of an MPP for a 70 kg human is from about 10 mg to about 30 mg of MPP. In another embodiment, an effective intraprostatic dose of an MPP is about 28 mg for a 70 kg human.

In Vivo Expression of MPPs

As an alternative to (or in addition to) administration of MPPs to treat BPH, long term or systemic treatment of BPH can be achieved by expressing nucleic acids encoding MPPs in vivo.

Nucleic Acids Encoding MPPs

The present invention contemplates the use of nucleic acids or DNA molecules encoding MPPs for the treatment of BPH. Such DNA molecules can be obtained through standard molecular biology laboratory techniques and the sequence information disclosed herein.

Suitable DNA molecules and nucleotide include those which hybridize under stringent conditions to the DNA sequences disclosed, or fragments thereof, provided that they encode a functional MPP. Hybridization conditions resulting in particular degrees of stringency vary depending upon the nature of the hybridization method and the composition and length of the hybridizing DNA used. Generally, the temperature of hybridization and the ionic strength (especially the $Na^+$ concentration) of the hybridization buffer determines hybridization stringency. Calculations regarding hybridization conditions required for attaining particular amounts of stringency are discussed by Sambrook et al. (Molecular Cloning: A Laboratory Manual, Cold Spring Harbor, N.Y., 1989, Chapters 9 and 11). Hybridization with a target probe labeled with [$^{32}P$]-dCTP is generally carried out in a solution of high ionic strength such as 6.times.SSC at a temperature that is about 5-25° C. below the melting temperature, $T_m$. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5.times.SSPE (750 mM NaCl, 50 mM Na phosphate, 5 mM EDTA, pH 7.4) at 25-30° C. are suitable for allele-specific probe hybridizations.

The degeneracy of the genetic code further allows for variations in the nucleotide sequence of a DNA molecule while maintaining the amino acid sequence of the encoded protein. For example, the amino acid Ala is encoded by the nucleotide codon triplet GCT, GCG, GCC and GCA. Thus, the nucleotide sequence could be changed without affecting the amino acid composition of the encoded protein or the characteristics of the protein. Based upon the degeneracy of the genetic code, variant DNA molecules may be derived from a reference DNA molecule using standard DNA mutagenesis techniques as described above, or by synthesis of DNA sequences. DNA sequences which do not hybridize under stringent conditions to the DNA sequences disclosed by virtue of sequence variation based on the degeneracy of the genetic code are also comprehended by this disclosure.

The present invention provides methods of expressing MPPs, for example a modified proaerolysin polypeptide in a cell or tissue in vivo. In one example, transfection of the cell or tissue occurs in vitro. In this example, the cell or tissue (such as a graft) is removed from a subject and then transfected with an expression vector containing a cDNA encoding the protein of interest. The transfected cells will produce functional protein and can be reintroduced into the subject. In another example, a nucleic acid encoding the protein of interest is administered to a subject directly (such as intravenous, or intraprostate), and transfection occurs in vivo.

The scientific and medical procedures required for human cell transfection are now routine. A general strategy for transferring genes into donor cells is disclosed in U.S. Pat. No. 5,529,774. Generally, a gene encoding a protein having therapeutically desired effects is cloned into a viral expression vector, and that vector is then introduced into the target organism. The virus infects the cells, and produces the protein sequence in vivo, where it has its desired therapeutic effect (Zabner et al. Cell 75:207-16, 1993).

It may only be necessary to introduce the DNA or protein elements into certain cells or tissues, for example, the prostate. However, in some instances, it may be more therapeutically effective and simple to treat all of a subject's cells, or more broadly disseminate the vector, for example by intravascular (i.v.) or oral administration.

The nucleic acid sequence encoding the MPP is under the control of a suitable promoter. Suitable promoters which can be used include, but are not limited to, the gene's native promoter, retroviral LTR promoter, or adenoviral promoters, such as the adenoviral major late promoter; the CMV promoter; the RSV promoter; inducible promoters, such as the MMTV promoter; the metallothionein promoter; heat shock promoters; the albumin promoter; the histone promoter; the x-actin promoter; TK promoters; B19 parvovirus promoters; and the ApoAI promoter. In one example, the promoter is a prostate-specific promoter, such as a probasin promoter. However the disclosure is not limited to specific foreign genes or promoters.

The recombinant nucleic acid can be administered to the subject by known methods which allows the recombinant nucleic acid to reach the appropriate cells. These methods include injection, infusion, deposition, implantation, or topical administration. Injections can be intradermal or subcutaneous. The recombinant nucleic acid can be delivered as part of a viral vector, such as avipox viruses, recombinant vaccinia virus, replication-deficient adenovirus strains or poliovirus, or as a non-infectious form such as naked DNA or liposome encapsulated DNA, as further described below.

Adenoviral vectors include essentially the complete adenoviral genome (Shenk et al., Curr. Top. Microbiol. Immunol. 111: 1-39, 1984). Alternatively, the adenoviral vector is a modified adenoviral vector in which at least a portion of the adenoviral genome has been deleted. In one example, the vector includes an adenoviral 5' ITR; an adenoviral 3' ITR; an adenoviral encapsidation signal; a DNA sequence encoding a therapeutic agent; and a promoter for expressing the DNA sequence encoding a therapeutic agent. The vector is free of at least the majority of adenoviral E1 and E3 DNA sequences, but is not necessarily free of all of the E2 and E4 DNA sequences, and DNA sequences encoding adenoviral proteins transcribed by the adenoviral major late promoter. In another example, the vector is an adeno-associated virus (AAV) such as described in U.S. Pat. No. 4,797,368 (Carter et al.) and in McLaughlin et al. (J. Virol. 62:1963-73, 1988) and AAV type 4 (Chiorini et al. J. Virol. 71:6823-33, 1997) and AAV type 5 (Chiorini et al. J. Virol. 73:1309-19, 1999).

Such a vector can be constructed according to standard techniques, using a shuttle plasmid which contains, beginning at the 5' end, an adenoviral 5' ITR, an adenoviral encapsidation signal, and an E1a enhancer sequence; a promoter (which may be an adenoviral promoter or a foreign promoter); a tripartite leader sequence, a multiple cloning site (which may be as herein described); a poly A signal; and a DNA segment which corresponds to a segment of the adenoviral genome. The DNA segment serves as a substrate for homologous recombination with a modified or mutated adenovirus, and may encompass, for example, a segment of the adenovirus 5' genome no longer than from base 3329 to base 6246. The plasmid can also include a selectable marker and an origin of replication. The origin of replication may be a bacterial origin of replication. A desired DNA sequence encoding a therapeutic agent can be inserted into the multiple cloning site of the plasmid.

Examples of vectors which can be used to practice the methods disclosed herein include, but are not limited to, those disclosed in: WO 95/27512 to Woo et al.; WO 01/127303 to Walsh et al.; U.S. Pat. No. 6,221,349 to Couto et al.; U.S. Pat. No. 6,093,392 to High et al.

Clinical Trials

One skilled in the art will appreciate that, following the demonstrated effectiveness of MPPs for the treatment of BPH in in vitro and in animal models, the MPPs should be tested in clinical trials in order to further evaluate their efficacy in the treatment of BPH and to obtain regulatory approval for therapeutic use. As is known in the art, clinical trials progress through phases of testing, which are identified as Phases I, II, III, and IV.

Initially the MPPs will be evaluated in a Phase I trial. Typically Phase I trials are used to determine the best mode of administration (for example, by pill or by injection), the frequency of administration, and the toxicity for the compounds. Phase I studies frequently include laboratory tests, such as blood tests and biopsies, to evaluate the effects of the potential therapeutic in the body of the patient. For a Phase I trial, a small group of patients with BPH are treated with a specific dose of MPP. During the trial, the dose is typically increased group by group in order to determine the maximum tolerated dose (MTD) and the dose-limiting toxicities (DLT) associated with the compound. This process determines an appropriate dose to use in a subsequent Phase II trial.

A Phase II trial can be conducted to further evaluate the effectiveness and safety of the MPP. In Phase II trials, the MPP is administered to groups of patients with BPH, using the dosage found to be effective in Phase I trials.

Phase III trials focus on determining how the MPP compares to the standard, or most widely accepted, treatment. In Phase III trials, patients are randomly assigned to one of two or more "arms". In a trial with two arms, for example, one arm will receive the standard treatment (control group) and the other arm will receive MPP treatment (investigational group).

Phase IV trials are used to further evaluate the long-term safety and effectiveness of an MPP. Phase IV trials are less common than Phase I, II and III trials and take place after the MPP has been approved for standard use.

Eligibility of Patients for Clinical Trials

Participant eligibility criteria can range from general (for example, age, sex, type of disease) to specific (for example, type and number of prior treatments, disease characteristics, blood cell counts, organ function). In one embodiment, eligible patients have been diagnosed with BPH. Eligibility criteria may also vary with trial phase. Patients eligible for clinical trials can also be chosen based on objective measurement of urinary obstruction, and failure to respond to oral treatment for BPH. For example, in Phase I and II trials, the criteria often exclude patients who may be at risk from the investigational treatment because of abnormal organ function or other factors. In Phase II and III trials additional criteria are often included regarding disease type and stage, and number and type of prior treatments.

Phase I trials usually comprise 15 to 30 participants for whom other treatment options have not been effective. Phase II trials typically comprise up to 100 participants who have already received drug therapy or surgery, but for whom the treatment has not been effective. Participation in Phase II trials is often restricted based on the previous treatment received. Phase III trials usually comprise hundreds to thousands of participants. This large number of participants is necessary in order to determine whether there are true differences between the effectiveness of MPP and the standard treatment. Phase III may comprise patients ranging from those newly diagnosed with BPH to those with extensive disease in order to cover the disease continuum.

One skilled in the art will appreciate that clinical trials should be designed to be as inclusive as possible without making the study population too diverse to determine whether the treatment might be as effective on a more narrowly defined population. The more diverse the population included in the trial, the more applicable the results could be to the general population, particularly in Phase III trials. Selection of appropriate participants in each phase of clinical trial is considered to be within the ordinary skills of a worker in the art.

Assessment of Patients Prior to Treatment

Prior to commencement of the study, several measures known in the art can be used to first classify the patients. Patients can first be assessed, for example, using the benign hyperplasia symptom index found on the Family Practice Notebook website. Patients can also be classified according to the type and/or stage of their disease and/or by prostate size.

Administration of MPP in Clinical Trials

MPP is typically administered to the trial participants by injection. In one embodiment, the MPP is administered by intraprostatic injection.

A range of doses of the MPP can be tested. Provided with information from preclinical testing, a skilled practitioner could readily determine appropriate dosages of MPP for use in clinical trials. In one embodiment, a dose range is from about 0.01 μg/g prostate to about 50 μg/g prostate. In one embodiment, a dose range is from about 0.02 μg/g prostate to about 40 μg/g prostate. In one embodiment, a dose range is from about 0.02 μg/g prostate to about 35 μg/g prostate. In one embodiment, a dose range is from about 0.03 μg/g prostate to about 25 μg/g prostate. In one embodiment, a dose range is from about 0.044 μg/g prostate to about 20 μg/g prostate. In one embodiment, a dose range is from about 0.04 μg/g prostate to about 10 μg/g prostate. In one embodiment, a dose range is from about 0.1 μg/g prostate to about 5 μg/g prostate. In one embodiment, a dose range is from about 0.2 μg/g prostate to about 3 μg/g prostate. In one embodiment, a dose range is from about 0.5 μg/g prostate to about 2 μg/g prostate.

Pharmacokinetic Monitoring

To fulfill Phase I criteria, distribution of the MPP is monitored, for example, by chemical analysis of samples, such as blood or urine, collected at regular intervals. For example, samples can be taken at regular intervals up until about 72 hours after the start of infusion.

If analysis is not conducted immediately, the samples can be placed on dry ice after collection and subsequently transported to a freezer to be stored at −70° C. until analysis can be conducted. Samples can be prepared for analysis using standard techniques known in the art and the amount of MPP present can be determined, for example, by high-performance liquid chromatography (HPLC).

Pharmacokinetic data can be generated and analyzed in collaboration with an expert clinical pharmacologist and used to determine, for example, clearance, half-life and maximum plasma concentration.

Monitoring of Patient Outcome

The endpoint of a clinical trial is a measurable outcome that indicates the effectiveness of a compound under evaluation. The endpoint is established prior to the commencement of the trial and will vary depending on the type and phase of the clinical trial. Examples of endpoints include, for example decline in prostate volume, decline in blood PSA levels, improved urinary tract symptoms, improved urinary flow, and reduction in acute urinary retention. Other endpoints include toxicity and quality of life.

Pharmaceutical Kits

The present invention additionally provides for therapeutic kits or packs containing one or more MPPs or a pharmaceutical composition comprising one or more MPPs for use in the treatment of BPH. The MPPs can be provided in the kit in unit dosage form. Individual components of the kit can be packaged in separate containers, associated with which, when applicable, can be a notice in the form prescribed by a governmental agency regulating the manufacture, use or sale of pharmaceuticals or biological products, which notice reflects approval by the agency of manufacture, use or sale for human or animal administration. The kit can optionally further contain one or more other therapeutic agents for use in combination with the MPPs of the invention. The kit may optionally contain instructions or directions outlining the method of use or dosing regimen for the MPPs and/or additional therapeutic agents.

When the components of the kit are provided in one or more liquid solutions, the liquid solution can be an aqueous solution, for example a sterile aqueous solution. In this case the container means may itself be an inhalant, syringe, pipette, eye dropper, or other such like apparatus, from which the composition may be administered to a patient or applied to and mixed with the other components of the kit.

The components of the kit may also be provided in dried or lyophilised form and the kit can additionally contain a suitable solvent for reconstitution of the lyophilised components. Irrespective of the number or type of containers, the kits of the invention also may comprise an instrument for assisting with the administration of the composition to a patient. Such an instrument may be an inhalant, syringe, pipette, forceps, measured spoon, eye dropper or similar medically approved delivery vehicle.

The invention will now be described with reference to specific examples. It will be understood that the following examples are intended to describe embodiments of the invention and are not intended to limit the invention in any way.

EXAMPLES

Example 1

Generation of MPPS Activated by PSA

This example describes methods used to produce the MPPs according to embodiments of the invention as shown in Table 6, which are activated by PSA. These MPPs are derived from proaerolysin. One skilled in the art will understand that similar methods can be used to produce other MPPs which are activated by PSA or any other prostate-specific protease. Such proteins can be produced by substituting the furin sequence of proaerolysin with a prostate-specific protease cleavage site, such as a PSA-specific cleavage sequence.

TABLE 6

Comparison of MPPs with an activation sequence containing a protease cleavage site cleaved by PSA with wild-type Proaerolysin

| MPP (SEQ ID NO:) | Change(s) made (SEQ ID NO:) | Comparison to wt Proaerolysin ADSKVRRARSVDGAGQGLRLEIPLD (aa 424-448 of SEQ ID NO: 2) |
|---|---|---|
| MPP1 (3 & 4) | KVRRAR (aa 427-432 of SEQ ID NO: 2) changed to HSSKLQ (5) | ADSHSSKLQSVDGAGQGLRLEIPLD) (aa 424-448 of SEQ ID NO: 4) |
| MPP2 (6 & 7) | KVRRARSV (aa 427-434 of SEQ ID NO: 2) changed to HSSKLQSA (8) | ADSHSSKLQSADGAGQGRLEIPLD (aa 424-448 of SEQ ID NO: 7) |
| MPP3 (9 & 10) | KVRRAR (aa 427-432 of (SEQ ID NO: 2) changed to QFYSSN (11) | ADSQFYSSNSVDGAGQGLRLEIPLD (aa 424-448 of SEQ ID NO: 10) |
| MPP4 (12 & 13) | KVRRAR (aa 427-432 of (SEQ ID NO: 2) changed to GISSFQS (14) | ADSGISSFQSSVDGAGQGLRLEIPLD (aa 424-448 of SEQ ID NO: 13) |

The MPPs shown in Table 6 include a proaerolysin sequence (wild-type PA shown in SEQ ID NOS: 1 and 2) in which the six amino acid furin protease recognition site (amino acids 427-432 of SEQ ID NO: 2) was replaced with a PSA cleavage site. For example, MPP1 (SEQ ID NOS: 3 and 4), includes a proaerolysin sequence in which the furin cleavage site was replaced by the PSA substrate HSSKLQ (SEQ ID NO: 5).

Recombinant PCR was used to substitute the furin site of aerolysin (amino acids 427-432 of SEQ ID NO: 2) with a PSA-specific cleavage site (SEQ ID NO: 5, 8, 11 or 14) using methods previously described (Vallette et al., Nucl. Acids Res. 17:723-33, 1988). Briefly, recombinant PCR was performed in a final volume of 50 μl which contained 0.2 mM deoxynucleoside triphosphate (dNTPs), 0.5 μM forward and reverse primers, 0.1 μg template DNA and 2.5 units cloned pfu polymerase in pfu Reaction Buffer [20 mM Tris-HCl (pH 8.8), 10 mM KCl, 10 mM $(NH_4)_2SO_4$, 2 mM $MgSO_4$, 0.1% Triton X-100, and 0.1 mg/ml BSA].

Screening transformed cells for the proaerolysin insert was performed by PCR using Taq polymerase. A cocktail was prepared in PCR reaction buffer [50 mM KCl, 1.5 mM $MgCl_2$, and 10 mM Tris-HCl (pH 9.0)] containing 0.2 mM dNTPs, 0.5 μM forward and reverse primers and 5 units of Taq polymerase. Ten μl samples of this cocktail were aliquoted into 0.2 ml tubes and transformed cells were added using sterile toothpicks.

The final PCR products were digested using appropriate restriction enzymes, then ligated into the cloning vector pTZ18u (BioRad) for amplification. Briefly, restriction digests were performed at 37° C. for 90 minutes in Pharmacia One-Phor-All buffer [10 mM Tris-acetate (pH 7.5), 10 mM Mg-acetate, and 50 mM K-acetate] containing about one unit of restriction enzyme for every μg of DNA. The resulting insert, and pTZ18u vector DNA, were mixed together in a ratio of approximately 5:1 and heated at 45° C. for 15 minutes. Subsequently, the samples were diluted in One-Phor All buffer and ATP added to a final concentration of 1 mM for cohesive-end ligations or 0.5 mM for blunt-end ligations. Then, 11 units of T4 DNA ligase were added to each sample and the samples mixed gently. Ligations were carried out at 13° C. for 4 hours (cohesive-end ligations) or 16 hours (blunt-end ligations).

DNA sequencing was performed to ensure the correct substitutions were made. The insert was subsequently isolated from the cloning vector and subcloned into the broad-host-range plasmid pMMB66HE (Furste et al., Gene 48:119-131, 1986) for expression in *E. coli*. *E. coli* DH5α cells were made competent using the $CaCl_2$ wash method described previously (Cohen et al. Proc. Nat. Acad. Sci. USA 69:2110-4, 1972). Cells in log-phase ($OD_{600}$=0.4-0.7) were harvested by centrifugation and washed in ¼ volume of cold 100 mM $MgCl_2$. The cells were pelleted again, and resuspended in two volumes of cold 100 mM $CaCl_2$. The cells were then incubated on ice for approximately 45 minutes. The cells were then centrifuged and resuspended in 1/10 volume of 100 mM $CaCl_2$. Incubation continued for an additional 45 minutes before the addition of glycerol to a final concentration of 15%. Competent cells were stored at −70° C. until use.

Transformation of recombinant plasmids into competent *E. coli* cells was performed according to the method of Inoue et al. (Gene 96: 23-8, 1990). Competent cells (200 μl aliquots) were incubated with 0.5-10 ng of DNA for one hour on ice. The cells were then subjected to heat shock at 42° C. for 4 minutes. The cells were quickly transferred back onto ice for 5 minutes. Subsequently, 500 μl of LB media was added to each sample and the cells incubated for 1 hour at 37° C. with mild agitation. Aliquots (150 μl) were plated onto LB agar containing 50 μg/ml ampicillin. These plates were incubated overnight at 37° C.

Recombinant pMMB66HE clones were transferred into *Aeromonas salmonicida* strain CB3 (see Buckley, Biochem. Cell. Biol. 68:221-4, 1990) by conjugation using the filter-mating technique of Harayama et al. (Mol. Gen. Genet. 180: 47-56, 1980). Use of this protease-deficient strain of *A. salmonicida* resulted in production of MPPs that were not contaminated by activated aerolysin and resulted in production of large quantities of protein. The MPPs were purified by hydroxyapatite chromatography and ion exchange chromatography as previously described (Buckley, Biochem. Cell. Biol. 68:221-4, 1990). This method resulted in preparations of the MPPs identical from batch to batch.

Example 2

MPP1 Specifically LYSES PSA-producing Cells In Vitro

This example describes methods used to determine the specificity of the MPPs according to embodiments of the invention as described in Example 1. Such methods can be used to test the specificity of MPPs that include a PSA-specific cleavage site.

MPP1 was tested against PSA-producing LNCaP cells (American Type Culture Collection, Manassas, Va.) and non-PSA-producing TSU cells (Dr. T. Itzumi, Teikyo University, Japan). Cells were incubated in the presence of $10^{-12}$ M to $10^{-6}$ M MPP1 for 24 hours. Subsequently, cells were counted and scored for percent viable cells based on ability to exclude Trypan Blue. Concentration required to kill 50% of cells ($IC_{50}$) was determined for MPP1 against both LNCaP and TSU lines.

The $LD_{50}$ for MPP1 against PSA-producing cells was $10^{-10}$ M. In contrast, against non-PSA producing TSU cells the $LD_{50}$ was about $5\times10^{-8}$ M. This result demonstrates that MPP1 is specifically activated by PSA as evidenced by a 500-fold difference in toxicity against PSA-producing versus non-PSA producing human cell lines.

Example 3

MPP1 is not Activated in Blood Containing PSA

MPPs which include a PSA cleavage site should not be activated in blood, because PSA is enzymatically inactivated in the blood due to the presence of a large molar excess of serum protease inhibitors such as alpha-1-antichymotrypsin and alpha-2-macroglobulin.

To test for non-specific activation of MPP1 by other serum proteases and PSA in human serum, a sensitive hemolysis assay was performed as follows. Red blood cells (RBCs, 2% v/v) were added to plasma or buffer containing MPP1±PSA. The extent of hemolysis was assayed by measuring release of hemoglobin into the supernatant. Addition of 0.1% Triton results in 100% hemolysis within a few seconds and was used as the positive control. Amount of hydrolysis was expressed as a ratio of sample absorbance at 540 nm to absorbance of Triton treated sample. Pre-incubation of the MPP1 ($10^{-8}$ M) with PSA in aqueous buffer alone for 1 hour prior to adding RBCs resulted in about 45% hemolysis (FIG. 2).

To determine whether MPP1 becomes activated in human plasma, MPP1 ($10^{-8}$ M) was incubated in 50% human plasma for 1 hour. In a related experiment, excess PSA (10,000 ng/ml) was first added to the human plasma and allowed to incubate for several hours. MPP1 containing plasma ±PSA was then incubated with human RBCs (2% v/v). The addition of MPP1 to human plasma, or human plasma spiked with high concentration of PSA, resulted in no appreciable hemolysis (i.e. <1% of Triton control, FIG. 2). These results demonstrate that MPP1 can be administered systemically without any significant activation in the blood, even if the blood contains measurable PSA.

Example 4

In Vitro and In Vivo Toxicity of MPP1, MPP2, and MPP3

This example describes methods used to determine the in vitro and in vivo toxicity of MPPs.

To determine in vitro toxicity, a cell viability assay was performed as follows. EL4 mouse T-cell lymphoma cells (ATCC TIB-39) were cultured at $10^5$ cells per well in MTS/PMS Cell Titer 96 (Promega). MPP1, MPP2 and MPP3 at $1\times10^{-13}$ M–$1\times10^{-7}$ M were added as shown in FIG. 3, and incubated with the cells for 4 hours at 37° C. Cell viability was subsequently determined by reading the plate on a plate reader, as directed by the manufacturer of the MTS/PMS kit. As shown in FIG. 3, the MPPs are less toxic than wild-type proaerolysin, with an $LC_{50}$ of $4\times10^{-9}$ (MPP1), $1\times10^{-9}$ (MPP2), and $1\times10^{-7}$ (MPP3), in contrast to an $LC_{50}$ of $1.5\times10^{-10}$ for wild-type.

To determine in vivo toxicity, MPPs were administered to mice intravenously. Wild-type proaerolysin (SEQ ID NO: 2) was highly toxic to mice; a dose of 1 μg caused death within one hour and the $LD_{100}$ at 24 hours (i.e. the dose that kills 100% of animals within 24 hours) following a single IV injection was 0.1 μg. In contrast, the $LD_{100}$ of MPP1 (SEQ ID NO: 4) at 24 hours post injection was 25-fold higher (i.e. 2.5 μg total dose).

Example 5

Preparation of MPP5 (A Histidine-Tagged MPP)

A histidine-tagged MPP according to the present invention (MPP5) was prepared as follows. The plasmid insert containing the gene encoding MPP1 was modified to improve ease of purification and yield. A stretch of 35 nucleotides, including the ribosome binding site and the ATG start codon, that when transcribed, forms a secondary loop structure, which causes reduction in production of the protein (Burr et al., J. Bacteriol. 183: 5956-63, 2001) was modified to prevent loop formation, leaving 23 nucleotides upstream of the ATG start codon (Diep et al., Mol. Microbiol. 30: 341-52, 1998). This increased the amount of MPP that could be released into the culture supernatant of CB3 (Burr et al., J. Bacteriol. 183: 5956-63, 2001). The construct with the new upstream sequence is designated as the γ123 promoter construct. The change was carried out by digesting the MPP1 construct with KpnI and EcoRI, followed by ligation of the resulting fragment into the KpnI/EcoRI site of γ123-aerA::pTZ18U. The resulting construct was called γ123-MPP1::pTZ18U.

Addition of a His tag was accomplished using a 2-step QuikChange (Stratagene) protocol. In the first step, 3 His residues were added to the end of the γ123-MPP1 DNA by synthesizing two primers (the 3 CAT codons encode the extra His residues):

```
EndHis1 (sense):
                                    (SEQ ID NO: 26)
5'-GCT GCC AAT CAA CAT CAT CAT TAA CGG CAG CGC-3'

EndHis1 (antisense)
                                       (SEQ ID: 27)
5'-GCG CTG CCG TTA ATG ATG ATG TTG ATT GGC AGC-3'
```

These primers were used in the protocol suggested by Stratagene for the QuikChange kit. Once the addition of the DNA for the 3 His residues was confirmed by sequencing, a second QuikChange reaction was performed to add nucleotides for the final 3 His residues. In this step, the primers used were:

```
EndHis2 (sense)
                                    (SEQ ID NO: 28)
5'-GCC AAT CAA CAT CAT CAT CAT CAT CAT TAA CGG CAG
CGC-3'

EndHis2 (antisense)
                                    (SEQ ID NO: 29)
5'-GCC AAT CAA CAT CAT CAT CAT CAT CAT TAA CGG CAG
CGC-3'
```

After the second round of PCR, clones were screened and sequenced to confirm that the 6 His residues were correctly inserted at the end of γ123-MPP1 in the correct reading frame, and that no other changes were made to the γ123-MPP1 sequence. The resulting plasmid was named γ123-MPP5::pTZ18U, and the γ123-PSAH6 insert region was sequenced (see FIG. 34).

The nucleic acid sequence of γ123-MPP5 differs from that of the MPP1 construct in the region before the ATG start codon, with the γ123 promoter replacing the normal aerA upstream sequence. The sequence also has the additional CAT repeats immediately before the TAA stop codon. When the open reading frame of γ123-MPP5 was translated into the amino acid sequence, the only difference seen compared to the MPP1 amino acid sequence was the addition of 6 histidine residues at the C-terminus of the protein.

Cloning of γ123-MPP5 into pMMB208 Expression Vector

The γ123-MPP5 created as a result of the addition of γ123 promoter and His-tag, was cloned into plasmid pMMB208. This plasmid was chosen as it confers chloramphenicol resistance, it contains an IPTG inducible tac promoter, and it can be mobilized into *Aeromonas salmonicida* by transconjugation. Thus the γ123-PSA PAH6 insert was cloned into the HindIII and EcoRI sites of the pMMB208 plasmid. The resultant plasmid, γ123-MPP5::208, was transconjugated into *A. salmonicida* strain CB3 for the production of MPP5.

In order to purify GLP MPP5, 30 L of sterile defined media set at an initial pH of 6.90±0.15 and temperature 27° C. was inoculated with approximately 1% v/v of shake flask inoculum. The pH of the medium was maintained at 6.90±0.15 by automatic addition of sterile acid/alkali during the fermentation. Fermenter RPM and SLM were adjusted to maintain Dissolved Oxygen Tension (DOT) of ≥20% in the vessel at all times. Expression of MPP5 was induced by addition of isopropyl thiogalactopyranoside (IPTG) when the cell density reached an OD at 600 nm of 0.3-0.6. Expressed protein was secreted into the medium and harvested several hours after induction. The supernatant containing MPP5 was recovered using a 60 SP CUNO filter. Following cell separation, the supernatant was concentrated using a 30,000 NMWC TFF membrane. Concentrated supernatant was purified using two chromatographic steps that yielded protein of acceptable purity; nickel chelating chromatography, followed by anion exchange chromatography. The MPP5 containing fractions from the anion exchange chromatography step were pooled and the resulting material was concentrated to approximately 1 mg/mL by ultrafiltration and subsequently diafiltered into formulation buffer. Purified MPP5 was sterile filtered using a 0.22 μm absolute filter in a certified biological safety cabinet and frozen to −70° C. until required. Final yield of purified MPP5 using this process was approximately 100 mg/L.

Example 6

An Acute Intraprostatic or Intravenous Bolus Injection Toxicity Study of MPP5 in the Albino Rat This example shows preliminary results of a study indicating that intraprostatic administration of a histidine-tagged MPP (MPP5) to rats was able to decrease the weight of the prostate gland.

Summary of Results

The objective of this study was to confirm the maximum tolerated dose (MTD) and to investigate the potential toxicity and toxicokinetics of an MPP (MPP5) following a single intraprostatic injection or intravenous bolus injection to male rats followed by a 1, 14, or 28-day observation period. MPP5 is a histidine tagged proaerolysin molecule which comprises a PSA cleavage site.

The study design is detailed in Tables 7 and 8:

TABLE 7

Study Design MTD Study

| Group | Treatment | Dose Level (μg) | Dose Volume (μL) IP | Dose Volume (μL) IV | Number of Males IP | Number of Males IV |
|---|---|---|---|---|---|---|
| 6 | MPP5 | 10 | 20 | 500 | 3 | 3 |
| 7 | MPP5 | 20 | 20 | 500 | 3 | 3 |
| 8 | MPP5 | 40 | 20 | 500 | 3 | 3 |
| 9 | MPP5 | 50 | — | 500 | — | 3 |

IP—Intraprostatic, IV—Intravenous, Animals were terminated following a 48-hour observation period

TABLE 8

Main and Toxicokinetic Study Design

| Group | Treatment | Dose Level (μg) | Route | Main Study Terminal Sacrifice Males per Group Day 2 | Day 15 | Day 29 | TK Study Animals |
|---|---|---|---|---|---|---|---|
| 1 | Control | 0 | IP | 7 | 7 | 6 | 9 |
| 2 | MPP5 | 2 | IP | 7 | 7 | 6 | 9 |
| 3 | MPP5 | 10 | IP | 7 | 7 | 6 | 9 |
| 4 | MPP5 | 25 | IP | 7 | 7 | 6 | 9 |
| 5 | MPP5 | 25 | IV | 7 | 7 | 6 | 9 |

IP—Intraprostatic (20 μL), IV—Intravenous (0.05 mL), TK—Toxicokinetic

The following were evaluated: clinical signs, body weight, food consumption, opthalmology, hematology, serum chemistry, urinalysis, toxicokinetics, macroscopic observations at necropsy, organ weights and histopathology. There were no effects on body weight, body weight gain, food consumption, opthalmology or urinalysis parameters. One MTD animal treated intraprostatically at 40 μg was found dead on Day 2. Prior to death there were no treatment-related clinical signs. Dark foci were seen in the stomach and a dark area and swelling were noted at the injection site (prostate). Two main study animals treated intraprostatically at 25 μg were found dead on Day 2. Prior to death there were no treatment-related clinical signs noted for one animal, but fur staining (muzzle), blue skin, decreased activity, weakness, decreased muscle tone, clear liquid discharge (periorbital), pale eyes, labored breathing, lying on side and cold to touch were noted in the other animal. Macroscopic findings in one animal included: a dark area at the injection site (prostate); dark foci in the testes; pale, clear fluid in the abdomen cavity, including pale material adjacent to the liver. In the other animal, lesions were seen in the fat and jejunum, including discoloration. Adhesions were seen in the liver, thickening of the pancreas, multiple dark areas in the stomach and thymus, and dark foci in the abdominal fat, adjacent to the epididymides. A specific cause of death was not identified for these two males, however, it was assumed that the severity of the prostatic inflammation with its proximity to kidneys and concurrent systemic degenerative alterations contributed to the death of these animals.

Treatment-related clinical signs were seen in animals treated at all MTD IP dose levels. Red fur staining was seen in some animals from all groups at one or more sites including the muzzle, jaw, forepaw, periorbital, and ventral/dorsal cervical between Days 1 and 4. Blue skin discoloration (surgical site, abdominal, urogenital or inguinal sites) was noted at 20 and 40 μg in 1/3 animals each, including urogenital swelling in one animal at 40 μg. In MTD animals treated intravenously, red fur staining (muzzle and/or periorbital), were noted with a greater incidence in animals treated at 50 μg.

Red fur staining (muzzle) was predominantly seen in main study animals from all IP dose levels including the controls, but generally with a higher incidence in treated animals. This clinical sign was considered likely treatment-related. Red fur staining (muzzle) was also observed in all main study IV animals. Additional clinical signs were noted at the site of injection (tail) and included skin scabs and/or redness or other discoloration. In addition, two animals required tail amputation due to lesions and suspected self-mutilation. These latter changes suggested an irritant potential of the test article formulation which was further supported following histopathological examinations.

A dose-related increase was seen in some white cell parameters in main study IP animals on Day 2. WBC, neutrophil, monocyte and basophil counts were increased in all treated groups at 10 and/or 25 μg. Increases were also seen in MCHC at 25 μg and in MPV at all dose levels. Decreases were recorded in percent and absolute reticulocytes at all dose levels. A slight, but dose-related increase in activated partial thromboplastin time was noted at all IP dose levels. Similar changes were observed in animals treated intravenously at 25 μg. WBC, neutrophil and basophil counts were increased. MCHC, MPV and red cell distribution width (RDW) were also increased and percent and absolute reticulocytes were decreased. In animals terminated after 14 days of observation, increases were seen in RDW and MPV only and after 28 days, there were no differences noted in hematology parameters. Changes noted in animals terminated after 1 day of observation were considered to be test article-related. Results shown following the 15-day and 28-day observation period demonstrate recovery from these changes.

Dose related increases in mean aspartate aminotransferase and alanine aminotransferase concentration were seen on Day 2 and considered marked at 25 μg. Increases in direct bilirubin, urea, creatinine and triglyceride concentration were also noted at 25 μg IP. Decreases were seen in glucose concentration at 25 μg and albumin concentration was decreased at ≥10 μg with an associated decrease in albumin to globulin ratio and decrease in total protein concentration at 25 μg only. In animals treated 25 μg IV, a slight increase was seen in urea and calcium concentration and a slight increase in globulin concentration was also noted with a corresponding decrease in albumin to globulin ratio. These changes were considered related to the inflammation observed at the site of injection. On Day 29, an increase in alanine aminophosphatase concentration and a decrease in indirect bilirubin concentration were noted at 25 μg IP only.

The composite terminal half-life was estimated at 12.8 hours for intravenous administration. The $C_{max}$ could be back extrapolated to time 0 hours with a value of 81.3 ng/mL. The observed peak value (at the first sampling time) was 74.3 ng/mL. The systemic clearance (CL) and volume of distribution ($V_z$) was estimated as 46.3 mL/h and 841 mL, respectively. Following intraprostatic administration, observed $t_{max}$ occurred at 4 hours post dose for all cases, with peak levels of 2.95 and 3.51 ng/mL at 10 and 25 μg, respectively. The observed $AUC_{0\text{-}tlast}$ appeared to decrease at the higher dose, due to the different $t_{last}$ observed. Dose linearity for the intraprostatic route was assessed using $C_{max}$ and $AUC_{0\text{-}tlast}$. Both dose normalized exposure parameters were decreased from 10 μg to 25 μg and the corresponding estimated bioavailabilities were 23.7 and 4.38%, all of which was indicative of limited absorption of MPP5 into the systemic circulation from the prostate with increasing dose level.

During the MTD phase, single IP doses of MPP5 at 40 μg in male rats were associated with mortality with no specific cause of death. A single IV dose of MPP5 in male rats was tolerated up to a maximum dose of 50 μg.

During the main study phase, single IP injection of MPP5 in male rats resulted in the death of 2 rats at 25 μg, prostate injection site macroscopic, microscopic and organ weight alterations at ≥2 μg. The cause of death of the two males could not be ascribed with certainty but it was assumed that the severity of the prostatic inflammation and associated changes contributed to the deterioration/death of these animals. The other test article related changes were observed at 2, 15, and/or 29 days of the recovery period. Macroscopic, microscopic and organ weight alterations in other tissues were considered to be secondary to the prostate injection site changes.

Single IV injection of MPP5 in male rats resulted in tail vein injection site macroscopic and/or microscopic alterations at a dose of ≥25 μg. These changes were observed at 2, 15 and 29 days of the recovery period with progressive recovery at 25 μg and were indicative of an irritant effect of the test article. Macroscopic and microscopic alterations in other tissues were considered to be secondary to the injection site changes. Liver and spleen organ weight changes on Day 2 were without microscopic correlation and recovered by Day 15.

In conclusion, the administration of MPP5 by single intraprostatic injection at dose levels up to 40 μg or intravenous injection at dose levels up to 50 μg resulted in mortality at 25 μg and 40 μg IP with no clear cause of death, however the extent of the test article related prostatic inflammation and with proximity to the kidneys and concurrent systemic degeneration were considered contributory factors to the deaths. Mostly reversible changes were seen in clinical signs (≥2 μg), hematology and clinical biochemistry parameters at ≥10 μg. Pathological changes persisted at all dose levels in a dose-related fashion but showed evidence of regression in animals treated intravenously. Consequently, the no-observable-effect-level (NOEL) was not determined for either the intraprostatic or the intravenous route.

Experimental Procedures 3.1. Test System

A total of 180 male Sprague Dawley (Crl:CD® (SD) IGS BR) rats (*Rattus norvegicus*) were used. At the start of treatment, animals were 12 to 15 weeks of age and ranged in weight from 399 to 495 g.

3.2 Veterinary Treatments

On Days 4 and 7, tail amputations were performed on animals 5010 and 5004, respectively, due to suspected self-mutilation. As these animals were treated intravenously, the amputated tissue was retained in neutral buffered 10% formalin for pathological evaluation.

Prior to treatment, all animals were weighed and randomly assigned to treatment groups using a computer-based randomization procedure. Randomization was by stratification using body weight as the parameter. Animals in poor health were not assigned to groups. The study design is detailed in Table 9 (MTD) and Table 7 (Main).

TABLE 9

MTD Study

| Group | Treatment | Dose Level (μg) | Dose Volume (μL) IP | IV | Number of Males IP | IV |
|---|---|---|---|---|---|---|
| 6 | MPP5 | 10 | 20 | 500 | 3 | 3 |
| 7 | MPP5 | 20 | 20 | 500 | 3 | 3 |
| 8 | MPP5 | 40 | 20 | 500 | 3 | 3 |
| 9 | MPP5 | 50 | — | 500 | — | 5 |

IP—Intraprostatic, IV—Intravenous

Animals assigned to the MTD Study were terminated following a 48-hour observation period. On Day 1, animals 6001 and 8001 assigned to the IP dose regimen were replaced by spare animals 6101 and 8101, respectively, due to a technical error (overdosed by 10 times their assigned dose). Later the same day, animal 8001 (400 μg) was found dead approximately 4 hours post dose and animal 6001 (100 μg) was euthanized at the end of Day 1 due to poor condition. These animals were subject to necropsy including a detailed external and internal examination, however; no tissues were retained for histopathological examination. Prior to death, clinical signs for animal 6001 included weakness, decreased muscle tone, eyes partly closed, cold to touch, decreased activity and abnormal gait. Clinical signs for animal 8001 included lying on side, labored breathing, decreased respiratory rate, blue skin, pale eyes, cold to touch, decreased activity, weakness and decreased muscle tone. Gross examination for animal 6001 revealed only a single dark area at the administration site (prostate). For animal 8001, bilateral dark discoloration was noted in the mandibular lymph nodes and swelling was noted at the injection site (prostate). These deaths were considered probably related to the high MPP5 administration and are reported in order to provide further reference for the MTD in this study.

On Day 13 (MTD study), additional animals were added at a dose level of 50 μg via the intravenous route in order to further explore MPP5 toxicity via this route due to limited observations seen at ≤40 μg.

Prior to initiation of dosing, animal 1025 was considered unsuitable for use in the study due to a malocclusion and was replaced by a spare animal, which became animal 1125. All animals remaining unassigned to groups were released from the study and their disposition documented.

3.3. Test and Vehicle Control Articles

The test article was MPP5 (Lot Number PTIC-MF-PAL-DS-001), at a concentration of 3.2 mg/mL. The test article was colorless solid when frozen, and was stored at −20° C., out of direct light. The vehicle control was Phosphate Buffered Saline-EDTA, pH 7.4.

3.4 Preparation of Dose Formulations

Dose formulations were prepared on the day of use. On each day, appropriate amounts of the 3.2 mg/mL stock solution of MPP5 was measured and diluted with appropriate amounts of PBS, 1 mM EDTA.

3.5 Administration of Test/Control Article

MTD Study

Groups of three rats were dosed either intraprostatically or intravenously as described in section 3.2 and in Table 9, on a single day and observed for clinical signs and potential toxicity for up to 48 hours post dose. For intravenous administration, the test article was administered by intravenous injection, via the tail vein at a dose volume of 0.5 mL.

For intraprostatic groups, prior to dose administration, animals were anesthetized using isoflurane. At least 1 hour prior to surgery and up to 2 days following surgery, animals received an intramuscular antibiotic injection of Benzathine penicillin G and Procaine Penicillin G (0.1 mL). Animals also received a subcutaneous injection of Buprenorphine (0.05 mg/kg) on the day of surgery.

Using a scalpel blade, a midline incision of approximately 2 cm was made, starting 0.5 cm cranially of the penis. The abdomen was cut on the same length. The two ventral lobes of the prostate were localized and 20 μL of formulated MPP5 or PBS/EDTA pH 7.4 was injected into the right ventral lobe using an appropriate syringe. Prior to closing, the site was irrigated with warm (approximately 37° C.) 0.9% Sodium Chloride Injection, U.S.P. The site was closed in layers using appropriate suture material.

For animals assigned to the intravenous route, the test article was administered intravenously, via the tail vein at a dose volume of 0.5 mL.

Main Study

Animals were dosed according to the procedures established during the MTD phase. For animals assigned to the intravenous route, the test article was administered intravenously, via the tail vein at a dose volume of 0.05 mL. After completion of treatment, main study animals were maintained undosed for a 1, 14 or 28-day recovery period.

3.6 Observations

Clinical Observations: All animals were observed twice daily (once on the day of arrival and necropsy) for mortality and signs of ill health and/or reaction to treatment throughout the study. In addition, a detailed examination was performed at least once prior to the start of treatment and daily throughout the treatment and recovery periods (main and MTD study animals).

Body Weights: Individual body weights were measured for all animals on the day of randomization and twice weekly throughout treatment and recovery periods (main study animals). In addition, each main study/recovery animal was weighed (fasted) before scheduled necropsy. MTD study animals were weighed prior to dosing and prior to terminal sacrifice.

Food Consumption: Individual food consumption for all main study animals was measured weekly commencing the last week of the pretreatment period and throughout the treatment and recovery periods.

Opthalmology: Once prior to the start of treatment (all animals) and again prior to necropsy (main study animals), funduscopic (indirect opthalmoscopy) and biomicroscopic (slit lamp) examinations were performed by a board-certified veterinary ophthalmologist.

Laboratory Investigations: Blood sampling for hematology and serum chemistry testing was performed on all main study animals at necropsy on Days 2, 15 and 29. Food was removed overnight from animals prior to blood sampling. Blood samples were collected from the abdominal aorta under isoflurane anesthesia.

Urine samples were collected prior to necropsy on Days 2, 15 and 29 from main study animals placed in metabolism cages for an approximate 16-hour collection period, during which the animals were deprived of food.

The hematological parameters examined were: activated partial thromboplastin time, blood cell morphology, erythrocyte indices (MCV, MCH, MCHC and RDW); hematocrit hemoglobin, mean platelet volume platelet count prothrombin time, red blood cell count, reticulocyte count (absolute and percent), white blood cell count (total, absolute and percent differential).

The Serum Chemistry, Parameters examined were: A/G ratio (calculated) alanine aminotransferase, albumin, alkaline phosphatase, aspartate aminotransferase, blood urea nitrogen, calcium chloride cholesterol creatinine, globulin (calculated), glucose, inorganic phosphorus potassium, sodium, total bilirubin, total protein, triglycerides.

The Urinalysis Parameters examined were: bilirubin, blood color and appearance, creatinine, glucose, ketones, microscopy of centrifuged deposit nitrite, pH, protein, specific gravity urobilinogen volume.

Immunogenicity Evaluation (Day 14 and Day 28 Main Study Only)

Blood samples were collected from each main study rat pre-dose (baseline) from a jugular vein and at terminal sacrifice from the abdominal aorta following isoflurane anesthesia (along with blood sampling for clinical pathology). Samples were placed in serum separation tubes, inverted several times, allowed to clot at room temperature for 20 to 30 minutes, and then centrifuged at approximately 1200 g for 10 minutes at approximately 4° C.

3.7 Toxicokinetics

On Study Day 1, blood samples (4.5 mL) were collected by venipuncture of the jugular vein into $K_3$ EDTA tubes alternately from three toxicokinetic study rats per group per time point, at pre-dose, 15, and 30 minutes and 1, 2, 4, 8, 24 and 48 hours post-dose. Blood samples were placed immediately on wet ice until separated by refrigerated centrifugation (approximately 2 to 8° C.) at approximately 2700 rpm for 10 minutes. Plasma was separated, transferred into a second tube and placed on dry ice. Plasma samples were stored at approximately −20° C. and analyzed for levels of MPP5.

Plasma samples were analyzed by Enzyme Linked Immunosorbent Assay (ELISA) based on the antibody sandwich principle. The capture antibody (mouse anti-aerolysin monoclonal antibody) specific to MPP5 was coated onto the 96-well microtitre plate to create the solid phase, which captured the analyte present in the standards and quality control samples. The secondary antibody (rabbit anti-aerolysin polyclonal antibody) that binds to a different epitope of the analyte molecule, was then added to complete the antibody-analyte-antibody sandwich. The detection antibody enzyme conjugate (goat anti-rabbit IgG, horse radish peroxidase conjugate) that binds to the constant region of the rabbit IgG antibody, was then added. The captured conjugate was visualized using the tetramethylbenzidine substrate and measured at 450 nm using a SpectraMAX plate reader.

For the intraprostatic dose route, non-compartmental toxicokinetic analysis was performed on the plasma concentration data. As practical, toxicokinetic analysis included assessment of the $t_{max}$, $C_{max}$, AUC, k and $t_{1/2}$. The $t_{max}$ and $C_{max}$ are observed values. Where possible, the AUC parameter was calculated by the trapezoidal rule method (Gibaldi and Perrier, 1982) using the standard computer software program WinNonlin (Version 3.2). The k was determined by linear regression analysis of selected time points in the apparent terminal phase of the concentration vs. time curves. The apparent terminal half-life was calculated as follows:

$$t_{1/2}=ln2/k.$$

For the intravenous dose route, non-compartmental toxicokinetic analysis was performed on the plasma concentration data. As practical, toxicokinetic analysis included assessment of the $t_{max}$, $C_{max}$, AUC, k, $t_{1/2}$, $V_z$ and CL. The $C_{max}$ will be back-extrapolated to time 0 hour. The AUC parameter was calculated by the trapezoidal rule method (Gibaldi and Perrier, 1982) using the standard computer software program WinNonlin (Version 3.2). The k was determined by linear regression analysis of selected time points in the apparent terminal phase of the concentration vs. time curves. The apparent terminal half-life was calculated as follows: $t_{1/2}$=ln2/k. Clearance (CL) was calculated by Dose/AUC and the apparent volume of distribution ($V_Z$) was calculated as CL/k.

3.8. Terminal Procedures

Gross Pathology: MTD study animals found dead during the study were subject to necropsy without tissue preservation. All main study and recovery animals found dead during the study were subjected to necropsy and tissue samples were preserved.

On completion of the treatment and recovery period, all surviving animals were exsanguinated from the abdominal aorta following isoflurane anesthesia and blood sample collection for laboratory investigations. In order to avoid autolytic change, a complete gross pathology examination of the carcass was performed as soon as possible after euthanasia of all main study animals.

Organ Weights: For each main study animal euthanized at scheduled necropsy, the following organs were dissected free of fat and weighed: adrenal glands, brain, heart, kidneys, liver, lungs, testes, pituitary, prostate, spleen, thymus, thyroid lobes (with parathyroids). Paired organs were weighed together and organ weight ratios relative to body weights were calculated.

Tissue Preservation: On completion of the necropsy of each main study animal, the following tissues and organs were retained: Abnormalities, animal identification, adrenals, aorta (thoracic), bone and marrow (sternum), brain (cerebrum, cerebellum, midbrain and medulla oblongata), cecum, colon, duodenum, epididymis, esophagus, eyes, Harderian glands, heart (including section of aorta), ileum, injection site (prostate) Groups 1 to 4, injection site (tail vein) Group 5, jejunum, kidneys, lacrimal glands, liver (sample of 2 lobes), lungs (sample of 2 lobes), lymph nodes (mandibular and mesenteric), mammary gland (inguinal), nasal cavities and sinuses (3 levels), optic nerves, pancreas, pituitary, prostate (uninjected lobes), rectum, salivary gland, sciatic nerve, seminal vesicles, skeletal muscle, skin (inguinal), spinal cord (cervical), spleen, stomach, testes, thymus, thyroid lobes (and parathyroids), tongue, trachea, ureter (bilateral), urinary bladder.

Neutral buffered 10% formalin was used for tissue fixation and preservation except for epididymis, eyes, optic nerves and testes, which were fixed in Zenker's fluid (euthanized animals only). For all euthanized animals, 3 femoral bone marrow smears, were prepared and stained. The smears were retained but not evaluated.

Histopathology: Tissues were embedded in paraffin wax, sectioned (nasal cavities and sinuses, sternum and tail vein injection site were decalcified prior to sectioning), and stained with hematoxylin and eosin and examined histopathologically as follows:

Groups 1, 4 and 5: Tissues listed under tissue preservation (except animal identification and rectum)

Group 2 and Group 3: Tissues showing treatment-related findings, all gross lesions and target tissues listed below:

Tissue samples of target tissues including brain, heart, kidneys, liver, lymph nodes, injection site (prostate), prostate (uninjected lobes), spleen, thyroid lobes (and parathyroids), ureter and urinary bladder, were processed and examined for all main study animals in all dose groups. Optic nerves, parathyroid glands and mammary gland were only examined histopathologically if present in routine sections of eyes, thyroid and skin, respectively.

Statistical Analyses

Numerical data obtained during the conduct of the study were subjected to calculation of group means and standard deviations. For each parameter of interest, group variances were compared using Levene's test at the 0.05 significance level. When differences between group variances were not found to be significant, a parametric one-way analysis of variance (ANOVA) was performed. If significant differences among the means were indicated by the ANOVA ($p \leq 0.05$), then Dunnett's "t" test was used to perform the group mean comparisons between the control group and each treated group.

Whenever Levene's test indicates heterogeneous group variances ($p \leq 0.05$), the non-parametric Kruskal-Wallis test was used to compare all considered groups. If the Kruskal-Wallis test was significant ($p \leq 0.05$), then the significance of the differences between the control group and each treated group was assessed using Dunn's test.

For each pairwise group comparison of interest, significance was reported at the 0.05, 0.01 and 0.001 levels.

Results and Discussion

1. Dose Formulation Analysis

The results of pH, osmolality and density assessments of the dose formulations used in the study are indicated in Table 10.

TABLE 10

Dose Formulation pH, Osmolality and Density

| Group No. | Dose Level (μg) | Route | pH | Osmolality (mOsm/kg) | Density ($g/cm^3$) |
|---|---|---|---|---|---|
| 1 | 0 | IP | 7.39 | 300 | 1.0037 |
| 2 | 2 | IP | 7.38 | 299 | 1.0030 |
| 3 | 10 | IP | 7.36 | 298 | 1.0041 |
| 4 | 25 | IP | 7.36 | 295 | 1.0049 |
| 5 | 25 | IV | 7.36 | 301 | 0.9999 |
| 6 | 10 | IV/IP | 7.35/7.35 | 308/304 | 0.9941/1.0043 |
| 7 | 20 | IV/IP | 7.35/7.34 | 307/302 | 1.0052/1.0002 |
| 8 | 40 | IV/IP | 7.35/7.32 | 305/297 | 1.0048/1.0040 |
| 9 | 50 | IV | 7.37 | 308 | 1.0057 |

2. Mortality

MTD Study

On Day 2, animal 8101 (40 μg, IP) was found dead. Prior to death, there were no treatment-related clinical signs. At necropsy, dark foci were seen in the stomach and a dark area and swelling were noted at the injection site (prostate). No clear cause of death was determined.

Main Study

On Day 2, animals 4005 and 4013 (25 μg, IP) were found dead. Prior to death, there were no treatment-related clinical signs noted for animal 4013. Fur staining (muzzle), blue skin, decreased activity, weakness, decreased muscle tone, clear liquid discharge (periorbital), pale eyes, labored breathing, lying on side and cold to touch were noted for animal 4005.

At necropsy for animal 4005, macroscopic findings included: a dark area at the injection site (prostate); dark foci in the testes; pale, clear fluid in the abdominal cavity, including pale material adjacent to the liver. For animal 4013, lesions were seen in the fat and jejunum, including discoloration. Adhesions were seen in the liver, thickening of the pancreas, multiple dark areas in the stomach and thymus, and dark foci in the abdominal fat, adjacent to the epididymis. The cause of death in both cases was uncertain, however, it was assumed that the severity of the prostatic inflammation observed histopathologically with its proximity to kidneys and concurrent systemic degenerative alterations contributed to the death of these animals.

3. Clinical Observations

MTD Study

Treatment-related effects were seen in animals treated at all MTD IP dose levels (10 to 40 μg). Red fur staining was seen in 2/3 animals from all groups at one or more sites including the muzzle, jaw, forepaw, periorbital, and ventral/dorsal cervical between Days 1 and 4. Blue skin discoloration (surgical site, abdominal, urogenital or inguinal sites) was noted at 20 and 40 μg in 1/3 animals each, including urogenital swelling in animal 8002 (40 μg). Although these observations may be related to the surgical procedure, the incidence and severity was increased at 40 μg.

In animals treated intravenously, treatment-related clinical signs were limited to red fur staining (muzzle and/or periorbital), which were noted with a greater incidence in animals treated at 50 μg. Up to 5/5 high dose animals were seen with these signs compared to 1/3 that were observed with these signs at <50 μg during Days 1 to 4.

Main Study

Day 2 Termination

Red fur staining (muzzle, periorbital, and/or cranium) was noted in some animals from all IP dose levels including 3/7 control animals, 1/7 animals at 2 μg, 5/7 animals at 10 μg and 3/7 animals at 25 μg. Animal 4014 (25 μg) was observed with reddish discharge from both eyes and animal 4015 had decreased activity and was cold to touch prior to necropsy on Day 2.

4. Food Consumption

There was no effect on food consumption.

5. Opthalmology

There were no opthalmologic findings.

6. Hematology

In IP animals terminated on Day 2, a dose-related 2-fold or greater increase was seen in some white cell parameters. White blood cell (WBC), neutrophil, monocyte and basophil counts were increased in all treated groups, attaining statistical significance at 10 and/or 25 μg. Statistically significant increases were also seen in mean corpuscular hemoglobin concentration (MCHC) at 25 μg and in mean platelet volume (MPV) at all dose levels. Decreases were recorded in percent and absolute reticulocytes at all dose levels. A slight, but dose-related increase in activated partial thromboplastin time was noted at all IP dose levels, attaining statistical significance at 25 μg.

Similar changes were observed in animals treated intravenously with 25 μg MPP5. WBC, neutrophil and basophil counts were increased. MCHC, MPV and red cell distribution width (RDW) were also increased and percent and absolute reticulocytes were decreased. In animals terminated after 14 days of observation, increases were seen in RDW and MPV only. After 28 days of observation, there were no differences noted in hematology parameters. The changes noted in animals terminated after 1 day of observation were considered test article-related and were correlated histopathologically. The results shown following the 15-day and 28-day observation period demonstrate evidence of recovery from these changes. Other minor differences were considered incidental and unrelated to treatment.

7. Serum Chemistry

On Day 2, dose related increases, attaining statistical significance at 25 μg IP, were seen in mean aspartate aminotransferase and alanine aminotransferase concentration. These were considered marked changes at 25 μg. Increases in direct bilirubin, urea, creatinine and triglyceride concentration were also noted at 25 μg IP. Decreases were seen in glucose concentration at 25 μg. Albumin concentration was decreased at ≥10 μg with an associated decrease in albumin to globulin ratio and decrease in total protein concentration at 25 μg only.

In animals treated 25 μg IV, a slight increase was seen in urea and calcium concentration. A slight increase in globulin concentration was also noted with a corresponding decrease in albumin to globulin (A/G) ratio. The changes in globulin (and consequently in A/G ratio) were considered possibly related to inflammation at the injection site.

At Day 15, statistically significant decreases were seen in triglyceride concentration at all dose levels including IV treated animals. These were considered of no toxicological significance and possibly related to minor alterations in lipid metabolism.

At Day 29, an increase in alanine aminophosphatase concentration and a decrease in indirect bilirubin concentration was noted at 25 μg IP only. These changes may be related the secondary changes described histopathologically.

There were no other toxicologically significant changes.

8. Urinalysis

There were no apparent effects on urinalysis parameters.

9. Toxicokinetics

Plasma concentrations of MPP5 were generally similar between individual animals of each group at each time point. Some variability in plasma concentration values was expected as dose levels were not normalized according to body or prostate weight. MPP5 was not quantifiable in samples collected from control animals or from samples collected pre dose.

In test groups, plasma concentrations of MPP5 generally increased with increasing dose levels of test article administered intraprostatically, with no detectable concentrations in any samples collected from animals at 2 μg. MPP5 was detectable up to 24 hours in animals treated at 10 μg, 8 hours in animals treated at 25 μg and 48 hours in Group 5 (25 μg, intravenous). In all, three composite profiles were obtained and considered for further evaluation.

A terminal phase could be estimated for the composite IV profile, where the terminal half-life was estimated as 12.8 hours. For the remaining profiles, a terminal phase could not be estimated with confidence. Therefore, all parameters derived from k ($t_{1/2}$, $AUC_{0\text{-}inf}$ and % extrapolated) were not reported. For the IV profile, the percent of $AUC_{0\text{-}inf}$ extrapolated from $AUC_{0\text{-}tlast}$ was less than 6%, indicating that this profile was well characterized from the experimental data.

Following intraprostatic dosing, observed $t_{max}$ occurred at 4 hours post dose for all cases, with peak levels of 2.95 and 3.51 ng/mL at 10 and 25 μg, respectively. The observed $AUC_{0\text{-}tlast}$ decreased at the higher dose (48.5 vs 22.4 ng·h/mL). This result was biased, however, by the shorter $t_{last}$ observed at 25 μg IP (8 hours vs 24 hours at 10 μg IP). Following IV dosing the $C_{max}$ could be back extrapolated to time 0 hours with a value of 81.3 ng/mL. The observed peak value (at the first sampling time) was 74.3 ng/mL. The systemic clearance (CL) and volume of distribution ($V_z$) was estimated as 46.3 mL/h and 841 mL, respectively.

Dose linearity following intraprostatic dosing was assessed at 10 to 25 μg dose levels using dose normalized mean peak plasma concentration and area under the curve exposure parameters ($C_{max}$ and $AUC_{0\text{-}tlast}$, respectively). Both dose normalized exposure parameters were decreased from 10 μg to 25 μg. This could be indicative of limited absorption of MPP5 into the systemic circulation from the prostate.

Based on the areas ($AUC_{0\text{-}tlast}$) observed in the mid to high doses following intraprostatic administration, the percent bioavailability was determined by comparing these areas (normalized to dose level) to the dose normalized area obtained following intravenous administration. The estimated bioavailabilities were 23.7 and 4.38%.

10. Organ Weights

Intraprostatic Injection

Changes in absolute and relative organ weights (organ weight to body weight), occasionally attaining statistical significance were noted in the prostate on all sacrifice days and in the spleen on sacrifice Day 2. Prostatic weights ranged from 26% to 45% higher in animals at 10 μg and 25 μg on Day 2 compared to controls. Prostate weights were 16% to 24% lower compared to controls in treated animals on Day 15 and 19% to 21% lower at ≥10 μg on Day 29. These changes were consistent with the observed microscopic findings. Spleen weights were approximately 36% lower at 25 μg on Day 2 compared to controls. This was considered a secondary change and recovered by Day 15.

Intravenous Injection

On Day 2, animals at 25 μg IV had higher liver and spleen weights of approximately 21% compared to controls without histological correlation and recovered by Day 15.

11. Gross Pathology

MTD Study

Prostatic injection site changes were identified at all IP dose levels. Alterations included dark discoloration/area, mottling, and enlargement/swelling. Animals replaced on Day 1 (Nos. 6001, 8001) or found dead (No. 8101) on Day 2 following IP injection had some of the prostatic injection site changes as described above. A specific cause of death was not determined. Intravenous (IV) injection in the tail vein was associated with scabs on the tail of Group 8 and 9 animals. Other changes were considered sporadic, procedure-related or agonal and not treatment-related.

Main Study

Prostatic injection site changes were identified on all sacrifice days. Day 2 changes were characterized by dark discoloration/area/foci, adhesion, and enlargement/swelling at all dose levels. Day 15 and 29 alterations were described as pale area, raised, firm, and/or small in animals at ≥10 μg. Adhesions and pale areas were frequently noted on the liver and spleen on sacrifice Day 15 and 29 at ≥10 μg and were likely secondary to the prostatic injection site alterations. Animal 4005 (25 μg IP) found dead on Day 2 had some of the prostatic injection site changes as described above. A specific cause of death was not determined.

Intravenous injection in the tail vein was associated with scabs on the tail on all sacrifice days. Ulceration was present on Day 15 and 29 with or without loss of the tail tip. Liver enlargement was noted on sacrifice Day 2.

Other changes were considered sporadic, procedure-related or agonal and not treatment-related.

12. Histopathology

Intraprostatic Injection

Microscopic changes attributed to MPP5 were observed at the prostate injection site at ≥2 μg on Day 2, 15 and 29. Minimal to severe acute inflammation was observed at all doses on Day 2, generally, with a dose-dependent increase in severity. The inflammation was characterized by fibrin, mixed cell infiltrate and acinar necrosis. Edema and hemorrhage were observed in treated and control animals and therefore, considered partially procedure-related. Minimal to marked chronic inflammation and/or fibrosis were observed at all doses on Day 15 and 29, generally, with a dose-dependent increase in the severity. Fibrosis, mononuclear infiltrate and acinar necrosis characterized the inflammation. These changes were frequently accompanied by concurrent acinar atrophy/dilatation. Minimal fibrosis and acinar atrophy/dilatation were infrequently observed in controls on Day 29 and therefore, considered primarily treatment-related. Acute and chronic changes were also observed in the adjacent prostatic lobe, generally, with a lower incidence and severity of change. Acute inflammation, edema and hemorrhage correlated with higher prostate weights on Day 2 and chronic inflammation, fibrosis and acinar atrophy/dilatation with lower prostate weights on Day 15 and 29 and generally correlated with the macroscopic findings. These alterations indicate an irritating effect of MPP5 at the prostatic injection site.

Numerous microscopic observations in other tissues were considered secondary to the prostatic injection site inflammation either by expansion into adjacent pelvic organs and throughout the abdominal cavity or systemic reactive and/or degenerative changes. Acute and chronic inflammation with or without hemorrhage and fibrosis of capsular or serosal surfaces, respectively, were observed in fat, liver, large and small intestines, pancreas, spleen, stomach, seminal vesicles, epididymis, testis and urinary bladder. Reactive and/or degenerative changes included: bone marrow myeloid hyperplasia; increased extramedullary hematopoiesis in the spleen; lymphoid atrophy and/or hyperplasia in lymph nodes, spleen and thymus; hepatic mononuclear infiltrate, single cell necrosis and increased mitotic figures, and; testicular atrophy (with concurrent epididymis oligo/aspermia). Splenic lymphoid atrophy would account for the low spleen weights noted in males at 25 μg on Day 2 and therefore, considered secondary.

A specific cause of death was not identified for two males (25 μg) found dead on Day 2. However, it was assumed that the severity of the prostatic inflammation with its proximity to kidneys and concurrent systemic degenerative alterations may have contributed to the death of these animals.

Other changes were sporadic, incidental, agonal or were expected in this age and breed of rat and not directly treatment-related.

Intravenous Injection

Microscopic changes attributed to MPP5 were observed at the tail vein injection site on Days 2, 15 and 29. Minimal to marked acute inflammation of the dermis and subcutis on Day 2 was characterized by fibrin, hemorrhage, necrosis and mixed cell infiltrate with or without epidermal ulceration and crust formation in the majority of animals. One animal had moderate necrosis spreading to adjacent tissues and regional lymph nodes. A reduced incidence and severity of changes on Day 15 and 29 suggested progressive recovery. Chronic inflammation characterized by fibrosis and mononuclear infiltrate was observed with or without epidermal ulceration and crust formation and infrequent necrosis and inflammation of the adjacent bone. Microscopic findings generally correlated with macroscopic alterations. These alterations indicate an irritating effect of MPP5, particularly in perivascular tissue at the injection site.

A low incidence of changes in other tissues was considered secondary to the injection site inflammatory changes observed on Day 2 and generally, recovered by Day 15 and 29. These included: necrosis and inflammation in the spleen; perivascular neutrophil, mononuclear or mixed cell infiltrate in the epididymis, seminal vesicles, testis and liver; bone marrow myeloid hyperplasia; lymph node edema; lymphoid atrophy in lymph nodes, spleen and thymus, and; testicular atrophy observed on Day 29. Increased liver and spleen weights on Day 2 had no microscopic correlate.

5. Conclusion

In conclusion, the administration of MPP5 by single intraprostatic injection at dose levels up to 40 μg or intravenous injection at dose levels up to 50 μg resulted in mortality at 25 μg and 40 μg IP with no clear cause of death, however the extent of the test article related prostatic inflammation and with proximity to the kidneys and concurrent systemic degeneration were considered potential contributory factors to the deaths. Mostly reversible changes were seen in clinical signs (≥2 μg), hematology and clinical biochemistry parameters at ≥10 μg. Pathological changes persisted at all dose levels in a dose-related fashion but showed evidence of regression in animals treated intravenously. Consequently, the no-observable-effect-level (NOEL) was not determined for either the intraprostatic or the intravenous route.

References

Dunn, O. J. 1964, Multiple Comparisons using Rank Sums, Technometrics, 6, 241-256.

SAS Institute Inc., 1999.5AS/STAT® User's Guide, Version 8, Cary, N.C.: SAS Institute Inc., 3884 pp.

Example 7

Acute Toxicity of MPP5 in Monkeys

This example shows preliminary results of a study indicating that intraprostatic administration of a histidine-tagged MPP comprising a PSA cleavage site (MPP5) results in dose-dependent damage to the prostate. The objective of this study was to assess the potential localized toxicity of a single intraprostatic injection of MPP5 in sexually mature male cynomolgus monkeys over a 2 week period.

Experimental Design Overview

General Description:

A total of 16 male cynomolgus monkeys (*Macaca fascicularis*) were assigned to treatment groups as shown in the Table 11 below. The animals were approximately 3.6 to 11.7 years of age and weighed approximately 2.8 to 7.9 kg. The animals were imported from China, Vietnam, Indonesia and Mauritius.

TABLE 11

| Group No. | Number of Males | Dose Level (μg/g prostate[1]) | Number Sacrificed: Day 3 | Number Sacrificed: Day 15 |
|---|---|---|---|---|
| 1 | 4 | 0 (control) | 2 | 2 |
| 2 | 4 | 1 | 2 | 2 |
| 3 | 4 | 5 | 2 | 2 |
| 4 | 4 | 25 | 2 | 2 |

[1]Prostate weight will be estimated from a previously established relationship between prostate weight and body weight. One-half of the dose will be injected into each lobe of the prostate.

All animals were dosed once under general anesthesia via perianal intraprostatic injection. The first day of dosing was designated Day 1. The animals were evaluated for changes in clinical signs (twice daily), food consumption (once daily), body weight (Days −1, 3, 8, and 15), electrocardiograms (prestudy and Days 2 and 14), and ophthalmic condition (prestudy and Day 14). Clinical pathology indices (serum chemistry [including C-reactive protein], hematology and coagulation) were determined prestudy and on Days 3 and 14. Blood samples were collected for toxicokinetic analysis, antibodies to the test article and prostate specific antigen (PSA) at various time points following dose administration. Eight animals were euthanized on Days 3 and 15 as indicated in the Table 11. At termination, a full necropsy was conducted on all animals, and tissues were collected (including selected periprostatic tissues), preserved, processed and examined microscopically. This study evaluated the acute localized toxicity of MPP5.

The test article was MPP5, Lot No. PTIC-MF-PAL-DS-001 and the control article was PBS-EDTA. A solution of the stock test article, in which the concentration of the active ingredient was 3.2 mg/mL, was filtered through a suitable 0.22 micron PVDF filter prior to dose solution preparation on the day of preparation. Dilutions of the filtered stock test article solution with the control vehicle were performed on the day of dosing to yield a dosing solution at appropriate concentrations for achieving the intended doses.

Animals were housed as specified in the USDA Animal Welfare Act (9 CFR, Parts 1, 2 and 3) and as described in the *Guide for the Care and Use of Laboratory Animals* (ILAR publication, 1996, National Academy Press).

Animals were initially assigned Provantis numbers that reflected the origin of the monkey as shown in the table below. Animals assigned Provantis numbers of 6001-6008 were of Chinese origin. Animals assigned Provantis numbers of 7001-7004 were of Indonesian origin. Animals assigned Provantis numbers of 8001-8003 were of Mauritius origin. The animal assigned Provantis number 9001 was of Vietnamese origin.

Due to the wide range of animal origins and bodyweights, the animals were randomly assigned to treatment groups according to the table below.

| | Set A | | Set B | |
|---|---|---|---|---|
| Group No. | Chinese/ Vietnamese | Indonesian/ Mauritius | Chinese/ Vietnamese | Indonesian/ Mauritius |
| 1 | 1 | 1 | 1 | 1 |
| 2 | 1 | 1 | 1 | 1 |
| 3 | 1 | 1 | 1 | 1 |
| 4 | 1 | 1 | 1 | 1 |

Test and control article administration, group assignments and dose levels:

| Group No. | Number of Males | Dose Level (μg/g prostate[1]) | Dose Volume (μL/g prostate[2]) | Dose Solution Conc. (μg/mL) |
|---|---|---|---|---|
| 1 | 4 | 0 (control) | 50 | 0 |
| 2 | 4 | 1 | 50 | 20 |
| 3 | 4 | 5 | 50 | 100 |
| 4 | 4 | 25 | 50 | 500 |

[1]Prostate weight was estimated from a previously established relationship between prostate weight and body weight.
[2]One-half of the dose was injected into each lobe of the prostate, that is, approximately 25 ul/g prostate per lobe.

Dosing was carried out as follows. The route of injection was Perianal intraprostatic bolus injection and the frequency was once. Monkeys were initially sedated with an intramuscular injection of ketamine and a temporary intravenous catheter was placed for administering sedatives and/or anesthetics during the surgical procedures. A small skin incision was made in the perianal region below the anus and muscle and subcutaneous tissues were blunt dissected to allow visualization and identification of the prostate gland. The test and control articles were administered on a prostate gland weight basis. Approximate weight of the prostate gland was estimated from the animal's body weight and a previously established relationship between the body weight and prostate gland weight (prostate weight (g)=0.07294+(−0.2309×kg)+(0.06296×kg$^2$), where kg is body weight). The test and control articles were administered in approximately equal volumes to each of the left and right lobes of the prostate gland.

The perianal route was chosen because it is the most precise means of administering the test article directly to the prostate gland. The test article will also be administered locally to the prostate in humans.

Cage side observations: These were made twice daily (a.m. and p.m.), beginning at least 7 days prior to the day of dosing and continuing through the last day of sample collection. Each animal was observed for changes in general appearance and behavior.

Food consumption was once daily, as part of the routine cage side observations, beginning at least 7 days prior to the day of dosing and continuing through the last day of sample collection (except as noted below). The number of biscuits remaining from the previous day's feeding were observed. Exceptions to this procedure were for days of fasting for study procedures Body weight measurements were taken prior to the first dose (Day −1), and on Days 3, 8 and 15 according to the following procedure. Food was withheld before body weights were measured.

Electrocardiograms were recorded Prestudy, on Day 2 and 14 using Leads: I, II, III, aVR, aVL and aVF. Monkeys were temporarily restrained for the procedure outside their cages in primate chairs, but were not sedated.

Ophthalmic Examinations were conducted by a veterinarian prestudy (within 3 weeks of Day 1) and on Day 14. Under light sedation with ketamine, a direct opthalmoscope was used to examine the anterior and posterior chambers of the eye. A few drops of a mydriatic solution (typically 1% tropicamide) was instilled into each eye to facilitate the examination.

Blood samples for evaluation of serum chemistry, hematology and coagulation parameters were collected from all animals during Week −1 and on Days 3 (prior to necropsy) and 14 (prior to ophthalmic examinations). The animals were fasted for at least 8 hours (but not more than 16 hours, without appropriate justification) prior to blood collections for serum chemistry.

Urine was collected for urinalysis by cage pan collection prestudy and on the morning following dosing (Day 2, approximately 24 hours after dosing) and in terminated animals by cystocentesis at each necropsy (Days 3 and 15)

a) Serum Chemistry Collection Procedures

Method of Collection: Venipuncture—Any available vein, preferably femoral

TABLE 12

| Serum Chemistry Parameters | |
|---|---|
| Sodium | Calcium |
| Potassium | Phosohorus |
| Chloride | Urea nitrogen (BUN) |
| Carbon dioxide | Creatinine |
| Total bilirubin* | Total protein |
| Alkaline phosohatase (ALP) | Albumin |
| Lactate dehydrogenase (LDH) | Globulin |
| Aspartate aminotransferase (AST) | Albumin/globulin ratio |
| Alanine aminotransferase (ALT) | Glucose |
| Gamma-glutamyltransferase (GGT) | Cholesterol |
| C-Reactive Protein (CRP) | Triglycerides |

*If suspected test article-related increases in total bilirubin occur, direct and indirect bilirubin concentrations will be determined.

b) Hematology

Blood samples were collected by venipuncture of any available vein, preferably femoral. The collection volume was 1 ml and the anticoagulant used was EDTA.

Parameters Analyzed:

TABLE 13

| Hematology Parameters | |
|---|---|
| Red blood cell (RBC) count | Mean corpuscular hemoglobin (MCH) |
| White blood cell (WBC) count* | Mean corpuscular volume (MCV) |
| Hemoglobin concentration | Mean corpuscular hemoglobin concentration (MCHC) |
| Hematocrit | Platelet counts |
| Reticulocyte counts | Blood cell morphology** |

*Includes total white blood cell, polysegmented neutrophil, band neutrophil, lymphocyte, monocyte, eosinophil, basophil, and other cell counts as appropriate.
**The blood smear from all animals will be examined at each timepoint (including pre-study).

c) Coagulation Parameters

Samples were collected by venipuncture of any available vein, preferably femoral. The collection volume was 1.8 mL and the anticoagulant was sodium citrate. The samples were processed to plasma and the following parameters analyzed: Activated partial thromboplastin time (APTT), prothrombin time (PT), and fibrinogen.

d) Urinalysis

Samples were collected by the cagepan collection method (Prestudy and at approximately 24 hours after dosing) and by cystocentesis; obtained at necropsy. The collection volume was as available, up to 5 mL. Samples were processed according to standard procedures known in the art.

The following parameters were analyzed:

| Urinalysis Parameters | |
|---|---|
| Color/Character | Ketones |
| pH | Bilirubin |
| Specific gravity | Occult blood |
| Protein | Microscopics |
| Glucose | |

F. Analysis Conducted of:

1. Toxicokinetic Samples

Samples were collected by venipuncture of any available vein, preferably femoral. Samples were taken prior to dosing and at 1, 2, 4, 8, 24 and 48 hours postdose. The collection volume was 2 mL and no anticoagulant was used. Samples were processed to serum.

Sera were divided into two aliquots of approximately equal volume. Each sample was labeled with the animal number, dose group, day of collection, date, nominal collection time, study number and aliquot number. Samples were stored at approximately −70° C., and were analyzed for MPP5 concentration by ELISA.

2. Antibody Samples

Samples from all available groups/animals were tested. Samples were collected by venipuncture of any available vein, preferably femoral, prior to dosing and on Day 14. The collection volume was 2 mL. No anticoagulant was used. Samples were processed to serum. Samples were stored at approximately −70° C.

Prostate Specific Antigen Analysis

Samples from all available groups/animals were tested. Samples were collected by venipuncture of any available vein, preferably femoral, pior to dosing and on Days 2, 3, and 10. The collection volume was 2 mL. No anticoagulant was used. Samples were processed to serum and stored at approximately −70° C.

Terminal Procedures and Anatomic Pathology

Termination: The animals were terminated by exsanguination while under deep anesthesia induced with ketamine and Beuthanasia®-D or equivalent. Food rations were withheld overnight prior to the day of sacrifice. The animals were sacrificed according to the following schedule:

| Group No. | Day 3, Set B, No. of Males | Day 15, Set A, No. of Males |
|---|---|---|
| 1 | 2 | 2 |
| 2 | 2 | 2 |
| 3 | 2 | 2 |
| 4 | 2 | 2 |

Final Body Weight: A terminal body weight was obtained at necropsy for all scheduled and unscheduled sacrifices. This body weight was used to calculate organ/body and organ/brain weight ratios.

Gross Necroscopy: A complete gross necropsy was conducted on all animals found dead or sacrificed during the study (both scheduled and unscheduled sacrifices). The necropsy included examination of: Carcass and musculoskeletal system, all external surfaces and orifices, cranial cavity and external surface of the brain, neck with associated organs and tissues, thoracic, abdominal and pelvic cavities with their associated organs and tissues.

Urine samples: Urine (as available to a maximum of 5 mL) was collected from the bladder at necropsy and analyzed as described in the Clinical Pathology section of this protocol.

Organ weights: The following organs (when present) were weighed before fixation. Paired organs will be weighed together unless gross abnormalities are present, in which case they will be weighed separately. The pituitary was weighed post fixation.

| Organs Weighed | |
|---|---|
| Adrenals | Brain |
| Epididymides | Heart |
| Kidneys | Liver |
| Lungs | Pituitary (post fixation) |
| Prostate (without seminal vesicles) | Spleen |
| Testes | Thymus |
| Thyroid with parathyroids | |

Organ/body weight ratios were calculated (using the final body weight obtained prior to necropsy), as well as organ/brain weight ratios.

Tissue collection and preservation: The following tissues and organs (or portions of), were collected and preserved in neutral-buffered 10% formalin (except for the eyes, which were preserved in Davidson's fixative for optimum fixation).

| Tissues Collected | |
|---|---|
| Cardiovascular | Urogenital |
| Aorta | Kidneys |
| Heart | Urinary Bladder |
| Digestive | Testes |
| Salivary Gland (mandibular) | Epididymides |
| Tongue | Prostate |
| Esophagus | Periprostate Tissues |
| Stomach | Anal Sphincter Muscle |
| Small Intestine | Bladder adjacent to Prostate |
| Duodenum | Prostatic Urethra |
| Jejunum | Seminal Vesicles |
| Ileum | Ureters |
| Large Intestine | Vas Deferens |
| Cecum | Endocrine |
| Colon | Adrenals |
| Rectum | Pituitary |

-continued

| Tissues Collected | |
|---|---|
| Pancreas | Thyroid/Parathyroids[a] |
| Liver | Skin/Musculoskeletal |
| Gall bladder | Skin |
| Respiratory | Bone (femoral head) |
| Trachea | Bone (7th rib) |
| Lung | Skeletal Muscle (psoas and diaphragm) |
| Lymphoid/Hematopoietic | Nervous/Special Sense |
| Bone Marrow (sternum) | Eyes with Optic Nerve |
| Thymus | Sciatic Nerve |
| Spleen | Brain |
| Lymph Nodes | Spinal Cord (thoracic) |
| Inguinal | Other |
| Mesenteric | Animal Number Tattoo |
| | Gross Lesions |

[a]The occasional absence of the parathyroid gland from the routine tissue section will not require a recut of the section.

Histopathology: For all animals necropsied, the tissues listed in the table above (except tattoos) were embedded in paraffin, sectioned, stained with hematoxylin and eosin, and examined by a Veterinary Pathologist certified by the ACVP.

Statistical Analyses

Group means and standard deviation values were calculated for all numerical data obtained by Sierra, including body weights, clinical pathology parameters (excluding non-numerical data), and organ weight data.

Further statistical analyses were performed with the SAS® System, Version 8.1. Significant intergroup differences will be evaluated by use of an analysis of variance (ANOVA), followed by a multiple comparisons test. The assumptions that permit use of a parametric ANOVA will be verified using the Shapiro-Wilkes test for normality of the data and Levene's test for homogeneity of variance, with $p \leq 0.001$ level of significance required for either test to reject the assumptions. If both assumptions are fulfilled, a single-factor ANOVA will be applied, with animal grouping as the factor, utilizing a $p \leq 0.05$ level of significance. If the parametric ANOVA is significant at $p \leq 0.05$, Dunnett's test will be used to identify statistically significant differences between the control group and each test article-treated group at the 0.05 level of significance. If either of the parametric assumptions is not satisfied, then the Kruskal-Wallis non-parametric ANOVA procedure will be used to evaluate intergroup differences ($p \leq 0.05$). The Dunn's multiple comparison test will be applied if this ANOVA is significant, again utilizing a significance level of $p \leq 0.05$.

Preliminary Results

Prostate: All treated animals had lesions in their prostates (See FIGS. 32C-H and 33C-H). Group 1 (Control) animals had minimal inflammation, hemorrhage, and fibrosis on Day 3 and fibrosis on Day 15 consistent with reaction to an injection, and healing. There were significant severe lesions in Groups 3 and 4 (FIGS. 32E-32H, FIGS. 33 E-H) and 33F). There was no difference in extent or severity of lesions between Groups 3 (5 μg/g prostate) and 4 (25 μg/g prostate). There were significant, less severe lesions in Group 2 (1 μg/g prostate). (FIGS. 32C, 32D, 33C, 33D).

On Day 3 the primary reaction to the test article was coagulative necrosis of large parts of the prostate with extensive hemorrhage, and mixed cell inflammation. Inflammation was primarily neutrophilic with lesser numbers of eosinophils, lymphocytes and macrophages. In some areas there was liquefactive necrosis. Coagulative necrosis was mild in Group 2 and moderate to marked in Groups 3 and 4.

On Day 3 in Group 2, extensive repair was underway with marked regenerative hyperplasia of gland epithelium that progressed to squamous metaplasia, at the margins of areas of coagulative necrosis, and mild to marked activation and proliferation of interstitial cells. On Day 3 in Groups 3 and 4 repair was just beginning evidenced by mild activation and proliferation of interstitial cells.

On Day 15 in Group 2 necrosis and hemorrhage had resolved. Cavitation of the prostate was not noted. The lesions had fibrosed in with minimal to mild ongoing regenerative hyperplasia and squamous metaplasia of glands. Inflammation was primarily macrophages and lymphocytes with lesser numbers of polymorphonuclear leukocytes. In one animal, these were primarily eosinophils.

On Day 15 in Groups 3 and 4, there was ongoing coagulative necrosis and hemorrhage with more severe liquefactive necrosis and cavitation of the prostate, and ongoing mixed cell inflammation. Repair in these groups consisted of moderate to marked fibrosis and fibroplasia of the interstitium at the margins of necrotic lesions, with regenerative hyperplasia progressing to squamous metaplasia of glands. Inflammation was primarily neutrophilic in areas with ongoing necrosis but had a relatively greater percentage of lymphocytes and macrophages at the margins of lesions in areas of fibrosis.

Periprostatic Tissues:

Seminal vesicles in 5/6 treated animals on Day 3 had minimal to moderate mineralization of the secretion in the gland lumen. This is seen occasionally as a background finding, but not to this extent or as frequently as seen here. Therefore this was likely secondary to changes in the prostates. On Day 15 the only affected animal was a control.

Prostatic urethras had some inflammatory cell infiltrates, likely secondary to changes in the prostates.

Example 8

Activation of MPP5 by Prostate Tissue

The ability of extracts from prostates of various animals to activate an MPP according to the present invention was examined. An in vitro study was performed in which extracts of rat, dog, monkey, and human prostate tissues were incubated with MPP5 to determine percent activation of the MPP.

The experimental protocol was as follows. Fresh prostate tissue was obtained from a Sprague Dawley rat and a single beagle dog. Frozen prostate tissues were obtained from a single Cynomolgus monkey and from a single human. Human prostate tissue was obtained as archived research material from Johns Hopkins University IRB approved clinical study. For this analysis, prostates were sectioned (~100-500 mg pieces) and suspended in serum-free RPMI 1640 cell culture media at a concentration of equal volume of media per volume of tissue. Tissue samples were incubated in this media at 37° C. for 2 hours. After centrifugation, supernatant was frozen at −80° C.

Hemolysis assay: Samples were thawed at 37° C., centrifuged, and the supernatants collected. Protein concentration of each supernatant was determined using the Bradford Assay. Samples were diluted to the same starting protein concentration. Aliquots of supernatant from monkey and human samples were obtained for PSA determination using a standard ELISA (Hybritech®, Beckman Coulter) methodology. A solution of 2% fresh human red blood cells (RBCs) suspended in phenol red-free Hanks Buffered Salt Solution (HBSS) was prepared each day. Red blood cells were pelleted, resuspended in three volumes of HBSS to remove excess serum and resuspended to produce a 50% solution in phenol red-free HBSS. To prepare test samples, a 50% RBC sample was gently vortexed to suspend RBCs. Aliquots of RBCs were added to 230 μL phenol red-free HBSS to produce a 4% (v/v) solution. To this suspension an aliquot of 240 μL of prostate section conditioned RPMI media was added, and subsequently, a 10 μl, aliquot of MPP5 from stock of 100 μg/mL was added so that total MPP5 added per assay was 1 μg and final volume of assay was 500 μL. This RBC/MPP5/Tissue solution was incubated for 1 hr at room temperature. Samples were then centrifuged to pellet non-lysed RBCs and 100 μL aliquot of supernatant from each sample was obtained and immediately measured spectrophotometrically at 540 nm for hemoglobin release due to RBC lysis. Controls included sham-treated RBCs (negative control) and RBCs lysed with 1% Triton-X100 (positive control). In order to compare the extent of hydrolysis, serial dilutions of each sample of prostate tissue-conditioned media were assayed. Dilutions of extract of 1:1, 1:2, 1:4, 1:8, 1:16, and 1:32 were used in this study. All samples were assayed for hemolysis in triplicate.

Figure 36:
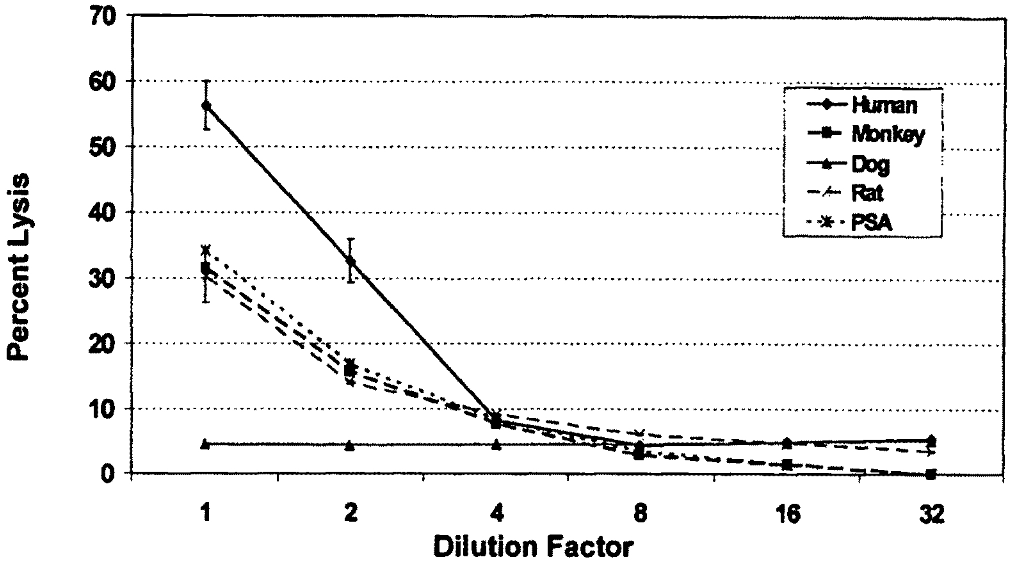
FIG. 36 depicts activation of MPP5 in prostate tissue fragment conditioned media assayed by degree of hydrolysis of washed red blood cells.

The results indicated that the human prostate tissue was most active in cleaving MPP5, while rat and monkey prostate tissues produced a lower response, whereas dog prostate tissue did not show any activity towards MPP5 (FIG. 36). Although the rat lacks the PSA gene, it has been shown to possess an S3 kallikrein homolog to human PSA (Onozawa et al., 2001). This PSA-like protein, identified in the rat ventral prostate, shows nucleotide and amino acid sequence homology of 64% and 49%, respectively, with human PSA. Furthermore, the rat S3 kallikrein and human PSA have similar isoelectric points and molecular weights. Thus, it is likely that MPP5 is activated in rat prostate tissue by this PSA-like S3 kallikrein.

Lack of activation by the dog prostate is consistent with the observation that the dog does not possess the PSA gene.

Example 9

Activation of MPP5 by Plasma/Serum

The ability of serum from human, monkey, dog, rat or mouse to cleave MPP5 was determined as follows.

MPP5 (1.073 mg/mL) was thawed on ice at 4° C., aliquoted, and refrozen at −80° C. Two assays were performed for each condition. 5 μg MPP5 was incubated in 20 mM HEPES buffer (pH 7.4) containing 150 mM NaCl and 25 μL human, monkey, dog, rat or mouse serum at 37° C. for 10 minutes in a total volume of 250 μL. In control experiments, 25 μg chymotrypsin was added to the reaction mixture before addition of serum (positive control). In other control experiments serum was replaced with an equal volume of buffer (negative control). The reaction was stopped by addition of 5 μL of 100 mM PMSF in isopropyl alcohol followed by cooling on ice. A 15 μL aliquot of stopped reaction mixture was added to an equal amount of 2× BioRad sample loading buffer containing 0.5% β-mercaptoethanol and heated at 95° C. for 5 min to denature all proteins and block protein-protein interactions. A 5 sample was electrophoresed on pre-cast 4-12% Bis-Tris gels (Invitrogen) using XT MOPS running buffer (BioRad Laboratories) at 100 V for 60 minutes. Proteins in the gels were transblotted onto nitrocellulose (BioRad Laboratories) and the membrane blocked with non-fat milk (5% in tris-buffered saline with 0.1% Tween 20 (TBST) for 1 hour at room temperature. MPP5 was detected by incubating the membranes in purified polyclonal rat anti-MPP5 at a dilution of 1:250,000 in TBST for 1 hour at room temperature. After washing three times with TBST, the blot was incubated in HRP-linked goat anti-rat antibody (Jackson ImmunoResearch) at a dilution of 1:20,000 in TBST. Antibody binding to the membrane was detected using chemiluminescence according to the kit manufacturer (Cell Signaling) and recorded real-time using an Alpha Innotech Fluor Chem SP with chemiluminescence autoexposure settings to avoid saturation using a 4 megapixel CCD camera. Blots were quantified densitometrically using a voxel based program (ImageQuant software; Alpha Innotech, San Leandro, Calif.). Percent of cleaved protein remaining was determined for each lane by dividing density of the cleaved band by the sum of the intact and cleaved bands, after correction for background. Percent cleaved was then compared to no-serum and serum plus chymotrypsin controls.

Figure 37:
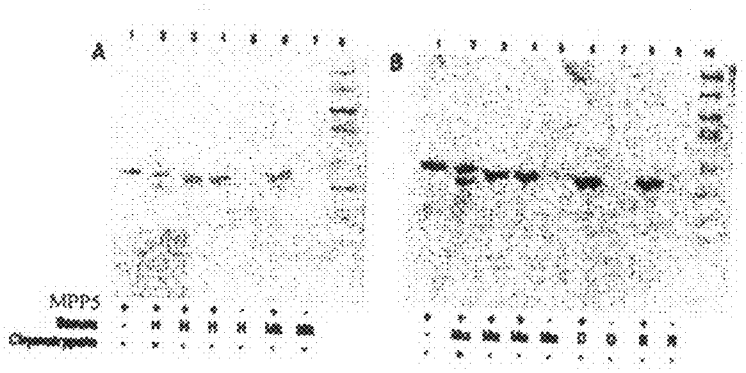
FIG. 37 depicts the ability of sera from various species to cleave MPP5.

Estimation of percent cleavage of MPP5 was accomplished by electrophoresis and densitometric quantification of western blots. The percent cleaved was then compared to MPP5 only (negative) and MPP5+ chymotrypsin (positive) controls to determine whether MPP5 is cleaved by serum enzymes. Under these experimental conditions, cleavage of MPP5 by human, monkey, dog, rat or mouse serum was not detectable. Table 14 shows the percentage of MPP5 that is cleaved after incubation with various sera. FIG. 37 shows western blots of MPP5 after incubation for 10 minutes in the absence or presence of various sera. Panel A shows MPP5 incubated with either 25 μL serum from human males (H) (lanes 2-5) or *Cynomolgous* monkey (Mk) (lanes 6-7) in 250 μL assay volume. Lane 3 contains MPP5, human serum and chymotrypsin, but was not incubated. Lane 8 is molecular weight marker. (B) MPP5 incubated with either 25 μL serum from Mouse (Mu) (lanes 2-5), Dog (D) (lanes 6-7) or Rat (R) (lanes 8-9) in 250 μL assay volume. Lane 3 contains MPP5, human serum and chymotrypsin, but was not incubated. Lane 10 is molecular weight marker.

TABLE 14

Species Comparison of Percent Cleavage of MPP5 in Serum

| | Buffer | Human | Monkey | Dog | Rat | Mouse |
|---|---|---|---|---|---|---|
| Percent Cleaved | 1.45 ± 1.08 | 0.90 ± 0.31 | 1.78 ± 1.51 | 1.20 ± 1.0 | 1.87 ± 0.32 | 1.33 ± 0.10 |

These results suggest that MPP5 is not activated in normal human serum and also suggest that MPP5 would not become activated in the event of leakage into the blood following intraprostatic injection even in men with extraordinarily high levels of serum PSA. These results are consistent with published data demonstrating that PSA is enzymatically inactivated in the blood by serum protease inhibitors, primarily α1-antichymotrypsin and α2-macroglobulin (Lilja et al., 1991; Otto et al., 1998).

Example 10

Activation Of MPP5 By Non-PSA Proteases

An in vitro study was performed to determine the sensitivity of MPP5 to non-PSA proteases that the prodrug could potentially encounter if it was inadvertently exposed to tissues outside of the prostate. Specifically, several common proteases including PSA, furin, trypsin, chymotrypsin, thrombin, MMP-7, cysteine protease cathepsin B, and the serine proteases hK1, hK2, and uPA were evaluated for their potential to cleave MPP5.

The assays were carried out as follows. Native proaerolysin (wt PA; 0.84 mg/mL) and MPP5 at 1.073 mg/mL were used for assays testing all proteases except for assay #2 with furin, in which MPP5 of Lot # N-PTIC-MF-PAL-BX; at 1 mg/ml was used.

To measure activation by PSA cleavage, 5 μg of native proaerolysin or MPP5 were incubated in 20 mM HEPES buffer (pH 7.4), containing 150 mM NaCl. Various amounts of PSA were added (0-10 μg PSA according to a logarithmic scale) and incubated at 37° C. for 60 minutes in a total volume of 250 μL. The reaction was stopped by addition of 5 μL of 100 mM PMSF in isopropyl alcohol followed by cooling on ice. A 15 μL aliquot of stopped reaction mixture was added to an equal amount of 2× BioRad sample loading buffer containing 0.5% (3-mercaptoethanol and heated at 95° C. for 5 minutes. The sample was electrophoresed on pre-cast 10% Tris-HCl gels using XT MOPS running buffer (BioRad Laboratories) at 200 V for 30 minutes. The proteins were detected by silver staining.

To measure activation by furin cleavage in study #1, five μg of Native PA or MPP5 were incubated in 20 mM HEPES buffer (pH 7.4) containing 150 mM NaCl and various amounts of furin (0-3.2 ng of furin according to a logarithmic scale) at 37° C. for 10 minutes in a total volume of 250 μL. The reaction was stopped by addition of 5 μL of 100 mM PMSF in isopropyl alcohol followed by cooling on ice. A 15 μL aliquot of stopped reaction mixture was added to an equal amount of 2× BioRad sample loading buffer containing 0.5% β-mercaptoethanol and heated at 95° C. for 5 minutes. The sample was electrophoresed on pre-cast 10% Tris-HCl gels using XT MOPS running buffer (BioRad Laboratories) at 200 V for 30 minutes. The proteins were detected by silver staining.

To measure activation by furin cleavage in study #2, five μg of native PA or MPP5 were incubated in 20 mM HEPES buffer (pH 7.4) containing 150 mM NaCl, 1 mM $CaCl_2$ and 0 to 3 units of furin at 37° C. for 60 minutes in a total volume of 250 μL. Note that in earlier experiment (Furin, Study # 1), the incubation time was 10 minutes at the same enzyme concentration. The reaction was stopped by addition of 2.5 μL of 100 mM PMSF in ethanol followed by cooling on ice. A 15 μL aliquot of stopped reaction mixture was added to an equal amount of 2× BioRad sample loading buffer containing 0.5% β-mercaptoethanol and heated at 95° C. for 5 minutes. The sample was electrophoresed on pre-cast 10% Novex Bis-Tris Nupage gels (Invitrogen) using 1×MOPS-SDS running buffer at 200V for 50 minutes. The proteins were detected by silver staining.

To measure activation by chymotrypsin, 5 μg of native PA or MPP5 were incubated in 20 mM HEPES buffer (pH 7.4) containing 150 mM NaCl and various amounts of chymotrypsin (0-500 ng chymotrypsin according to a logarithmic scale) at 37° C. for 10 minutes in a total volume of 250 μL. The reaction was stopped by addition of 5 μL of 100 mM PMSF in isopropyl alcohol followed by cooling on ice. A 15 μL aliquot of stopped reaction mixture was added to an equal amount of 2× BioRad sample loading buffer containing 0.5% β-mercaptoethanol and heated at 95° C. for 5 minutes. The sample was electrophoresed on pre-cast 10% Tris-HCl gels using XT MOPS running buffer (BioRad Laboratories) at 200 V for 30 minutes. The proteins were detected by silver staining.

To measure activation of MPP5 by thrombin in Study #1, 5 μg aerolysin-related protein (native PA or MPP5) was incubated in 20 mM HEPES buffer (pH 7.4) containing 150 mM NaCl and various amounts of thrombin (0-12 μg of 0.23 Unit/μg thrombin according to a logarithmic scale) at 37° C. for 10 minutes in a total volume of 250 μL. The reaction was stopped by addition of 5 μL of 100 mM PMSF in isopropyl alcohol followed by cooling on ice. A 15 μL aliquot of stopped reaction mixture was added to an equal amount of 2× BioRad sample loading buffer containing 0.5% (3-mercaptoethanol and heated at 95° C. for 5 minutes. The sample was electrophoresed on pre-cast 10% Tris-HCl gels using XT MOPS running buffer (BioRad Laboratories) at 200 V for 30 minutes. The proteins were detected by silver staining.

To measure activation of MPP5 by thrombin in Study #2, two thrombin dilutions, 1/66 and 1/25, were made in the thrombin dilution buffer provided with the thrombin kit (Novagen) used in these experiments. Two reaction mixtures were prepared containing 10 μg of MPP5 (N-PTIC-MF-PAL-BX) in 1× cleavage buffer as provided with the thrombin kit. Two reaction mixtures containing native proaerolysin with a His tag (PA-EndHis) were prepared the same way. Thrombin was added to one of the PA-EndHis mixtures at 0.15 units and to one of the MPP5 mixtures at 0.4 units. Total incubation volume was 50 μl in each case. The reaction mixtures were incubated at room temperature for 6.5 hours, and this was followed by inhibition of proteolysis by the addition of phenylmethyl sulfonyl fluoride (Sigma) to a final concentration of 1 mM. The samples were stored overnight on ice at 4° C. They were then prepared in 1×LDS sample buffer (Invitrogen) and heated at 70° C. for 10 minutes before being loaded and run on a 10% Bis-Tris NuPAGE gel (Invitrogen) under non-reducing conditions at 200 V constant voltage for 50 minutes in 1×MOPS-SDS running buffer. The proteins were detected by silver staining.

To measure activation by trypsin, 5 μg aerolysin-related protein (wt PA or MPP5) was incubated in 20 mM HEPES buffer (pH 7.4) containing 150 mM NaCl and various amounts of Type I trypsin (0-500 ng Trypsin according to a logarithmic scale) at 37° C. for 10 minutes in a total volume of μL. The reaction was stopped by addition of 5 μL of 100 mM PMSF in isopropyl alcohol followed by cooling on ice. A 15 μL aliquot of stopped reaction mixture was added to an equal amount of 2× BioRad sample loading buffer containing 0.5% (β-mercaptoethanol and heated at 95° C. for 5 minutes. The sample was electrophoresed on pre-cast 10% Tris-HCl gels using XT MOPS running buffer (BioRad Laboratories) at 200 V for 30 minutes. The proteins were detected by silver staining.

To measure activation by uPA, 5 μg of PA and MPP5 were incubated separately in 20 mM HEPES buffer (pH 7.4) containing 150 mM NaCl and 10-0.16 μg of uPA at 37° C. for 4 hours in a total volume of 250 μL. The reaction was stopped by addition of 5 μL of 100 mM PMSF in isopropyl alcohol followed by cooling on ice. A 15 μL aliquot of stopped reaction mixture was prepared in 1× sample buffer (Invitrogen) containing 0.5% 2-mercaptoethanol and heated at 95° C. for 5 min. The sample (100 ng) was electrophoresed on pre-cast 10% Novex Bis-Tris NuPAGE gels (Invitrogen) using 1×MOPS-SDS running buffer under reducing conditions at 200V for 50 minutes. The proteins were detected by silver staining.

To measure activation by cathepsin B, 5 μg of PA and MPP5 were incubated separately in 20 mM HEPES buffer (pH 7.4) containing 150 mM NaCl, 1 mM EDTA, 5 mM L-cysteine and 24-0.375 units of cathepsin B at 37° C. for 4 hours in a total volume of 250 μL. The reaction was stopped by addition of leupeptin to a final concentration of 2 μM (Sigma method), followed by cooling on ice. A 15 μL aliquot of stopped reaction mixture was prepared in 1× sample buffer (Invitrogen) containing 0.5% 2-mercaptoethanol and heated at 95° C. for 5 min. The sample (100 ng) was electrophoresed on pre-cast 10% Novex Bis-Tris NuPAGE gels (Invitrogen) using 1×MOPS-SDS running buffer under reducing conditions at 200V for 50 minutes. The proteins were detected by silver staining.

To measure activation by MMP-7, 5 μg of PA and MPP5 were incubated separately in 20 mM HEPES buffer (pH 7.4) containing 150 mM NaCl, 10 mM $CaCl_2$ and 1.5-0.0234 μg of MMP-7 at 37° C. for 3 hours in a total volume of 250 μL. The reaction was stopped by addition of 8.4 μL of 31 mM 1,10-phenanthroline monohydrate (1 μM final) in ethanol followed by cooling on ice. A 15 μL aliquot of stopped reaction mixture was prepared in 1× sample buffer (Invitrogen) containing 0.5% 2-mercaptoethanol and heated at 95° C. for 5 min. The sample (100 ng) was electrophoresed on pre-cast 10% Novex Bis-Tris NuPAGE gels (Invitrogen) using 1×MOPS-SDS running buffer under reducing conditions at 200V for 50 minutes The proteins were detected by silver staining.

To measure activation by hK1, 5 μg of hK1 was activated by 0.05 μg thermolysin in a final volume of 50 μl of TCN buffer (50 mM Tris, 10 mM $CaCl_2$, 0.15 M NaCl, pH 7.5), incubated at 37° C. for 1 hour and inhibited with 2.5 μl 200 mM 1,10-phenanthroline monohydrate in 95% ethanol (R & D Systems method). One μg of PA and PSA-PAH1 were incubated separately in 20 mM HEPES buffer (pH 7.4) containing 150 mM NaCl, 1 mM EDTA, and 1-0.015625 μg of activated hK1 at 37° C. for 4 hours in a total volume of 50 μL. The reaction was stopped by addition of PMSF in isopropyl alcohol to a final concentration of 2 mM, followed by cooling on ice. A 5 μL aliquot of stopped reaction mixture was prepared in 1× sample buffer (Invitrogen) containing 0.5% 2-mercaptoethanol and heated at 95° C. for 5 min. The sample (100 ng) was electrophoresed on pre-cast 10% Novex Bis-Tris NuPAGE gels (Invitrogen) using 1×MOPS-SDS running buffer under reducing conditions at 200V for 50 minutes. The proteins were detected by silver staining.

To measure activation by hK2, 1 μg of PA and MPP5 were incubated separately in 20 mM HEPES buffer (pH 7.4) containing 150 mM NaCl and 0.25-0.0039 μg of hK2 at 37° C. for 1 hour in a total volume of 50 μL. The reaction was stopped by addition of PMSF in isopropyl alcohol to a final concentration of 2 mM, followed by cooling on ice. A 10 μL aliquot of stopped reaction mixture was prepared in 1× sample buffer (Invitrogen) containing 0.5% 2-mercaptoethanol and heated at 95° C. for 5 min. The sample (100 ng) was electrophoresed on pre-cast 10% Novex Bis-Tris NuPAGE gels (Invitrogen) using 1×MOPS-SDS running buffer under reducing conditions at 200 V for 50 minutes. The proteins were detected by silver staining.

Results of this study indicated that the sensitivity profiles between MPP5 and proaerolysin (PA) are very different, with native proaerolysin (PA) being more sensitive to the range of proteases (except PSA) than MPP5 (Table 15).

TABLE 15

In Vitro Protease Sensitivity Study Results

| Protease Name | Amount Required for 50% Cleavage of MPP5 | Amount Required for 50% Cleavage of Native Proaerolysin | Specific Activity Towards MPP5 | Specific Activity Towards Proaerolysin |
|---|---|---|---|---|
| Furin | >3.2 ng | 1.2 ng | 0.24 nM/μg/min | 9.69 nM/μg/min |
| Trypsin | 813 ng | 9.5 ng | 5,700 nM/μg/min | 489,000 nM/μg/min |
| Chymotrypsin | 31 μg | 3.0 μg | 150 nM/μg/min | 1550 nM/μg/min |
| Thrombin | >12 μg | >12 μg | <0.00000078 nM/μg/min | <0.00000078 nM/μg/min |
| MMP-7 | Inactive | Inactive | 0 | 0 |
| Cathepsin B | 170 units | 51.6 units | 1.2 fmol/μg/min | 3.9 fmol/μg/min |
| hK1 | Inactive | 2.63 μg | 0 | 15.3 fmol/μg/min |
| hK2 | Inactive | 0.1 μg | 0 | 1.61 pmol/μg/min |
| Prostate-specific antigen (PSA), also referred as hK3 | 12.2 μg | 49.7 μg | 0.0635 nM/μg/min | 0.0156 nM/μg/min |
| uPA | 173 μg | 7.79 μg | 1.1 fmol/μg/min | 25.8 fmol/μg/min |

Note:
Units reported reflect those as recorded in the raw data.

Example 11

Biodistribution of MPP5 in RATS

In order to establish the biodistribution of MPP5 in the prostate and potential distribution to surrounding tissues following single-dose intraprostatic administration, a radiolabeled quantitative whole body autoradiography study using $^{125}$I-MPP5 was performed in male Sprague-Dawley rats. The radioactivity concentration (±S.D.) in the dose formulation was $1.6\times10^9\pm44.02\times106$ dpm/g (730.94 μC/g). Based on the standard deviation and the coefficient of variation around the mean concentration value, the dose formulation was considered homogeneous. The mean dose of formulated $^{125}$I-MPP5 administered by injection into the prostate gland was 8.73 μg/animal (5.86 μCi/animal in a volume of 10 μL.

Duplicate aliquots of blood (2×50 μL) were sampled for radioactivity analysis. Blood was centrifuged at 3500 rpm and 4° C. for approximately 10 minutes (within 60 minutes of collection) and duplicate aliquots of plasma (2×50 μL) were sampled for radioactivity analysis. Duplicate weighed aliquots of whole blood were solubilized (Soluene-350) and decolorized with hydrogen peroxide (30% w/v) prior to mixing with liquid scintillation fluid for radioactivity measurement. Duplicate aliquots of plasma were mixed directly with liquid scintillation fluid for radioactivity measurement.

For quantitative whole body autoradioluminography, animals were deep frozen in a mixture of hexane and dry ice for 20 minutes. Animals were then embedded lying on their right side in a 2% CMC medium using a freezing frame according to Standard Operating Procedures in order to collect sagittal whole-body sections. Twelve holes were made in each frozen CMC block in order to incorporate ten $^{125}I$ standard solutions and the two quality control solutions. Blood spiked with $^{14}C$ or $^{125}I$ were inserted in four drilled holes of each CMC block, which were used, if required, as reference dots for identification of structures presenting a low radioactivity level or low contrast. Each animal specimen block was sectioned using the Leica CM 3600 cryomicrotome. 30 μm sections were collected and identified the animal no., time point, section no., section date and knife position.

The results indicated that following a single-dose intraprostatic administration, the concentration of radioactivity in the blood and plasma were low, suggesting little apparent absorption following intraprostatic administration. The highest concentration of radioactivity (9.445 μg Eq/g) was obtained at the first sampling time point (3 h) from the right ventral prostate injection site. High levels of radioactivity were also observed in other lobes of the prostate (left ventral, and right and left dorsal lobes) but decreased over time to the final sampling point of 96 h. At this final time point, the concentration of radioactivity in the prostate was low for all areas of the prostate except the right ventral prostate injection site (0.268 μg Eq/g). Other than the prostate, only the bladder and the thyroid exhibited radioactivity concentrations higher than either blood or plasma. Thyroid levels of radioactivity ($^{125}I$) increased over time from 12 to 48-h post dose and remained elevated until the final time point at 96-h post treatment. Sequestration of $^{125}I$ in the thyroid may be indicative of free $^{125}I$ distributing to the thyroid. Low concentrations of radioactivity were observed in the adrenal gland (≤0.034 μg Eq/g), kidney (≤0.032 μg Eq/g), liver (≤0.045 μg Eq/g), lung (≤0.041 μg Eq/g) and pancreas (≤0.022 μg Eq/g). The brain exhibited the lowest concentration of radioactivity (≤0.003 μg Eq/g). Extremely low levels of radioactivity were noted in all other major organs at all times, suggesting that significant systemic distribution did not occur. Tissue to plasma levels increased over time, suggesting that the MPP5 was cleared faster from plasma than from tissues. Therefore, this biodistribution study suggests that MPP5 remains largely at the local site of administration, with only limited peripheral distribution and toxicity to surrounding cells.

Example 12

Toxicokinetics of MPP5 in Monkeys

The toxicokinetics of MPP5 were also established following intraprostatic administration in sexually mature male Cynomolgus monkeys as described in Example 7. Four monkeys per group were dosed intraprostatically with control saline or 0.35, 4.14, or 25.79 μg MPP5/g prostate tissue using 2×25 μL injections (25 μL/lobe). Blood samples were obtained from all monkeys (16) prior to dose and at 1, 2, 4, 8, 24, and 48-h post-dose. Preliminary results of this study are also described in Example 7. The following represents the finalized toxicokinetic results of this study.

Study samples were analyzed for MPP5 using a validated ELISA method. The lower limit of quantitation (LLOQ) of the ELISA method was 5 ng/mL using 50 μL serum in duplicate analysis. No appreciable systemic levels of MPP5 were detected following intraprostatic administration. One animal in Group 2 presented concentrations over the LLOQ (5 ng/mL) for all time points. This was considered unusual compared to animals from the same dose group, and all samples from this animal were repeated in a subsequent assay for confirmation. All original results were confirmed in the repeat analysis. As the pre-dose sample was also over the LLOQ, it was determined that the observed concentrations in this animal were likely due to matrix interference and were not treatment related.

Example 13

Evaluation of Prostate Morphology of MPP5 Treated Monkeys

Further analyses of sections of monkey prostate collected in the study described in Examples 7 and 12 were conducted. Hematoxylin & Eosin (H&E) staining was performed to examine morphology of treated prostate, immunohistochemical staining for PSA was performed to examine distribution of PSA, and MPP5 staining was performed in order to examine distribution of MPP5. The protocols used are described following.

Materials and Reagents: 96 slides (6 per monkey) of sections from control and MPP5 treated monkey prostate from were stored in a sealed container at room temperature. Sections of prostate tissue from monkeys dosed intraprostatically with vehicle or 0.35, 4.1 or 25 μg MPP5/gram of prostate were prepared and stained with H&E. Sections were also immunohistochemically stained for PSA and MPP5 according to methods known in the art.

Image analysis: Histological sections of monkey prostate were evaluated using 1.25× objective. Metamorph™ software package (Molecular Devices, Sunnyvale, Calif.) was used to outline the total area of the prostate gland and the total area of MPP5 induced injury. This software provides total area as number of pixels. A 1×1 cm square was placed on each slide as a standard to determine number of pixels/$cm^2$. The area of damage from each dose of MPP5 was then determined and converted into $cm^2$ of damage. Percent area of damage was determined by ratio of injured area/total prostate area multiplied by 100.

Analysis of control (normal) monkey prostate demonstrated that the Cynomolgus monkey prostate is similar to the human prostate in terms of glandular morphology, and distribution of PSA is restricted to columnar epithelial cells lining the ducts. The monkey prostate gland, like the human, surrounds the urethra. Therefore, the monkey prostate represents the best available animal model for studying activation and toxicity of the PSA-activated protein toxin, MPP5, when injected intraprostatically.

Morphological characterization of the prostate tissue and distribution of PSA and MPP5 in the prostates from this study showed a dose-response in the area/percent of prostate damage from doses of 0.35 to 4.14 μg/g prostate; however, there was no significant increase from 4.14 to 25.79 μg/g prostate (Table 15). The largest area of calculated damage was observed in monkeys receiving a dose of 4.14 μg/g prostate, in which a single injection of 25 μL per lobe damaged approximately 50% of the total gland. The results suggest that the maximum damage may be limited by the total distribution of the 25 μL injection volume per lobe of prostate.

Figure 38:
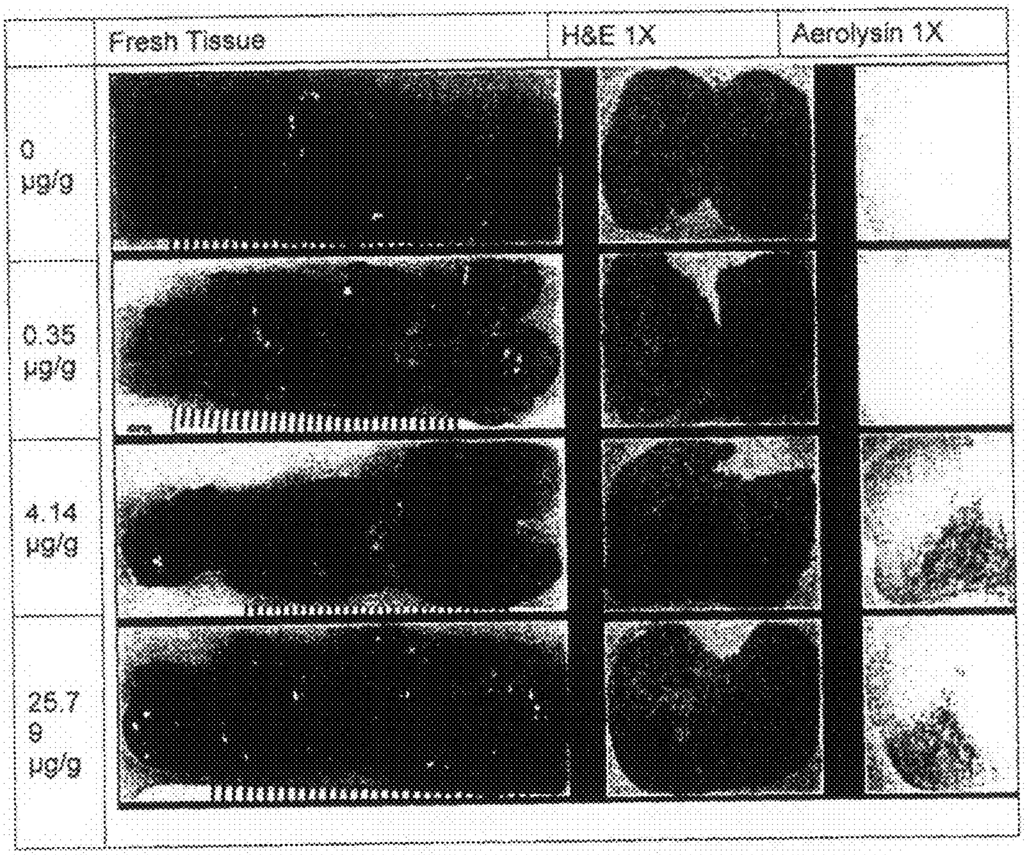
FIG. 38 depicts the effect of MPP5 on monkey prostates.

In treated areas where MPP5 induced significant infarction of normal glandular tissue, PSA staining was markedly decreased, while in adjacent, uninjured areas of the prostate, PSA staining was normal in distribution and degree. These results suggest that MPP5 killing of columnar epithelial cells within the gland eliminates PSA production. The results also demonstrated that the distribution of MPP5 overlapped with the infarct area at the mid- and high-dose levels as shown in FIG. 38. At 15 days post-dose, no residual MPP5 was observed at the mid-dose level. In addition, MPP5 did not appear to penetrate the prostate capsule in any of the sections evaluated in this study.

TABLE 15

Area and Percent of Prostate Damage[1] from MPP5

| | Dose | | | | | |
|---|---|---|---|---|---|---|
| | 0.35 μg/g prostate | | 4.14 μg/g prostate | | 25.79 μg/g prostate | |
| | Area ($cm^2$) | Percent | Area ($cm^2$) | Percent | Area ($cm^2$) | Percent |
| | 0.33 | 20.2 | 0.78 | 46.6 | 0.57 | 63.4 |
| | 0.36 | 30.2 | 0.87 | 47.9 | 0.32 | 23.2 |
| | 0.20 | 13.8 | 0.89 | 54.9 | 0.51 | 41.0 |
| | 0.46 | 36.8 | 1.23 | 56.6 | 0.47 | 51.0 |
| Average (±Standard Deviation) | 0.33 ± 0.11 | 25.3 ± 5.9 | 0.94 ± 0.20 | 51.5 ± 2.9 | 0.47 ± 0.11 | 44.7 ± 9.8 |

[1]Damage (area/percent of total gland) following injection of 25 μL per lobe

In treated areas where MPP5 induced significant infarction of normal glandular tissue, PSA staining was markedly decreased. In adjacent uninjured areas, PSA staining was normal in distribution and degree. These results suggest that MPP5 killing of columnar epithelial cells within the gland eliminates PSA production. However, MPP5 does not alter PSA production in uninjured areas, nor does it select for epithelial cells that produce lower levels of PSA. No PSA staining was observed in the muscular cuff surrounding the urethra. This lack of PSA present in the urethral tissue may partly explain the lack of any significant injury to the urethra. Thus, a small volume (25 μL) injection of MPP5 into a single lobe of the prostate can produce significant infarction of a large area of PSA-producing glandular tissue in the normal monkey prostate without significant injury to non-PSA producing structures (e.g., urethra).

Example 14

Toxicity of MPP5 in Dogs

A pilot toxicology study was performed in male beagle dogs in order to establish the potential direct intraprostatic toxicity and MTD following a single intraprostatic dose of MPP5. MPP5 was administered to male beagle dogs (1/group) via intraprostatic injection (left lobe) of 0, 50, 107, 200, or 400 μg in a dose volume of 100 μL (based on prostate weight, these doses were equivalent to 0, 22, 24.4, 40, and 72.2 μg/g prostate, respectively). The animals were observed for 1-week post-dose. There was no mortality, or treatment-related effects on clinical observations, body weight, food consumption, or clinical pathology. There was no apparent MPP5-related effect on prostate weight. Gross pathological changes were identified in the left lobe of the prostate and adjacent abdominal fat and consisted of dark areas of the prostate extending into the prostatic parenchyma. Adhesions to and/or dark areas in the abdominal fat were associated with the MPP5-related effects noted within the prostate. In the dog treated at 400 μg, the dark areas were more numerous, and the left lobe of the prostate was enlarged. Increases in the severity of these pathological changes were considered attributable to the anticipated pharmacological effect of MPP5. There did not appear to be any significant extraprostatic toxicity. Overall, apparent treatment-related macroscopic changes were observed in the prostate, with limited associated effects on surrounding or adjacent abdominal fat tissue, with an increased severity at the 400 μg level.

The dog prostate shares structural similarities with the human prostate, including a 2-lobe structure, nature of the acinar ducts and the existence of abundant stroma (Wientjes et al., 2005). Although man possesses a higher fraction of stromal tissue than the dog prostate gland, it is not known to what degree the architecture of fibrous partitions, and the blood and lymphatic drainage patterns, differ between man and dog prostate. Nonetheless, the dog has previously been demonstrated as a useful model to study the effects of intraprostatic injection (Rosser et al., 2004). However, in the case of MPP5, beagle dogs did not appear overtly sensitive to the cytolytic effects of this compound. This is likely attributed to a lack of PSA expression in dogs (or other nonspecific enzymes capable of cleaving MPP5). The canine model shows that in the absence of PSA, MPP5 is not activated at extremely high doses, demonstrating the safety of the non-activated prodrug. Rats and nonhuman primates, in contrast, are known to express a PSA-like kallikrein and PSA, respectively, and have been shown to be sensitive to even low concentrations of MPP5. Thus, although the dog prostate is anatomically similar to the human prostate, it does not appear to exhibit a functional relation to the human gland in terms of MPP5 activation, and, therefore, the dog was not pursued further as a toxicology model for MPP5. However, the dog study served to demonstrate that MPP5 appears to be pharmacologically inactive when not cleaved by PSA, providing confidence that MPP5 would not produce significant toxicity if found in non-PSA-producing tissues.

Example 15

Toxicity of MPP5 in Monkeys

In order to establish the toxicity of MPP5 in an endogenous PSA-producing nonrodent species, an intraprostatic toxicity study was conducted in male Cynomolgus monkeys (4/group) injected with 0.35, 4.14, or 25.79 μg MPP5/g prostate tissue as described in Example 7. Two perineal injections were administered, one to each lobe of the prostate (25 μL/lobe). Preliminary results of this study are shown in Example 7. A description of the finalized results follows.

Following direct intraprostatic administration and a 2- or 14-day observation period, toxicity associated with MPP5 was confined to the prostate, with little damage to the surrounding tissues or other overt systemic effects. Results of blood analysis indicated that male Cynomolgus monkeys express detectable levels of PSA and that intraprostatic administration of MPP5 releases significant amounts of PSA into the blood/serum. PSA levels returned to near baseline levels 10 days following treatment. No treatment-related effects were observed at any dose level on clinical signs, body weight, ophthalmic condition, urinalysis, or electrocardiogram (ECG) evaluations. Serum chemistry and hematology assessments revealed a transient cellular and inflammatory response. Transient acute phase immunological responses were observed in all groups on Study Day 3 and were attributed to inflammation associated with the surgical procedure and inflammation localized to the prostate. Increases in C-reactive proteins (CRP) noted on Study Day 3 were generally dose-related and consistent with the extent of mixed cell inflammation and necrosis of the prostate observed microscopically.

Gross and microscopic pathologic changes were observed in prostate glands at all MPP5 dose levels on Day 3. These changes were characterized by necrosis, hemorrhage, and mixed cell infiltrates and were more severe in animals receiving MPP5 at the mid- and high doses. Monkeys in the low-dose group also exhibited histologic changes on Day 3 that were consistent with repair, including regenerative hyperplasia and squamous metaplasia in epithelial tissues and fibroplasia in interstitial (mesenchymal) tissues. Repair in the mid- and high-dose groups was minimal to absent on Day 3. By Day 15, necrosis had resolved and repair was ongoing in the low-dose group. In the mid- and high-dose groups, necrosis was ongoing on Day 15 and changes consistent with repair were confined to the margins of necrotic lesions. In contrast, there were no changes in peri-prostatic or systemic tissues attributable to MPP5 on either Days 3 or 15.

Example 16

Immune Response to MPP5 in Monkeys

The potential immune response to MPP5 was also evaluated. The animals were treated with MPP5 as described in Example 7. The potential immune response to MPP5 was determined as follows.

Groups of monkeys received administration of various doses of MPP5 directly into the prostate according to the table below. Serum (approximately 0.5 mL) was collected from the animals prior to the day of injection and again at day 14 after injection. Serum was stored at −70° C. until assay. Immunoglobulin response was measured by ELISA as described separately. Briefly, proaerolysin (0.5 μg/mL in phosphate buffered saline) was bound to an EIA plate by coating overnight at 4° C. Non-specific binding was inhibited by coating with 5% BSA (Sigma) at room temperature. A series of ten-fold dilutions (1:100-1:1,000,000) of pooled normal monkey serum was used in quadruplicate to form a comparison curve for titer determination in serum from animals taken at various times after MPP5 administration. Samples of serum from MPP5-treated monkeys were diluted ten-fold (1:100-1:1,000,000) to provide concentrations with the normal serum. Peroxidase conjugated goat anti-rat IgG (Jackson ImmunoResearch) was bound to antibody that was bound to the proaerolysin-coated well. Color was developed by addition of OPD peroxidase substrate according to manufacturer's instructions. Absorbance at 490 nm was measured on a Molecular Dynamics VERSAmax microplate reader. Titer was defined as the dilution above which the absorbance reading was less than that of normal pooled serum +2 standard deviations for the same dilution.

Prior to MPP5 administration, all monkeys except one of the vehicle-control animals had no detectable titer. That control animal appears to have been exposed to an immunogen prior to the study as the appearance of a small titer was confirmed in the 14 day sample and reconfirmed by reassay. One of the two animals that received 1 μg/g MPP5 exhibited a titer. Similarly, one of the two animals that received 5 μg/g MPP5 exhibited a titer. Both animals that received 25 μg/g MPP5 exhibited a titer.

Titers for each animal at the pre- and post-administration blood draws are listed in Table 16.

TABLE 16

Antibody titers in monkeys after administration of MPP5

| Group | Monkey | Dose (μg/g Prostate) | Route of Administration | Antibody Titer Day 1 | Antibody Titer Day 14 |
|---|---|---|---|---|---|
| 1 | 6001 | 0 | IP | 1:1000* | 1:1000* |
| 1 | 8001 | 0 | IP | <1:100 | <1:100 |
| 2 | 6003 | 1 | IP | <1:100 | 1:10,000 |
| 2 | 7002 | 1 | IP | <1:100 | <1:100 |
| 3 | 6005 | 5 | IP | <1:100 | 1:10,000 |
| 3 | 8002 | 5 | IP | <1:100 | 1:100 |
| 4 | 6007 | 25 | IP | <1:100 | 1:10,000 |
| 4 | 8003 | 25 | IP | <1:100 | 1:10,000 |

*This animal demonstrated the same small titer prior to administration.

Figure 39:
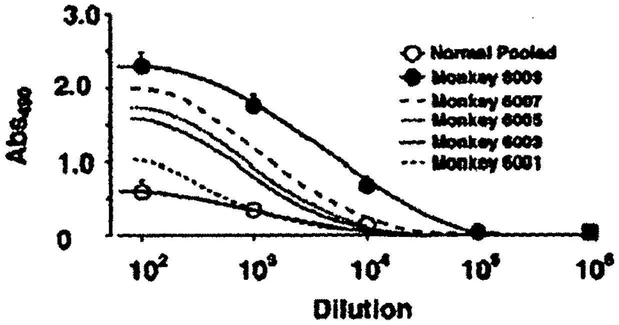
FIG. 39 depicts the humoral response to administration of MPP5 in monkeys.

FIG. 39 demonstrates the antibody titer in monkeys after administration of MPP5. None of the titers were above $10^4$. This suggests that intraprostatic administration of MPP5 does not elicit a strong immune response. However, 4 of 6 animals treated exhibited a titer above pooled serum.

Antibody titers were noted in one of two monkeys treated with 0.35 or 4.14 μg/g prostate and both animals that received 25.79 μg/g prostate exhibited a titer. Thus, administration of MPP5 induced a detectable, but low-titer immune response in some monkeys.

Based on the findings in Examples 11, 12 and 15, there was no indication of extraprostatic toxicity at any dose level; thus, the systemic NOAEL was the highest MPP5 dose tested, 25.79 μg/g prostate (based on actual prostate weight). The effects observed in the prostate were both dose-dependent and anticipated based on the known mechanism of action of MPP5. Effects in the prostate were observed at all dose levels, including the lowest dose tested, 0.35 μg/g prostate, which damaged approximately 25% of the prostate. Therefore, the Lowest-Observed-Adverse-Effect Level (LOAEL) for local prostate effects was 0.35 μg/g prostate in this study.

The previous examples describe the investigation of the drug metabolism and toxicokinetics of MPP5 following intravenous or intraprostatic administration in male albino rats and following intraprostatic injection in nonhuman primates. A summary of the nonclinical drug metabolism and pharmacokinetics (DMPK) studies conducted with MPP5 is presented in Table 17.

TABLE 17

List of nonclinical drug metabolism and pharmacokinetic studies conducted with MPP5

| Study Title | Results |
|---|---|
| An Acute Intraprostatic or Intravenous Bolus Injection Toxicity Study of MPP5 in the | Provided toxicokinetic data following a single intraprostatic (2, 10, or 25 μg) or IV injection (25 μg). MPP5 was not detectable following intraprostatic |

TABLE 17-continued

List of nonclinical drug metabolism and pharmacokinetic studies conducted with MPP5

| Study Title | Results |
| --- | --- |
| Albino Rat (with a 1-, 14-, or 28-Day Observation Period) [Example 6] | injection of 2 μg. $C_{max}$ increased with increasing dose at 10 and 25 μg; however, the AUC at 10 μg was double that at 25 μg. After IV injection, $t_{max}$ was 0 (immediate). |
| Tissue Distribution of Radioactivity in Male Sprague-Dawley Rats following Single Injection of $^{125}$I-MPP5 into the Prostate Gland [Example 11] | Demonstrated that MPP5 had limited systemic bioavailability/distribution following intraprostatic administration and nonhomogeneous distribution throughout the prostate. |
| MPP5: A 2-Week Intraprostatic Acute Toxicity Study in Sexually Mature Male Cynomolgus Monkeys [Examples 7, 12, 13, and 15] | Demonstrated a lack of systemic exposure following intraprostatic injection (1, 5, or 25 μg/g prostate). All serum concentrations were below the LLOQ (5.00 ng/mL), with the exception of 1 low-dose animal which had concentrations above LLOQ at all timepoints including pre-dose. |

Example 17

Selection Of Dosage and Method of Administration of MPP5 in Clinical Trials for BPH An exemplary rationale for selecting a starting dose for clinical trials of MPP5 in BPH is described below. An exemplary method of administering MPP 5 is also described.

Based on the expression of PSA and the physiologic similarities between the Cynomolgus monkey prostate and the human prostate, the single dose monkey studies described herein are selected as the basis for estimating a safe intraprostatic starting dose in humans. The dog was not sensitive to the effects of MPP5 in comparison to rats and monkeys; thus, the dog was not considered to be an appropriate model for estimating the safe starting dose of MPP5. Data from the rat studies described herein suggest that, despite the fact that the rat does not have the PSA coding gene, MPP5 is likely activated by a PSA-like S3 kallikrein identified in the rat ventral prostate (Onozawa et al., 2001).

The starting dose of MPP5 in a BPH clinical trial is selected from the range of 0.03 μg/g to 0.25 μg/g prostate. A potential starting dose is set at 0.03 μg/g prostate, based on the application of a 10-fold safety factor to the lowest dose tested in the single dose monkey study (0.35 μg/g prostate). In monkeys that received the 0.35 μg/g prostate dose, no systemic toxicity was observed, while local prostate gland changes were noted. While all 3 doses showed local ablation of prostate tissue, the mid and higher doses demonstrated the most marked alterations and lack of healing at 14 days post injection. It was concluded that the lowest dose (0.35 μg/g prostate tissue) had the therapeutically useful combination of no systemic findings, either by histological or laboratory analysis, and limited but clearly observable local prostatic effect with approximately 25% ablation of the prostate. This was considered a safe dose in the monkey. Using these data, a safety factor of at least 10-fold is applied and a starting dose of 0.03 μg of MPP5 per gram of human prostate is chosen for the first cohort of the BPH trial.

An exemplary method of administration of MPP5 in the BPH trials is the common transurethral route of administration with only 4 injections per dose (2 injections into each lateral lobe). For guidance during injection, for example, transrectal ultrasound can be used. The total volume to be administered in the BPH trial is 50 μL/gram of prostate. To reduce backflow during injection, for example, a gel or viscous formulation can be used.

Although the invention has been described with reference to certain specific embodiments, various modifications thereof will be apparent to those skilled in the art without departing from the spirit and scope of the invention as outlined in the claims appended hereto.

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

SEQUENCE LISTING

<160> NUMBER OF SEQ ID NOS: 74

<210> SEQ ID NO 1
<211> LENGTH: 1410
<212> TYPE: DNA
<213> ORGANISM: Aeromonas hydrophila
<220> FEATURE:
<221> NAME/KEY: CDS
<222> LOCATION: (1)...(1410)

<400> SEQUENCE: 1 gca gag ccc gtc tat cca gac cag ctt cgc ttg ttt tca ttg ggc caa 48
Ala Glu Pro Val Tyr Pro Asp Gln Leu Arg Leu Phe Ser Leu Gly Gln
1 5 10 15 ggg gtc tgt ggc gac aag tat cgc ccc gtc aat cga gaa gaa gcc caa 96
Gly Val Cys Gly Asp Lys Tyr Arg Pro Val Asn Arg Glu Glu Ala Gln
20 25 30 agc gtt aaa agc aat att gtc ggc atg atg ggg caa tgg caa ata agc 144
Ser Val Lys Ser Asn Ile Val Gly Met Met Gly Gln Trp Gln Ile Ser
35 40 45 ggg ctg gcc aac ggc tgg gtc att atg ggg ccg ggt tat aac ggt gaa 192
Gly Leu Ala Asn Gly Trp Val Ile Met Gly Pro Gly Tyr Asn Gly Glu -continued

```
     50                  55                  60

ata aaa cca ggg aca gcg tcc aat acc tgg tgt tat ccg acc aat cct      240
Ile Lys Pro Gly Thr Ala Ser Asn Thr Trp Cys Tyr Pro Thr Asn Pro
 65                  70                  75                  80

gtt acc ggt gaa ata ccg aca ctg tct gcc ctg gat att cca gat ggt      288
Val Thr Gly Glu Ile Pro Thr Leu Ser Ala Leu Asp Ile Pro Asp Gly
                 85                  90                  95

gac gaa gtc gat gtg cag tgg cga ctg gta cat gac agt gcg aat ttc      336
Asp Glu Val Asp Val Gln Trp Arg Leu Val His Asp Ser Ala Asn Phe
            100                 105                 110

atc aaa cca acc agc tat ctg gcc cat tac ctc ggt tat gcc tgg gtg      384
Ile Lys Pro Thr Ser Tyr Leu Ala His Tyr Leu Gly Tyr Ala Trp Val
        115                 120                 125

ggc ggc aat cac agc caa tat gtc ggc gaa gac atg gat gtg acc cgt      432
Gly Gly Asn His Ser Gln Tyr Val Gly Glu Asp Met Asp Val Thr Arg
    130                 135                 140

gat ggc gac ggc tgg gtg atc cgt ggc aac aat gac ggc ggc tgt gac      480
Asp Gly Asp Gly Trp Val Ile Arg Gly Asn Asn Asp Gly Gly Cys Asp
145                 150                 155                 160

ggc tat cgc tgt ggt gac aag acg gcc atc aag gtc agc aac ttc gcc      528
Gly Tyr Arg Cys Gly Asp Lys Thr Ala Ile Lys Val Ser Asn Phe Ala
                165                 170                 175

tat aac ctg gat ccc gac agc ttc aag cat ggc gat gtc acc cag tcc      576
Tyr Asn Leu Asp Pro Asp Ser Phe Lys His Gly Asp Val Thr Gln Ser
            180                 185                 190

gac cgc cag ctg gtc aag act gtg gtg ggc tgg gcg gtc aac gac agc      624
Asp Arg Gln Leu Val Lys Thr Val Val Gly Trp Ala Val Asn Asp Ser
        195                 200                 205

gac acc ccc caa tcc ggc tat gac gtc acc ctg cgc tac gac aca gcc      672
Asp Thr Pro Gln Ser Gly Tyr Asp Val Thr Leu Arg Tyr Asp Thr Ala
    210                 215                 220

acc aac tgg tcc aag acc aac acc tat ggc ctg agc gag aag gtg acc      720
Thr Asn Trp Ser Lys Thr Asn Thr Tyr Gly Leu Ser Glu Lys Val Thr
225                 230                 235                 240

acc aag aac aag ttc aag tgg cca ctg gtg ggg gaa acc caa ctc tcc      768
Thr Lys Asn Lys Phe Lys Trp Pro Leu Val Gly Glu Thr Gln Leu Ser
                245                 250                 255

atc gag att gct gcc aat cag tcc tgg gcg tcc cag aac ggg ggc tcg      816
Ile Glu Ile Ala Ala Asn Gln Ser Trp Ala Ser Gln Asn Gly Gly Ser
            260                 265                 270

acc acc acc tcc ctg tct cag tcc gtg cga ccg act gtg ccg gcc cgc      864
Thr Thr Thr Ser Leu Ser Gln Ser Val Arg Pro Thr Val Pro Ala Arg
        275                 280                 285

tcc aag atc ccg gtg aag ata gag ctc tac aag gcc gac atc tcc tat      912
Ser Lys Ile Pro Val Lys Ile Glu Leu Tyr Lys Ala Asp Ile Ser Tyr
    290                 295                 300

ccc tat gag ttc aag gcc gat gtc agc tat gac ctg acc ctg agc ggc      960
Pro Tyr Glu Phe Lys Ala Asp Val Ser Tyr Asp Leu Thr Leu Ser Gly
305                 310                 315                 320

ttc ctg cgc tgg ggc ggc aac gcc tgg tat acc cac ccg gac aac cgt     1008
Phe Leu Arg Trp Gly Gly Asn Ala Trp Tyr Thr His Pro Asp Asn Arg
                325                 330                 335

ccg aac tgg aac cac acc ttc gtc ata ggt ccg tac aag gac aag gcg     1056
Pro Asn Trp Asn His Thr Phe Val Ile Gly Pro Tyr Lys Asp Lys Ala
            340                 345                 350

agc agc att cgg tac cag tgg gac aag cgt tac atc ccg ggt gaa gtg     1104
Ser Ser Ile Arg Tyr Gln Trp Asp Lys Arg Tyr Ile Pro Gly Glu Val
        355                 360                 365

aag tgg tgg gac tgg aac tgg acc ata cag cag aac ggt ctg tct acc     1152
```

```
Lys Trp Trp Asp Trp Asn Trp Thr Ile Gln Gln Asn Gly Leu Ser Thr
    370                 375                 380

atg cag aac aac ctg gcc aga gtg ctg cgc ccg gtg cgg gcg ggg atc      1200
Met Gln Asn Asn Leu Ala Arg Val Leu Arg Pro Val Arg Ala Gly Ile
385                 390                 395                 400

acc ggt gat ttc agt gcc gag agc cag ttt gcc ggc aac ata gag atc      1248
Thr Gly Asp Phe Ser Ala Glu Ser Gln Phe Ala Gly Asn Ile Glu Ile
                405                 410                 415

ggt gct ccc gtg ccg ctc gcg gct gac agc aag gtg cgt cgt gct cgc      1296
Gly Ala Pro Val Pro Leu Ala Ala Asp Ser Lys Val Arg Arg Ala Arg
            420                 425                 430

agt gtg gac ggc gct ggt caa ggc ctg agg ctg gag atc ccg ctc gat      1344
Ser Val Asp Gly Ala Gly Gln Gly Leu Arg Leu Glu Ile Pro Leu Asp
        435                 440                 445

gcg caa gag ctc tcc ggg ctt ggc ttc aac aac gtc agc ctc agc gtg      1392
Ala Gln Glu Leu Ser Gly Leu Gly Phe Asn Asn Val Ser Leu Ser Val
    450                 455                 460

acc cct gct gcc aat caa                                              1410
Thr Pro Ala Ala Asn Gln
465                 470


<210> SEQ ID NO 2
<211> LENGTH: 470
<212> TYPE: PRT
<213> ORGANISM: Aeromonas hydrophila

<400> SEQUENCE: 2

Ala Glu Pro Val Tyr Pro Asp Gln Leu Arg Leu Phe Ser Leu Gly Gln
 1               5                  10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240
```

```
Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Gln Asn Gly Leu Ser Thr
    370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Ser Lys Val Arg Arg Ala Arg
            420                 425                 430

Ser Val Asp Gly Ala Gly Gln Gly Leu Arg Leu Glu Ile Pro Leu Asp
        435                 440                 445

Ala Gln Glu Leu Ser Gly Leu Gly Phe Asn Asn Val Ser Leu Ser Val
    450                 455                 460

Thr Pro Ala Ala Asn Gln
465                 470


<210> SEQ ID NO 3
<211> LENGTH: 1410
<212> TYPE: DNA
<213> ORGANISM: Artificial Sequence
<220> FEATURE:
<221> NAME/KEY: CDS
<222> LOCATION: (1)...(1410)
<223> OTHER INFORMATION: Proaerolysin with a PSA sequence substituted
      for the furin site.

<400> SEQUENCE: 3

gca gag ccc gtc tat cca gac cag ctt cgc ttg ttt tca ttg ggc caa       48
Ala Glu Pro Val Tyr Pro Asp Gln Leu Arg Leu Phe Ser Leu Gly Gln
 1               5                  10                  15

ggg gtc tgt ggc gac aag tat cgc ccc gtc aat cga gaa gaa gcc caa       96
Gly Val Cys Gly Asp Lys Tyr Arg Pro Val Asn Arg Glu Glu Ala Gln
            20                  25                  30

agc gtt aaa agc aat att gtc ggc atg atg ggg caa tgg caa ata agc      144
Ser Val Lys Ser Asn Ile Val Gly Met Met Gly Gln Trp Gln Ile Ser
        35                  40                  45

ggg ctg gcc aac ggc tgg gtc att atg ggg ccg ggt tat aac ggt gaa      192
Gly Leu Ala Asn Gly Trp Val Ile Met Gly Pro Gly Tyr Asn Gly Glu
     50                  55                  60

ata aaa cca ggg aca gcg tcc aat acc tgg tgt tat ccg acc aat cct      240
Ile Lys Pro Gly Thr Ala Ser Asn Thr Trp Cys Tyr Pro Thr Asn Pro
 65                  70                  75                  80
```

-continued

```
gtt acc ggt gaa ata ccg aca ctg tct gcc ctg gat att cca gat ggt      288
Val Thr Gly Glu Ile Pro Thr Leu Ser Ala Leu Asp Ile Pro Asp Gly
                 85                  90                  95

gac gaa gtc gat gtg cag tgg cga ctg gta cat gac agt gcg aat ttc      336
Asp Glu Val Asp Val Gln Trp Arg Leu Val His Asp Ser Ala Asn Phe
            100                 105                 110

atc aaa cca acc agc tat ctg gcc cat tac ctc ggt tat gcc tgg gtg      384
Ile Lys Pro Thr Ser Tyr Leu Ala His Tyr Leu Gly Tyr Ala Trp Val
        115                 120                 125

ggc ggc aat cac agc caa tat gtc ggc gaa gac atg gat gtg acc cgt      432
Gly Gly Asn His Ser Gln Tyr Val Gly Glu Asp Met Asp Val Thr Arg
    130                 135                 140

gat ggc gac ggc tgg gtg atc cgt ggc aac aat gac ggc ggc tgt gac      480
Asp Gly Asp Gly Trp Val Ile Arg Gly Asn Asn Asp Gly Gly Cys Asp
145                 150                 155                 160

ggc tat cgc tgt ggt gac aag acg gcc atc aag gtc agc aac ttc gcc      528
Gly Tyr Arg Cys Gly Asp Lys Thr Ala Ile Lys Val Ser Asn Phe Ala
                165                 170                 175

tat aac ctg gat ccc gac agc ttc aag cat ggc gat gtc acc cag tcc      576
Tyr Asn Leu Asp Pro Asp Ser Phe Lys His Gly Asp Val Thr Gln Ser
            180                 185                 190

gac cgc cag ctg gtc aag act gtg gtg ggc tgg gcg gtc aac gac agc      624
Asp Arg Gln Leu Val Lys Thr Val Val Gly Trp Ala Val Asn Asp Ser
        195                 200                 205

gac acc ccc caa tcc ggc tat gac gtc acc ctg cgc tac gac aca gcc      672
Asp Thr Pro Gln Ser Gly Tyr Asp Val Thr Leu Arg Tyr Asp Thr Ala
    210                 215                 220

acc aac tgg tcc aag acc aac acc tat ggc ctg agc gag aag gtg acc      720
Thr Asn Trp Ser Lys Thr Asn Thr Tyr Gly Leu Ser Glu Lys Val Thr
225                 230                 235                 240

acc aag aac aag ttc aag tgg cca ctg gtg ggg gaa acc caa ctc tcc      768
Thr Lys Asn Lys Phe Lys Trp Pro Leu Val Gly Glu Thr Gln Leu Ser
                245                 250                 255

atc gag att gct gcc aat cag tcc tgg gcg tcc cag aac ggg ggc tcg      816
Ile Glu Ile Ala Ala Asn Gln Ser Trp Ala Ser Gln Asn Gly Gly Ser
            260                 265                 270

acc acc acc tcc ctg tct cag tcc gtg cga ccg act gtg ccg gcc cgc      864
Thr Thr Thr Ser Leu Ser Gln Ser Val Arg Pro Thr Val Pro Ala Arg
        275                 280                 285

tcc aag atc ccg gtg aag ata gag ctc tac aag gcc gac atc tcc tat      912
Ser Lys Ile Pro Val Lys Ile Glu Leu Tyr Lys Ala Asp Ile Ser Tyr
    290                 295                 300

ccc tat gag ttc aag gcc gat gtc agc tat gac ctg acc ctg agc ggc      960
Pro Tyr Glu Phe Lys Ala Asp Val Ser Tyr Asp Leu Thr Leu Ser Gly
305                 310                 315                 320

ttc ctg cgc tgg ggc ggc aac gcc tgg tat acc cac ccg gac aac cgt     1008
Phe Leu Arg Trp Gly Gly Asn Ala Trp Tyr Thr His Pro Asp Asn Arg
                325                 330                 335

ccg aac tgg aac cac acc ttc gtc ata ggt ccg tac aag gac aag gcg     1056
Pro Asn Trp Asn His Thr Phe Val Ile Gly Pro Tyr Lys Asp Lys Ala
            340                 345                 350

agc agc att cgg tac cag tgg gac aag cgt tac atc ccg ggt gaa gtg     1104
Ser Ser Ile Arg Tyr Gln Trp Asp Lys Arg Tyr Ile Pro Gly Glu Val
        355                 360                 365

aag tgg tgg gac tgg aac tgg acc ata cag cag aac ggt ctg tct acc     1152
Lys Trp Trp Asp Trp Asn Trp Thr Ile Gln Gln Asn Gly Leu Ser Thr
    370                 375                 380

atg cag aac aac ctg gcc aga gtg ctg cgc ccg gtg cgg gcg ggg atc     1200
Met Gln Asn Asn Leu Ala Arg Val Leu Arg Pro Val Arg Ala Gly Ile
385                 390                 395                 400
```

```
acc ggt gat ttc agt gcc gag agc cag ttt gcc ggc aac ata gag atc     1248
Thr Gly Asp Phe Ser Ala Glu Ser Gln Phe Ala Gly Asn Ile Glu Ile
                405                 410                 415

ggt gct ccc gtg ccg ctc gcg gct gac agc cat tcc tcc aag ctg cag     1296
Gly Ala Pro Val Pro Leu Ala Ala Asp Ser His Ser Ser Lys Leu Gln
            420                 425                 430

agt gtg gac ggc gct ggt caa ggc ctg agg ctg gag atc ccg ctc gat     1344
Ser Val Asp Gly Ala Gly Gln Gly Leu Arg Leu Glu Ile Pro Leu Asp
        435                 440                 445

gcg caa gag ctc tcc ggg ctt ggc ttc aac aac gtc agc ctc agc gtg     1392
Ala Gln Glu Leu Ser Gly Leu Gly Phe Asn Asn Val Ser Leu Ser Val
    450                 455                 460

acc cct gct gcc aat caa                                             1410
Thr Pro Ala Ala Asn Gln
465                 470


<210> SEQ ID NO 4
<211> LENGTH: 470
<212> TYPE: PRT
<213> ORGANISM: Artificial Sequence
<220> FEATURE:
<223> OTHER INFORMATION: Proaerolysin with a PSA sequence substituted
      for the furin site.

<400> SEQUENCE: 4

Ala Glu Pro Val Tyr Pro Asp Gln Leu Arg Leu Phe Ser Leu Gly Gln
 1               5                  10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255
```

```
Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Gln Asn Gly Leu Ser Thr
    370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Ser His Ser Ser Lys Leu Gln
            420                 425                 430

Ser Val Asp Gly Ala Gly Gln Gly Leu Arg Leu Glu Ile Pro Leu Asp
        435                 440                 445

Ala Gln Glu Leu Ser Gly Leu Gly Phe Asn Asn Val Ser Leu Ser Val
    450                 455                 460

Thr Pro Ala Ala Asn Gln
465                 470


<210> SEQ ID NO 5
<211> LENGTH: 6
<212> TYPE: PRT
<213> ORGANISM: Homo Sapiens

<400> SEQUENCE: 5

His Ser Ser Lys Leu Gln
 1               5


<210> SEQ ID NO 6
<211> LENGTH: 1410
<212> TYPE: DNA
<213> ORGANISM: Artificial Sequence
<220> FEATURE:
<223> OTHER INFORMATION: Proaerolysin with a PSA sequence substituted
      for the furin site.
<220> FEATURE:
<221> NAME/KEY: CDS
<222> LOCATION: (1)...(1410)

<400> SEQUENCE: 6

gca gag ccc gtc tat cca gac cag ctt cgc ttg ttt tca ttg ggc caa       48
Ala Glu Pro Val Tyr Pro Asp Gln Leu Arg Leu Phe Ser Leu Gly Gln
 1               5                  10                  15

ggg gtc tgt ggc gac aag tat cgc ccc gtc aat cga gaa gaa gcc caa       96
Gly Val Cys Gly Asp Lys Tyr Arg Pro Val Asn Arg Glu Glu Ala Gln
            20                  25                  30

agc gtt aaa agc aat att gtc ggc atg atg ggg caa tgg caa ata agc      144
Ser Val Lys Ser Asn Ile Val Gly Met Met Gly Gln Trp Gln Ile Ser
         35                  40                  45
```

-continued

```
ggg ctg gcc aac ggc tgg gtc att atg ggg ccg ggt tat aac ggt gaa      192
Gly Leu Ala Asn Gly Trp Val Ile Met Gly Pro Gly Tyr Asn Gly Glu
     50                  55                  60

ata aaa cca ggg aca gcg tcc aat acc tgg tgt tat ccg acc aat cct      240
Ile Lys Pro Gly Thr Ala Ser Asn Thr Trp Cys Tyr Pro Thr Asn Pro
 65                  70                  75                  80

gtt acc ggt gaa ata ccg aca ctg tct gcc ctg gat att cca gat ggt      288
Val Thr Gly Glu Ile Pro Thr Leu Ser Ala Leu Asp Ile Pro Asp Gly
                 85                  90                  95

gac gaa gtc gat gtg cag tgg cga ctg gta cat gac agt gcg aat ttc      336
Asp Glu Val Asp Val Gln Trp Arg Leu Val His Asp Ser Ala Asn Phe
            100                 105                 110

atc aaa cca acc agc tat ctg gcc cat tac ctc ggt tat gcc tgg gtg      384
Ile Lys Pro Thr Ser Tyr Leu Ala His Tyr Leu Gly Tyr Ala Trp Val
        115                 120                 125

ggc ggc aat cac agc caa tat gtc ggc gaa gac atg gat gtg acc cgt      432
Gly Gly Asn His Ser Gln Tyr Val Gly Glu Asp Met Asp Val Thr Arg
    130                 135                 140

gat ggc gac ggc tgg gtg atc cgt ggc aac aat gac ggc ggc tgt gac      480
Asp Gly Asp Gly Trp Val Ile Arg Gly Asn Asn Asp Gly Gly Cys Asp
145                 150                 155                 160

ggc tat cgc tgt ggt gac aag acg gcc atc aag gtc agc aac ttc gcc      528
Gly Tyr Arg Cys Gly Asp Lys Thr Ala Ile Lys Val Ser Asn Phe Ala
                165                 170                 175

tat aac ctg gat ccc gac agc ttc aag cat ggc gat gtc acc cag tcc      576
Tyr Asn Leu Asp Pro Asp Ser Phe Lys His Gly Asp Val Thr Gln Ser
            180                 185                 190

gac cgc cag ctg gtc aag act gtg gtg ggc tgg gcg gtc aac gac agc      624
Asp Arg Gln Leu Val Lys Thr Val Val Gly Trp Ala Val Asn Asp Ser
        195                 200                 205

gac acc ccc caa tcc ggc tat gac gtc acc ctg cgc tac gac aca gcc      672
Asp Thr Pro Gln Ser Gly Tyr Asp Val Thr Leu Arg Tyr Asp Thr Ala
    210                 215                 220

acc aac tgg tcc aag acc aac acc tat ggc ctg agc gag aag gtg acc      720
Thr Asn Trp Ser Lys Thr Asn Thr Tyr Gly Leu Ser Glu Lys Val Thr
225                 230                 235                 240

acc aag aac aag ttc aag tgg cca ctg gtg ggg gaa acc caa ctc tcc      768
Thr Lys Asn Lys Phe Lys Trp Pro Leu Val Gly Glu Thr Gln Leu Ser
                245                 250                 255

atc gag att gct gcc aat cag tcc tgg gcg tcc cag aac ggg ggc tcg      816
Ile Glu Ile Ala Ala Asn Gln Ser Trp Ala Ser Gln Asn Gly Gly Ser
            260                 265                 270

acc acc acc tcc ctg tct cag tcc gtg cga ccg act gtg ccg gcc cgc      864
Thr Thr Thr Ser Leu Ser Gln Ser Val Arg Pro Thr Val Pro Ala Arg
        275                 280                 285

tcc aag atc ccg gtg aag ata gag ctc tac aag gcc gac atc tcc tat      912
Ser Lys Ile Pro Val Lys Ile Glu Leu Tyr Lys Ala Asp Ile Ser Tyr
    290                 295                 300

ccc tat gag ttc aag gcc gat gtc agc tat gac ctg acc ctg agc ggc      960
Pro Tyr Glu Phe Lys Ala Asp Val Ser Tyr Asp Leu Thr Leu Ser Gly
305                 310                 315                 320

ttc ctg cgc tgg ggc ggc aac gcc tgg tat acc cac ccg gac aac cgt     1008
Phe Leu Arg Trp Gly Gly Asn Ala Trp Tyr Thr His Pro Asp Asn Arg
                325                 330                 335

ccg aac tgg aac cac acc ttc gtc ata ggt ccg tac aag gac aag gcg     1056
Pro Asn Trp Asn His Thr Phe Val Ile Gly Pro Tyr Lys Asp Lys Ala
            340                 345                 350

agc agc att cgg tac cag tgg gac aag cgt tac atc ccg ggt gaa gtg     1104
Ser Ser Ile Arg Tyr Gln Trp Asp Lys Arg Tyr Ile Pro Gly Glu Val
```

-continued

```
        355                 360                 365

aag tgg tgg gac tgg aac tgg acc ata cag cag aac ggt ctg tct acc      1152
Lys Trp Trp Asp Trp Asn Trp Thr Ile Gln Gln Asn Gly Leu Ser Thr
    370                 375                 380

atg cag aac aac ctg gcc aga gtg ctg cgc ccg gtg cgg gcg ggg atc      1200
Met Gln Asn Asn Leu Ala Arg Val Leu Arg Pro Val Arg Ala Gly Ile
385                 390                 395                 400

acc ggt gat ttc agt gcc gag agc cag ttt gcc ggc aac ata gag atc      1248
Thr Gly Asp Phe Ser Ala Glu Ser Gln Phe Ala Gly Asn Ile Glu Ile
                405                 410                 415

ggt gct ccc gtg ccg ctc gcg gct gac agc cat tcc tcc aag ctg cag      1296
Gly Ala Pro Val Pro Leu Ala Ala Asp Ser His Ser Ser Lys Leu Gln
            420                 425                 430

agt gcc gac ggc gct ggt caa ggc ctg agg ctg gag atc ccg ctc gat      1344
Ser Ala Asp Gly Ala Gly Gln Gly Leu Arg Leu Glu Ile Pro Leu Asp
        435                 440                 445

gcg caa gag ctc tcc ggg ctt ggc ttc aac aac gtc agc ctc agc gtg      1392
Ala Gln Glu Leu Ser Gly Leu Gly Phe Asn Asn Val Ser Leu Ser Val
    450                 455                 460

acc cct gct gcc aat caa                                              1410
Thr Pro Ala Ala Asn Gln
465                 470


<210> SEQ ID NO 7
<211> LENGTH: 470
<212> TYPE: PRT
<213> ORGANISM: Artificial Sequence
<220> FEATURE:
<223> OTHER INFORMATION: Proaerolysin with a PSA sequence substituted
      for the furin site.

<400> SEQUENCE: 7

Ala Glu Pro Val Tyr Pro Asp Gln Leu Arg Leu Phe Ser Leu Gly Gln
 1               5                  10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205
```

```
Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Gln Asn Gly Leu Ser Thr
    370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Ser His Ser Ser Lys Leu Gln
            420                 425                 430

Ser Ala Asp Gly Ala Gly Gln Gly Leu Arg Leu Glu Ile Pro Leu Asp
        435                 440                 445

Ala Gln Glu Leu Ser Gly Leu Gly Phe Asn Asn Val Ser Leu Ser Val
    450                 455                 460

Thr Pro Ala Ala Asn Gln
465                 470


<210> SEQ ID NO 8
<211> LENGTH: 8
<212> TYPE: PRT
<213> ORGANISM: Artificial Sequence
<220> FEATURE:
<223> OTHER INFORMATION: PSA cleavage site

<400> SEQUENCE: 8

His Ser Ser Lys Leu Gln Ser Ala
 1               5


<210> SEQ ID NO 9
<211> LENGTH: 1410
<212> TYPE: DNA
<213> ORGANISM: Artificial Sequence
<220> FEATURE:
<223> OTHER INFORMATION: Proaerolysin with a PSA sequence substituted
      for the furin site.
<220> FEATURE:
<221> NAME/KEY: CDS
<222> LOCATION: (1)...(1410)

<400> SEQUENCE: 9
```

-continued

```
gca gag ccc gtc tat cca gac cag ctt cgc ttg ttt tca ttg ggc caa        48
Ala Glu Pro Val Tyr Pro Asp Gln Leu Arg Leu Phe Ser Leu Gly Gln
 1               5                  10                  15

ggg gtc tgt ggc gac aag tat cgc ccc gtc aat cga gaa gaa gcc caa        96
Gly Val Cys Gly Asp Lys Tyr Arg Pro Val Asn Arg Glu Glu Ala Gln
            20                  25                  30

agc gtt aaa agc aat att gtc ggc atg atg ggg caa tgg caa ata agc       144
Ser Val Lys Ser Asn Ile Val Gly Met Met Gly Gln Trp Gln Ile Ser
        35                  40                  45

ggg ctg gcc aac ggc tgg gtc att atg ggg ccg ggt tat aac ggt gaa       192
Gly Leu Ala Asn Gly Trp Val Ile Met Gly Pro Gly Tyr Asn Gly Glu
    50                  55                  60

ata aaa cca ggg aca gcg tcc aat acc tgg tgt tat ccg acc aat cct       240
Ile Lys Pro Gly Thr Ala Ser Asn Thr Trp Cys Tyr Pro Thr Asn Pro
 65                  70                  75                  80

gtt acc ggt gaa ata ccg aca ctg tct gcc ctg gat att cca gat ggt       288
Val Thr Gly Glu Ile Pro Thr Leu Ser Ala Leu Asp Ile Pro Asp Gly
                85                  90                  95

gac gaa gtc gat gtg cag tgg cga ctg gta cat gac agt gcg aat ttc       336
Asp Glu Val Asp Val Gln Trp Arg Leu Val His Asp Ser Ala Asn Phe
            100                 105                 110

atc aaa cca acc agc tat ctg gcc cat tac ctc ggt tat gcc tgg gtg       384
Ile Lys Pro Thr Ser Tyr Leu Ala His Tyr Leu Gly Tyr Ala Trp Val
        115                 120                 125

ggc ggc aat cac agc caa tat gtc ggc gaa gac atg gat gtg acc cgt       432
Gly Gly Asn His Ser Gln Tyr Val Gly Glu Asp Met Asp Val Thr Arg
    130                 135                 140

gat ggc gac ggc tgg gtg atc cgt ggc aac aat gac ggc ggc tgt gac       480
Asp Gly Asp Gly Trp Val Ile Arg Gly Asn Asn Asp Gly Gly Cys Asp
145                 150                 155                 160

ggc tat cgc tgt ggt gac aag acg gcc atc aag gtc agc aac ttc gcc       528
Gly Tyr Arg Cys Gly Asp Lys Thr Ala Ile Lys Val Ser Asn Phe Ala
                165                 170                 175

tat aac ctg gat ccc gac agc ttc aag cat ggc gat gtc acc cag tcc       576
Tyr Asn Leu Asp Pro Asp Ser Phe Lys His Gly Asp Val Thr Gln Ser
            180                 185                 190

gac cgc cag ctg gtc aag act gtg gtg ggc tgg gcg gtc aac gac agc       624
Asp Arg Gln Leu Val Lys Thr Val Val Gly Trp Ala Val Asn Asp Ser
        195                 200                 205

gac acc ccc caa tcc ggc tat gac gtc acc ctg cgc tac gac aca gcc       672
Asp Thr Pro Gln Ser Gly Tyr Asp Val Thr Leu Arg Tyr Asp Thr Ala
    210                 215                 220

acc aac tgg tcc aag acc aac acc tat ggc ctg agc gag aag gtg acc       720
Thr Asn Trp Ser Lys Thr Asn Thr Tyr Gly Leu Ser Glu Lys Val Thr
225                 230                 235                 240

acc aag aac aag ttc aag tgg cca ctg gtg ggg gaa acc caa ctc tcc       768
Thr Lys Asn Lys Phe Lys Trp Pro Leu Val Gly Glu Thr Gln Leu Ser
                245                 250                 255

atc gag att gct gcc aat cag tcc tgg gcg tcc cag aac ggg ggc tcg       816
Ile Glu Ile Ala Ala Asn Gln Ser Trp Ala Ser Gln Asn Gly Gly Ser
            260                 265                 270

acc acc acc tcc ctg tct cag tcc gtg cga ccg act gtg ccg gcc cgc       864
Thr Thr Thr Ser Leu Ser Gln Ser Val Arg Pro Thr Val Pro Ala Arg
        275                 280                 285

tcc aag atc ccg gtg aag ata gag ctc tac aag gcc gac atc tcc tat       912
Ser Lys Ile Pro Val Lys Ile Glu Leu Tyr Lys Ala Asp Ile Ser Tyr
    290                 295                 300

ccc tat gag ttc aag gcc gat gtc agc tat gac ctg acc ctg agc ggc       960
Pro Tyr Glu Phe Lys Ala Asp Val Ser Tyr Asp Leu Thr Leu Ser Gly
305                 310                 315                 320
```

```
ttc ctg cgc tgg ggc ggc aac gcc tgg tat acc cac ccg gac aac cgt      1008
Phe Leu Arg Trp Gly Gly Asn Ala Trp Tyr Thr His Pro Asp Asn Arg
                325                 330                 335

ccg aac tgg aac cac acc ttc gtc ata ggt ccg tac aag gac aag gcg      1056
Pro Asn Trp Asn His Thr Phe Val Ile Gly Pro Tyr Lys Asp Lys Ala
            340                 345                 350

agc agc att cgg tac cag tgg gac aag cgt tac atc ccg ggt gaa gtg      1104
Ser Ser Ile Arg Tyr Gln Trp Asp Lys Arg Tyr Ile Pro Gly Glu Val
        355                 360                 365

aag tgg tgg gac tgg aac tgg acc ata cag cag aac ggt ctg tct acc      1152
Lys Trp Trp Asp Trp Asn Trp Thr Ile Gln Gln Asn Gly Leu Ser Thr
    370                 375                 380

atg cag aac aac ctg gcc aga gtg ctg cgc ccg gtg cgg gcg ggg atc      1200
Met Gln Asn Asn Leu Ala Arg Val Leu Arg Pro Val Arg Ala Gly Ile
385                 390                 395                 400

acc ggt gat ttc agt gcc gag agc cag ttt gcc ggc aac ata gag atc      1248
Thr Gly Asp Phe Ser Ala Glu Ser Gln Phe Ala Gly Asn Ile Glu Ile
                405                 410                 415

ggt gct ccc gtg ccg ctc gcg gct gac tcc cag ttc tat agc agc aat      1296
Gly Ala Pro Val Pro Leu Ala Ala Asp Ser Gln Phe Tyr Ser Ser Asn
            420                 425                 430

agt gtg gac ggc gct ggt caa ggc ctg agg ctg gag atc ccg ctc gat      1344
Ser Val Asp Gly Ala Gly Gln Gly Leu Arg Leu Glu Ile Pro Leu Asp
        435                 440                 445

gcg caa gag ctc tcc ggg ctt ggc ttc aac aac gtc agc ctc agc gtg      1392
Ala Gln Glu Leu Ser Gly Leu Gly Phe Asn Asn Val Ser Leu Ser Val
    450                 455                 460

acc cct gct gcc aat caa                                              1410
Thr Pro Ala Ala Asn Gln
465                 470


<210> SEQ ID NO 10
<211> LENGTH: 470
<212> TYPE: PRT
<213> ORGANISM: Artificial Sequence
<220> FEATURE:
<223> OTHER INFORMATION: Proaerolysin with a PSA sequence substituted
      for the furin site.

<400> SEQUENCE: 10

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140
```

```
Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Gln Asn Gly Leu Ser Thr
    370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Ser Gln Phe Tyr Ser Ser Asn
            420                 425                 430

Ser Val Asp Gly Ala Gly Gln Gly Leu Arg Leu Glu Ile Pro Leu Asp
        435                 440                 445

Ala Gln Glu Leu Ser Gly Leu Gly Phe Asn Asn Val Ser Leu Ser Val
    450                 455                 460

Thr Pro Ala Ala Asn Gln
465                 470


<210> SEQ ID NO 11
<211> LENGTH: 6
<212> TYPE: PRT
<213> ORGANISM: Artificial Sequence
<220> FEATURE:
<223> OTHER INFORMATION: PSA cleavage site

<400> SEQUENCE: 11

Gln Phe Tyr Ser Ser Asn
 1               5


<210> SEQ ID NO 12
<211> LENGTH: 1410
```

```
<212> TYPE: DNA
<213> ORGANISM: Artificial Sequence
<220> FEATURE:
<223> OTHER INFORMATION: Proaerolysin with a PSA sequence substituted
      for the furin site.
<220> FEATURE:
<221> NAME/KEY: CDS
<222> LOCATION: (1)...(1410)

<400> SEQUENCE: 12

gca gag ccc gtc tat cca gac cag ctt cgc ttg ttt tca ttg ggc caa       48
Ala Glu Pro Val Tyr Pro Asp Gln Leu Arg Leu Phe Ser Leu Gly Gln
 1               5                  10                  15

ggg gtc tgt ggc gac aag tat cgc ccc gtc aat cga gaa gaa gcc caa       96
Gly Val Cys Gly Asp Lys Tyr Arg Pro Val Asn Arg Glu Glu Ala Gln
            20                  25                  30

agc gtt aaa agc aat att gtc ggc atg atg ggg caa tgg caa ata agc      144
Ser Val Lys Ser Asn Ile Val Gly Met Met Gly Gln Trp Gln Ile Ser
        35                  40                  45

ggg ctg gcc aac ggc tgg gtc att atg ggg ccg ggt tat aac ggt gaa      192
Gly Leu Ala Asn Gly Trp Val Ile Met Gly Pro Gly Tyr Asn Gly Glu
    50                  55                  60

ata aaa cca ggg aca gcg tcc aat acc tgg tgt tat ccg acc aat cct      240
Ile Lys Pro Gly Thr Ala Ser Asn Thr Trp Cys Tyr Pro Thr Asn Pro
 65                  70                  75                  80

gtt acc ggt gaa ata ccg aca ctg tct gcc ctg gat att cca gat ggt      288
Val Thr Gly Glu Ile Pro Thr Leu Ser Ala Leu Asp Ile Pro Asp Gly
                85                  90                  95

gac gaa gtc gat gtg cag tgg cga ctg gta cat gac agt gcg aat ttc      336
Asp Glu Val Asp Val Gln Trp Arg Leu Val His Asp Ser Ala Asn Phe
            100                 105                 110

atc aaa cca acc agc tat ctg gcc cat tac ctc ggt tat gcc tgg gtg      384
Ile Lys Pro Thr Ser Tyr Leu Ala His Tyr Leu Gly Tyr Ala Trp Val
        115                 120                 125

ggc ggc aat cac agc caa tat gtc ggc gaa gac atg gat gtg acc cgt      432
Gly Gly Asn His Ser Gln Tyr Val Gly Glu Asp Met Asp Val Thr Arg
    130                 135                 140

gat ggc gac ggc tgg gtg atc cgt ggc aac aat gac ggc ggc tgt gac      480
Asp Gly Asp Gly Trp Val Ile Arg Gly Asn Asn Asp Gly Gly Cys Asp
145                 150                 155                 160

ggc tat cgc tgt ggt gac aag acg gcc atc aag gtc agc aac ttc gcc      528
Gly Tyr Arg Cys Gly Asp Lys Thr Ala Ile Lys Val Ser Asn Phe Ala
                165                 170                 175

tat aac ctg gat ccc gac agc ttc aag cat ggc gat gtc acc cag tcc      576
Tyr Asn Leu Asp Pro Asp Ser Phe Lys His Gly Asp Val Thr Gln Ser
            180                 185                 190

gac cgc cag ctg gtc aag act gtg gtg ggc tgg gcg gtc aac gac agc      624
Asp Arg Gln Leu Val Lys Thr Val Val Gly Trp Ala Val Asn Asp Ser
        195                 200                 205

gac acc ccc caa tcc ggc tat gac gtc acc ctg cgc tac gac aca gcc      672
Asp Thr Pro Gln Ser Gly Tyr Asp Val Thr Leu Arg Tyr Asp Thr Ala
    210                 215                 220

acc aac tgg tcc aag acc aac acc tat ggc ctg agc gag aag gtg acc      720
Thr Asn Trp Ser Lys Thr Asn Thr Tyr Gly Leu Ser Glu Lys Val Thr
225                 230                 235                 240

acc aag aac aag ttc aag tgg cca ctg gtg ggg gaa acc caa ctc tcc      768
Thr Lys Asn Lys Phe Lys Trp Pro Leu Val Gly Glu Thr Gln Leu Ser
                245                 250                 255

atc gag att gct gcc aat cag tcc tgg gcg tcc cag aac ggg ggc tcg      816
Ile Glu Ile Ala Ala Asn Gln Ser Trp Ala Ser Gln Asn Gly Gly Ser
            260                 265                 270
```

```
acc acc acc tcc ctg tct cag tcc gtg cga ccg act gtg ccg gcc cgc      864
Thr Thr Thr Ser Leu Ser Gln Ser Val Arg Pro Thr Val Pro Ala Arg
        275                 280                 285

tcc aag atc ccg gtg aag ata gag ctc tac aag gcc gac atc tcc tat      912
Ser Lys Ile Pro Val Lys Ile Glu Leu Tyr Lys Ala Asp Ile Ser Tyr
    290                 295                 300

ccc tat gag ttc aag gcc gat gtc agc tat gac ctg acc ctg agc ggc      960
Pro Tyr Glu Phe Lys Ala Asp Val Ser Tyr Asp Leu Thr Leu Ser Gly
305                 310                 315                 320

ttc ctg cgc tgg ggc ggc aac gcc tgg tat acc cac ccg gac aac cgt     1008
Phe Leu Arg Trp Gly Gly Asn Ala Trp Tyr Thr His Pro Asp Asn Arg
                325                 330                 335

ccg aac tgg aac cac acc ttc gtc ata ggt ccg tac aag gac aag gcg     1056
Pro Asn Trp Asn His Thr Phe Val Ile Gly Pro Tyr Lys Asp Lys Ala
            340                 345                 350

agc agc att cgg tac cag tgg gac aag cgt tac atc ccg ggt gaa gtg     1104
Ser Ser Ile Arg Tyr Gln Trp Asp Lys Arg Tyr Ile Pro Gly Glu Val
        355                 360                 365

aag tgg tgg gac tgg aac tgg acc ata cag cag aac ggt ctg tct acc     1152
Lys Trp Trp Asp Trp Asn Trp Thr Ile Gln Gln Asn Gly Leu Ser Thr
    370                 375                 380

atg cag aac aac ctg gcc aga gtg ctg cgc ccg gtg cgg gcg ggg atc     1200
Met Gln Asn Asn Leu Ala Arg Val Leu Arg Pro Val Arg Ala Gly Ile
385                 390                 395                 400

acc ggt gat ttc agt gcc gag agc cag ttt gcc ggc aac ata gag atc     1248
Thr Gly Asp Phe Ser Ala Glu Ser Gln Phe Ala Gly Asn Ile Glu Ile
                405                 410                 415

ggt gct ccc gtg ccg ctc gcg gct gac ggt ata agt agt ttc cag agt     1296
Gly Ala Pro Val Pro Leu Ala Ala Asp Gly Ile Ser Ser Phe Gln Ser
            420                 425                 430

agt gtg gac ggc gct ggt caa ggc ctg agg ctg gag atc ccg ctc gat     1344
Ser Val Asp Gly Ala Gly Gln Gly Leu Arg Leu Glu Ile Pro Leu Asp
        435                 440                 445

gcg caa gag ctc tcc ggg ctt ggc ttc aac aac gtc agc ctc agc gtg     1392
Ala Gln Glu Leu Ser Gly Leu Gly Phe Asn Asn Val Ser Leu Ser Val
    450                 455                 460

acc cct gct gcc aat caa                                             1410
Thr Pro Ala Ala Asn Gln
465                 470


<210> SEQ ID NO 13
<211> LENGTH: 470
<212> TYPE: PRT
<213> ORGANISM: Artificial Sequence
<220> FEATURE:
<223> OTHER INFORMATION: Proaerolysin with a PSA sequence substituted
      for the furin site.

<400> SEQUENCE: 13

Ala Glu Pro Val Tyr Pro Asp Gln Leu Arg Leu Phe Ser Leu Gly Gln
 1               5                  10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
```

-continued

```
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Gln Asn Gly Leu Ser Thr
    370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Gly Ile Ser Ser Phe Gln Ser
            420                 425                 430

Ser Val Asp Gly Ala Gly Gln Gly Leu Arg Leu Glu Ile Pro Leu Asp
        435                 440                 445

Ala Gln Glu Leu Ser Gly Leu Gly Phe Asn Asn Val Ser Leu Ser Val
    450                 455                 460

Thr Pro Ala Ala Asn Gln
465                 470


<210> SEQ ID NO 14
<211> LENGTH: 7
<212> TYPE: PRT
<213> ORGANISM: Artificial Sequence
```

<220> FEATURE:
<223> OTHER INFORMATION: PSA cleavage site

<400> SEQUENCE: 14

Gly Ile Ser Ser Phe Gln Ser
1 5

<210> SEQ ID NO 15
<211> LENGTH: 7
<212> TYPE: PRT
<213> ORGANISM: Homo sapiens

<400> SEQUENCE: 15

Lys Gly Ile Ser Ser Gln Tyr
1 5

<210> SEQ ID NO 16
<211> LENGTH: 7
<212> TYPE: PRT
<213> ORGANISM: Homo sapiens

<400> SEQUENCE: 16

Ser Arg Lys Ser Gln Gln Tyr
1 5

<210> SEQ ID NO 17
<211> LENGTH: 7
<212> TYPE: PRT
<213> ORGANISM: Homo sapiens

<400> SEQUENCE: 17

Ala Thr Lys Ser Lys Gln His
1 5

<210> SEQ ID NO 18
<211> LENGTH: 7
<212> TYPE: PRT
<213> ORGANISM: Homo sapiens

<400> SEQUENCE: 18

Lys Gly Leu Ser Ser Gln Cys
1 5

<210> SEQ ID NO 19
<211> LENGTH: 7
<212> TYPE: PRT
<213> ORGANISM: Homo sapiens

<400> SEQUENCE: 19

Leu Gly Gly Ser Ser Gln Leu
1 5

<210> SEQ ID NO 20
<211> LENGTH: 7
<212> TYPE: PRT
<213> ORGANISM: Homo sapiens

<400> SEQUENCE: 20

Glu His Ser Ser Lys Leu Gln
1 5

<210> SEQ ID NO 21
<211> LENGTH: 4
<212> TYPE: PRT
<213> ORGANISM: Homo sapiens

<400> SEQUENCE: 21

Ser Lys Leu Gln
1

<210> SEQ ID NO 22
<211> LENGTH: 10
<212> TYPE: PRT
<213> ORGANISM: Homo sapiens

<400> SEQUENCE: 22

Gln His Trp Ser Tyr Gly Leu Arg Pro Gly
1 5 10

<210> SEQ ID NO 23
<211> LENGTH: 10
<212> TYPE: PRT
<213> ORGANISM: Artificial Sequence
<220> FEATURE:
<223> OTHER INFORMATION: LHRH variant sequence.
<220> FEATURE:
<221> NAME/KEY: SITE
<222> LOCATION: (1)...(1)
<223> OTHER INFORMATION: Glu is a pyroglutamate
<220> FEATURE:
<221> NAME/KEY: SITE
<222> LOCATION: (6)...(6)
<223> OTHER INFORMATION: Lys is a D-Lys

<400> SEQUENCE: 23

Glu His Trp Ser Tyr Lys Leu Arg Pro Gly
1 5 10

<210> SEQ ID NO 24
<211> LENGTH: 397
<212> TYPE: PRT
<213> ORGANISM: Artificial Sequence
<220> FEATURE:
<223> OTHER INFORMATION: Variant proaerolysin peptide.
<220> FEATURE:
<221> NAME/KEY: SITE
<222> LOCATION: (1)...(1)
<223> OTHER INFORMATION: pyroglutamate
<220> FEATURE:
<221> NAME/KEY: SITE
<222> LOCATION: (6)...(6)
<223> OTHER INFORMATION: D-Lys

<400> SEQUENCE: 24

Glu His Trp Ser Tyr Lys Leu Arg Pro Gly Glu Ile Pro Thr Leu Ser
1 5 10 15

Ala Leu Asp Ile Pro Asp Gly Asp Glu Val Asp Val Gln Trp Arg Leu
20 25 30

Val His Asp Ser Ala Asn Phe Ile Lys Pro Thr Ser Tyr Leu Ala His
35 40 45

Tyr Leu Gly Tyr Ala Trp Val Gly Gly Asn His Ser Gln Tyr Val Gly
50 55 60

Glu Asp Met Asp Val Thr Arg Asp Gly Asp Gly Trp Val Ile Arg Gly
65 70 75 80

Asn Asn Asp Gly Gly Cys Asp Gly Tyr Arg Cys Gly Asp Lys Thr Ala
85 90 95

Ile Lys Val Ser Asn Phe Ala Tyr Asn Leu Asp Pro Asp Ser Phe Lys
100 105 110

His Gly Asp Val Thr Gln Ser Asp Arg Gln Leu Val Lys Thr Val Val
115 120 125

```
Gly Trp Ala Val Asn Asp Ser Asp Thr Pro Gln Ser Gly Tyr Asp Val
    130                 135                 140

Thr Leu Arg Tyr Asp Thr Ala Thr Asn Trp Ser Lys Thr Asn Thr Tyr
145                 150                 155                 160

Gly Leu Ser Glu Lys Val Thr Thr Lys Asn Lys Phe Lys Trp Pro Leu
                165                 170                 175

Val Gly Glu Thr Gln Leu Ser Ile Glu Ile Ala Ala Asn Gln Ser Trp
            180                 185                 190

Ala Ser Gln Asn Gly Gly Ser Thr Thr Thr Ser Leu Ser Gln Ser Val
        195                 200                 205

Arg Pro Thr Val Pro Ala Arg Ser Lys Ile Pro Val Lys Ile Glu Leu
    210                 215                 220

Tyr Lys Ala Asp Ile Ser Tyr Pro Tyr Glu Phe Lys Ala Asp Val Ser
225                 230                 235                 240

Tyr Asp Leu Thr Leu Ser Gly Phe Leu Arg Trp Gly Gly Asn Ala Trp
                245                 250                 255

Tyr Thr His Pro Asp Asn Arg Pro Asn Trp Asn His Thr Phe Val Ile
            260                 265                 270

Gly Pro Tyr Lys Asp Lys Ala Ser Ser Ile Arg Tyr Gln Trp Asp Lys
        275                 280                 285

Arg Tyr Ile Pro Gly Glu Val Lys Trp Trp Asp Trp Asn Trp Thr Ile
    290                 295                 300

Gln Gln Asn Gly Leu Ser Thr Met Gln Asn Asn Leu Ala Arg Val Leu
305                 310                 315                 320

Arg Pro Val Arg Ala Gly Ile Thr Gly Asp Phe Ser Ala Glu Ser Gln
                325                 330                 335

Phe Ala Gly Asn Ile Glu Ile Gly Ala Pro Val Pro Leu Ala Ala Asp
            340                 345                 350

Ser His Ser Ser Lys Leu Gln Ser Val Asp Gly Ala Gly Gln Gly Leu
        355                 360                 365

Arg Leu Glu Ile Pro Leu Asp Ala Gln Glu Leu Ser Gly Leu Gly Phe
    370                 375                 380

Asn Asn Val Ser Leu Ser Val Thr Pro Ala Ala Asn Gln
385                 390                 395
```

```
<210> SEQ ID NO 25
<211> LENGTH: 397
<212> TYPE: PRT
<213> ORGANISM: Artificial Sequence
<220> FEATURE:
<223> OTHER INFORMATION: Variant proaerolysin peptide.
<220> FEATURE:
<221> NAME/KEY: SITE
<222> LOCATION: (1)...(1)
<223> OTHER INFORMATION: pyroglutamate
<220> FEATURE:
<221> NAME/KEY: SITE
<222> LOCATION: (6)...(6)
<223> OTHER INFORMATION: D-Lys

<400> SEQUENCE: 25

Glu His Trp Ser Tyr Lys Leu Arg Pro Gly Glu Ile Pro Thr Leu Ser
 1               5                  10                  15

Ala Leu Asp Ile Pro Asp Gly Asp Glu Val Asp Val Gln Trp Arg Leu
            20                  25                  30

Val His Asp Ser Ala Asn Phe Ile Lys Pro Thr Ser Tyr Leu Ala His
        35                  40                  45
```

-continued

```
Tyr Leu Gly Tyr Ala Trp Val Gly Gly Asn His Ser Gln Tyr Val Gly
    50                  55                  60

Glu Asp Met Asp Val Thr Arg Asp Gly Asp Gly Trp Val Ile Arg Gly
65                  70                  75                  80

Asn Asn Asp Gly Gly Cys Asp Gly Tyr Arg Cys Gly Asp Lys Thr Ala
                85                  90                  95

Ile Lys Val Ser Asn Phe Ala Tyr Asn Leu Asp Pro Asp Ser Phe Lys
            100                 105                 110

His Gly Asp Val Thr Gln Ser Asp Arg Gln Leu Val Lys Thr Val Val
        115                 120                 125

Gly Trp Ala Val Asn Asp Ser Asp Thr Pro Gln Ser Gly Tyr Asp Val
    130                 135                 140

Thr Leu Arg Tyr Asp Thr Ala Thr Asn Trp Ser Lys Thr Asn Thr Tyr
145                 150                 155                 160

Gly Leu Ser Glu Lys Val Thr Thr Lys Asn Lys Phe Lys Trp Pro Leu
                165                 170                 175

Val Gly Glu Thr Gln Leu Ser Ile Glu Ile Ala Ala Asn Gln Ser Trp
            180                 185                 190

Ala Ser Gln Asn Gly Gly Ser Thr Thr Thr Ser Leu Ser Gln Ser Val
        195                 200                 205

Arg Pro Thr Val Pro Ala Arg Ser Lys Ile Pro Val Lys Ile Glu Leu
    210                 215                 220

Tyr Lys Ala Asp Ile Ser Tyr Pro Tyr Glu Phe Lys Ala Asp Val Ser
225                 230                 235                 240

Tyr Asp Leu Thr Leu Ser Gly Phe Leu Arg Trp Gly Gly Asn Ala Trp
                245                 250                 255

Tyr Thr His Pro Asp Asn Arg Pro Asn Trp Asn His Thr Phe Val Ile
            260                 265                 270

Gly Pro Tyr Lys Asp Lys Ala Ser Ser Ile Arg Tyr Gln Trp Asp Lys
        275                 280                 285

Arg Tyr Ile Pro Gly Glu Val Lys Trp Trp Asp Trp Asn Trp Thr Ile
    290                 295                 300

Gln Gln Asn Gly Leu Ser Thr Met Gln Asn Asn Leu Ala Arg Val Leu
305                 310                 315                 320

Arg Pro Val Arg Ala Gly Ile Thr Gly Asp Phe Ser Ala Glu Ser Gln
                325                 330                 335

Phe Ala Gly Asn Ile Glu Ile Gly Ala Pro Val Pro Leu Ala Ala Asp
            340                 345                 350

Ser Lys Val Arg Arg Ala Arg Ser Val Asp Gly Ala Gly Gln Gly Leu
        355                 360                 365

Arg Leu Glu Ile Pro Leu Asp Ala Gln Glu Leu Ser Gly Leu Gly Phe
    370                 375                 380

Asn Asn Val Ser Leu Ser Val Thr Pro Ala Ala Asn Gln
385                 390                 395
```

<210> SEQ ID NO 26
<211> LENGTH: 33
<212> TYPE: DNA
<213> ORGANISM: Artificial Sequence
<220> FEATURE:
<223> OTHER INFORMATION: Primer

<400> SEQUENCE: 26
gctgccaatc aacatcatca ttaacggcag cgc 33

```
<210> SEQ ID NO 27
<211> LENGTH: 33
<212> TYPE: DNA
<213> ORGANISM: Artificial Sequence
<220> FEATURE:
<223> OTHER INFORMATION: Primer

<400> SEQUENCE: 27

gcgctgccgt taatgatgat gttgattggc agc                                    33


<210> SEQ ID NO 28
<211> LENGTH: 39
<212> TYPE: DNA
<213> ORGANISM: Artificial Sequence
<220> FEATURE:
<223> OTHER INFORMATION: Primer

<400> SEQUENCE: 28

gccaatcaac atcatcatca tcatcattaa cggcagcgc                              39


<210> SEQ ID NO 29
<211> LENGTH: 39
<212> TYPE: DNA
<213> ORGANISM: Artificial Sequence
<220> FEATURE:
<223> OTHER INFORMATION: Primer

<400> SEQUENCE: 29

gccaatcaac atcatcatca tcatcattaa cggcagcgc                              39


<210> SEQ ID NO 30
<211> LENGTH: 1762
<212> TYPE: DNA
<213> ORGANISM: Artificial Sequence
<220> FEATURE:
<223> OTHER INFORMATION: Proaerolysin with a PSA sequence substituted
      for the furin site, and a histidine tag.

<400> SEQUENCE: 30

aagcttgcat gcctgcagaa gaaggagata tacatatgca aaaaataaaa ctaactggct      60

tgtcattaat catatccggc ctgctgatgg cacaggcgca agcggcagag cccgtctatc     120

cagaccagct tcgcttgttt tcattgggcc aaggggtctg tggcgacaag tatcgccccg     180

tcaatcgaga agaagcccaa agcgttaaaa gcaatattgt cggcatgatg ggcaatggc      240

aaataagcgg gctggccaac ggctgggtca ttatggggcc gggttataac ggtgaaataa     300

aaccagggac agcgtccaat acctggtgtt atccgaccaa tcctgttacc ggtgaaatac     360

cgacactgtc tgccctggat attccagatg gtgacgaagt cgatgtgcag tggcgactgg     420

tacatgacag tgcgaatttc atcaaaccaa ccagctatct ggcccattac ctcggttatg     480

cctgggtggg cggcaatcac agccaatatg tcggcgaaga catggatgtg acccgtgatg     540

gcgacggctg ggtgatccgt ggcaacaatg acggcggctg tgacggctat cgctgtggtg     600

acaagacggc catcaaggtc agcaacttcg cctataacct agatcccgac agcttcaagc     660

atggcgatgt cacccagtcc gaccgccagc tggtcaagac tgtggtgggc tgggcggtca     720

acgacagcga caccccccaa tccggctatg acgtcaccct gcgctacgac acagccacca     780

actggtccaa gaccaacacc tatggcctga gcgagaaggt gaccaccaag aacaagttca     840

agtggccact ggtgggggaa accgaactct ccatcgagat tgctgccaat cagtcctggg     900

cgtcccagaa cgggggctcg accaccacct ccctgtctca gtccgtgcga ccgactgtgc     960

cggcccgctc caagatcccg gtgaagatag agctctacaa ggccgacatc tcctatccct    1020
```

atgagttcaa ggccgatgtc agctatgacc tgaccctgag cggcttcctg cgctggggcg 1080
gcaacgcctg gtatacccac ccggacaacc gtccgaactg gaaccacacc ttcgtcatag 1140
gtccgtacaa ggacaaggcg agcagcattc ggtaccagtg ggacaagcgt tacatcccgg 1200
gtgaagtgaa gtggtgggac tggaactgga ccatacagca gaacggtctg tctaccatgc 1260
agaacaacct ggccagagtg ctgcgcccgg tgcgggcggg gatcaccggt gatttcagtg 1320
ccgagagcca gtttgccggc aacatagaga tcggtgctcc cgtgccgctc gcggctgaca 1380
gccattcctc caagctgcag agtgtggacg gcgctggtca aggcctgagg ctggagatcc 1440
cgctcgatgc gcaagagctc tccgggcttg gcttcaacaa cgtcagcctc agcgtgaccc 1500
ctgctgccaa tcaacatcat catcatcatc attaacggca gcgctaacaa catcatcatc 1560
atcatcatta acggcagcgc gttgtagtga tggaaccggg cctctggccc ggtttttgtt 1620
tgcactggtc gggcttgtta aaggcttgtg ctttccattt ccccacttat actggcgcca 1680
tcttgtcgga gtgccaaccg tcgaacgacg cgaggctgag accgttaatt cgggatccgt 1740
ggaacctgat ccccgggaat tc 1762

<210> SEQ ID NO 31
<211> LENGTH: 476
<212> TYPE: PRT
<213> ORGANISM: Artificial Sequence
<220> FEATURE:
<223> OTHER INFORMATION: Proaerolysin with a PSA sequence substituted for the furin site.

<400> SEQUENCE: 31

```
Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220
```

Thr Asn Trp Ser Lys Thr Asn Thr Tyr Gly Leu Ser Glu Lys Val Thr
225 230 235 240

Thr Lys Asn Lys Phe Lys Trp Pro Leu Val Gly Glu Thr Glu Leu Ser
245 250 255

Ile Glu Ile Ala Ala Asn Gln Ser Trp Ala Ser Gln Asn Gly Gly Ser
260 265 270

Thr Thr Thr Ser Leu Ser Gln Ser Val Arg Pro Thr Val Pro Ala Arg
275 280 285

Ser Lys Ile Pro Val Lys Ile Glu Leu Tyr Lys Ala Asp Ile Ser Tyr
290 295 300

Pro Tyr Glu Phe Lys Ala Asp Val Ser Tyr Asp Leu Thr Leu Ser Gly
305 310 315 320

Phe Leu Arg Trp Gly Gly Asn Ala Trp Tyr Thr His Pro Asp Asn Arg
325 330 335

Pro Asn Trp Asn His Thr Phe Val Ile Gly Pro Tyr Lys Asp Lys Ala
340 345 350

Ser Ser Ile Arg Tyr Gln Trp Asp Lys Arg Tyr Ile Pro Gly Glu Val
355 360 365

Lys Trp Trp Asp Trp Asn Trp Thr Ile Gln Gln Asn Gly Leu Ser Thr
370 375 380

Met Gln Asn Asn Leu Ala Arg Val Leu Arg Pro Val Arg Ala Gly Ile
385 390 395 400

Thr Gly Asp Phe Ser Ala Glu Ser Gln Phe Ala Gly Asn Ile Glu Ile
405 410 415

Gly Ala Pro Val Pro Leu Ala Ala Asp Ser His Ser Ser Lys Leu Gln
420 425 430

Ser Val Asp Gly Ala Gly Gln Gly Leu Arg Leu Glu Ile Pro Leu Asp
435 440 445

Ala Gln Glu Leu Ser Gly Leu Gly Phe Asn Asn Val Ser Leu Ser Val
450 455 460

Thr Pro Ala Ala Asn Gln His His His His His His
465 470 475

<210> SEQ ID NO 32
<211> LENGTH: 3
<212> TYPE: PRT
<213> ORGANISM: Artificial Sequence
<220> FEATURE:
<223> OTHER INFORMATION: HK2 Cleavage Site

<400> SEQUENCE: 32

Lys Arg Arg
1

<210> SEQ ID NO 33
<211> LENGTH: 3
<212> TYPE: PRT
<213> ORGANISM: Artificial Sequence
<220> FEATURE:
<223> OTHER INFORMATION: HK2 Cleavage Site

<400> SEQUENCE: 33

Ser Arg Arg
1

<210> SEQ ID NO 34
<211> LENGTH: 3
<212> TYPE: PRT

<213> ORGANISM: Artificial Sequence
<220> FEATURE:
<223> OTHER INFORMATION: HK2 Cleavage Site

<400> SEQUENCE: 34

Ala Arg Arg
1

<210> SEQ ID NO 35
<211> LENGTH: 3
<212> TYPE: PRT
<213> ORGANISM: Artificial Sequence
<220> FEATURE:
<223> OTHER INFORMATION: HK2 Cleavage Site

<400> SEQUENCE: 35

His Arg Arg
1

<210> SEQ ID NO 36
<211> LENGTH: 3
<212> TYPE: PRT
<213> ORGANISM: Artificial Sequence
<220> FEATURE:
<223> OTHER INFORMATION: HK2 Cleavage Site

<400> SEQUENCE: 36

Gln Arg Arg
1

<210> SEQ ID NO 37
<211> LENGTH: 3
<212> TYPE: PRT
<213> ORGANISM: Artificial Sequence
<220> FEATURE:
<223> OTHER INFORMATION: HK2 Cleavage Site

<400> SEQUENCE: 37

Ala Phe Arg
1

<210> SEQ ID NO 38
<211> LENGTH: 3
<212> TYPE: PRT
<213> ORGANISM: Artificial Sequence
<220> FEATURE:
<223> OTHER INFORMATION: HK2 Cleavage Site

<400> SEQUENCE: 38

Ala Gln Arg
1

<210> SEQ ID NO 39
<211> LENGTH: 3
<212> TYPE: PRT
<213> ORGANISM: Artificial Sequence
<220> FEATURE:
<223> OTHER INFORMATION: HK2 Cleavage Site

<400> SEQUENCE: 39

Ala Lys Arg
1

<210> SEQ ID NO 40
<211> LENGTH: 3
<212> TYPE: PRT
<213> ORGANISM: Artificial Sequence -continued
<220> FEATURE:
<223> OTHER INFORMATION: HK2 Cleavage Site

<400> SEQUENCE: 40

Ala Arg Lys
1

<210> SEQ ID NO 41
<211> LENGTH: 3
<212> TYPE: PRT
<213> ORGANISM: Artificial Sequence
<220> FEATURE:
<223> OTHER INFORMATION: HK2 Cleavage Site

<400> SEQUENCE: 41

Ala His Arg
1

<210> SEQ ID NO 42
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 42

Gln Lys Arg Arg
1

<210> SEQ ID NO 43
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 43

Lys Ser Arg Arg
1

<210> SEQ ID NO 44
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 44

Ala Lys Arg Arg
1

<210> SEQ ID NO 45
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 45

Lys Lys Arg Arg
1

<210> SEQ ID NO 46
<211> LENGTH: 4
<212> TYPE: PRT
<213> ORGANISM: Artificial Sequence
<220> FEATURE:

<223> OTHER INFORMATION: HK2 Cleavage Site

<400> SEQUENCE: 46

His Lys Arg Arg
1

<210> SEQ ID NO 47
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 47

Lys Ala Phe Arg
1

<210> SEQ ID NO 48
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 48

Lys Ala Gln Arg
1

<210> SEQ ID NO 49
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 49

Lys Ala Lys Arg
1

<210> SEQ ID NO 50
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 50

Lys Ala Arg Lys
1

<210> SEQ ID NO 51
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 51

Lys Ala His Arg
1

<210> SEQ ID NO 52
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 52

Lys Arg Arg Leu
1

<210> SEQ ID NO 53
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 53

Ser Arg Arg Leu
1

<210> SEQ ID NO 54
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 54

Ala Arg Arg Leu
1

<210> SEQ ID NO 55
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 55

Ala Arg Arg Ser
1

<210> SEQ ID NO 56
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 56

His Arg Arg Ala
1

<210> SEQ ID NO 57
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 57

Gln Arg Arg Leu
1

<210> SEQ ID NO 58
<211> LENGTH: 4
<212> TYPE: PRT
<213> ORGANISM: Artificial Sequence
<220> FEATURE:
<223> OTHER INFORMATION: HK2 Cleavage Site -continued

<400> SEQUENCE: 58

Ala Phe Arg Leu
1

<210> SEQ ID NO 59
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 59

Ala Gln Arg Leu
1

<210> SEQ ID NO 60
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 60

Ala Lys Arg Leu
1

<210> SEQ ID NO 61
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 61

Ala Arg Lys Leu
1

<210> SEQ ID NO 62
<211> LENGTH: 4
<212> TYPE: PRT
<213> ORGANISM: Artificial Sequence
<220> FEATURE:
<223> OTHER INFORMATION: HK2 Cleavage Site

<400> SEQUENCE: 62

Ala His Arg Leu
1

<210> SEQ ID NO 63
<211> LENGTH: 7
<212> TYPE: PRT
<213> ORGANISM: Artificial Sequence
<220> FEATURE:
<223> OTHER INFORMATION: HK2 Cleavage Site

<400> SEQUENCE: 63

His Ala Gln Lys Arg Arg Leu
1 5

<210> SEQ ID NO 64
<211> LENGTH: 7
<212> TYPE: PRT
<213> ORGANISM: Artificial Sequence
<220> FEATURE:
<223> OTHER INFORMATION: HK2 Cleavage Site

<400> SEQUENCE: 64

```
Gly Gly Lys Ser Arg Arg Leu
 1               5


<210> SEQ ID NO 65
<211> LENGTH: 7
<212> TYPE: PRT
<213> ORGANISM: Artificial Sequence
<220> FEATURE:
<223> OTHER INFORMATION: HK2 Cleavage Site

<400> SEQUENCE: 65

His Glu Gln Lys Arg Arg Leu
 1               5


<210> SEQ ID NO 66
<211> LENGTH: 7
<212> TYPE: PRT
<213> ORGANISM: Artificial Sequence
<220> FEATURE:
<223> OTHER INFORMATION: HK2 Cleavage Site

<400> SEQUENCE: 66

His Glu Ala Lys Arg Arg Leu
 1               5


<210> SEQ ID NO 67
<211> LENGTH: 7
<212> TYPE: PRT
<213> ORGANISM: Artificial Sequence
<220> FEATURE:
<223> OTHER INFORMATION: HK2 Cleavage Site

<400> SEQUENCE: 67

Gly Gly Gln Lys Arg Arg Leu
 1               5


<210> SEQ ID NO 68
<211> LENGTH: 7
<212> TYPE: PRT
<213> ORGANISM: Artificial Sequence
<220> FEATURE:
<223> OTHER INFORMATION: HK2 Cleavage Site

<400> SEQUENCE: 68

His Glu Gln Lys Arg Arg Ala
 1               5


<210> SEQ ID NO 69
<211> LENGTH: 7
<212> TYPE: PRT
<213> ORGANISM: Artificial Sequence
<220> FEATURE:
<223> OTHER INFORMATION: HK2 Cleavage Site

<400> SEQUENCE: 69

Gly Gly Ala Lys Arg Arg Leu
 1               5


<210> SEQ ID NO 70
<211> LENGTH: 7
<212> TYPE: PRT
<213> ORGANISM: Artificial Sequence
<220> FEATURE:
<223> OTHER INFORMATION: HK2 Cleavage Site

<400> SEQUENCE: 70
```

-continued

```
His Glu Gln Lys Arg Arg Ser
 1               5


<210> SEQ ID NO 71
<211> LENGTH: 7
<212> TYPE: PRT
<213> ORGANISM: Artificial Sequence
<220> FEATURE:
<223> OTHER INFORMATION: HK2 Cleavage Site

<400> SEQUENCE: 71

Gly Gly Lys Lys Arg Arg Leu
 1               5


<210> SEQ ID NO 72
<211> LENGTH: 7
<212> TYPE: PRT
<213> ORGANISM: Artificial Sequence
<220> FEATURE:
<223> OTHER INFORMATION: HK2 Cleavage Site

<400> SEQUENCE: 72

Gly Gly His Lys Arg Arg Leu
 1               5


<210> SEQ ID NO 73
<211> LENGTH: 1542
<212> TYPE: DNA
<213> ORGANISM: Clostridium septicum

<400> SEQUENCE: 73

tgttaataat atgttaatat tttgataaca tttattatat aataaattat ttattttaaa     60

attaaaggga gggatattta tgtcaaaaaa atcttttgct aaaaaagtaa tttgtacatc    120

tatgattgca attcagtgtg cggcagtagt accacatgta caagcttatg cacttacaaa    180

tcttgaagag gggggatatg caaatcataa taatgcttct tcaattaaaa tatttggata    240

tgaagacaat gaagatttaa aagctaaaat tattcaagat ccagagttta taagaaattg    300

ggcaaatgta gctcattcat taggatttgg atggtgcggt ggaacggcta atccaaacgt    360

tggacaaggt tttgaattta aaagagaagt tggggcaggt ggaaaagtat cttatttatt    420

atctgctaga tacaatccaa atgatcctta tgcaagtgga tatcgtgcaa aagatagact    480

ttctatgaaa atatcaaatg ttagatttgt tattgataat gattctataa aattaggtac    540

acctaaagtg aaaaaattag cacctttaaa ctctgctagt tttgatttaa taaatgaaag    600

taaaactgag tctaaattat caaaaacatt taattataca acttctaaaa cagtttctaa    660

aacagataac tttaaatttg gagaaaaaat aggagtaaaa acatcattta aagtaggtct    720

tgaagctata gctgacagta aagttgagac aagctttgaa tttaatgcag aacaaggttg    780

gtcaaataca aatagtacta ctgaaactaa acaagaaagt actacatata ctgcaacagt    840

ttctccacaa actaaaaaga gattattcct agatgtgtta ggatcacaaa ttgatattcc    900

ttatgaagga aaaatatata tggaatacga catagaatta atgggatttt taagatatac    960

aggaaatgct cgtgaagatc atactgaaga tagaccaaca gttaaactta aatttggtaa   1020

aaacggtatg agtgctgagg aacatcttaa agatttatat agtcataaga atattaatgg   1080

atattcagaa tgggattgga aatgggtaga tgagaaattt ggttatttat ttaaaaattc   1140

atacgatgct cttactagta gaaaattagg aggaataata aaaggctcat ttactaacat   1200

taatggaaca aaaatagtaa ttagagaagg taaagaaatt ccacttcctg ataagaagag   1260
```

-continued

```
aagaggaaaa cgttcagtag attctttaga tgctagatta caaaatgaag gtattagaat   1320

agaaaatatt gaaacacaag atgttccagg atttagacta aatagcataa catacaatga   1380

taaaaaattg atattaatta ataatatata attataattt attaaaatat gcttctctat   1440

actttatatt aatatttaaa gtataaaaac taacaaaatc tcacttagta ggtagaattg   1500

tataaaaaca aatctaccta ctattttttt attatttagt cg                      1542
```

<210> SEQ ID NO 74
<211> LENGTH: 443
<212> TYPE: PRT
<213> ORGANISM: Clostridium septicum

<400> SEQUENCE: 74

```
Met Ser Lys Lys Ser Phe Ala Lys Lys Val Ile Cys Thr Ser Met Ile
1               5                   10                  15

Ala Ile Gln Cys Ala Ala Val Val Pro His Val Gln Ala Tyr Ala Leu
            20                  25                  30

Thr Asn Leu Glu Glu Gly Gly Tyr Ala Asn His Asn Asn Ala Ser Ser
        35                  40                  45

Ile Lys Ile Phe Gly Tyr Glu Asp Asn Glu Asp Leu Lys Ala Lys Ile
    50                  55                  60

Ile Gln Asp Pro Glu Phe Ile Arg Asn Trp Ala Asn Val Ala His Ser
65                  70                  75                  80

Leu Gly Phe Gly Trp Cys Gly Gly Thr Ala Asn Pro Asn Val Gly Gln
                85                  90                  95

Gly Phe Glu Phe Lys Arg Glu Val Gly Ala Gly Gly Lys Val Ser Tyr
            100                 105                 110

Leu Leu Ser Ala Arg Tyr Asn Pro Asn Asp Pro Tyr Ala Ser Gly Tyr
        115                 120                 125

Arg Ala Lys Asp Arg Leu Ser Met Lys Ile Ser Asn Val Arg Phe Val
    130                 135                 140

Ile Asp Asn Asp Ser Ile Lys Leu Gly Thr Pro Lys Val Lys Lys Leu
145                 150                 155                 160

Ala Pro Leu Asn Ser Ala Ser Phe Asp Leu Ile Asn Glu Ser Lys Thr
                165                 170                 175

Glu Ser Lys Leu Ser Lys Thr Phe Asn Tyr Thr Thr Ser Lys Thr Val
            180                 185                 190

Ser Lys Thr Asp Asn Phe Lys Phe Gly Glu Lys Ile Gly Val Lys Thr
        195                 200                 205

Ser Phe Lys Val Gly Leu Glu Ala Ile Ala Asp Ser Lys Val Glu Thr
    210                 215                 220

Ser Phe Glu Phe Asn Ala Glu Gln Gly Trp Ser Asn Thr Asn Ser Thr
225                 230                 235                 240

Thr Glu Thr Lys Gln Glu Ser Thr Thr Tyr Thr Ala Thr Val Ser Pro
                245                 250                 255

Gln Thr Lys Lys Arg Leu Phe Leu Asp Val Leu Gly Ser Gln Ile Asp
            260                 265                 270

Ile Pro Tyr Glu Gly Lys Ile Tyr Met Glu Tyr Asp Ile Glu Leu Met
        275                 280                 285

Gly Phe Leu Arg Tyr Thr Gly Asn Ala Arg Glu Asp His Thr Glu Asp
    290                 295                 300

Arg Pro Thr Val Lys Leu Lys Phe Gly Lys Asn Gly Met Ser Ala Glu
305                 310                 315                 320

Glu His Leu Lys Asp Leu Tyr Ser His Lys Asn Ile Asn Gly Tyr Ser
```

-continued

```
            325                 330                 335

Glu Trp Asp Trp Lys Trp Val Asp Glu Lys Phe Gly Tyr Leu Phe Lys
            340                 345                 350

Asn Ser Tyr Asp Ala Leu Thr Ser Arg Lys Leu Gly Gly Ile Ile Lys
        355                 360                 365

Gly Ser Phe Thr Asn Ile Asn Gly Thr Lys Ile Val Ile Arg Glu Gly
    370                 375                 380

Lys Glu Ile Pro Leu Pro Asp Lys Lys Arg Arg Gly Lys Arg Ser Val
385                 390                 395                 400

Asp Ser Leu Asp Ala Arg Leu Gln Asn Glu Gly Ile Arg Ile Glu Asn
            405                 410                 415

Ile Glu Thr Gln Asp Val Pro Gly Phe Arg Leu Asn Ser Ile Thr Tyr
            420                 425                 430

Asn Asp Lys Lys Leu Ile Leu Ile Asn Asn Ile
        435                 440
```

The embodiments of the invention in which an exclusive property or privilege is claimed are defined as follows:

1. A method of treating benign prostatic hyperplasia (BPH), comprising intraprostatically administering to a patient in need thereof an effective amount of a modified pore-forming protein comprising the amino acid sequence shown in SEQ ID NO:31.

2. The method of claim 1, wherein said modified pore-forming protein is administered in combination with one or more other treatments for benign prostatic hyperplasia.

3. The method according to claim 2, wherein said one or more other treatments for benign pro static hyperplasia is selected from the group consisting of an alpha blocker, an inhibitor of an intracellular enzyme that converts testosterone into 5alpha-dihydrotestosterone, dutasteride, finasteride, an alpha-1 adrenoceptor blocking agent, a phytotherapy, balloon dilation, transurethral incision of the prostate, transurethral resection of the prostate, transurethral needle ablation, transurethral microwave thermotherapy, electrical vaporization, and prostatectomy.

4. The method according to claim 3, wherein said alpha-1 adrenoceptor blocking agent is selected from the group consisting of tamsulosin, terazosin, alfuzosin, doxazosin, and prazosin.

5. The method according to claim 3 wherein said phytotherapy is selected from the group consisting of saw palmetto berry/dwarf palm, African plum bark, South African star grass/beta-sitosterol, purple cone flower, pumpkin seeds, rye, and stinging nettle.

6. The method according to claim 3, wherein said prostatectomy is laser prostatectomy or open prostatectomy.

7. The method according to claim 1, further comprising administering an immunosuppressive therapy.

8. The method according to claim 7, wherein said immunosuppressive therapy is selected from the group consisting of a systemic corticosteroid, a topical corticosteroid, cyclosporin A, cyclophosphamide, deoxyspergualin, an antibody to T cells, an antibody to B cells, and an antiboby to T and B cells.

9. A method of treating benign prostatic hyperplasia (BPH), comprising intraprostatically administering to a patient in need thereof an effective amount of a modified pore-forming protein comprising an amino acid sequence having 98% or greater sequence identity to the amino acid sequence shown in SEQ ID NO:31, wherein said modified pore-forming protein maintains the ability to selectively target and kill normal prostate cells.

* * * * *